(12) United States Patent (10) Patent No.: US 11,759,224 B2
Shelton, IV et al. (45) Date of Patent: Sep. 19, 2023

(54) SURGICAL INSTRUMENT SYSTEMS COMPRISING HANDLE ARRANGEMENTS

(71) Applicant: Cilag GmbH International, Zug (CH)

(72) Inventors: Frederick E. Shelton, IV, Hillsboro, OH (US); Jason L. Harris, Lebanon, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 467 days.

(21) Appl. No.: 16/112,109

(22) Filed: Aug. 24, 2018

(65) Prior Publication Data

US 2019/0125388 A1 May 2, 2019

Related U.S. Application Data

(60) Provisional application No. 62/665,134, filed on May 1, 2018, provisional application No. 62/665,128, filed
(Continued)

(51) Int. Cl.
*A61B 5/05* (2021.01)
*A61B 17/3205* (2006.01)
(Continued)

(52) U.S. Cl.
CPC .......... *A61B 17/2909* (2013.01); *A61B 17/00* (2013.01); *A61B 17/105* (2013.01); *A61B 17/1285* (2013.01); *A61B 17/282* (2013.01); *A61B 17/2841* (2013.01); *A61B 17/29* (2013.01); *A61B 17/0469* (2013.01); *A61B 17/0482* (2013.01); *A61B 17/0483* (2013.01);
(Continued)

(58) Field of Classification Search
CPC ............ A61B 2017/00398; A61B 2017/07285
See application file for complete search history.

(56) References Cited

U.S. PATENT DOCUMENTS 1,853,416 A 4/1932 Hall
2,222,125 A 11/1940 Stehlik
(Continued)

FOREIGN PATENT DOCUMENTS

AU 2015201140 A1 3/2015
CA 2795323 A1 5/2014
(Continued)

OTHER PUBLICATIONS

US 10,504,709, 8/2018, Karancsi et al. (withdrawn)
(Continued)

*Primary Examiner* — Kawing Chan
*Assistant Examiner* — Charles S Laughlin

(57) ABSTRACT

A surgical instrument system comprising a first motor, a second motor, and a third motor is disclosed. The surgical instrument system comprises a first handle comprising a first number of controls, a second handle comprising a second number of controls, and a shaft assembly. The shaft assembly is attachable to the first handle in a first orientation in order to engage one of the motors. The shaft assembly is attachable to the second handle in a second orientation to engage a different motor. The surgical instrument system is configured to perform a different function of an end effector in the first orientation and the second orientation.

16 Claims, 92 Drawing Sheets

Related U.S. Application Data on May 1, 2018, provisional application No. 62/665,139, filed on May 1, 2018, provisional application No. 62/665,177, filed on May 1, 2018, provisional application No. 62/665,129, filed on May 1, 2018, provisional application No. 62/665,192, filed on May 1, 2018, provisional application No. 62/578,817, filed on Oct. 30, 2017, provisional application No. 62/578,835, filed on Oct. 30, 2017, provisional application No. 62/578,844, filed on Oct. 30, 2017, provisional application No. 62/578,855, filed on Oct. 30, 2017, provisional application No. 62/578,804, filed on Oct. 30, 2017, provisional application No. 62/578,793, filed on Oct. 30, 2017.

(51) Int. Cl.

| | |
|---|---|
| *A61B 17/29* | (2006.01) |
| *A61B 17/00* | (2006.01) |
| *A61B 17/128* | (2006.01) |
| *A61B 17/28* | (2006.01) |
| *A61B 17/10* | (2006.01) |
| A61B 18/14 | (2006.01) |
| B33Y 80/00 | (2015.01) |
| A61B 90/00 | (2016.01) |
| A61B 17/32 | (2006.01) |
| A61B 18/00 | (2006.01) |
| A61B 18/12 | (2006.01) |
| F16D 27/00 | (2006.01) |
| F16D 27/108 | (2006.01) |
| F16D 27/12 | (2006.01) |
| G09G 3/34 | (2006.01) |
| G09G 3/36 | (2006.01) |
| G09G 3/38 | (2006.01) |
| A61B 17/04 | (2006.01) |
| A61B 17/06 | (2006.01) |
| A61B 34/30 | (2016.01) |
| A61B 17/3201 | (2006.01) |
| A61B 90/98 | (2016.01) |
| A61B 17/062 | (2006.01) |
| A61B 17/068 | (2006.01) |
| A61B 17/285 | (2006.01) |
| A61B 17/295 | (2006.01) |
| A61B 17/34 | (2006.01) |
| G06F 3/147 | (2006.01) |
| A61B 34/00 | (2016.01) |

(52) U.S. Cl.
CPC ......... *A61B 17/0491* (2013.01); *A61B 17/062* (2013.01); *A61B 17/06004* (2013.01); *A61B 17/068* (2013.01); *A61B 17/0625* (2013.01); *A61B 17/06066* (2013.01); *A61B 17/06114* (2013.01); *A61B 17/06133* (2013.01); *A61B 17/128* (2013.01); *A61B 17/285* (2013.01); *A61B 17/2833* (2013.01); *A61B 17/295* (2013.01); *A61B 17/3201* (2013.01); *A61B 17/3421* (2013.01); *A61B 17/3468* (2013.01); *A61B 18/1206* (2013.01); *A61B 18/1445* (2013.01); *A61B 34/30* (2016.02); *A61B 34/76* (2016.02); *A61B 90/03* (2016.02); *A61B 90/98* (2016.02); *A61B 2017/0003* (2013.01); *A61B 2017/00017* (2013.01); *A61B 2017/00026* (2013.01); *A61B 2017/00039* (2013.01); *A61B 2017/0046* (2013.01); *A61B 2017/00057* (2013.01); *A61B 2017/00061* (2013.01); *A61B 2017/00075* (2013.01); *A61B 2017/00115* (2013.01); *A61B 2017/00119* (2013.01); *A61B 2017/00128* (2013.01); *A61B 2017/00212* (2013.01); *A61B 2017/00221* (2013.01); *A61B 2017/00327* (2013.01); *A61B 2017/00367* (2013.01); *A61B 2017/00393* (2013.01); *A61B 2017/00398* (2013.01); *A61B 2017/00407* (2013.01); *A61B 2017/00424* (2013.01); *A61B 2017/00438* (2013.01); *A61B 2017/00464* (2013.01); *A61B 2017/00473* (2013.01); *A61B 2017/00477* (2013.01); *A61B 2017/00526* (2013.01); *A61B 2017/00734* (2013.01); *A61B 2017/06052* (2013.01); *A61B 2017/06076* (2013.01); *A61B 2017/2825* (2013.01); *A61B 2017/2845* (2013.01); *A61B 2017/2902* (2013.01); *A61B 2017/2903* (2013.01); *A61B 2017/2911* (2013.01); *A61B 2017/2923* (2013.01); *A61B 2017/2925* (2013.01); *A61B 2017/2926* (2013.01); *A61B 2017/2927* (2013.01); *A61B 2017/2929* (2013.01); *A61B 2017/2931* (2013.01); *A61B 2017/2943* (2013.01); *A61B 2017/2945* (2013.01); *A61B 2017/320044* (2013.01); *A61B 2018/0063* (2013.01); *A61B 2018/0072* (2013.01); *A61B 2018/00077* (2013.01); *A61B 2018/00083* (2013.01); *A61B 2018/00136* (2013.01); *A61B 2018/00178* (2013.01); *A61B 2018/00208* (2013.01); *A61B 2018/00404* (2013.01); *A61B 2018/00577* (2013.01); *A61B 2018/00595* (2013.01); *A61B 2018/00601* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01); *A61B 2018/1253* (2013.01); *A61B 2018/1266* (2013.01); *A61B 2018/146* (2013.01); *A61B 2018/1452* (2013.01); *A61B 2018/1457* (2013.01); *A61B 2090/035* (2016.02); *A61B 2090/0811* (2016.02); *B33Y 80/00* (2014.12); *F16D 27/004* (2013.01); *F16D 27/108* (2013.01); *F16D 27/12* (2013.01); *G06F 3/147* (2013.01); *G09G 3/344* (2013.01); *G09G 3/3648* (2013.01); *G09G 3/38* (2013.01); *G09G 2380/08* (2013.01)

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffer |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |

(56) References Cited

U.S. PATENT DOCUMENTS

| | | |
|---|---|---|
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |

(56) References Cited

U.S. PATENT DOCUMENTS

| | | |
|---|---|---|
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |

(56) References Cited

U.S. PATENT DOCUMENTS

| | | |
|---|---|---|
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,540,709 B2 | 9/2013 | Allen |

(56) References Cited

U.S. PATENT DOCUMENTS

| | | |
|---|---|---|
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |

(56) References Cited

U.S. PATENT DOCUMENTS

| | | |
|---|---|---|
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,685 B2 | 6/2016 | Meier et al. |
| 9,360,449 B2 | 6/2016 | Duric |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |

(56) References Cited

U.S. PATENT DOCUMENTS

| | | |
|---|---|---|
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,737,371 B2 | 8/2017 | Romo et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,560 B2 | 9/2017 | Ballakur et al. |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |

(56) References Cited

U.S. PATENT DOCUMENTS

| | | |
|---|---|---|
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |

(56) References Cited

U.S. PATENT DOCUMENTS

| | | |
|---|---|---|
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |

(56) References Cited

U.S. PATENT DOCUMENTS

| | | |
|---|---|---|
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,930 B2 | 3/2020 | Scheib et al. |
| 10,595,952 B2 | 3/2020 | Forrest et al. |
| 10,602,007 B2 | 3/2020 | Takano |
| 10,610,223 B2 | 4/2020 | Wellman et al. |
| 10,617,482 B2 | 4/2020 | Houser et al. |
| 10,624,667 B2 | 4/2020 | Faller et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,639,027 B2 | 5/2020 | Shelton, IV et al. |
| 10,639,036 B2 | 5/2020 | Yates et al. |
| 10,639,098 B2 | 5/2020 | Cosman et al. |
| 10,639,185 B2 | 5/2020 | Agrawal et al. |
| 10,653,476 B2 | 5/2020 | Ross |
| 10,656,720 B1 | 5/2020 | Holz |
| 10,660,705 B2 | 5/2020 | Piron et al. |
| 10,674,897 B2 | 6/2020 | Levy |
| 10,675,035 B2 | 6/2020 | Zingman |
| 10,675,100 B2 | 6/2020 | Frushour |
| 10,679,758 B2 | 6/2020 | Fox et al. |
| 10,695,134 B2 | 6/2020 | Barral et al. |
| 10,716,489 B2 | 7/2020 | Kalvoy et al. |
| 10,716,615 B2 | 7/2020 | Shelton, IV et al. |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |

(56) References Cited

U.S. PATENT DOCUMENTS

| | | |
|---|---|---|
| 10,751,052 B2 | 8/2020 | Stokes et al. |
| 10,751,768 B2 | 8/2020 | Hersey et al. |
| D896,379 S | 9/2020 | Shelton, IV et al. |
| 10,765,376 B2 | 9/2020 | Brown et al. |
| 10,772,630 B2 | 9/2020 | Wixey |
| 10,772,673 B2 | 9/2020 | Allen, IV et al. |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,803,977 B2 | 10/2020 | Sanmugalingham |
| 10,806,499 B2 | 10/2020 | Castaneda et al. |
| 10,835,206 B2 | 11/2020 | Bell et al. |
| 10,835,247 B2 | 11/2020 | Shelton, IV et al. |
| 10,842,897 B2 | 11/2020 | Schwartz et al. |
| D904,612 S | 12/2020 | Wynn et al. |
| 10,856,768 B2 | 12/2020 | Osadchy et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,446 B2 | 1/2021 | Strobl |
| 10,898,256 B2 | 1/2021 | Yates et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,912,567 B2 | 2/2021 | Shelton, IV et al. |
| 10,916,415 B2 | 2/2021 | Karancsi et al. |
| D914,878 S | 3/2021 | Shelton, IV et al. |
| 10,932,705 B2 | 3/2021 | Muhsin et al. |
| 10,932,784 B2 | 3/2021 | Mozdzierz et al. |
| 10,939,313 B2 | 3/2021 | Eom et al. |
| 10,950,982 B2 | 3/2021 | Regnier et al. |
| 10,959,729 B2 | 3/2021 | Ehrenfels et al. |
| 10,960,150 B2 | 3/2021 | Zergiebel et al. |
| 10,966,590 B2 | 4/2021 | Takahashi et al. |
| 10,966,798 B2 | 4/2021 | Tesar et al. |
| 10,980,595 B2 | 4/2021 | Wham |
| 11,000,276 B2 | 5/2021 | Shelton, IV et al. |
| 11,051,817 B2 | 7/2021 | Shelton, IV et al. |
| 11,051,902 B2 | 7/2021 | Kruecker et al. |
| 11,058,501 B2 | 7/2021 | Tokarchuk et al. |
| 11,071,595 B2 | 7/2021 | Johnson et al. |
| 11,141,213 B2 | 10/2021 | Yates et al. |
| 11,185,325 B2 | 11/2021 | Shelton, IV et al. |
| 11,218,822 B2 | 1/2022 | Morgan et al. |
| 11,273,290 B2 | 3/2022 | Kowshik |
| D950,728 S | 5/2022 | Bakos et al. |
| D952,144 S | 5/2022 | Boudreaux |
| 11,350,978 B2 | 6/2022 | Henderson et al. |
| 11,382,715 B2 | 7/2022 | Arai et al. |
| D964,564 S | 9/2022 | Boudreaux |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0169584 A1 | 11/2002 | Fu et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0046109 A1 | 3/2003 | Uchikubo |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0287645 A1 | 12/2006 | Tashiro et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0023477 A1 | 2/2007 | Whitman et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |

(56) References Cited

U.S. PATENT DOCUMENTS

| | | |
|---|---|---|
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0235052 A1 | 9/2008 | Node-Langlois et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0121049 A1 | 5/2011 | Malinouskas et al. |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0105552 A1 | 5/2013 | Weir et al. |
| 2013/0116218 A1 | 5/2013 | Kaplan et al. |
| 2013/0131845 A1 | 5/2013 | Guilleminot |
| 2013/0144284 A1 | 6/2013 | Behnke et al. |

(56) References Cited

U.S. PATENT DOCUMENTS

| | | |
|---|---|---|
| 2013/0153635 A1 | 6/2013 | Hodgkinson |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331874 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0117256 A1 | 5/2014 | Mueller et al. |
| 2014/0121669 A1 | 5/2014 | Claus |
| 2014/0128885 A1 | 5/2014 | Dachs, II et al. |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171923 A1* | 6/2014 | Aranyi .................. A61B 17/00 606/1 |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246473 A1* | 9/2014 | Auld .................. A61B 90/90 227/175.1 |
| 2014/0246474 A1* | 9/2014 | Hall .................. A61B 17/07207 227/175.1 |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0263564 A1* | 9/2014 | Leimbach ............ A61B 17/105 227/180.1 |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053740 A1* | 2/2015 | Shelton, IV .............. G09G 5/14 227/175.2 |
| 2015/0053743 A1 | 2/2015 | Yates et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0066001 A1 | 3/2015 | Jeong et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0108198 A1 | 4/2015 | Estrella et al. |
| 2015/0122870 A1 | 5/2015 | Zemlok et al. |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0257816 A1 | 9/2015 | Ineson |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2015/0374369 A1 | 12/2015 | Yates et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |

(56) References Cited

U.S. PATENT DOCUMENTS

| | | |
|---|---|---|
| 2016/0078190 A1 | 3/2016 | Greene et al. |
| 2016/0095585 A1 | 4/2016 | Zergiebel et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166256 A1 | 6/2016 | Baxter, III et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0199125 A1 | 7/2016 | Jones |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0253472 A1 | 9/2016 | Pedersen et al. |
| 2016/0256154 A1 | 9/2016 | Shelton, IV et al. |
| 2016/0256160 A1 | 9/2016 | Shelton, IV et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310203 A1 | 10/2016 | Gaspredes et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374665 A1 | 12/2016 | DiNardo et al. |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0000554 A1 | 1/2017 | Yates et al. |
| 2017/0005911 A1 | 1/2017 | Kasargod et al. |
| 2017/0007247 A1 | 1/2017 | Shelton, IV et al. |
| 2017/0020291 A1 | 1/2017 | Magana |
| 2017/0027603 A1 | 2/2017 | Pandey |
| 2017/0042604 A1 | 2/2017 | McFarland et al. |
| 2017/0056017 A1 | 3/2017 | Vendely et al. |
| 2017/0056116 A1 | 3/2017 | Kostrzewski |
| 2017/0061375 A1 | 3/2017 | Laster et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086910 A1 | 3/2017 | Wiener et al. |
| 2017/0086911 A1 | 3/2017 | Wiener et al. |
| 2017/0086914 A1 | 3/2017 | Wiener et al. |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0151026 A1 | 6/2017 | Panescu et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0171231 A1 | 6/2017 | Reybok, Jr. et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172672 A1 | 6/2017 | Bailey et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0181745 A1 | 6/2017 | Penna et al. |
| 2017/0185732 A1 | 6/2017 | Niklewski et al. |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224428 A1 | 8/2017 | Kopp |
| 2017/0231553 A1 | 8/2017 | Igarashi et al. |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0252095 A1 | 9/2017 | Johnson |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281164 A1 | 10/2017 | Harris et al. |
| 2017/0281169 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0290586 A1 | 10/2017 | Wellman |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303419 A1 | 10/2017 | Collins et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325813 A1 | 11/2017 | Aranyi et al. |

(56) References Cited

U.S. PATENT DOCUMENTS

| | | |
|---|---|---|
| 2017/0325876 A1 | 11/2017 | Nakadate et al. |
| 2017/0325878 A1 | 11/2017 | Messerly et al. |
| 2017/0333152 A1 | 11/2017 | Wade |
| 2017/0337043 A1 | 11/2017 | Brincat et al. |
| 2017/0354470 A1 | 12/2017 | Farritor et al. |
| 2017/0360358 A1 | 12/2017 | Amiot et al. |
| 2017/0360438 A1 | 12/2017 | Cappola |
| 2017/0360439 A1 | 12/2017 | Chen et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008260 A1 | 1/2018 | Baxter, III et al. |
| 2018/0008359 A1 | 1/2018 | Randle |
| 2018/0011983 A1 | 1/2018 | Zuhars et al. |
| 2018/0014848 A1 | 1/2018 | Messerly et al. |
| 2018/0021058 A1 | 1/2018 | Meglan |
| 2018/0042659 A1 | 2/2018 | Rupp et al. |
| 2018/0049817 A1 | 2/2018 | Swayze et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0064498 A1 | 3/2018 | Kapadia et al. |
| 2018/0065248 A1 | 3/2018 | Barral et al. |
| 2018/0078170 A1 | 3/2018 | Panescu et al. |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0110576 A1 | 4/2018 | Kopp |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0140366 A1 | 5/2018 | Kapadia |
| 2018/0144243 A1 | 5/2018 | Hsieh et al. |
| 2018/0153436 A1 | 6/2018 | Olson |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168597 A1 | 6/2018 | Fanelli et al. |
| 2018/0168598 A1 | 6/2018 | Shelton, IV et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168635 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168748 A1 | 6/2018 | Kapadia |
| 2018/0168759 A1 | 6/2018 | Kilroy et al. |
| 2018/0168763 A1 | 6/2018 | Scheib et al. |
| 2018/0172420 A1 | 6/2018 | Hein et al. |
| 2018/0177383 A1 | 6/2018 | Noonan et al. |
| 2018/0177557 A1 | 6/2018 | Kapadia et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0199995 A1 | 7/2018 | Odermatt et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0243035 A1 | 8/2018 | Kopp |
| 2018/0247128 A1 | 8/2018 | Alvi et al. |
| 2018/0247711 A1 | 8/2018 | Terry |
| 2018/0250080 A1 | 9/2018 | Kopp |
| 2018/0250084 A1 | 9/2018 | Kopp et al. |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0310997 A1 | 11/2018 | Peine et al. |
| 2018/0315492 A1 | 11/2018 | Bishop et al. |
| 2018/0317915 A1 | 11/2018 | McDonald, II |

(56) References Cited

U.S. PATENT DOCUMENTS

| | | |
|---|---|---|
| 2018/0317916 A1 | 11/2018 | Wixey |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0338806 A1 | 11/2018 | Grubbs |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0358112 A1 | 12/2018 | Sharifi Sedeh et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000446 A1 | 1/2019 | Shelton, IV et al. |
| 2019/0000448 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0008600 A1 | 1/2019 | Pedros et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0054620 A1 | 2/2019 | Griffiths et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0090969 A1 | 3/2019 | Jarc et al. |
| 2019/0099180 A1 | 4/2019 | Leimbach et al. |
| 2019/0099221 A1 | 4/2019 | Schmidt et al. |
| 2019/0099227 A1 | 4/2019 | Rockrohr |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125365 A1 | 5/2019 | Parfett et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125381 A1 | 5/2019 | Scheib et al. |
| 2019/0125382 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125389 A1 | 5/2019 | Shelton, IV et al. |
| 2019/0125390 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0164285 A1 | 5/2019 | Nye et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201018 A1 | 7/2019 | Shelton, IV et al. |
| 2019/0201019 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |

(56) References Cited

U.S. PATENT DOCUMENTS

| | | |
|---|---|---|
| 2019/0201074 A1 | 7/2019 | Yates et al. |
| 2019/0201075 A1 | 7/2019 | Shelton, IV et al. |
| 2019/0201076 A1 | 7/2019 | Honda et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201122 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201593 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0223291 A1 | 7/2019 | Seow et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054325 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0078070 A1 | 3/2020 | Henderson et al. |
| 2020/0078071 A1 | 3/2020 | Asher |

(56) References Cited

U.S. PATENT DOCUMENTS

| | | |
|---|---|---|
| 2020/0078076 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |
| 2022/0323092 A1 | 10/2022 | Shelton, IV et al. |
| 2022/0323095 A1 | 10/2022 | Nott et al. |
| 2022/0323150 A1 | 10/2022 | Yates et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 107811710 A | 3/2018 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |

(56) References Cited

FOREIGN PATENT DOCUMENTS

| | | |
|---|---|---|
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5373315 A | 6/1978 |
| JP | H07132122 A | 5/1995 |
| JP | H08332169 A | 12/1996 |
| JP | 2001029353 A | 2/2001 |
| JP | 2001340350 A | 12/2001 |
| JP | 2002272758 A | 9/2002 |
| JP | 2007123394 A | 5/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2012065698 A | 4/2012 |
| JP | 2014155207 A | 8/2014 |
| JP | 2016174836 A | 10/2016 |
| JP | 2017047022 A | 3/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A3 | 11/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (Percom Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%

(56) References Cited

OTHER PUBLICATIONS

20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "*ARCM*", Video, Sep. 2012, YouTube, 5 screenshots, Retrieved from internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
Lalys, et al., "Automatic knowledge-based recognition of low-level tasks in ophthalmological procedures", Int J CARS, vol. 8, No. 1, pp. 1-49, Apr. 19, 2012.
Hu, Jinwen, Stimulations of adaptive temperature control with self-focused hyperthermia system for tumor treatment, Jan. 9, 2012, Ultrasonics 53, pp. 171-177, (Year: 2012).
Hussain et al., "A survey on resource allocation in high performance distributed computing systems", Parallel Computing, vol. 39, No. 11, pp. 709-736 (2013).

\* cited by examiner

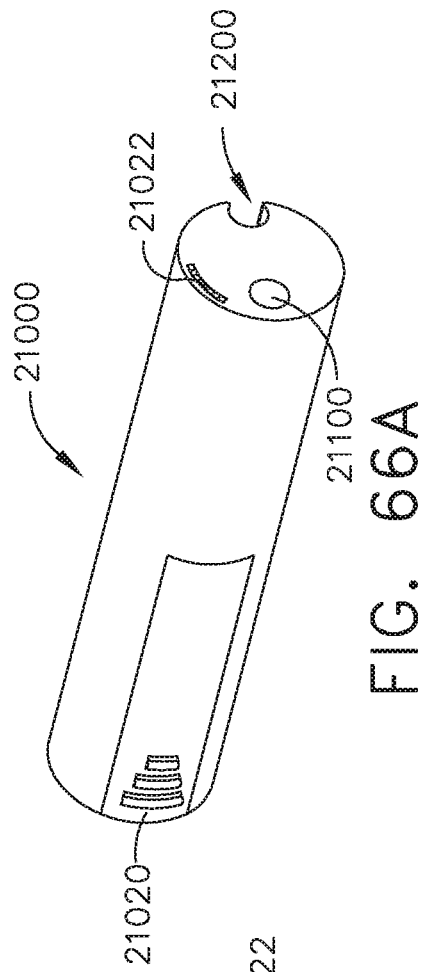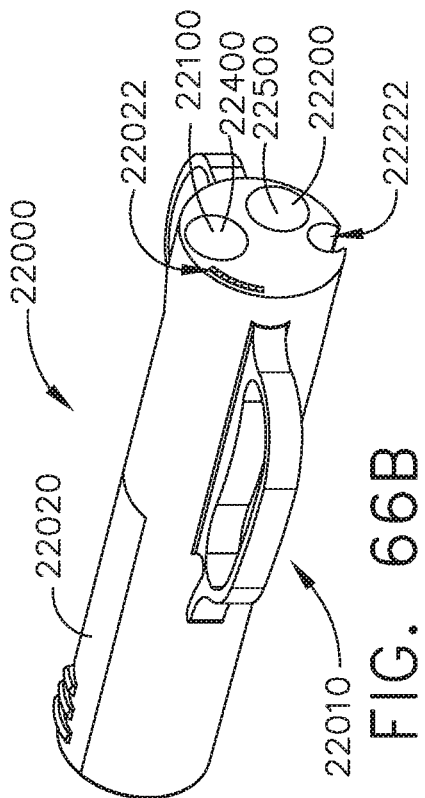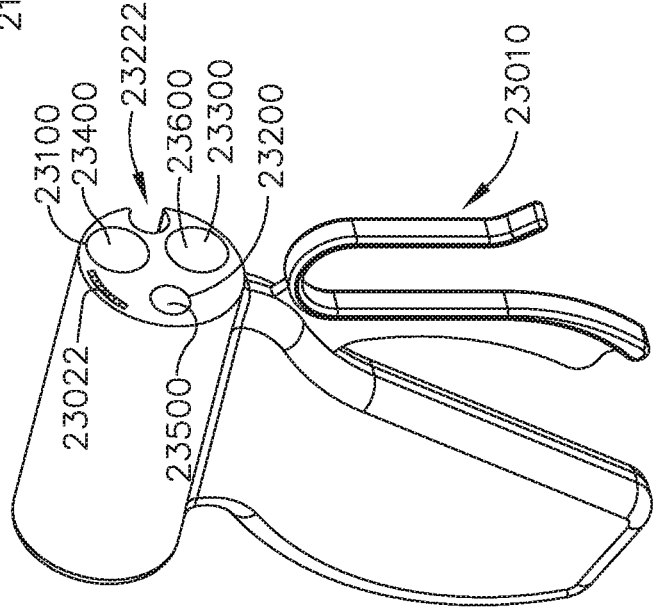

|  | RT/LE SHAFT ARTICULATION | DISTAL HEAD ROTATION | END-EFFECTOR ACTUATION #1 | END-EFFECTOR ACTUATION #2 | SHAFT ROTATION |
|---|---|---|---|---|---|
| 1 PENCIL HANDLE (8) | 8mm MOTOR/ +30° | MANUAL/ >360° | LOCKED OUT | LOCKED OUT | LOCKED OUT |
| 2 SCISSOR HANDLE (12) | 12mm MOTOR 1/ ±45° | MANUAL/ >360° | MOTOR 2 | LOCKED OUT | LOCKED OUT |
| 3 PISTOL HANDLE (12) | 12mm MOTOR1/ 5mm±45° 10mm±90° | 12mm MOTOR 3/ >360° | MOTOR 2 | MOTOR 2 WITH SHIFT | MANUAL/ >360° |

FIG. 69

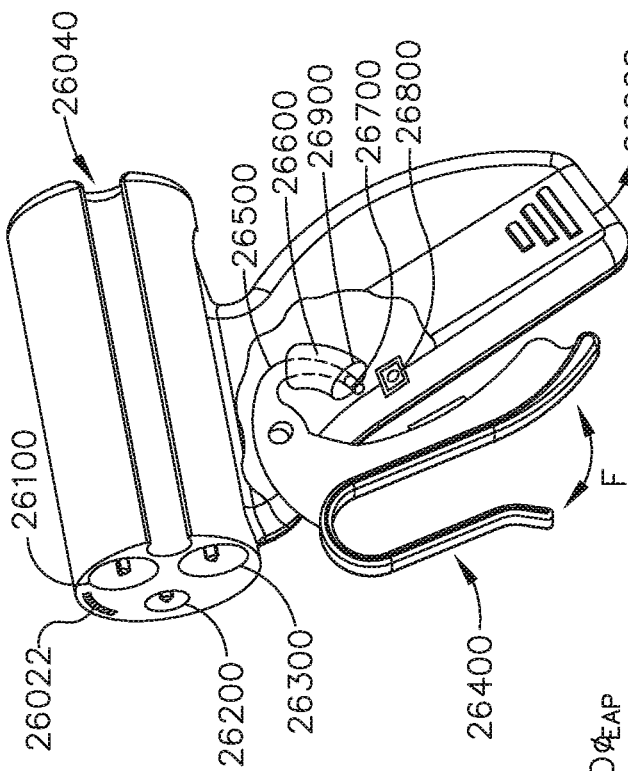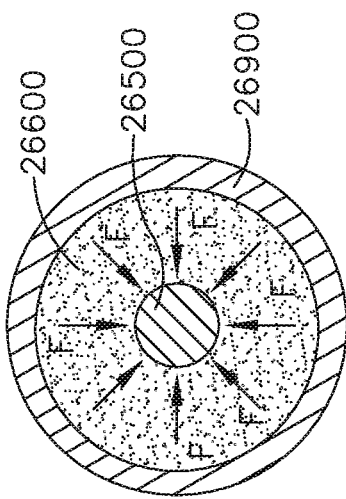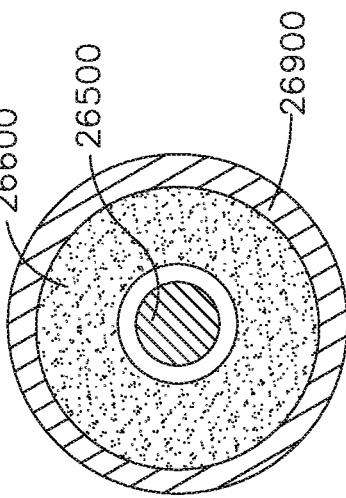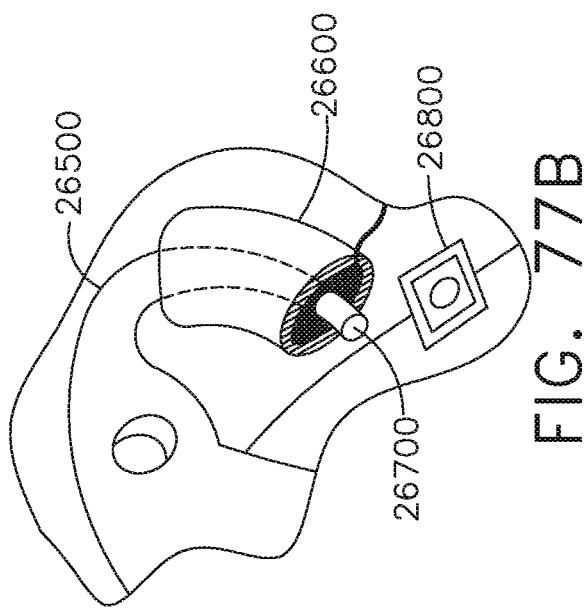

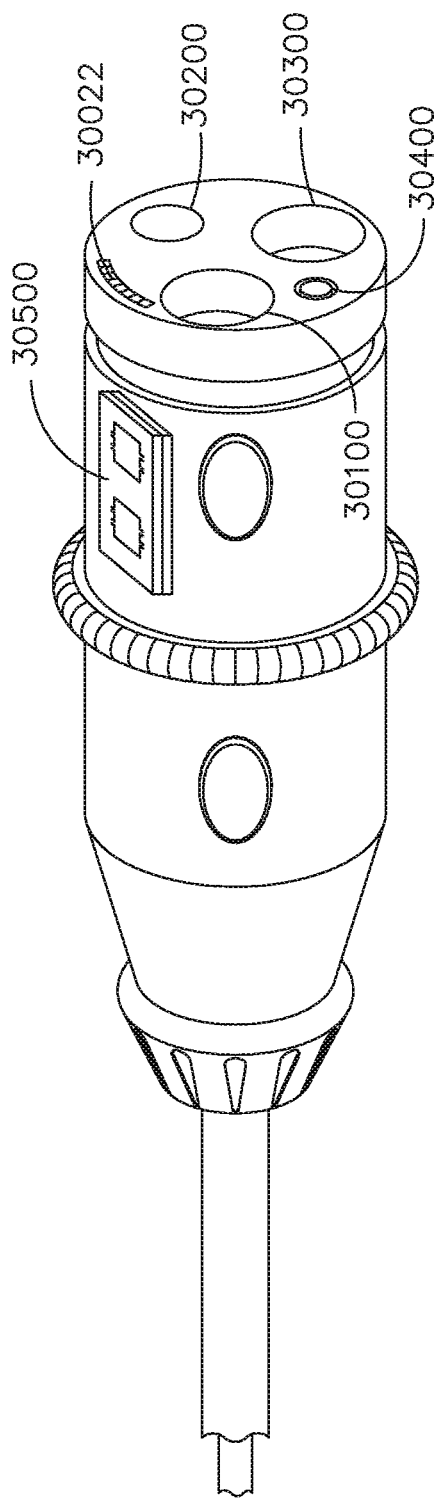
FIG. 83
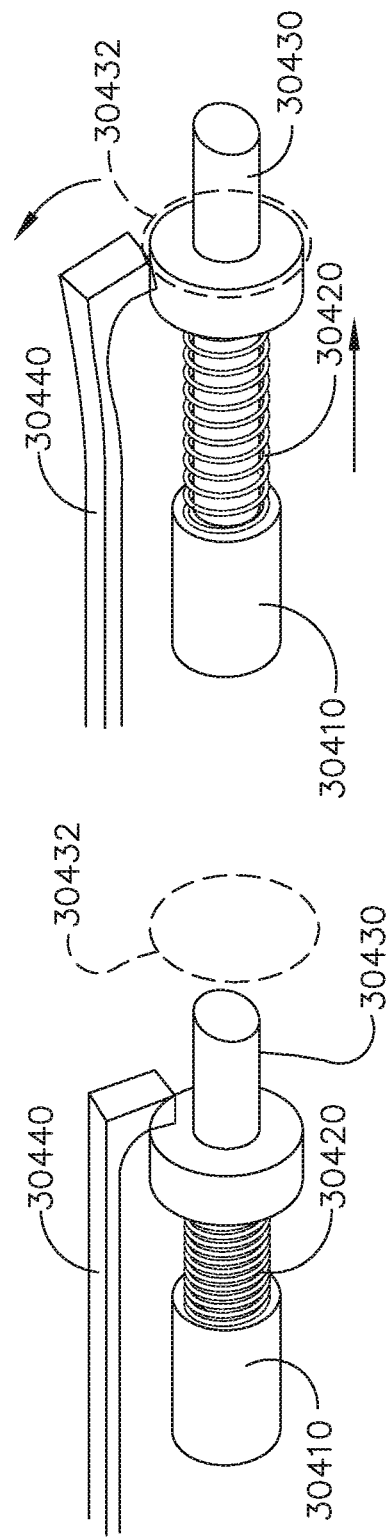
FIG. 84
FIG. 85

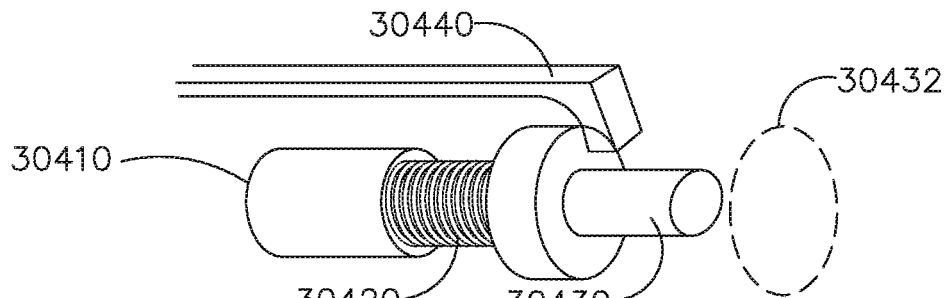
FIG. 85A Unfired, Attached/Detached
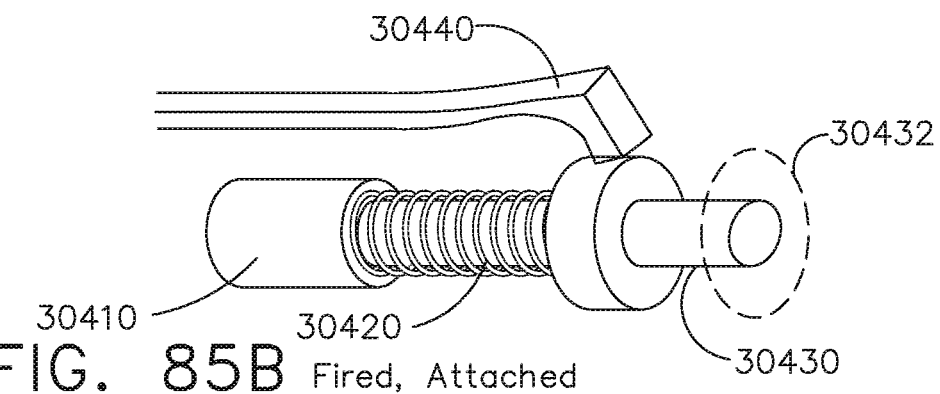
FIG. 85B Fired, Attached
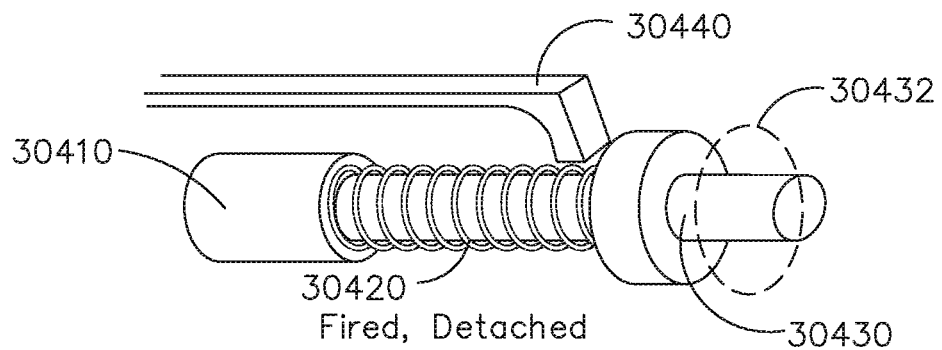
FIG. 85C

SURGICAL INSTRUMENT SYSTEMS COMPRISING HANDLE ARRANGEMENTS

CROSS-REFERENCE TO RELATED APPLICATIONS

This non-provisional application claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety. This non-provisional application claims the benefit under 35 U.S.C. § 119(e) of U.S. Provisional Patent Application Ser. No. 62/665,129, entitled SURGICAL SUTURING SYSTEMS, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, of U.S. Provisional Patent Application Ser. No. 62/665,128, entitled MODULAR SURGICAL INSTRUMENTS, filed May 1, 2018, of U.S. Provisional Patent Application Ser. No. 62/665,192, entitled SURGICAL DISSECTORS, filed May 1, 2018, and of U.S. Provisional Patent Application Ser. No. 62/665,134, entitled SURGICAL CLIP APPLIER, filed May 1, 2018, the disclosures of which are incorporated by reference herein in their entirety.

BACKGROUND

The present invention relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 66A is an elevational view of a handle assembly of FIG. 66 in accordance with at least one embodiment;

FIG. 66B is an elevational view of a handle assembly of FIG. 66 in accordance with at least one embodiment;

FIG. 66C is an elevational view of a handle assembly of FIG. 66 in accordance with at least one embodiment;

FIG. 69 illustrates a chart depicting various functions of the surgical instrument system of FIG. 66;

FIG. 73A is a proximal end view of the handle assembly of FIG. 72;

FIG. 73B illustrates a chart depicting various functions of the handle assembly of FIG. 72;

FIG. 75A is a proximal end view of the handle assembly of FIG. 74;

FIG. 75B illustrates a chart depicting various functions of the handle assembly of FIG. 74;

FIG. 77A is a perspective view of the handle assembly of FIG. 77;

FIG. 77B is a cut-away view of a curved cylinder of the handle assembly of FIG. 77;

FIG. 78A is a partial cross-sectional view of the curved cylinder of FIG. 77A illustrating an electroactive polymer located in the cylinder in a non-energized state;

FIG. 78B is a partial cross-sectional view of the curved cylinder of FIG. 77A illustrating the electroactive polymer located in the cylinder in an energized state;

FIG. 83 is a partial perspective view of the shaft assembly of FIG. 82 comprising a locking mechanism;

FIG. 84 is a perspective view of the locking mechanism of FIG. 83 in an unlocked configuration;

FIG. 85 is a perspective view of the locking mechanism of FIG. 83 in a locked configuration;

FIGS. 85A-85C illustrate the locking mechanism of FIG. 83 in three different states during the operation of the surgical instrument system;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
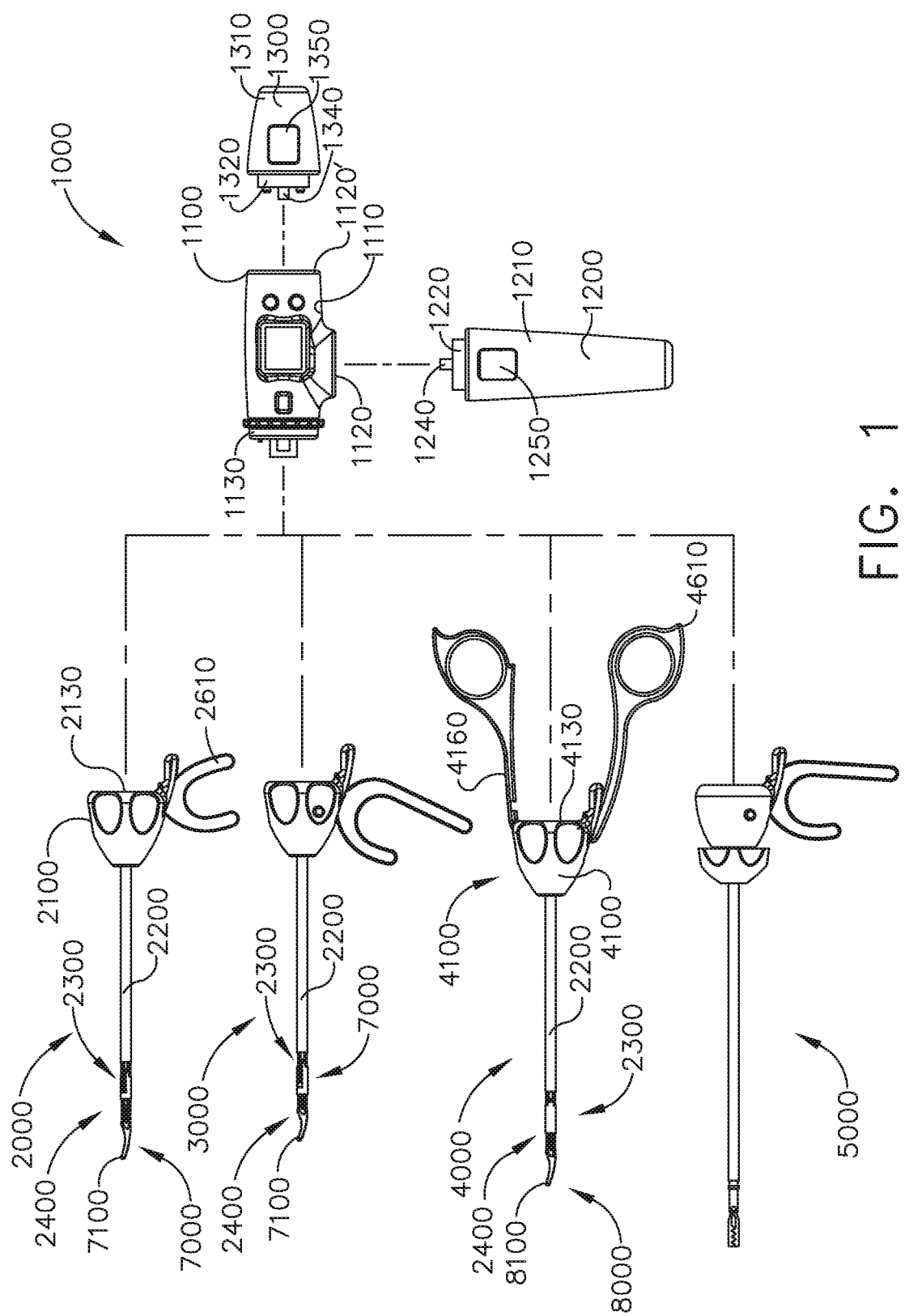
FIG. 1 illustrates a surgical system comprising a handle and several shaft assemblies—each of which are selectively attachable to the handle in accordance with at least one embodiment.

Applicant of the present application owns the following U.S. Patent Applications that were filed Aug. 24, 2018 and which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER, now U.S. Pat. No. 11,602,366;

U.S. patent application Ser. No. 16/112,155, entitled SURGICAL SUTURING INSTRUMENT COMPRISING A CAPTURE WIDTH WHICH IS LARGER THAN TROCAR DIAMETER, now U.S. Pat. No. 11,564,703;

U.S. patent application Ser. No. 16/112,168, entitled SURGICAL SUTURING INSTRUMENT COMPRISING A NON-CIRCULAR NEEDLE, now U.S. Patent Application Publication No. 2019/0125336;

U.S. patent application Ser. No. 116/112,180, entitled ELECTRICAL POWER OUTPUT CONTROL BASED ON MECHANICAL FORCES, now U.S. Patent Application Publication No. 2019/0125432;

U.S. patent application Ser. No. 16/112,193, entitled REACTIVE ALGORITHM FOR SURGICAL SYSTEM, now U.S. Pat. No. 10,932,806;

U.S. patent application Ser. No. 16/112,099, entitled SURGICAL INSTRUMENT COMPRISING AN ADAPTIVE ELECTRICAL SYSTEM, now U.S. Patent Application Publication No. 2019/0125378;

U.S. patent application Ser. No. 16/112,112, entitled CONTROL SYSTEM ARRANGEMENTS FOR A MODULAR SURGICAL INSTRUMENT, now U.S. Patent application Publication No. 2019/0125320;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE, now U.S. Patent Application Publication No. 2019/0125338;

U.S. patent application Ser. No. 16/112,097, entitled SURGICAL INSTRUMENT SYSTEMS COMPRISING BATTERY ARRANGEMENTS, now U.S. Pat. No. 11,648,022;

U.S. patent application Ser. No. 16/112,114, entitled SURGICAL INSTRUMENT SYSTEMS COMPRISING FEEDBACK MECHANISMS, now U.S. Pat. No. 10,980,560;

U.S. patent application Ser. No. 16/112,117, entitled SURGICAL INSTRUMENT SYSTEMS COMPRISING LOCKOUT MECHANISMS, now U.S. Patent Application Publication No. 2019/0125476;

U.S. patent application Ser. No. 16/112,095, entitled SURGICAL INSTRUMENTS COMPRISING A LOCKABLE END EFFECTOR SOCKET, now U.S. Pat. No. 11,291,465;

U.S. patent application Ser. No. 16/112,121, entitled SURGICAL INSTRUMENTS COMPRISING A SHIFTING MECHANISM, now U.S. Pat. No. 11,026,712;

U.S. patent application Ser. No. 16/112,151, entitled SURGICAL INSTRUMENTS COMPRISING A SYS- TEM FOR ARTICULATION AND ROTATION COMPENSATION, now U.S. Pat. No. 10,772,651;

U.S. patent application Ser. No. 16/112,154, entitled SURGICAL INSTRUMENTS COMPRISING A BIASED SHIFTING MECHANISM, now U.S. Pat. No. 11,207,090;

U.S. patent application Ser. No. 16/112,226, entitled SURGICAL INSTRUMENTS COMPRISING AN ARTICULATION DRIVE THAT PROVIDES FOR HIGH ARTICULATION ANGLES, now U.S. Pat. No. 11,129,636;

U.S. patent application Ser. No. 16/112,062, entitled SURGICAL DISSECTORS AND MANUFACTURING TECHNIQUES, now U.S. Pat. No. 10,959,744;

U.S. patent application Ser. No. 16/112,098, entitled SURGICAL DISSECTORS CONFIGURED TO APPLY MECHANICAL AND ELECTRICAL ENERGY, now U.S. Patent Application Publication No. 2019/0125430;

U.S. patent application Ser. No. 16/112,237, entitled SURGICAL CLIP APPLIER CONFIGURED TO STORE CLIPS IN A STORED STATE, now U.S. Pat. No. 11,026,713;

U.S. patent application Ser. No. 16/112,245, entitled SURGICAL CLIP APPLIER COMPRISING AN EMPTY CLIP CARTRIDGE LOCKOUT, now U.S. Pat. No. 11,051,836;

U.S. patent application Ser. No. 16/112,249, entitled SURGICAL CLIP APPLIER COMPRISING AN AUTOMATIC CLIP FEEDING SYSTEM, now U.S. Pat. No. 11,109,878;

U.S. patent application Ser. No. 16/112,253, entitled SURGICAL CLIP APPLIER COMPRISING ADAPTIVE FIRING CONTROL, now U.S. Pat. No. 11,103,268; and U.S. patent application Ser. No. 16/112,257, entitled SURGICAL CLIP APPLIER COMPRISING ADAPTIVE CONTROL IN RESPONSE TO A STRAIN GAUGE CIRCUIT, now U.S. Pat. No. 11,071,560.

Applicant of the present application owns the following U.S. Patent Applications that were filed on May 1, 2018 and which are each herein incorporated by reference in their respective entireties:

U.S. Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Patent Application Ser. No. 62/665,177, entitled SURGICAL INSTRUMENTS COMPRISING HANDLE ARRANGEMENTS;

U.S. Patent Application Ser. No. 62/665,128, entitled MODULAR SURGICAL INSTRUMENTS;

U.S. Patent Application Ser. No. 62/665,192, entitled SURGICAL DISSECTORS; and

U.S. Patent Application Ser. No. 62/665,134, entitled SURGICAL CLIP APPLIER.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR

SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

Figure 2:
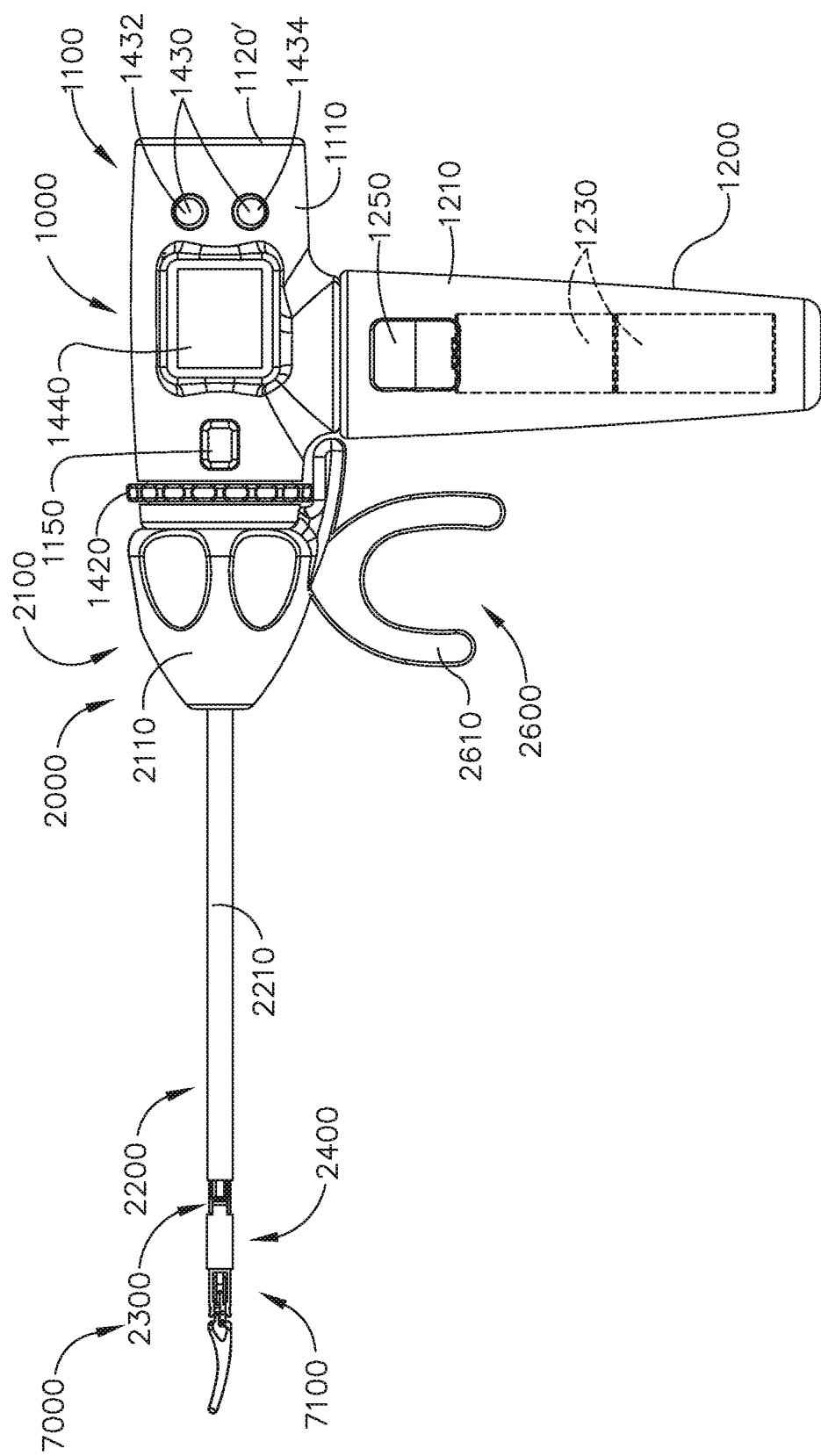
FIG. 2 is an elevational view of the handle and one of the shaft assemblies of the surgical system of FIG. 1.
Figure 3:
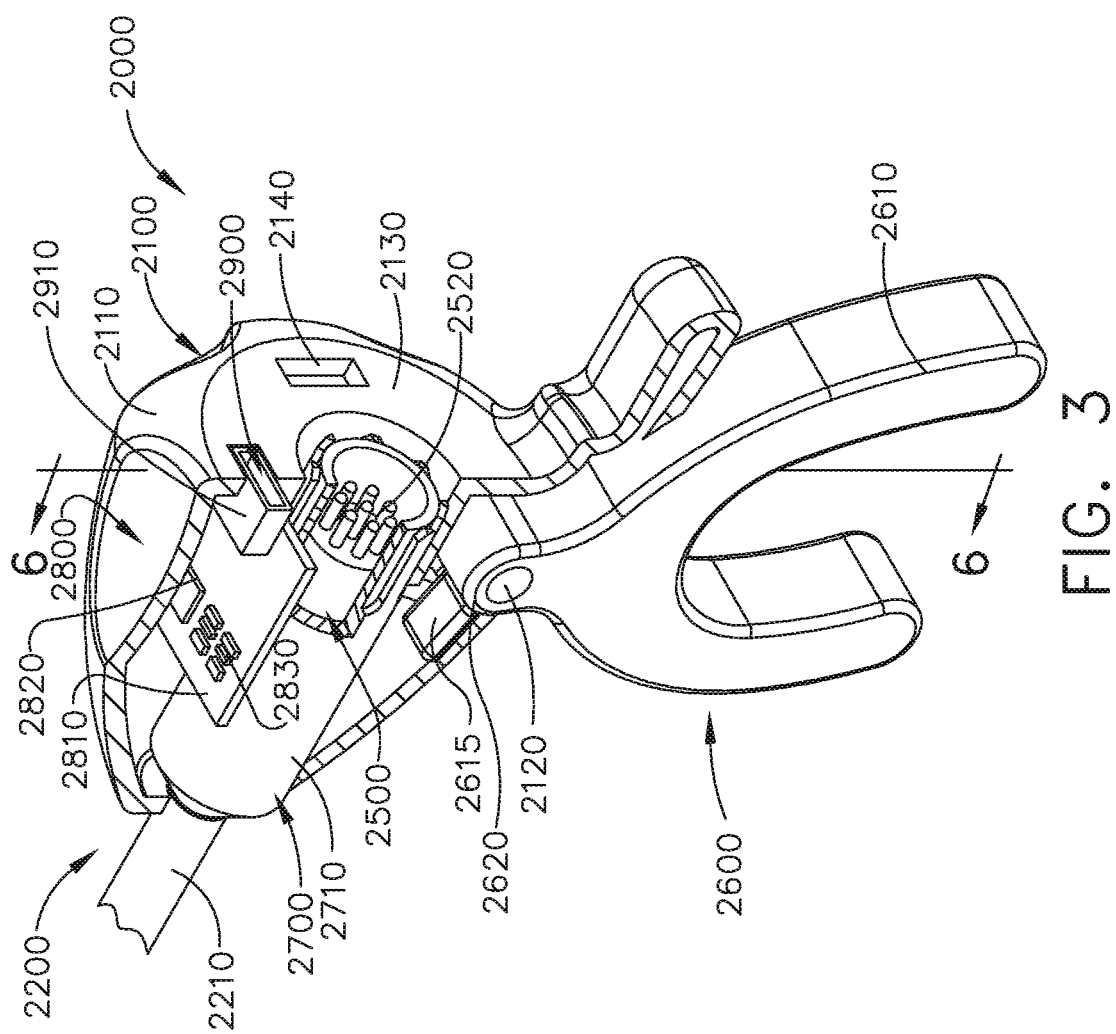
FIG. 3 is a partial cross-sectional perspective view of the shaft assembly of FIG. 2.
Figure 4:
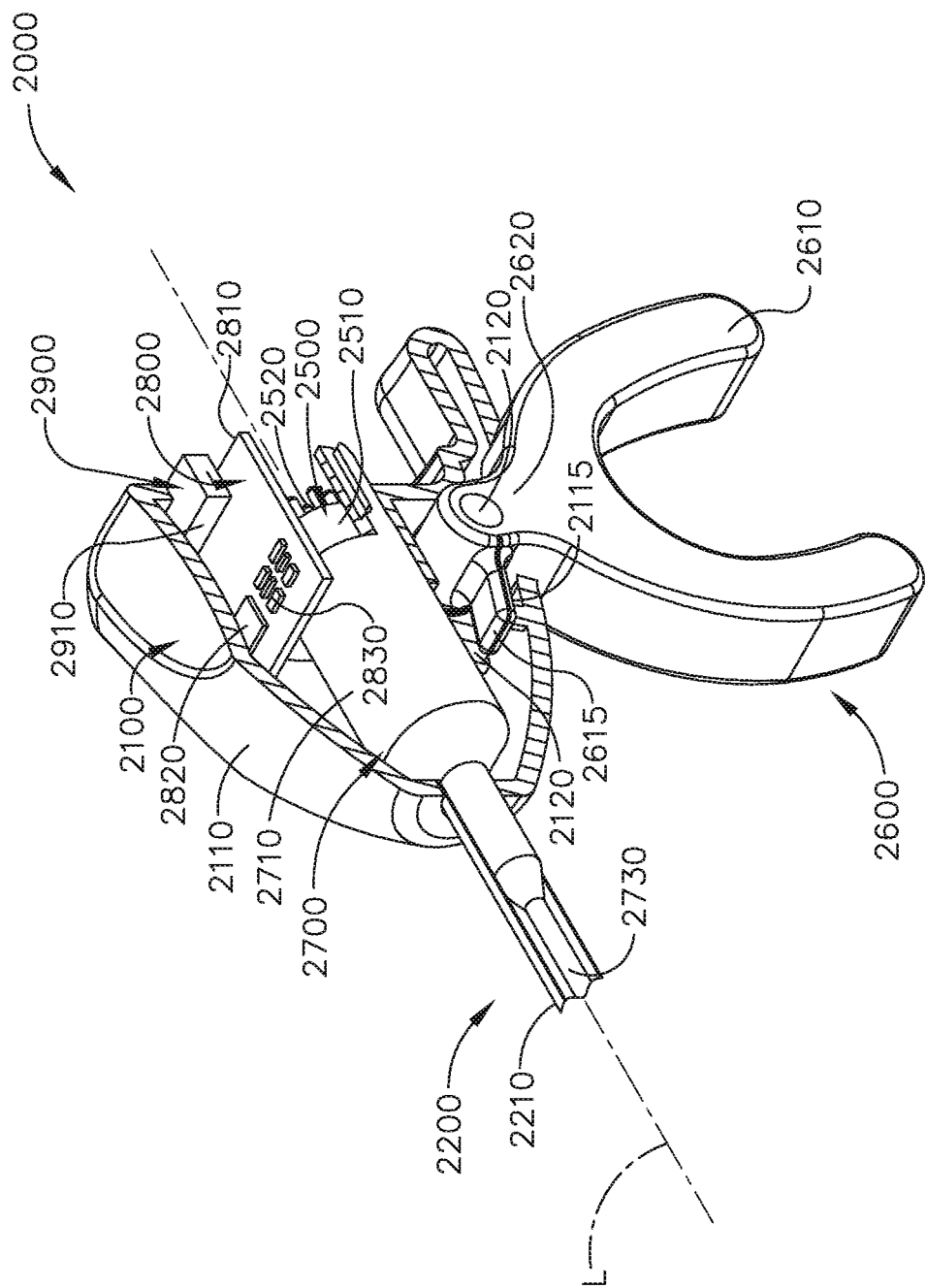
FIG. 4 is another partial cross-sectional perspective view of the shaft assembly of FIG. 2.
Figure 45:
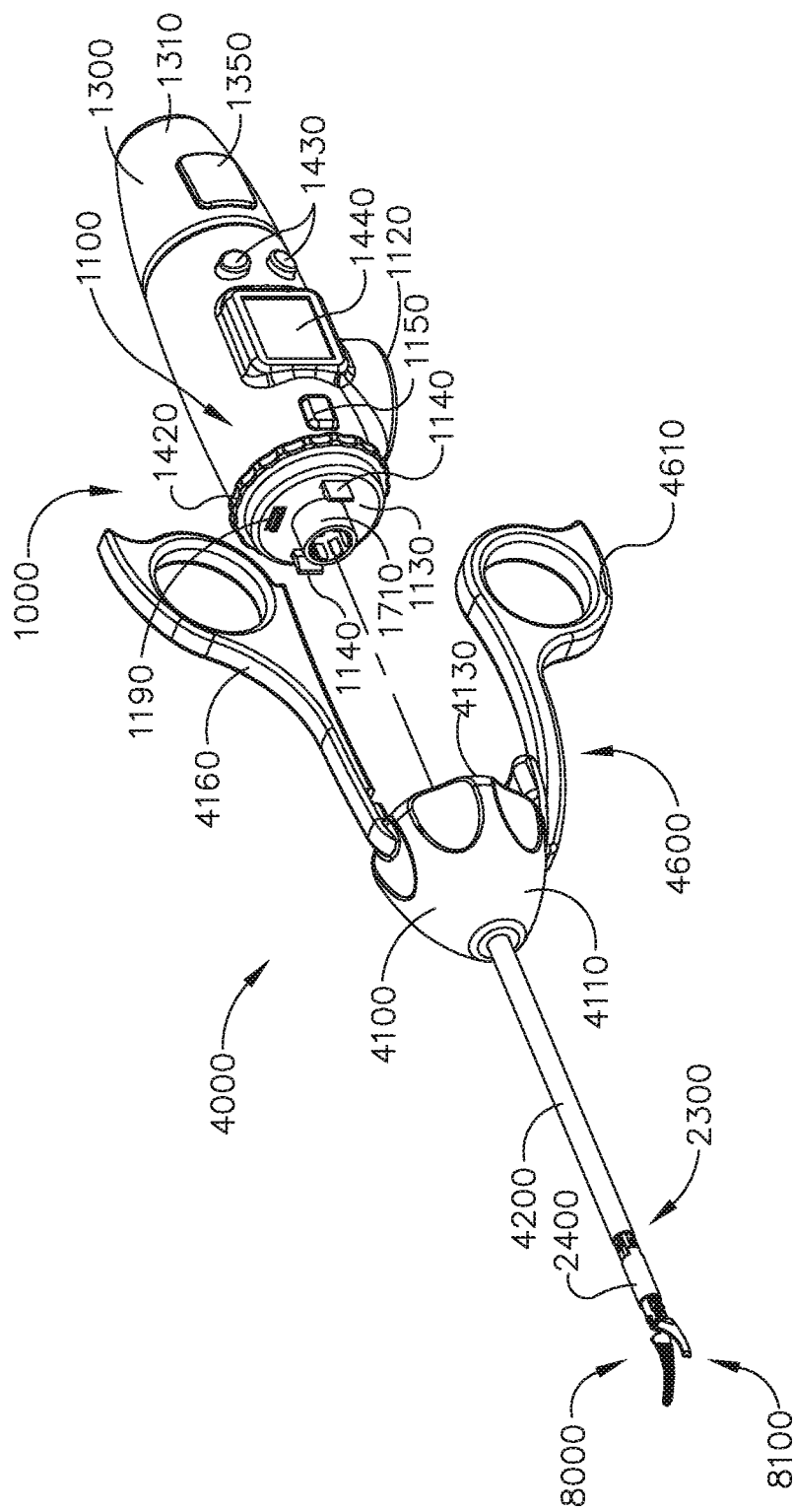
FIG. 45 is a perspective view of the handle drive module of FIG. 7 and one of the shaft assemblies of the surgical system of FIG. 1.
Figure 46:
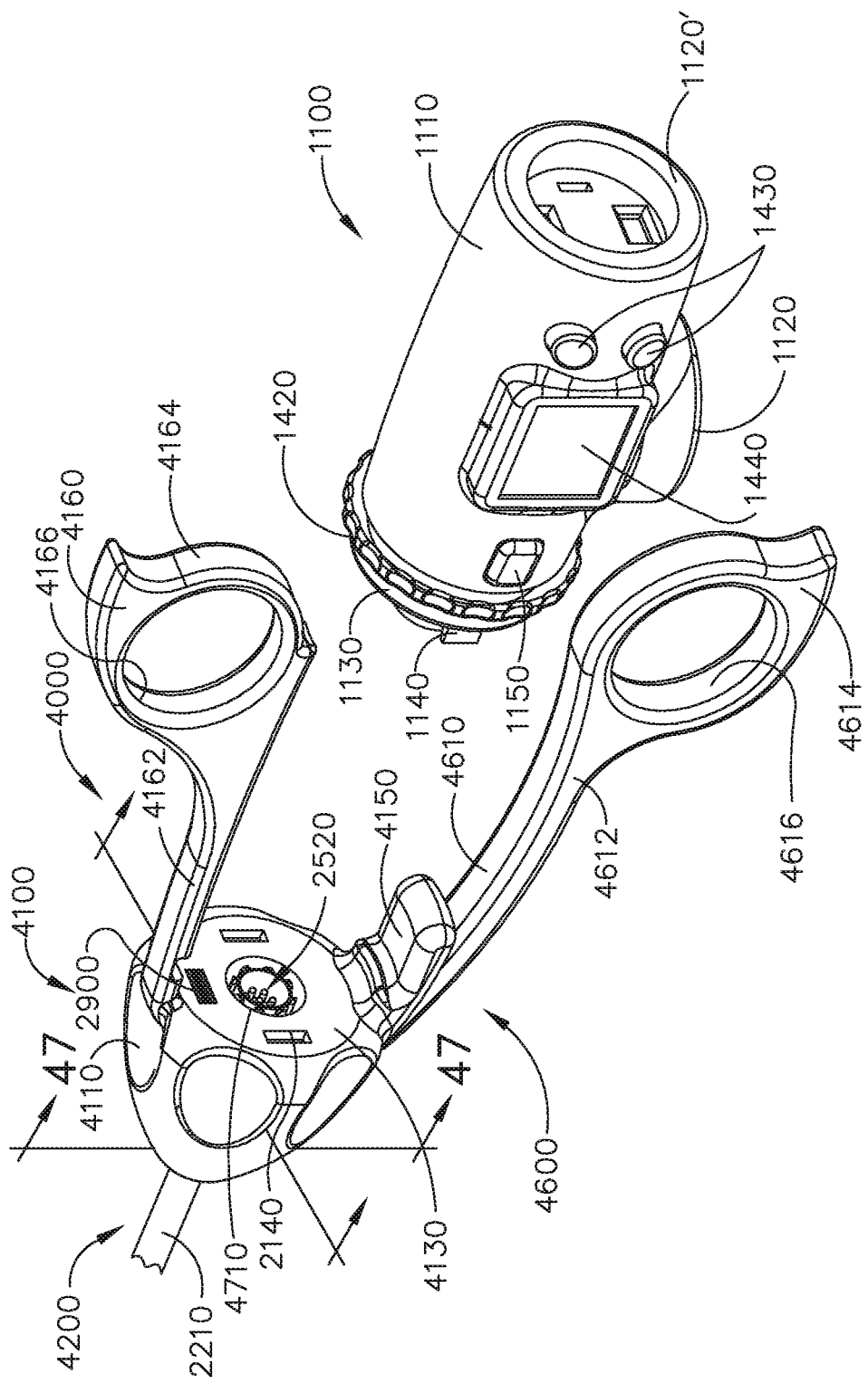
FIG. 46 is another perspective view of the handle drive module of FIG. 7 and the shaft assembly of FIG. 45.

A surgical instrument system is depicted in FIG. 1. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 2 and the shaft assembly 4000 is attached to the handle assembly 1000 in FIG. 45. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 1, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one ore more power modules, such as power modules 1200 and 1300, for example, which are operably attachable to the drive module 1100 to supply power thereto.

Further to the above, referring again to FIGS. 1 and 2, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Figure 47:
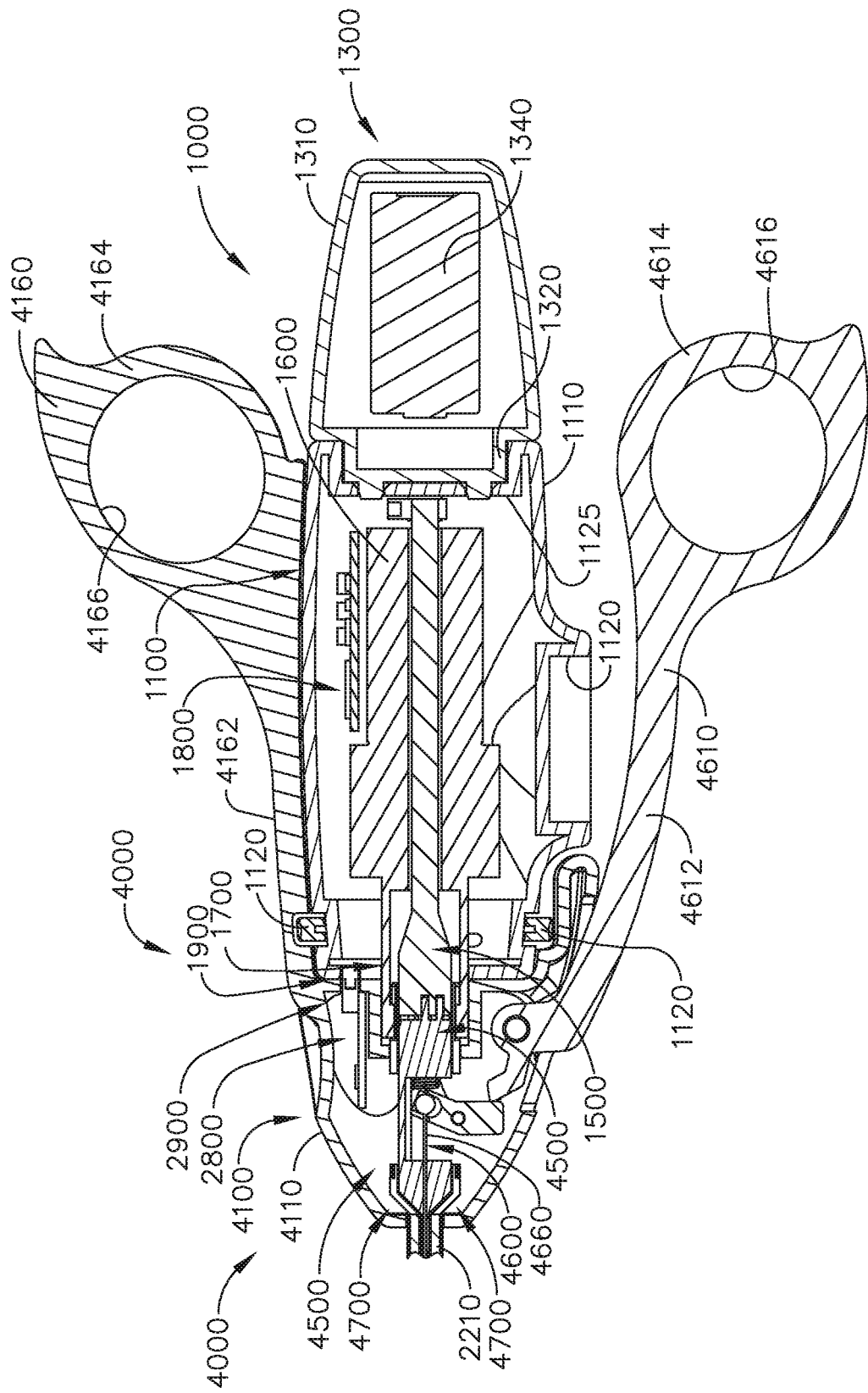
FIG. 47 is a partial cross-sectional view of the shaft assembly of FIG. 45 attached to the handle of FIG. 1.

Further to the above, referring again to FIGS. 1 and 2, the power module 1300 comprises a housing 1310, a connector 1320, one or more release latches 1350, and one or more batteries 1330 (FIG. 47). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Figure 7:
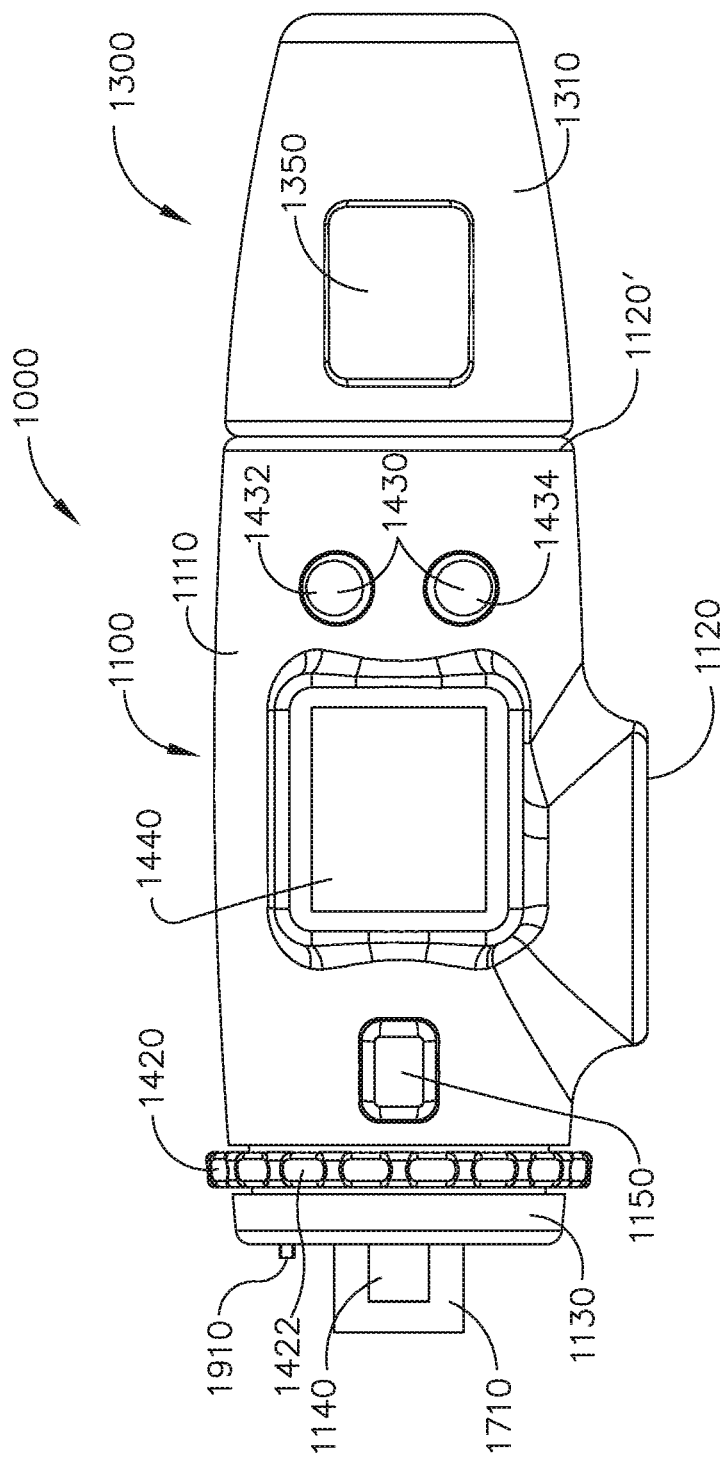
FIG. 7 is an elevational view of a drive module of the handle of FIG. 1.
Figure 8:
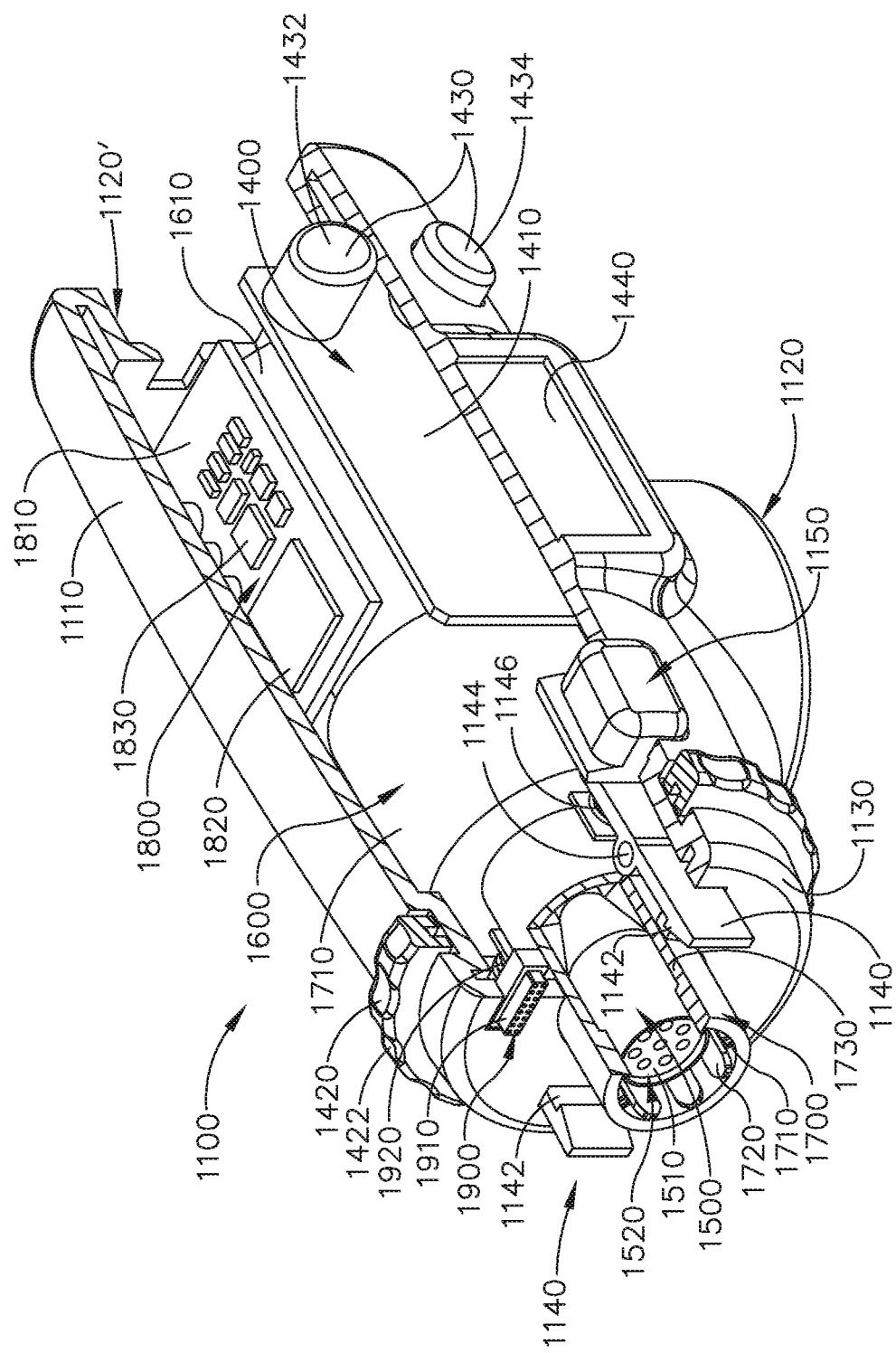
FIG. 8 is a cross-sectional perspective view of the drive module of FIG. 7.

Referring to FIGS. 7 and 8, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830. The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Figure 12:
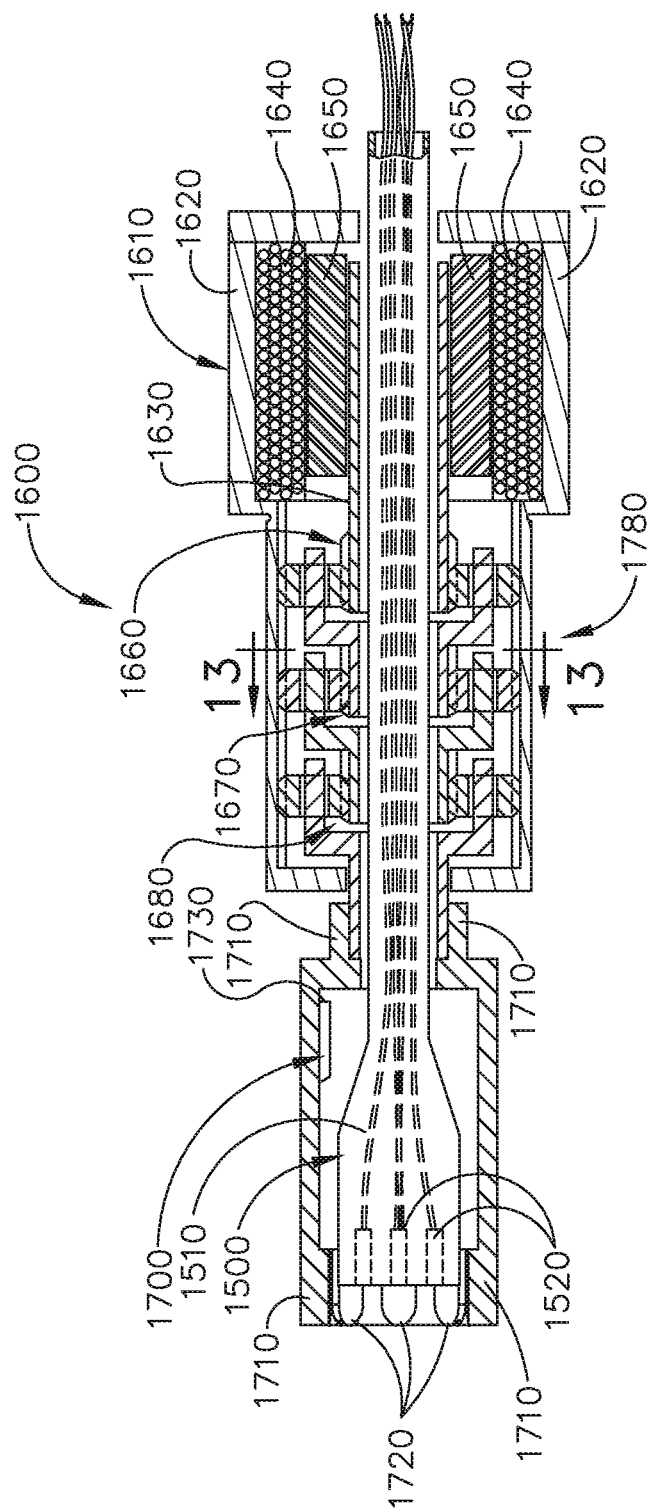
FIG. 12 is a cross-sectional perspective view of a motor and a speed reduction gear assembly of the drive module of FIG. 7.
Figure 13:
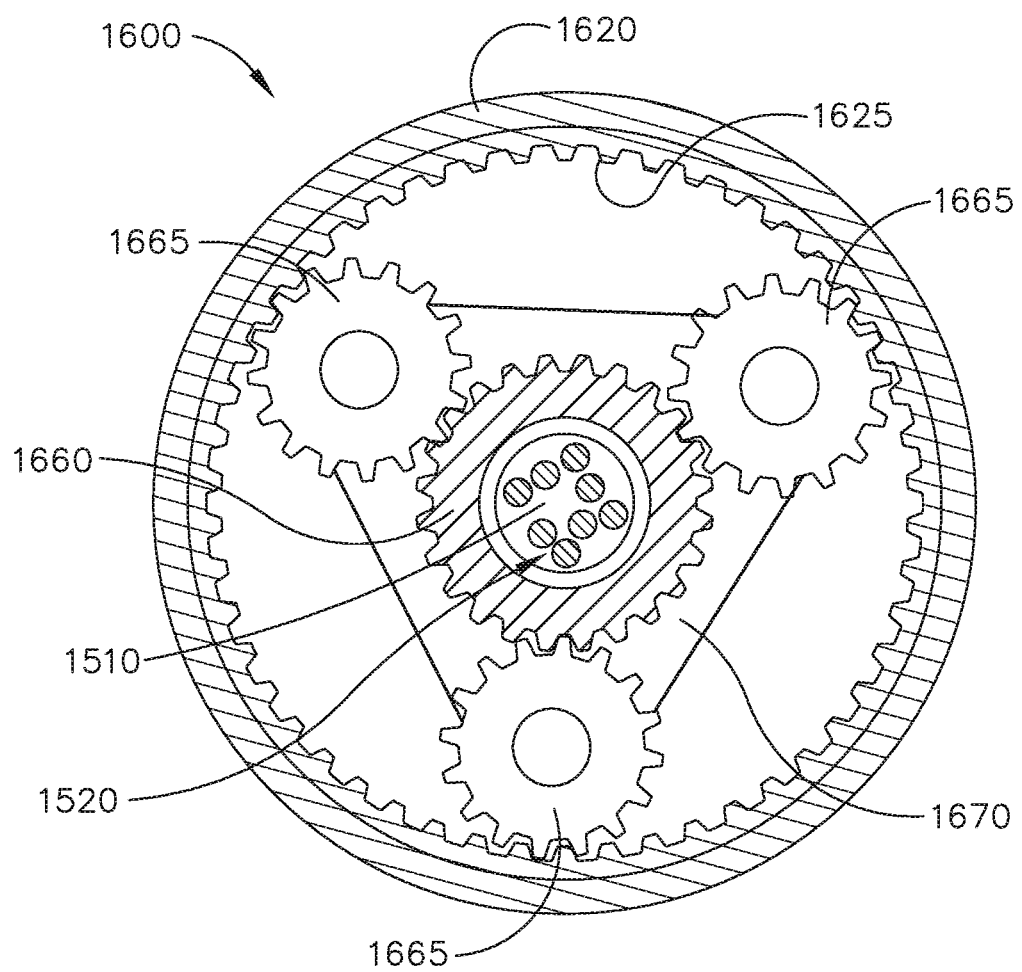
FIG. 13 is an end view of the speed reduction gear assembly of FIG. 12.
Figure 14:
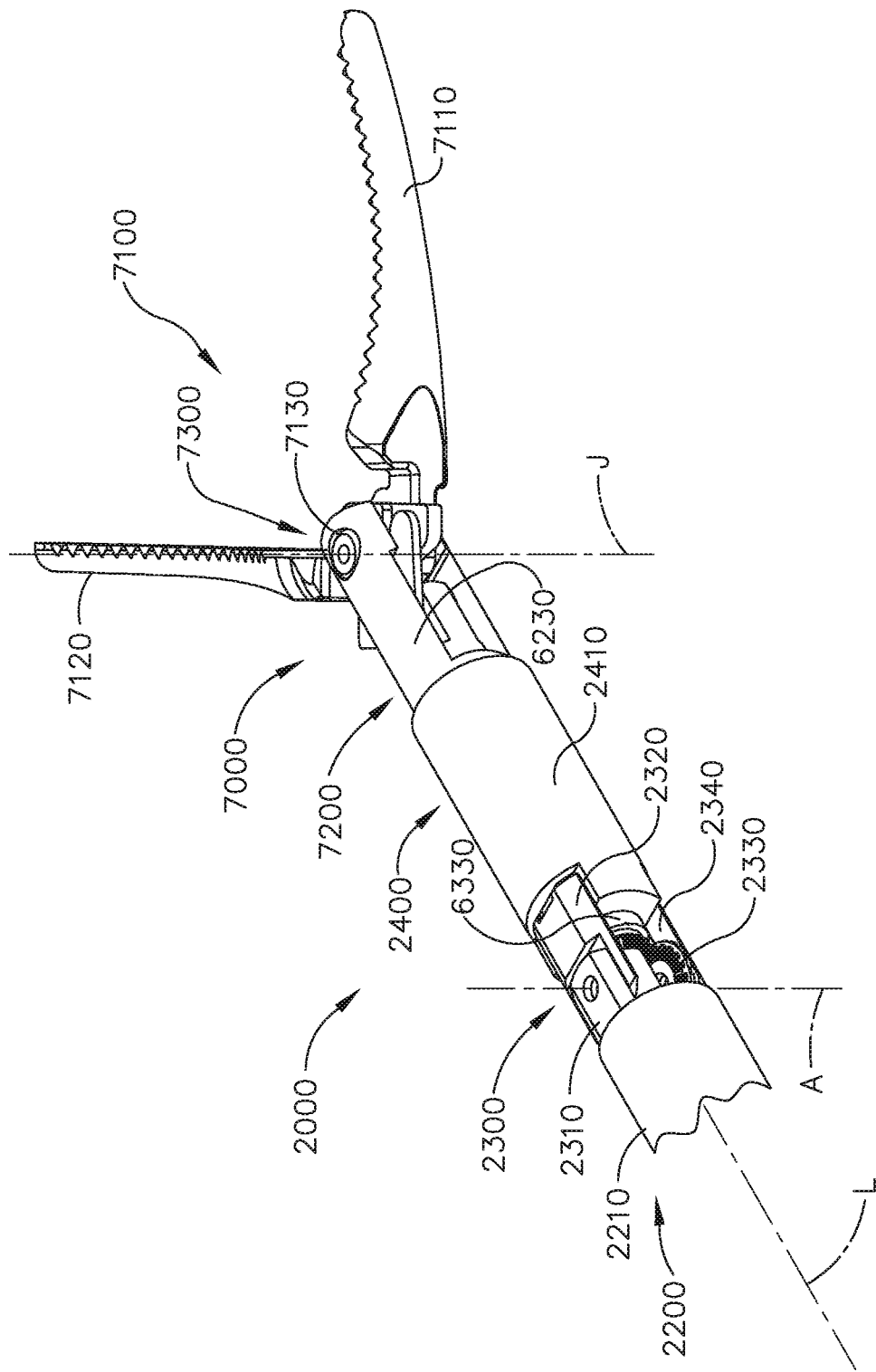
FIG. 14 is a partial perspective view of an end effector of the shaft assembly of FIG. 2 in an open configuration.

Referring to FIGS. 12 and 13, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 13) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 7 and 8, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 3-6, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

Figure 10:
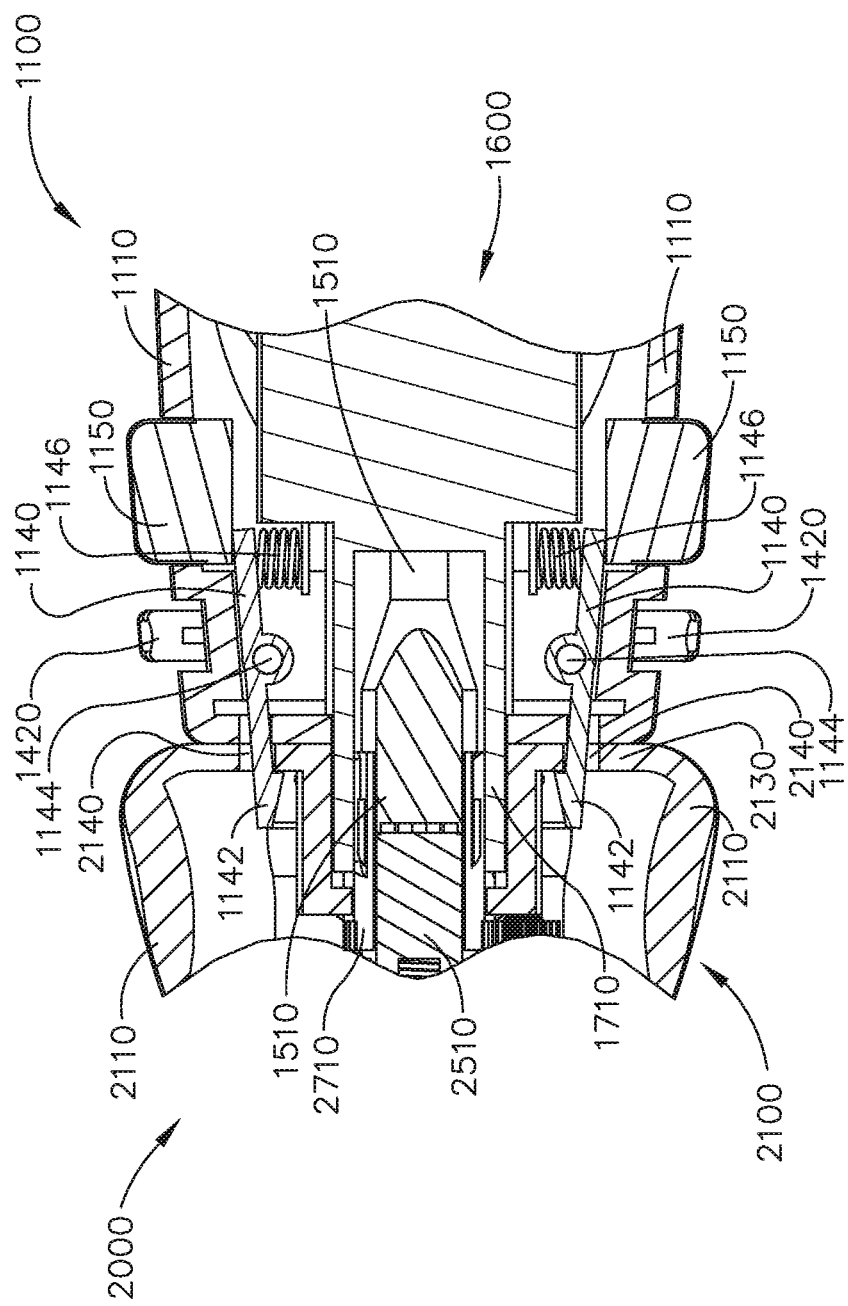
FIG. 10 is a partial cross-sectional view of the interconnection between the handle and shaft assembly of FIG. 2 in a locked configuration.
Figure 11:
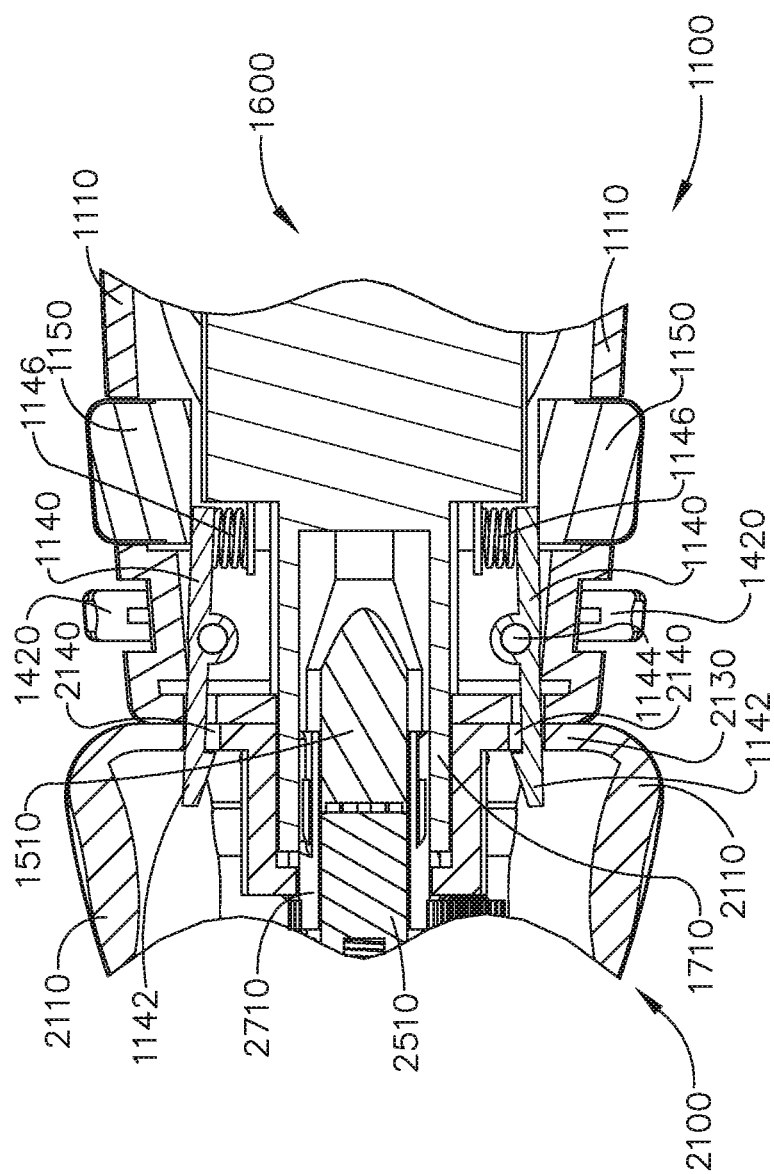
FIG. 11 is a partial cross-sectional view of the interconnection between the handle and shaft assembly of FIG. 2 in an unlocked configuration.

As discussed above, referring to FIGS. 3-8, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 8, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 8, 10, and 11, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be re-opened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 3-6, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor 2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an and electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 7 and 8, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 8, 10, and 11, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a conformational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 7 and 8, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

Figure 15:
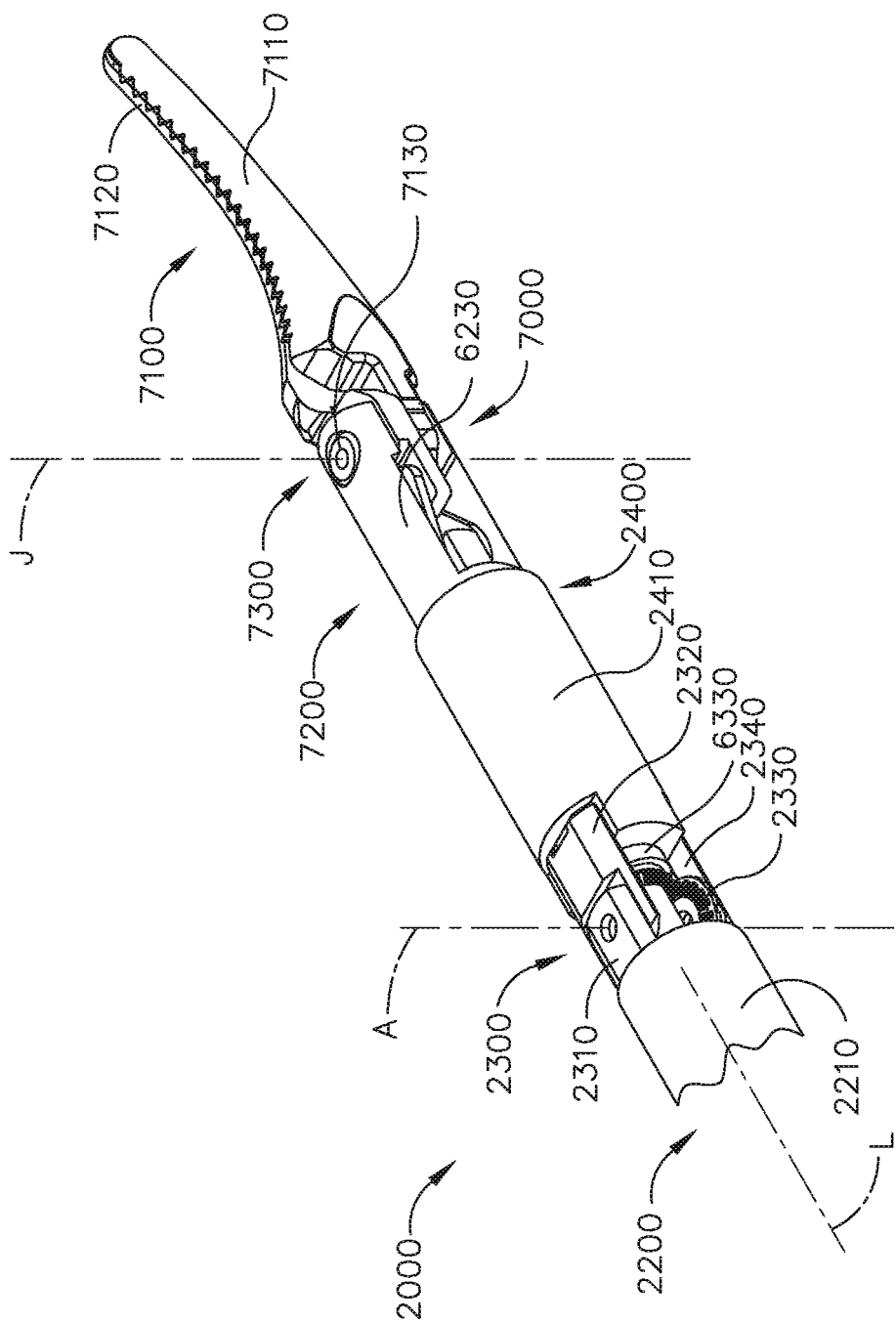
FIG. 15 is a partial perspective view of the end effector of FIG. 14 in a closed configuration.

As described above, the end effector 7000 is articulatable in a first direction (FIG. 16) and/or a second direction (FIG. 17) from a center, or unarticulated, position (FIG. 15). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector 7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Figure 5:
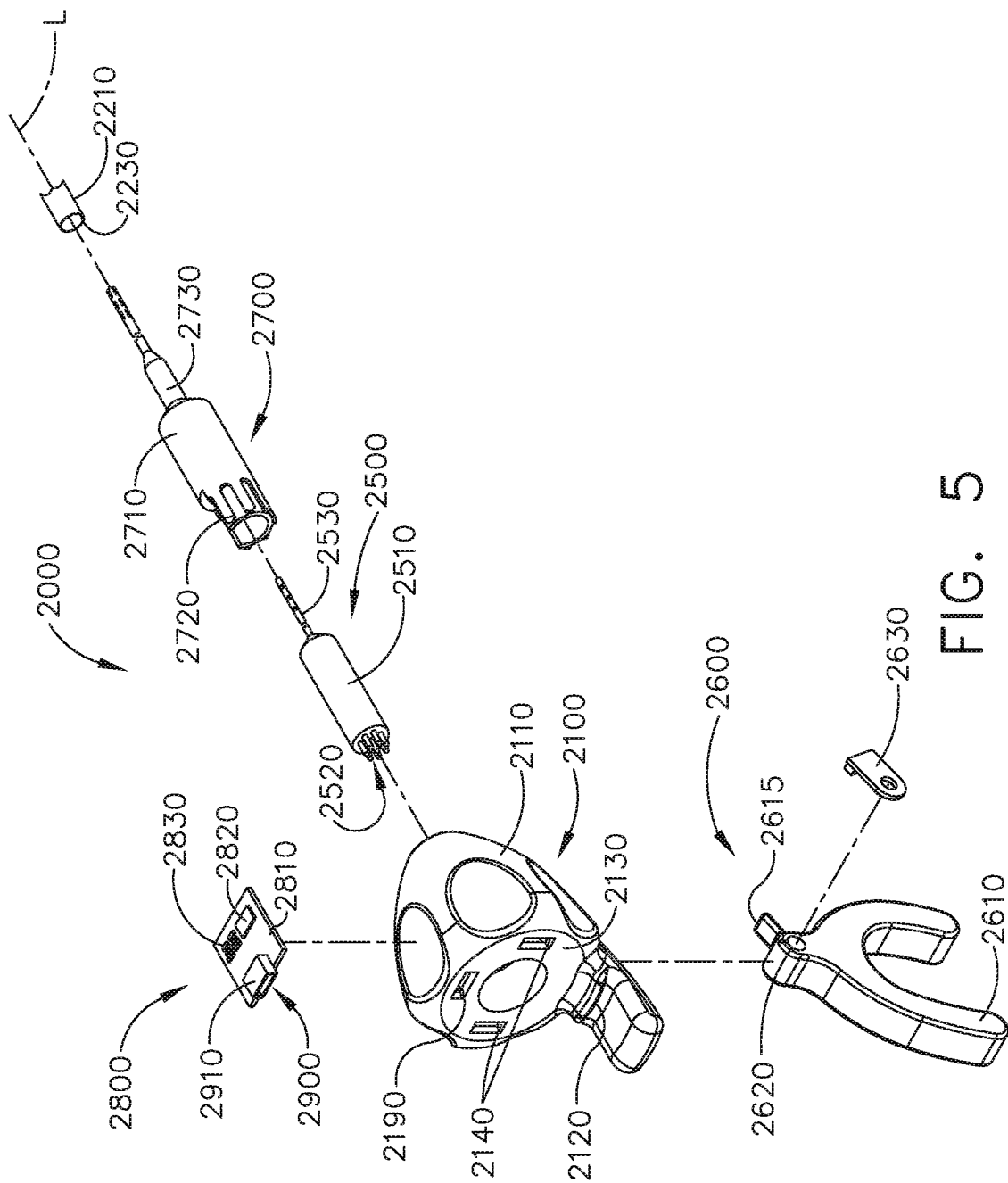
FIG. 5 is a partial exploded view of the shaft assembly of FIG. 2.
Figure 6:
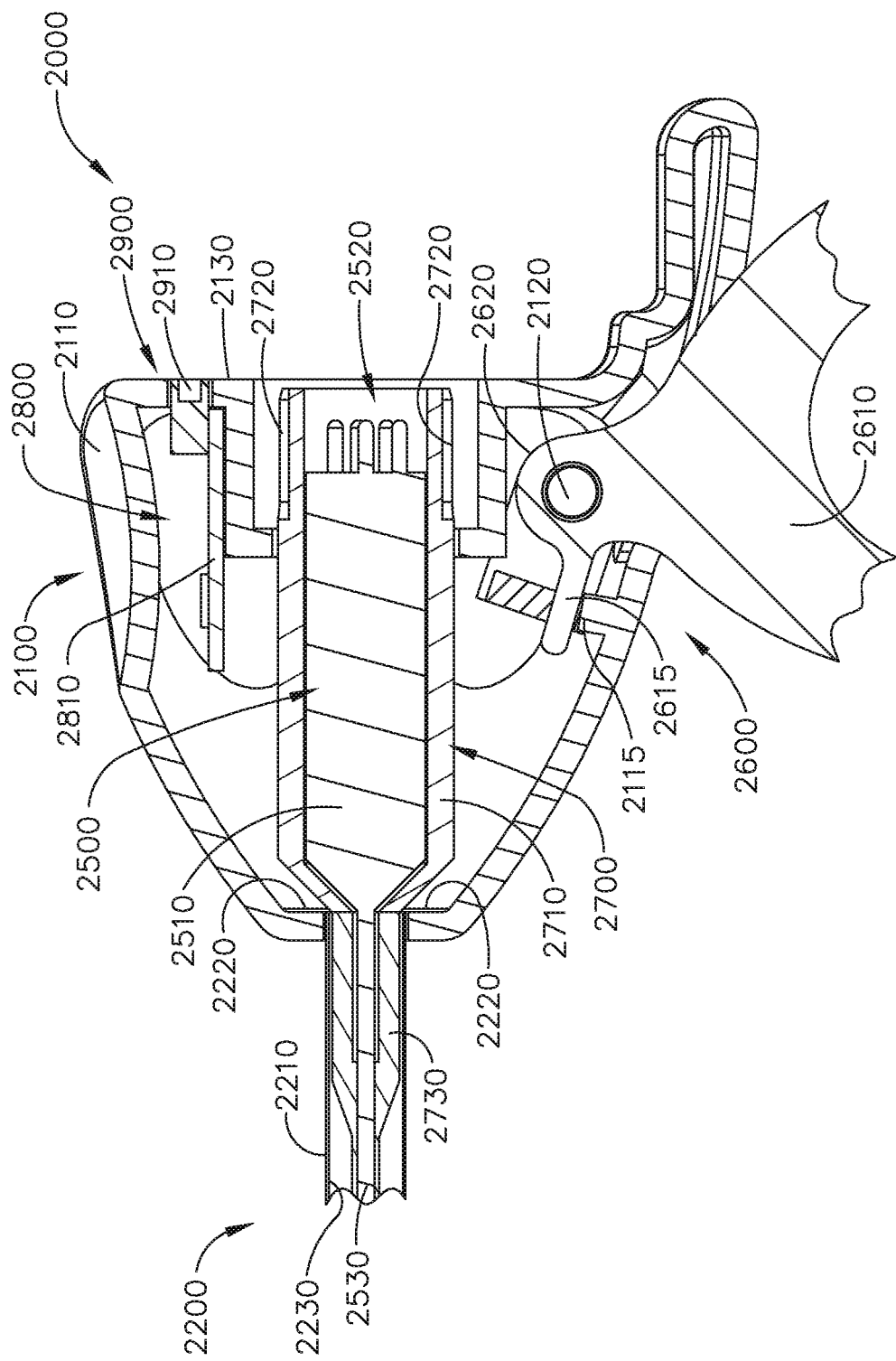
FIG. 6 is a partial cross-sectional elevational view of the shaft assembly of FIG. 2.

Referring primarily to FIGS. 5 and 6, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Figure 20:
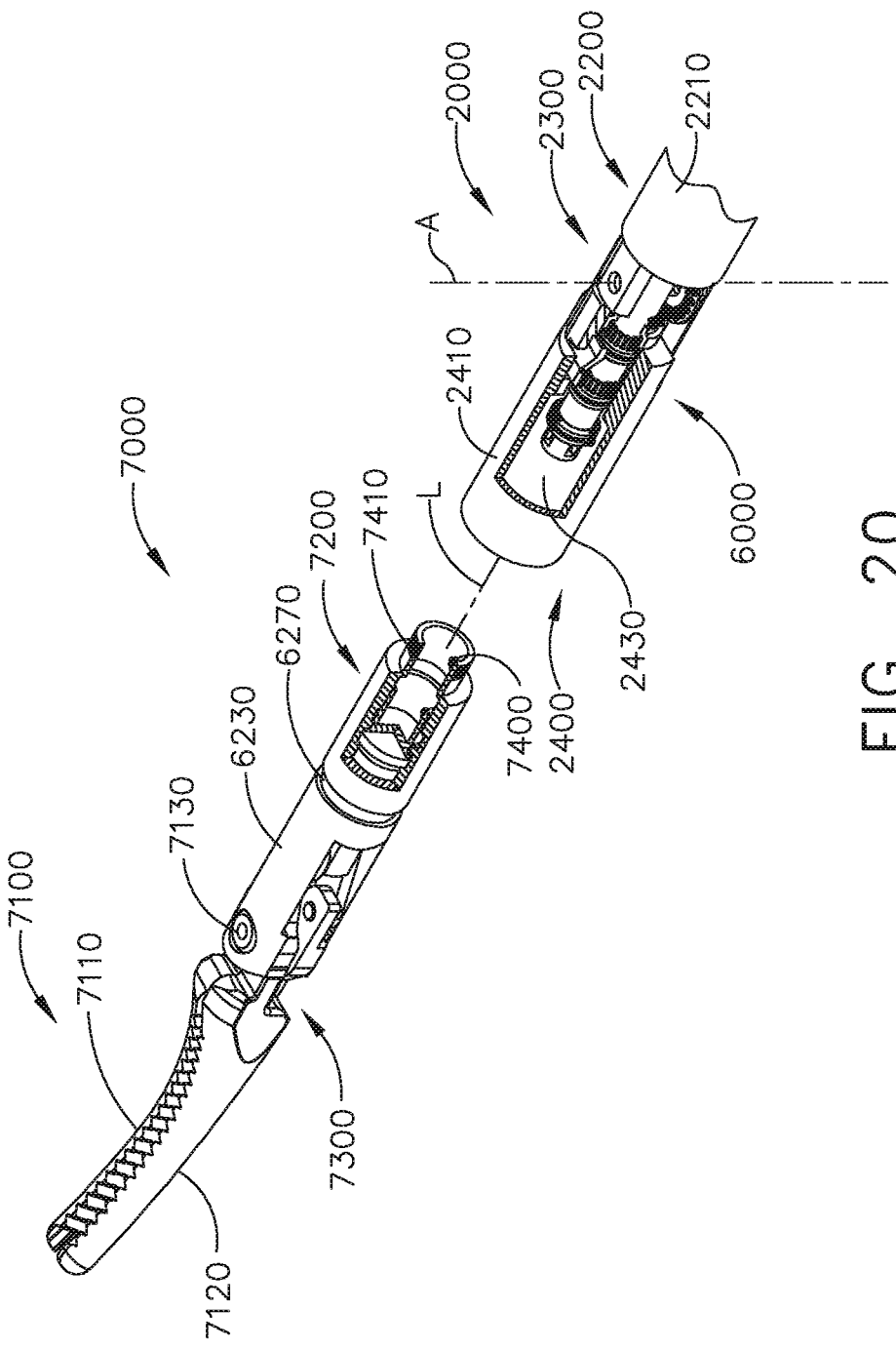
FIG. 20 is a partial cross-sectional perspective view of the end effector of FIG. 14 detached from the shaft assembly of FIG. 2.
Figure 22:
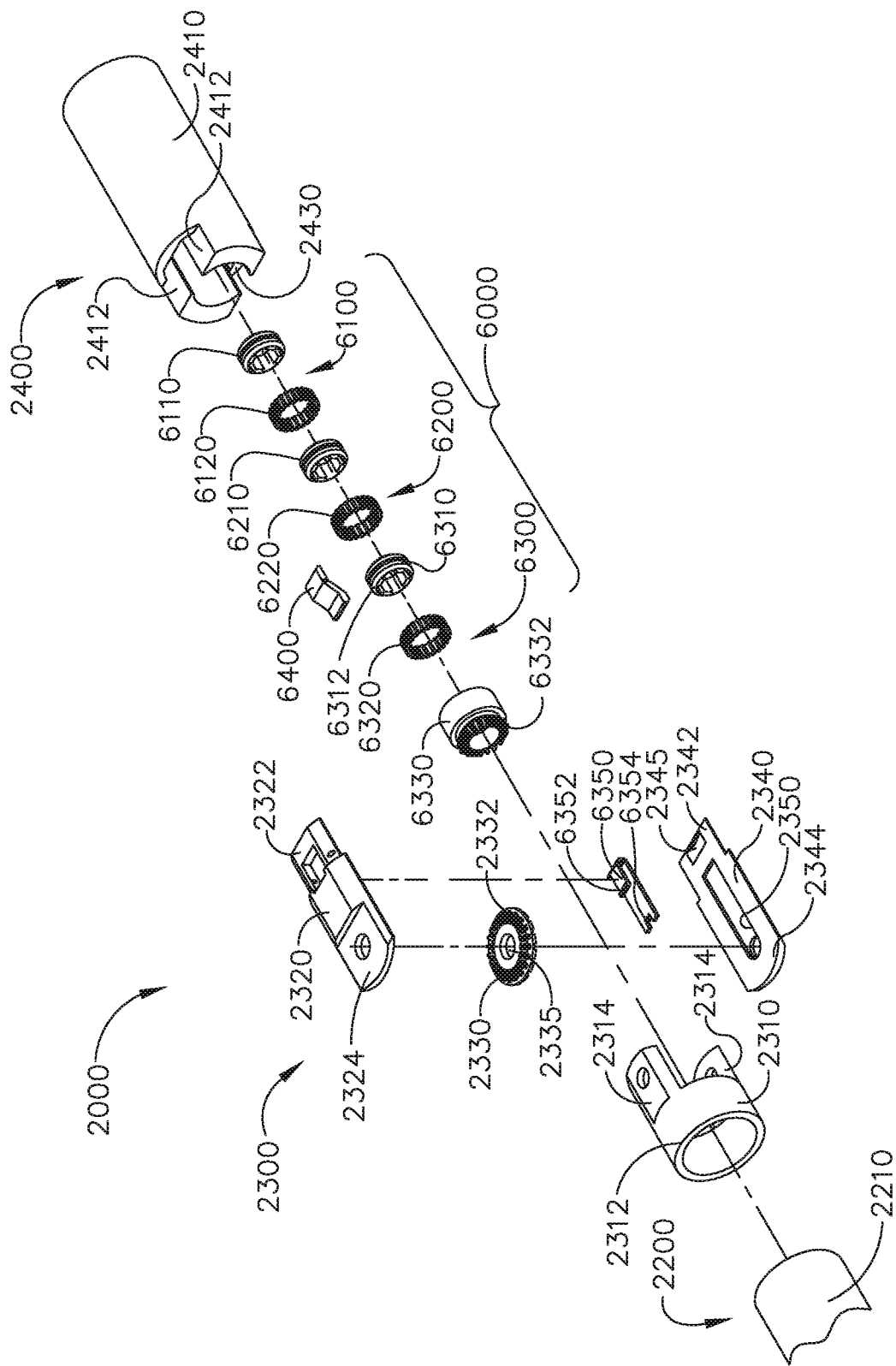
FIG. 22 is an exploded view of a distal attachment portion of the shaft assembly of FIG. 2.
Figure 23:
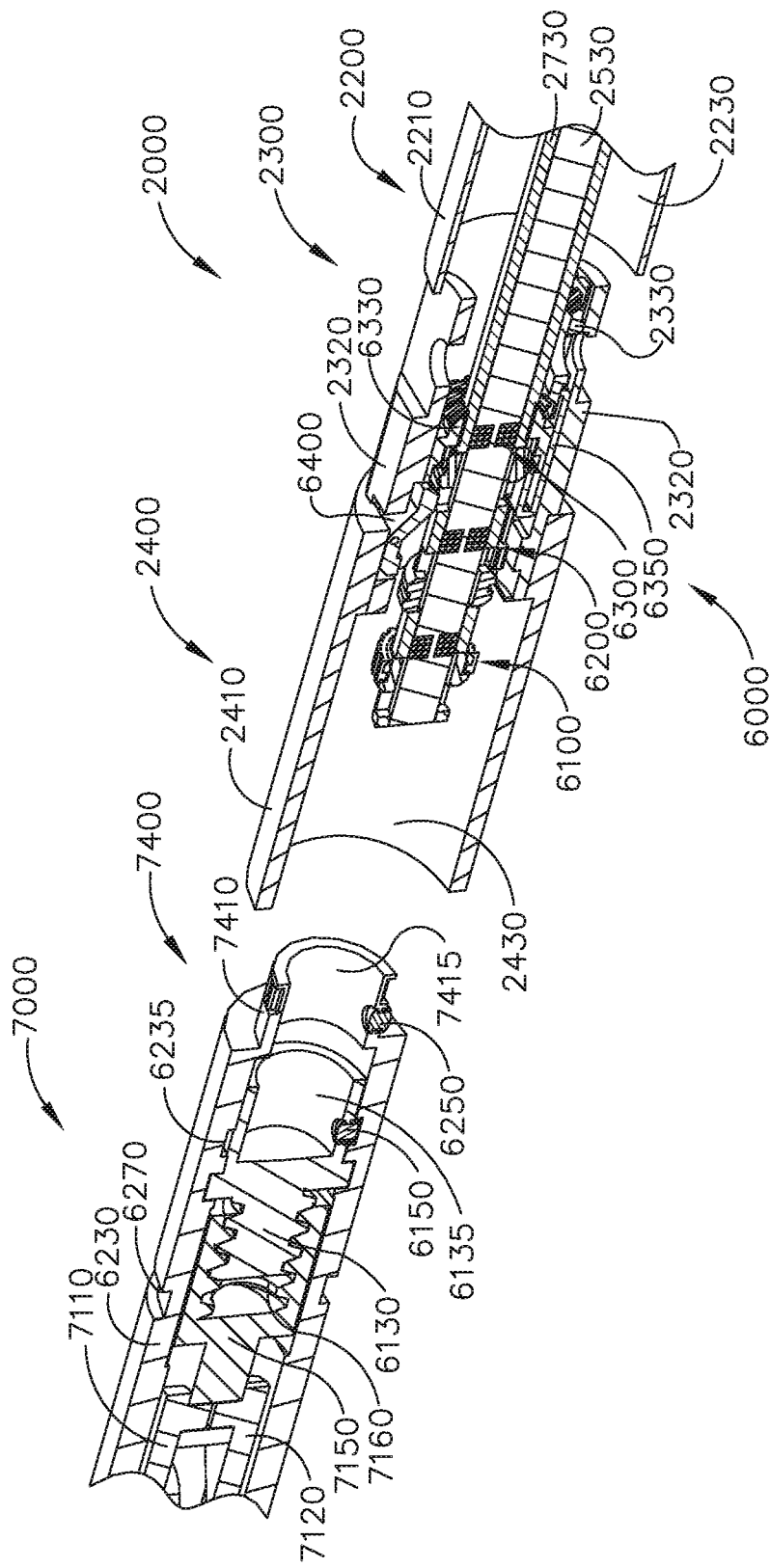
FIG. 23 is another partial cross-sectional perspective view of the end effector of FIG. 14 detached from the shaft assembly of FIG. 2.
Figure 24:
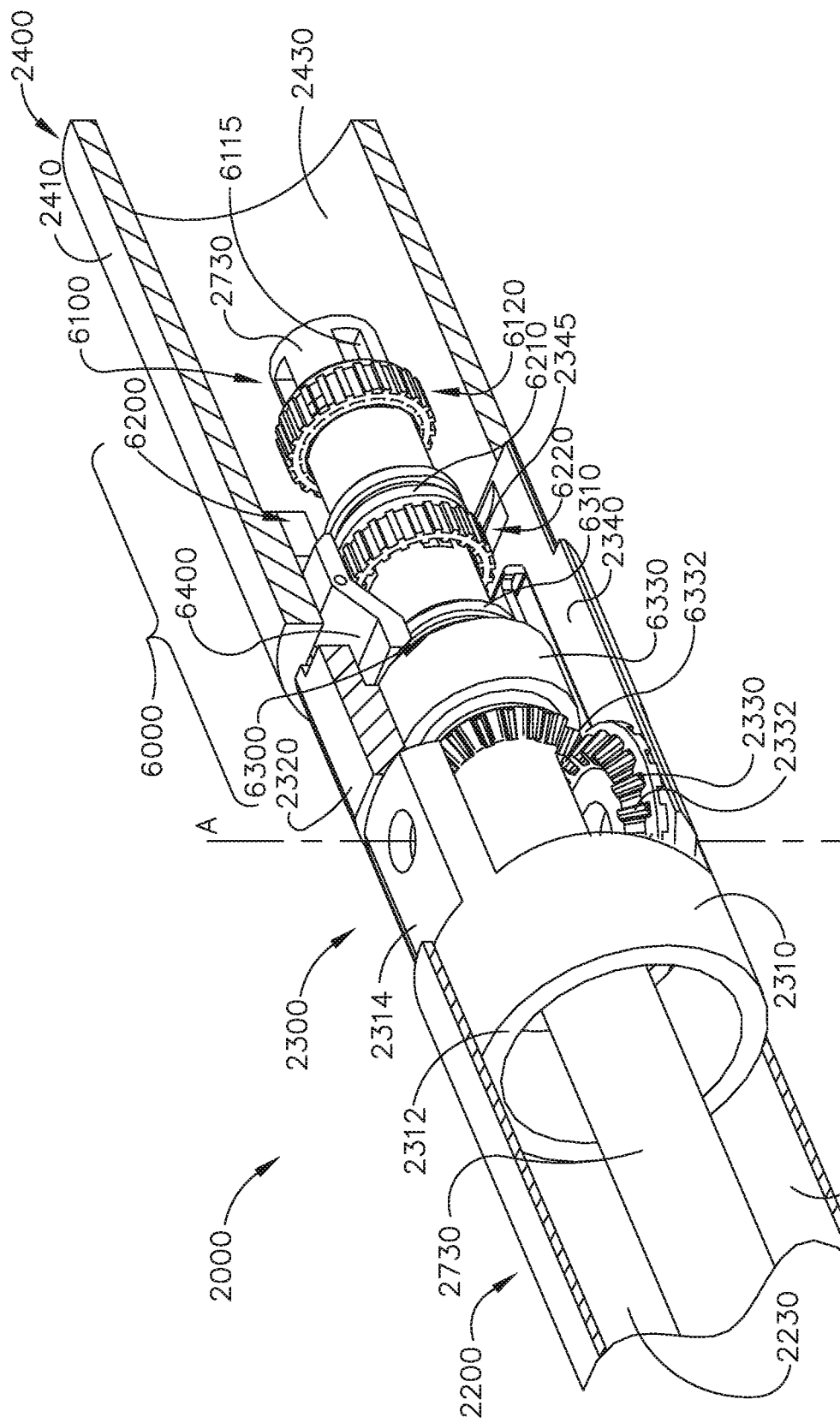
FIG. 24 is a partial cross-sectional perspective view of the end effector of FIG. 14 attached to the shaft assembly of FIG. 2.

Referring primarily to FIGS. 20, 23, and 24, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 22, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 22, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 22, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 20, 23, and 24, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Figure 21:
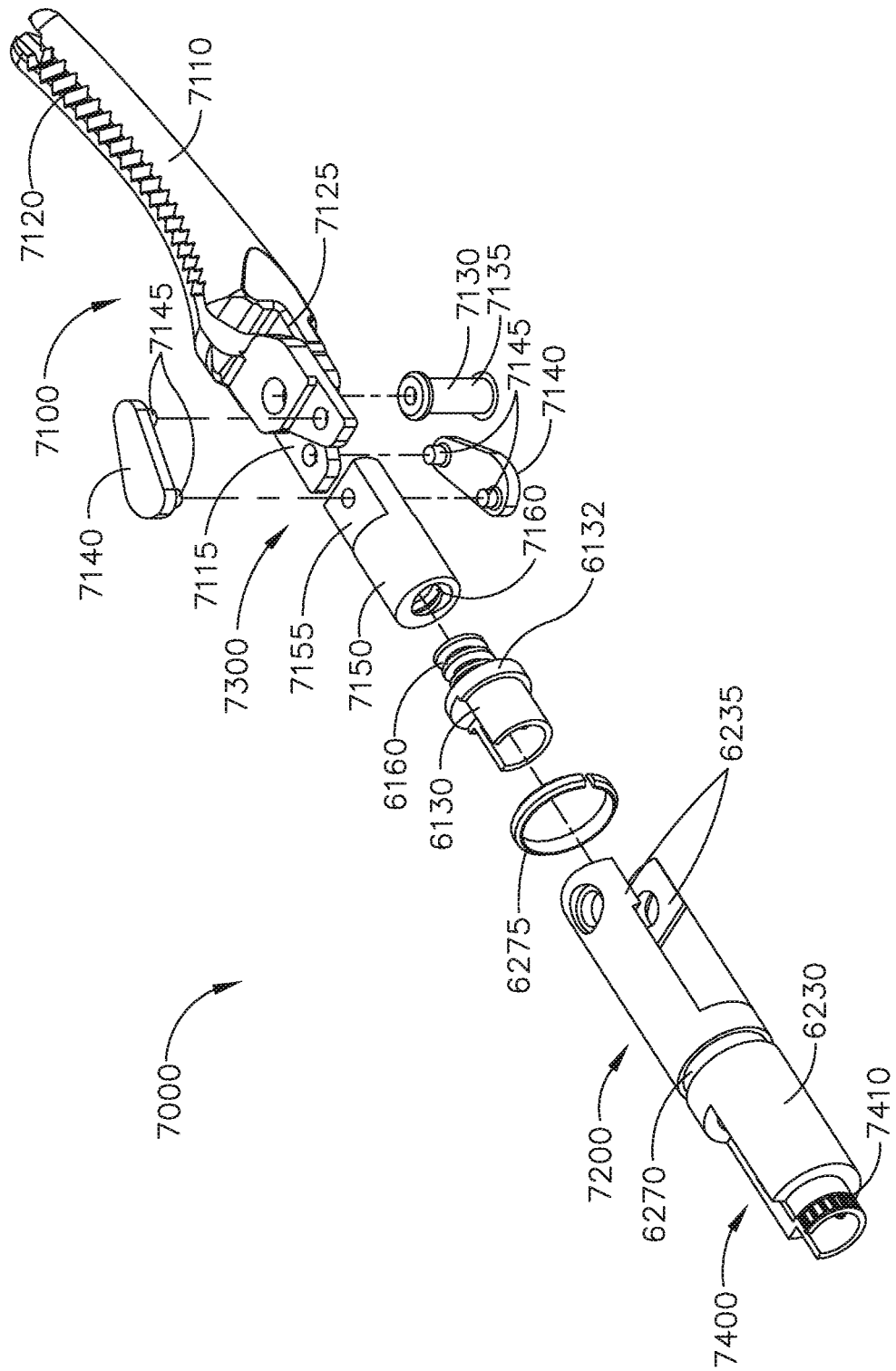
FIG. 21 is an exploded view of the end effector of FIG. 14 illustrated with some components removed.

Further to the above, referring to FIG. 21, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 14-21, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 21, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 21 and 23, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 25) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 21, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

Figure 16:
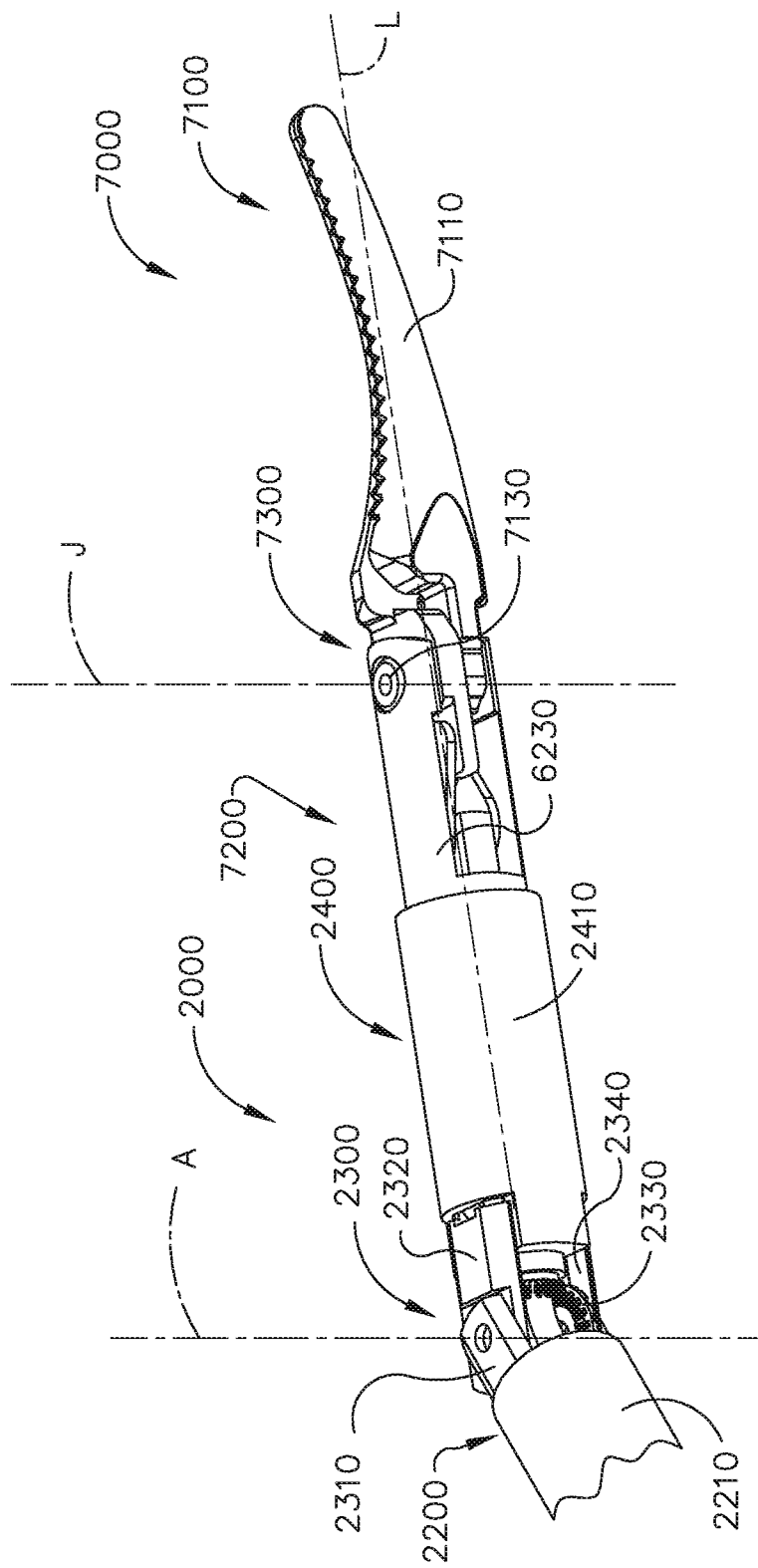
FIG. 16 is a partial perspective view of the end effector of FIG. 14 articulated in a first direction.
Figure 17:
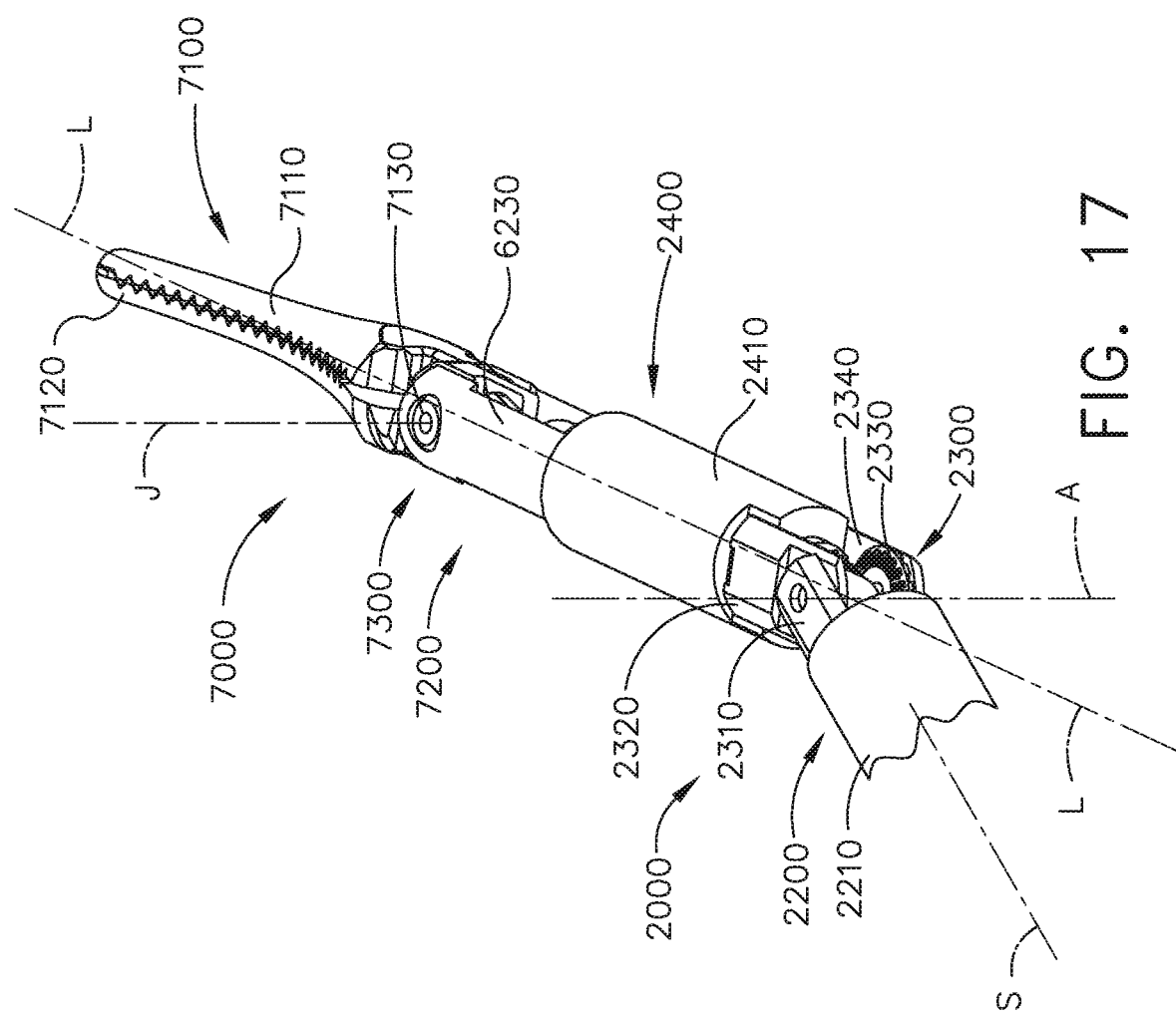
FIG. 17 is a partial perspective view of the end effector of FIG. 14 articulated in a second direction.
Figure 18:
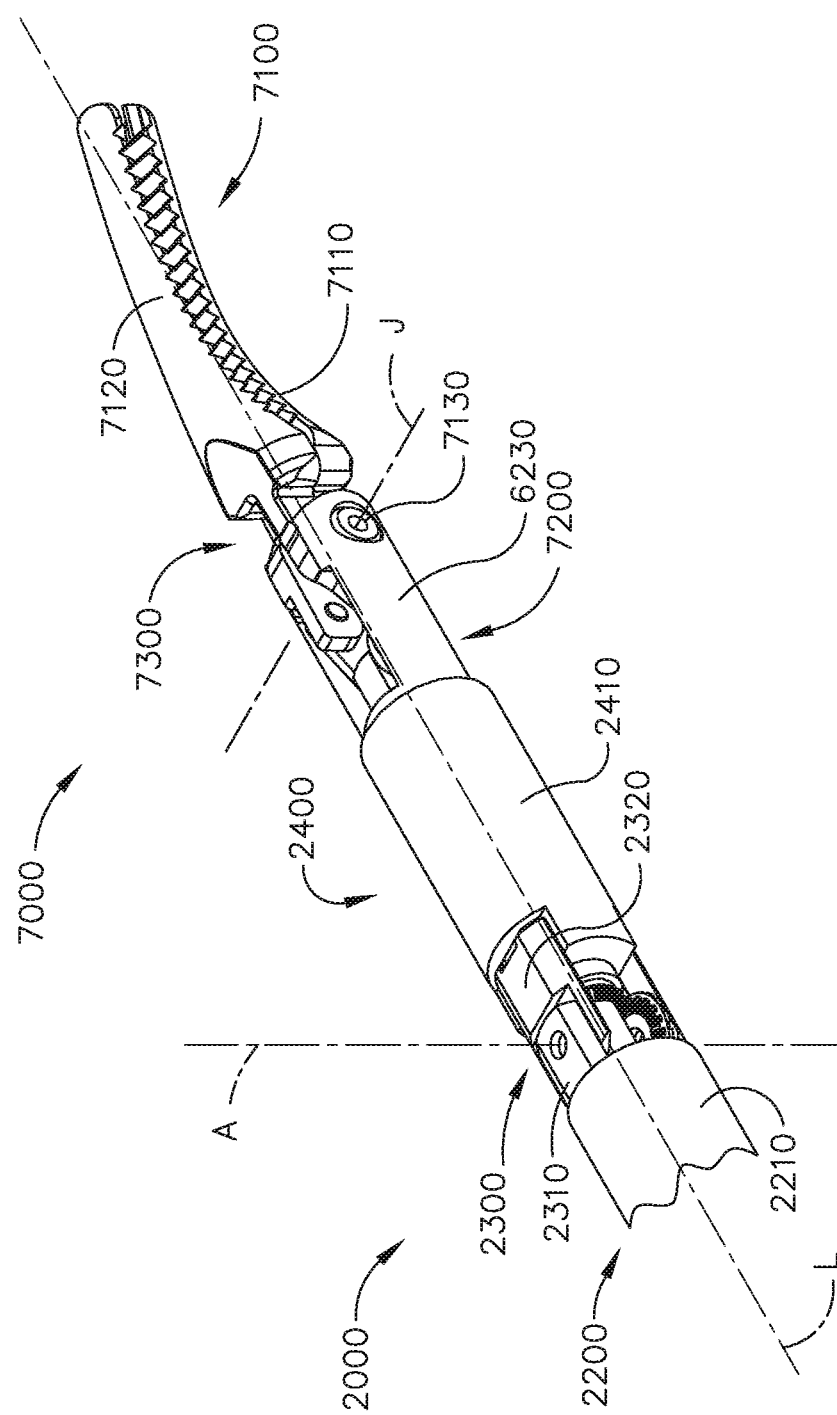
FIG. 18 is a partial perspective view of the end effector of FIG. 14 rotated in a first direction.
Figure 19:
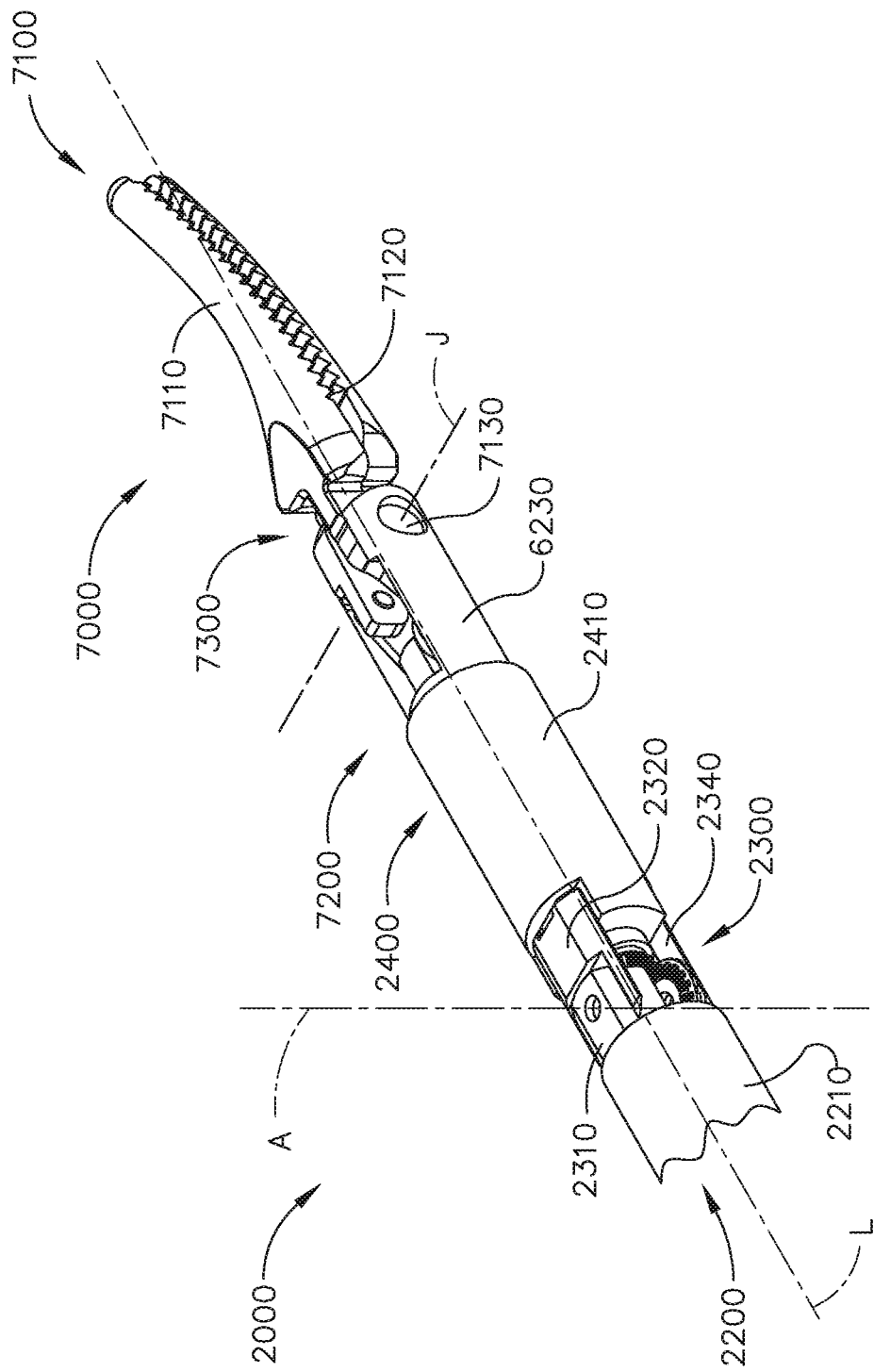
FIG. 19 is a partial perspective view of the end effector of FIG. 14 rotated in a second direction.
Figure 26:
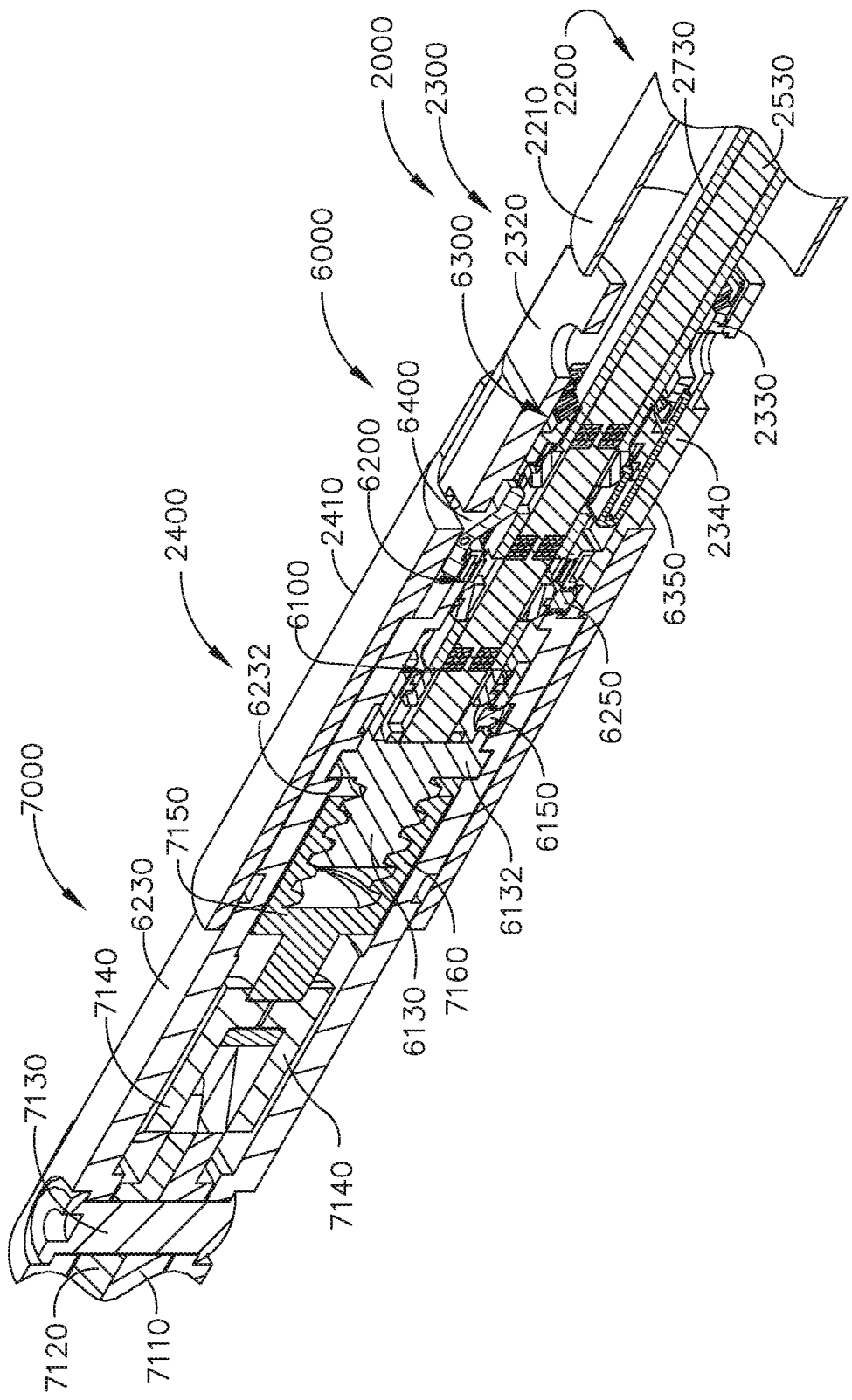
FIG. 26 is another partial cross-sectional perspective view of the end effector of FIG. 14 attached to the shaft assembly of FIG. 2.
Figure 27:
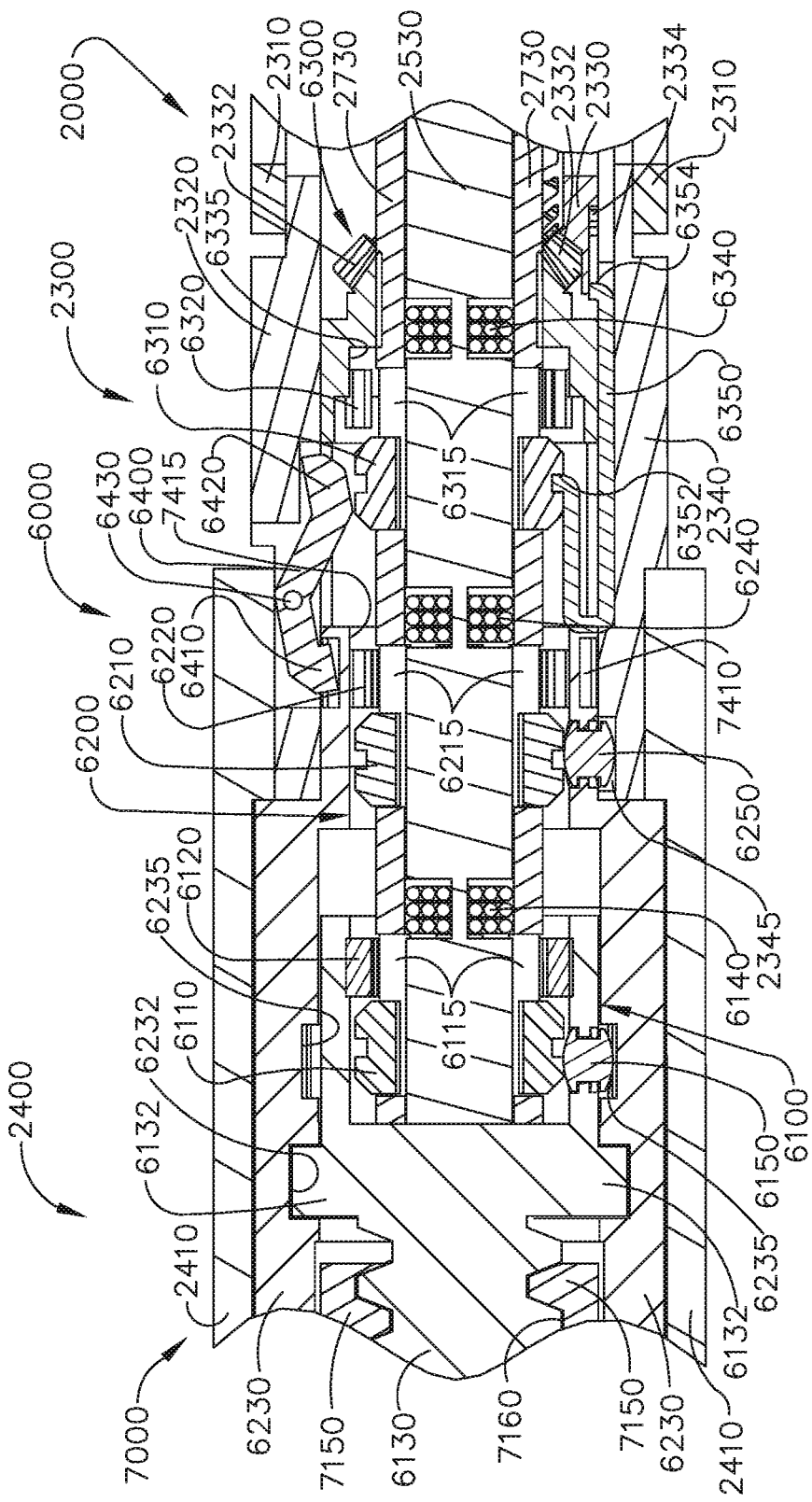
FIG. 27 is a partial cross-sectional view of the end effector of FIG. 14 attached to the shaft assembly of FIG. 2 depicting a first, second, and third clutch of the end effector.

As discussed above, the control system 1800 is configured to actuate the electric motor 1610 to perform three different end effector functions—clamping/opening the jaw assembly 7100 (FIGS. 14 and 15), rotating the end effector 7000 about a longitudinal axis (FIGS. 18 and 19), and articulating the end effector 7000 about an articulation axis (FIGS. 16 and 17). Referring primarily to FIGS. 26 and 27, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Figure 22A:
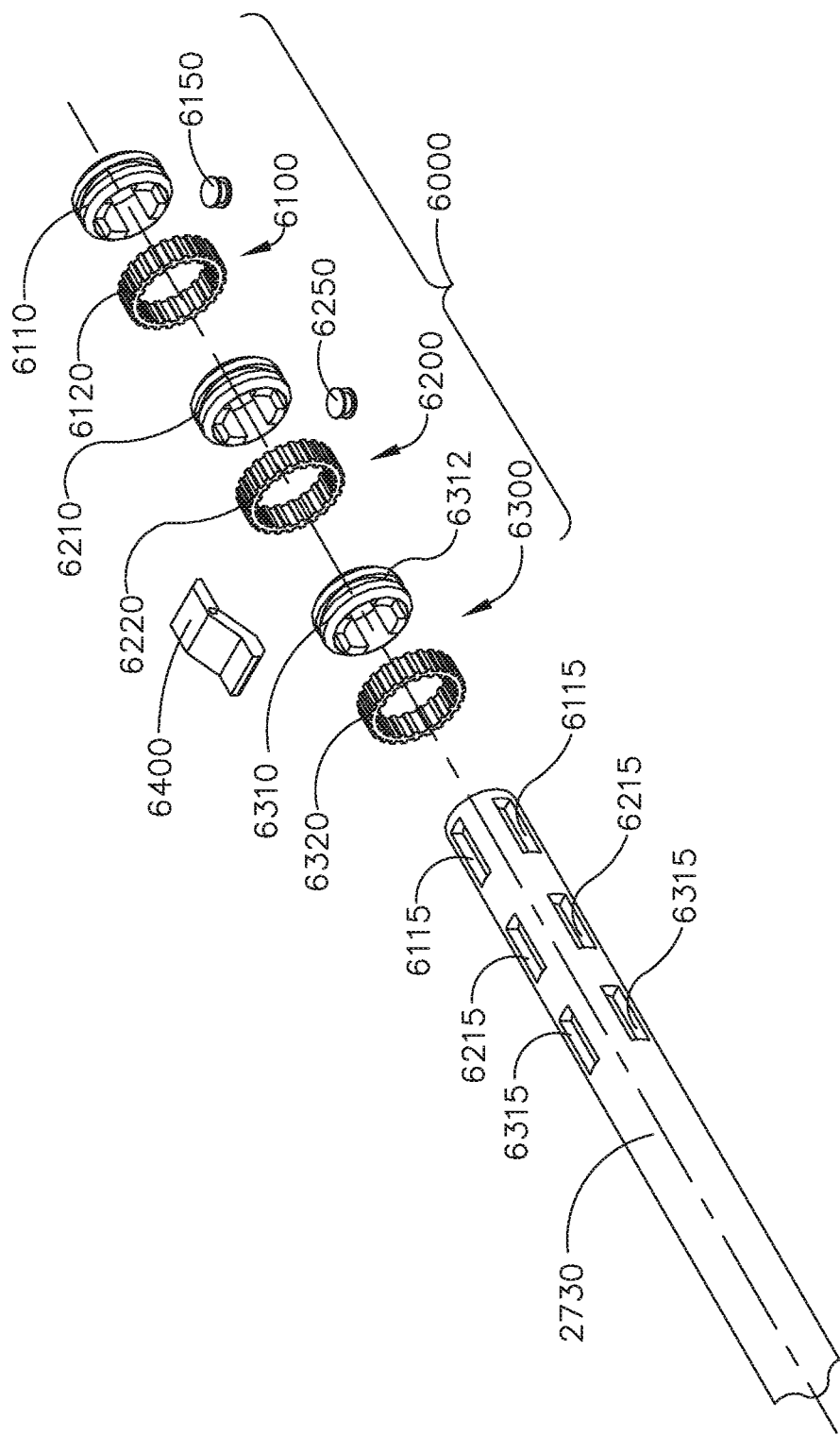
FIG. 22A is an exploded view of the distal portion of the shaft assembly of FIG. 2 illustrated with some components removed.
Figure 28:
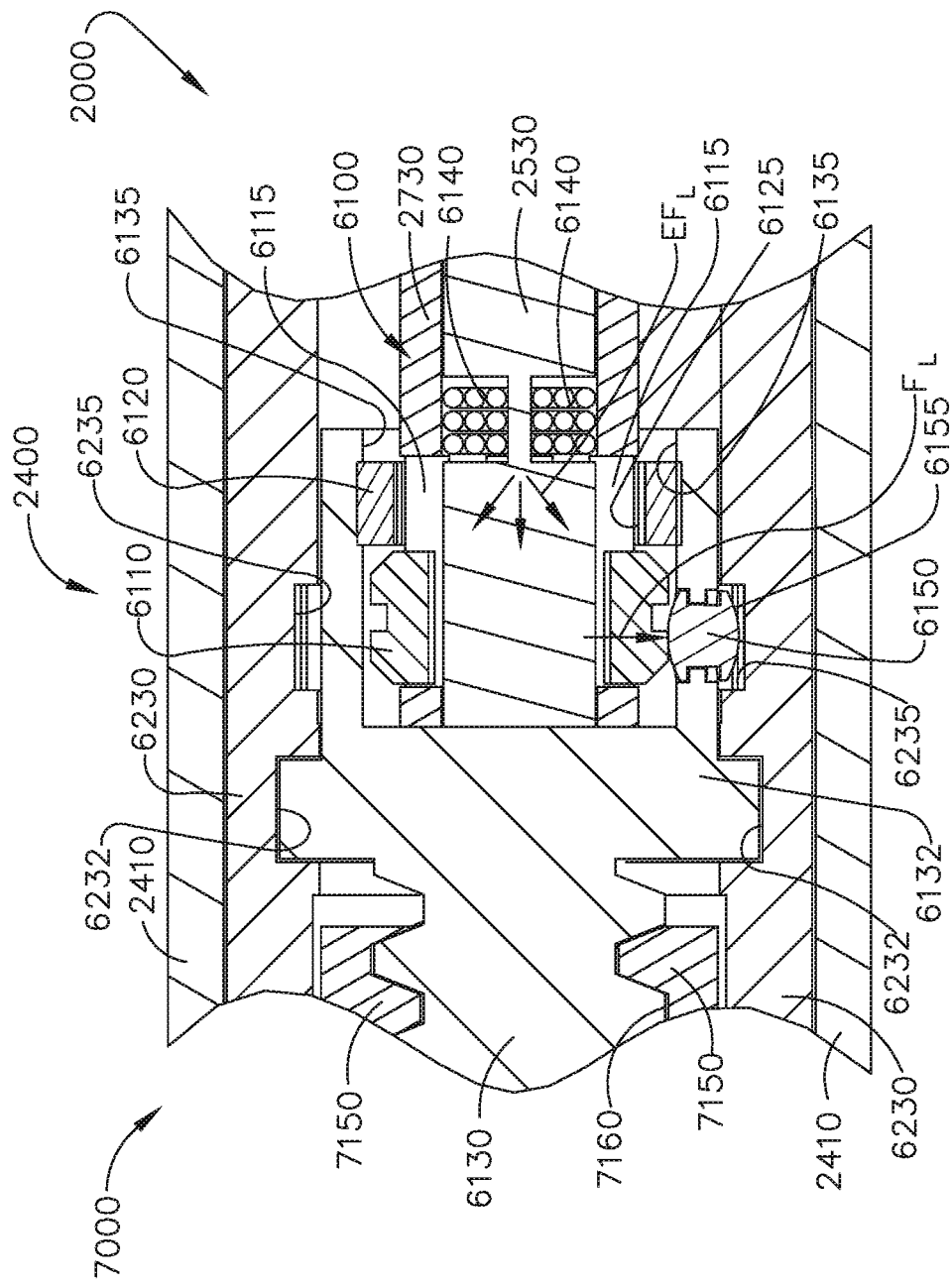
FIG. 28 depicts the first clutch of FIG. 27 in an unactuated condition.

Referring primarily to FIG. 28, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 28) and an engaged, or actuated, position (FIG. 29) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 22A, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

Figure 29:
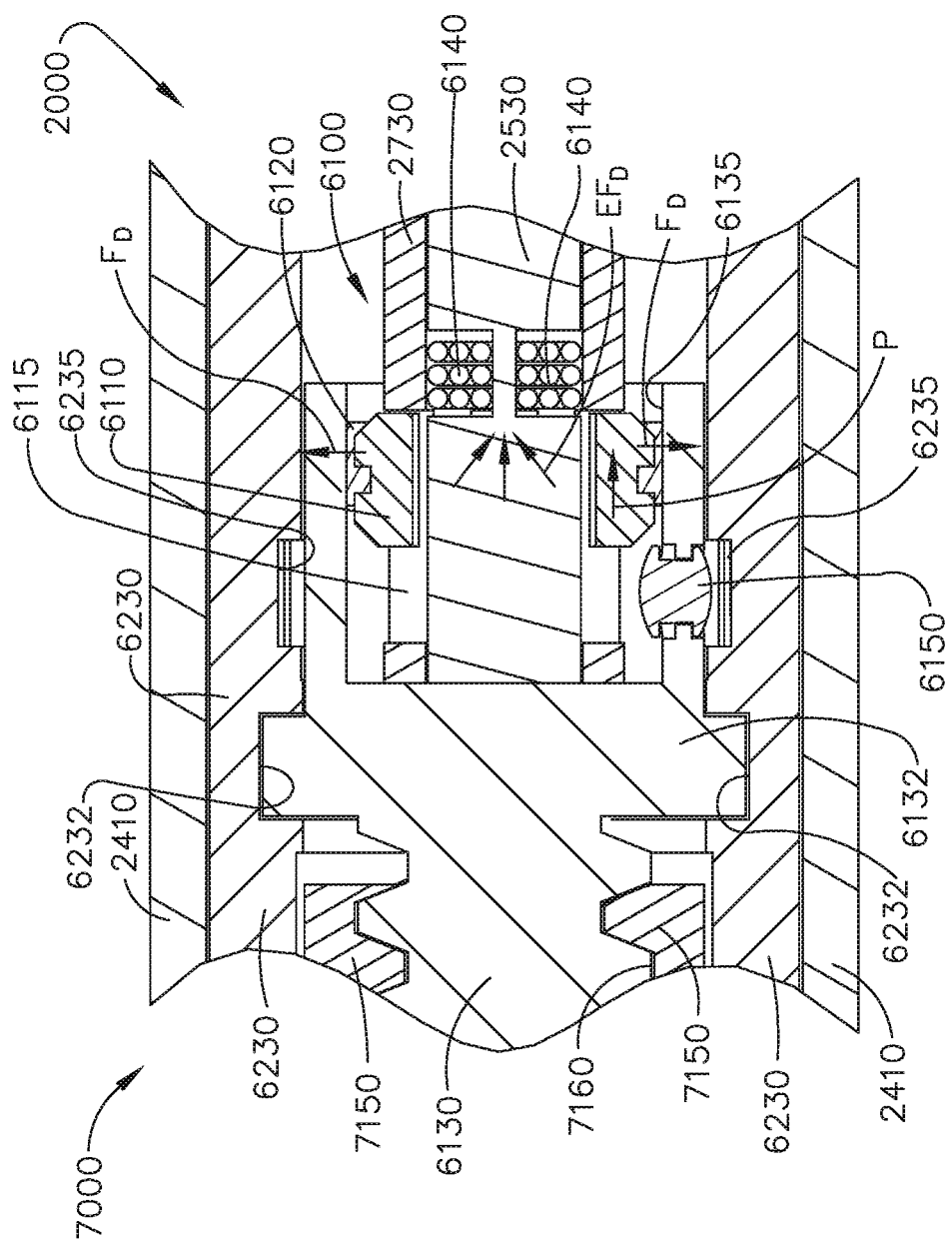
FIG. 29 depicts the first clutch of FIG. 27 in an actuated condition.

When the first clutch 6110 is in its disengaged position (FIG. 28), the first clutch 6110 rotates with the drive shaft 2130 but does not transmit rotational motion to the first drive ring 6120. As can be seen in FIG. 28, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 29), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 29, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 28) and engaged (FIG. 29) positions. For instance, referring to FIG. 28, the first electromagnetic actuator 6140 is configured to emit a magnetic field $EF_L$ which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field $EF_L$ when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 28, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 29, the first electromagnetic actuator 6140 is configured to emit a magnetic field $EF_D$ which pulls, or drives, the first clutch 6110 toward the first drive ring 6120 when the first clutch assembly 6100 is in its engaged state. The coils of the first electromagnetic actuator 6140 generate the magnetic field $EF_D$ when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 28, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 29, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Figure 30:
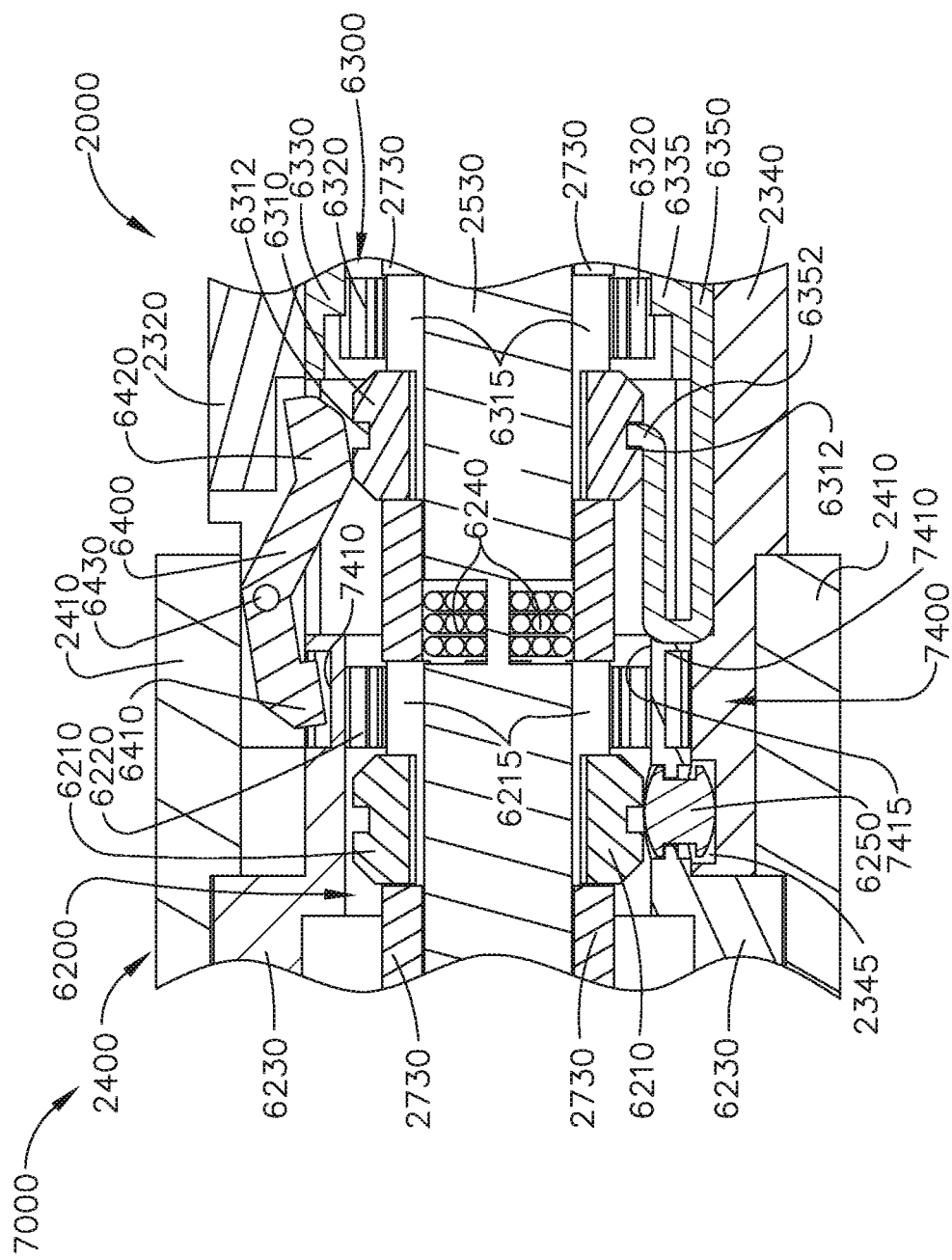
FIG. 30 depicts the second clutch of FIG. 27 in an unactuated condition.

Referring primarily to FIG. 30, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 30) and an engaged, or actuated, position (FIG. 31) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 22A, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

Figure 31:
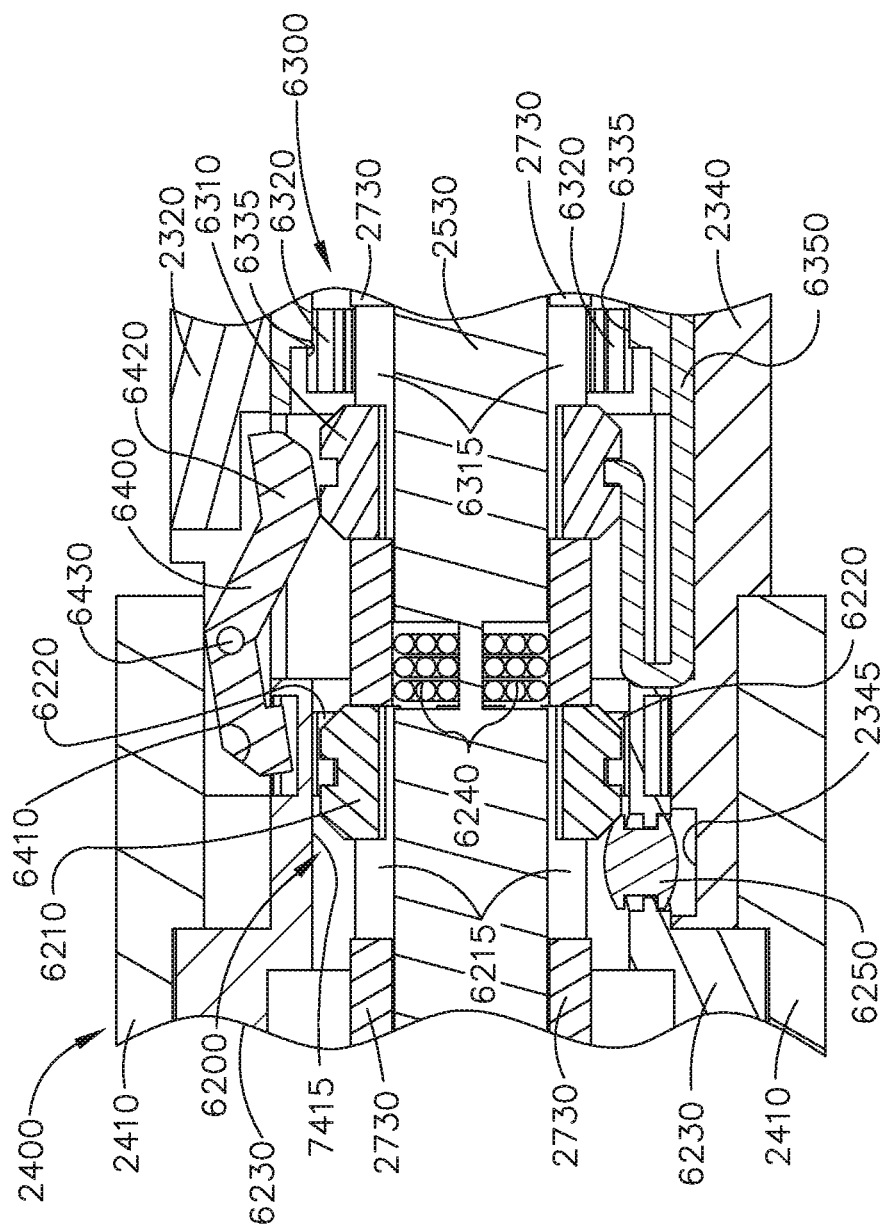
FIG. 31 depicts the second clutch of FIG. 27 in an actuated condition.

When the second clutch 6210 is in its disengaged position, referring to FIG. 30, the second clutch 6210 rotates with the drive shaft 2730 but does not transmit rotational motion to the second drive ring 6220. As can be seen in FIG. 30, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 31), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 31, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 30) and engaged (FIG. 31) positions. For instance, the second electromagnetic actuator 6240 is configured to emit a magnetic field $EF_L$ which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field $EF_L$ when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 30, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 31, the second electromagnetic actuator 6240 is configured to emit a magnetic field $EF_D$ which pulls, or drives, the second clutch 6210 toward the second drive ring 6220 when the second clutch assembly 6200 is in its engaged state. The coils of the second electromagnetic actuator 6240 generate the magnetic field $EF_D$ when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 30, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 27, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things— operate the end effector rotation drive when the second clutch 6210 is in its engaged position and lock out the end effector rotation drive when the second clutch 6210 is in its disengaged position.

Figure 25:
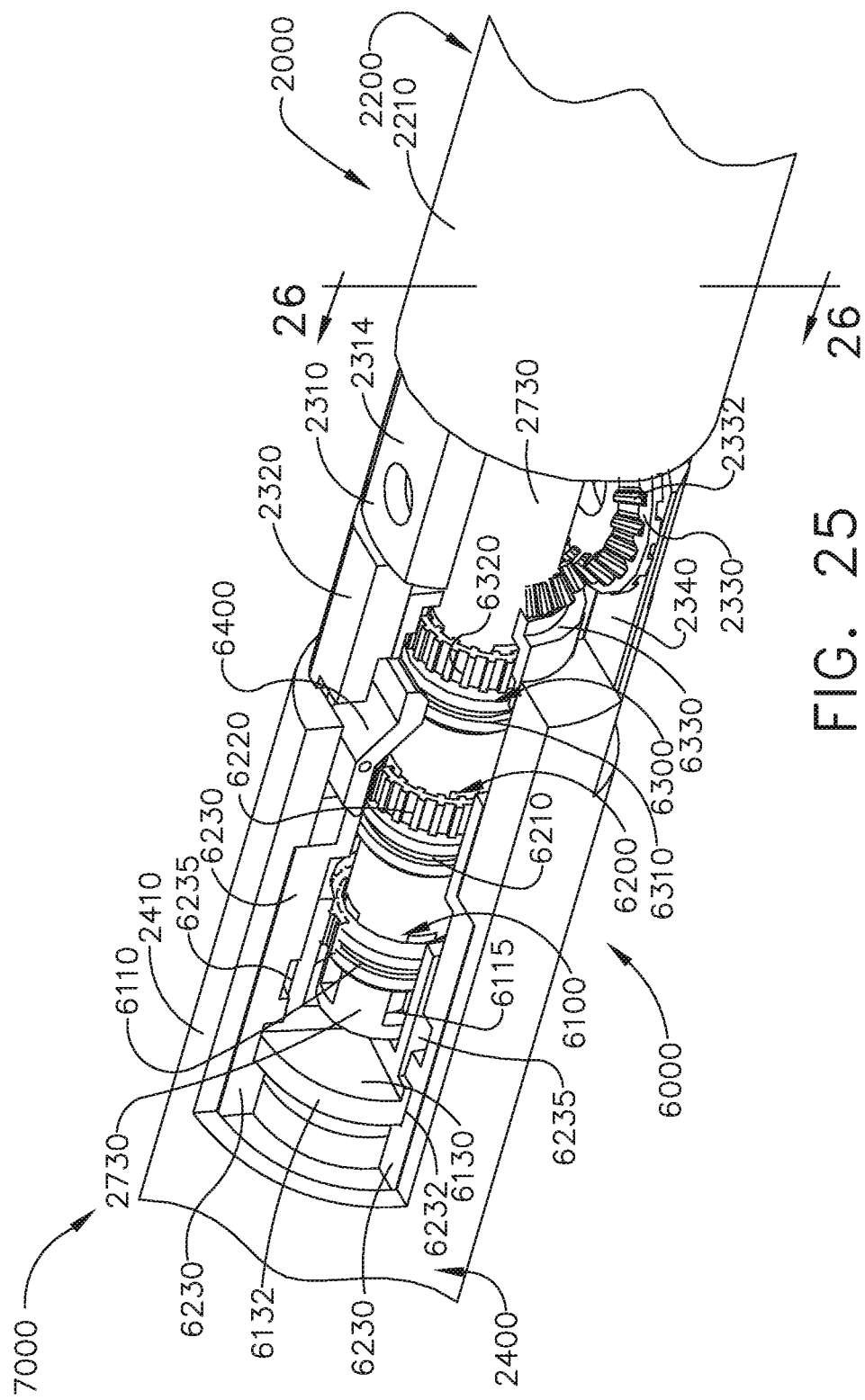
FIG. 25 is a partial cross-sectional perspective view of the end effector of FIG. 14 attached to the shaft assembly of FIG. 2.

Referring primarily to FIGS. 22, 24, and 25, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Figure 32:
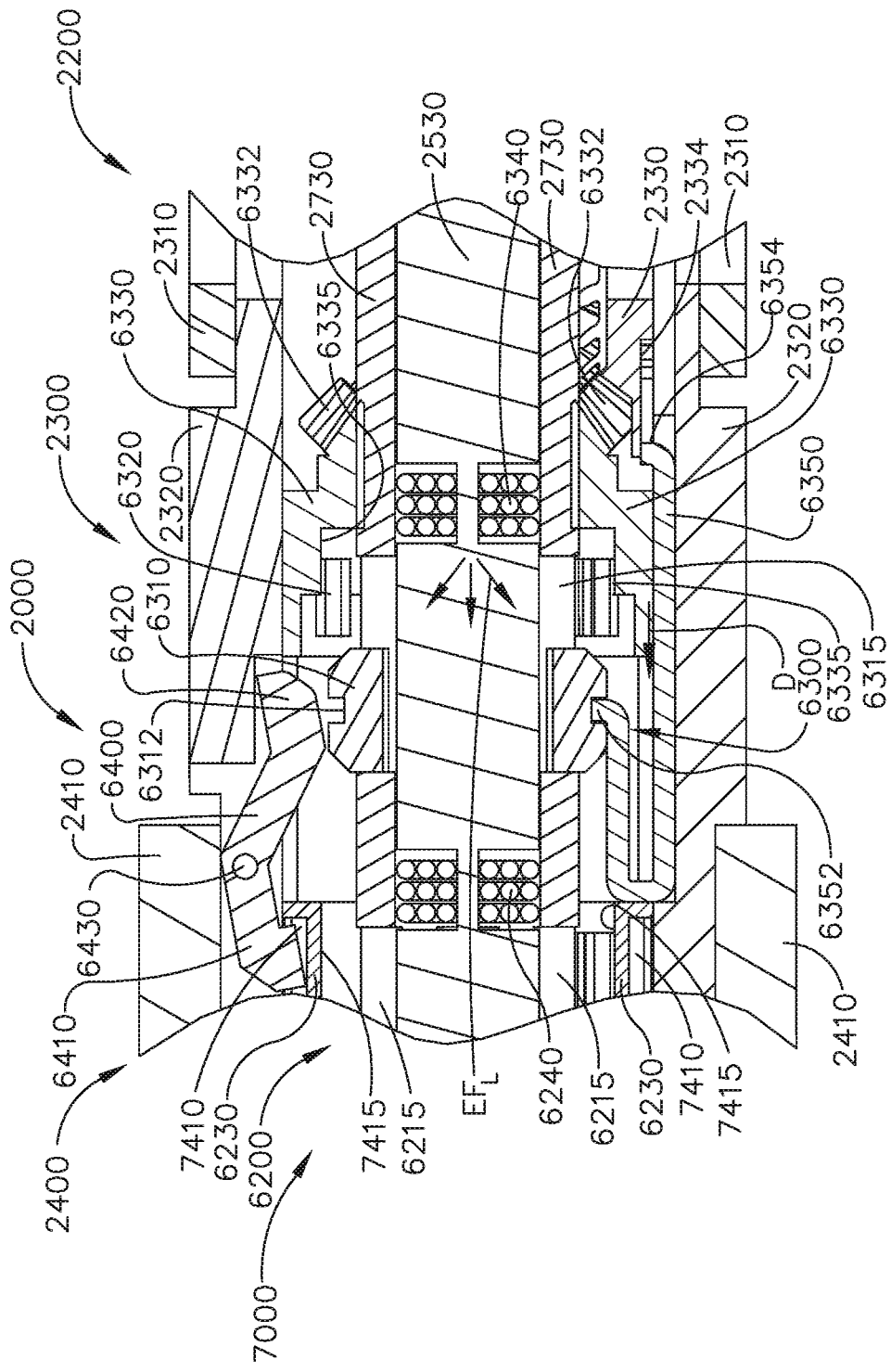
FIG. 32 depicts the third clutch of FIG. 27 in an unactuated condition.

Referring primarily to FIG. 32, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 32) and an engaged, or actuated, position (FIG. 33) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 22A, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

Figure 33:
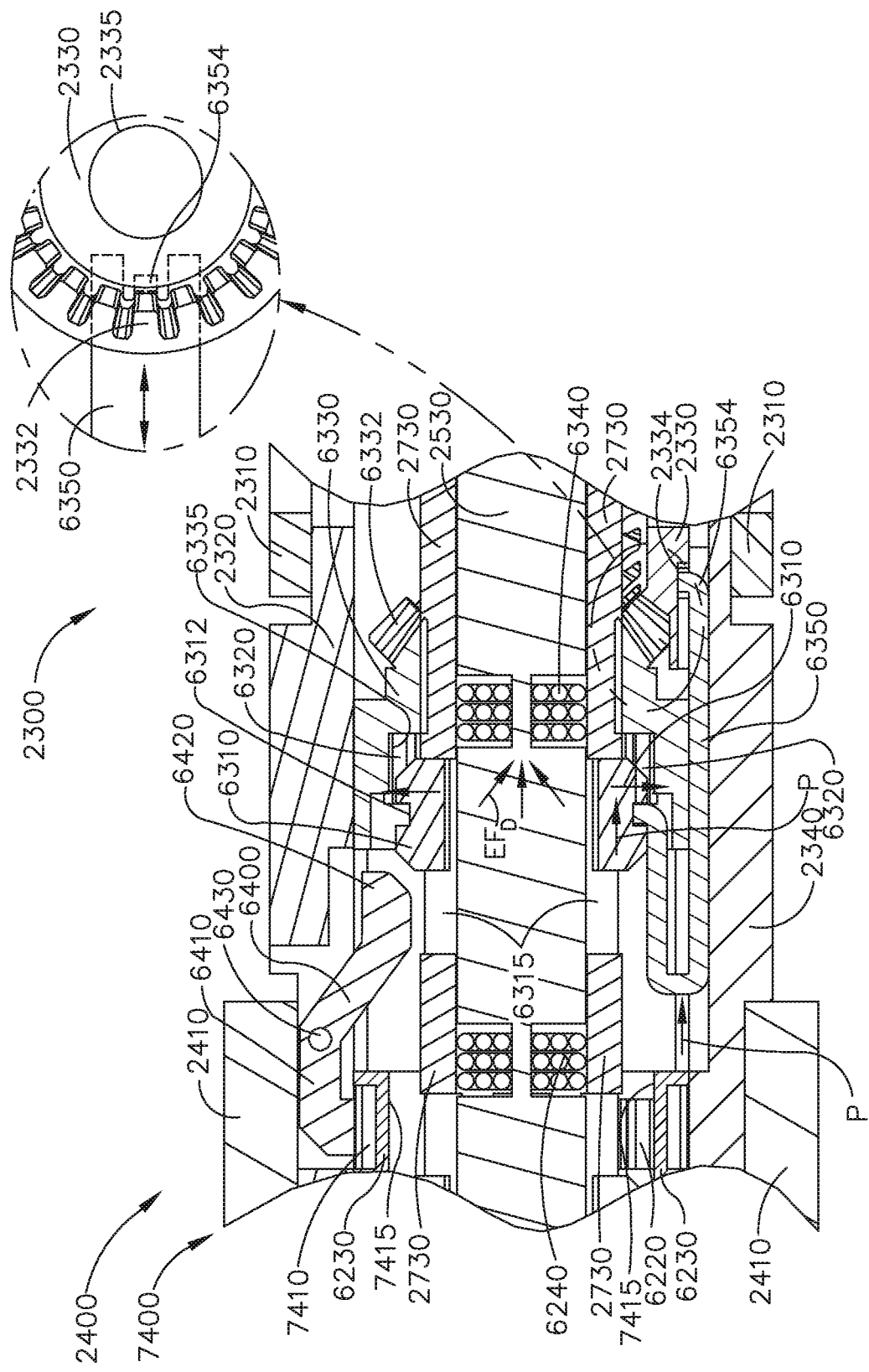
FIG. 33 depicts the third clutch of FIG. 27 in an actuated condition.

When the third clutch 6310 is in its disengaged position, referring to FIG. 32, the third clutch 6310 rotates with the drive shaft 2730 but does not transmit rotational motion to the third drive ring 6320. As can be seen in FIG. 32, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 33, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 33, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 32) and engaged (FIG. 33) positions. For instance, referring to FIG. 32, the third electromagnetic actuator 6340 is configured to emit a magnetic field $EF_L$ which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field $EF_L$ when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field $EF_D$ which pulls, or drives, the third clutch 6310 toward the third drive ring 6320 when the third clutch assembly 6300 is in its engaged state. The coils of the third electromagnetic actuator 6340 generate the magnetic field $EF_D$ when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 22, 32, and 33, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 32). Referring primarily to FIG. 22, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 32, the lockout 6350 is in a locked position in which the lockout hook 6354 prevents the end effector 7000 from rotating about the articulation joint 2300. When the third clutch 6310 is in its engaged position, as illustrated in FIG. 33, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 32 and 33 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactivated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 24 and 25, the shaft frame 2530 and the drive shaft 2730 extend through the articulation joint 2300 into the distal attachment portion 2400. When the end effector 7000 is articulated, as illustrated in FIGS. 16 and 17, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

Figure 34:
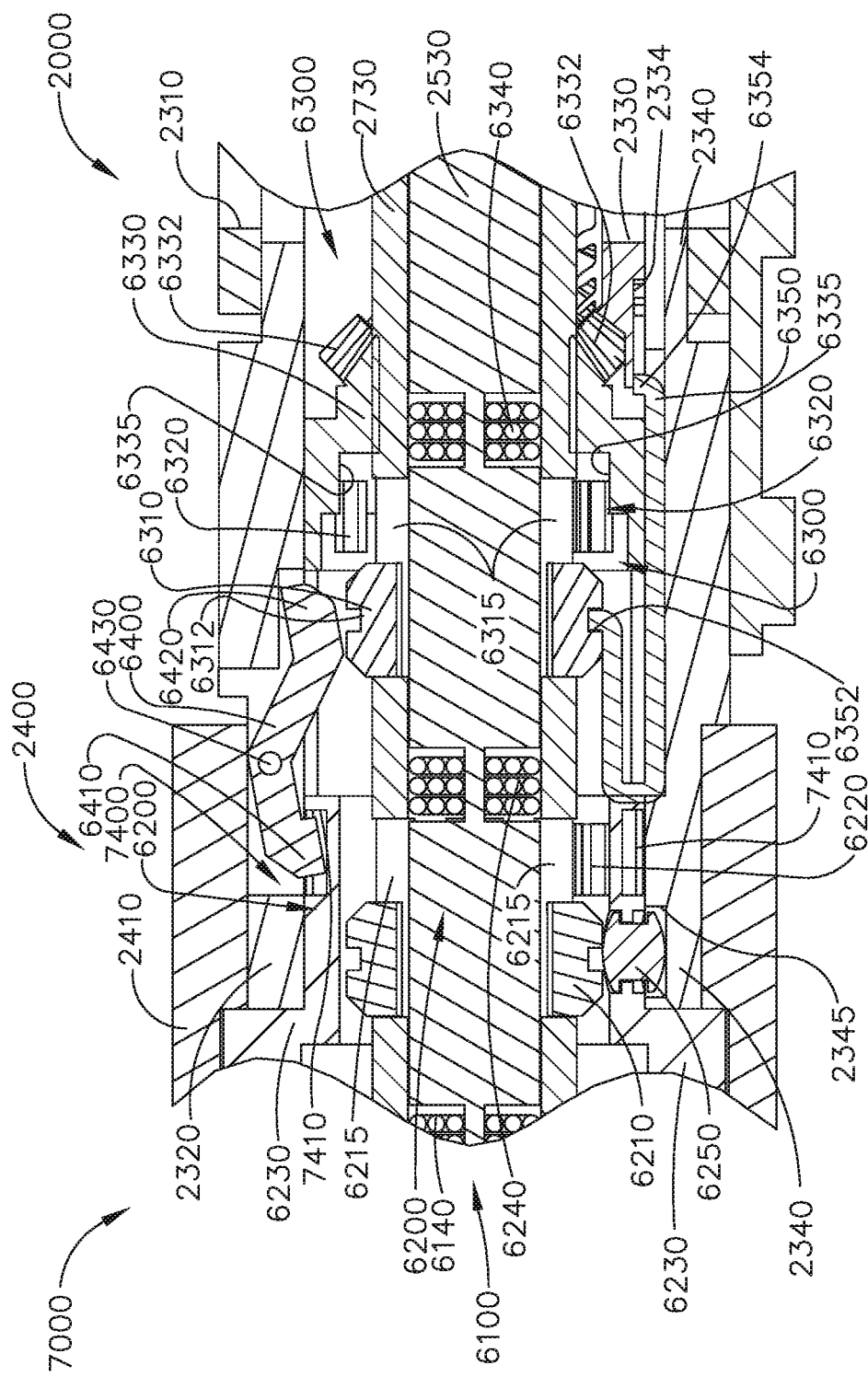
FIG. 34 depicts the second and third clutches of FIG. 27 in their unactuated conditions and the end effector of FIG. 14 locked to the shaft assembly of FIG. 2.
Figure 35:
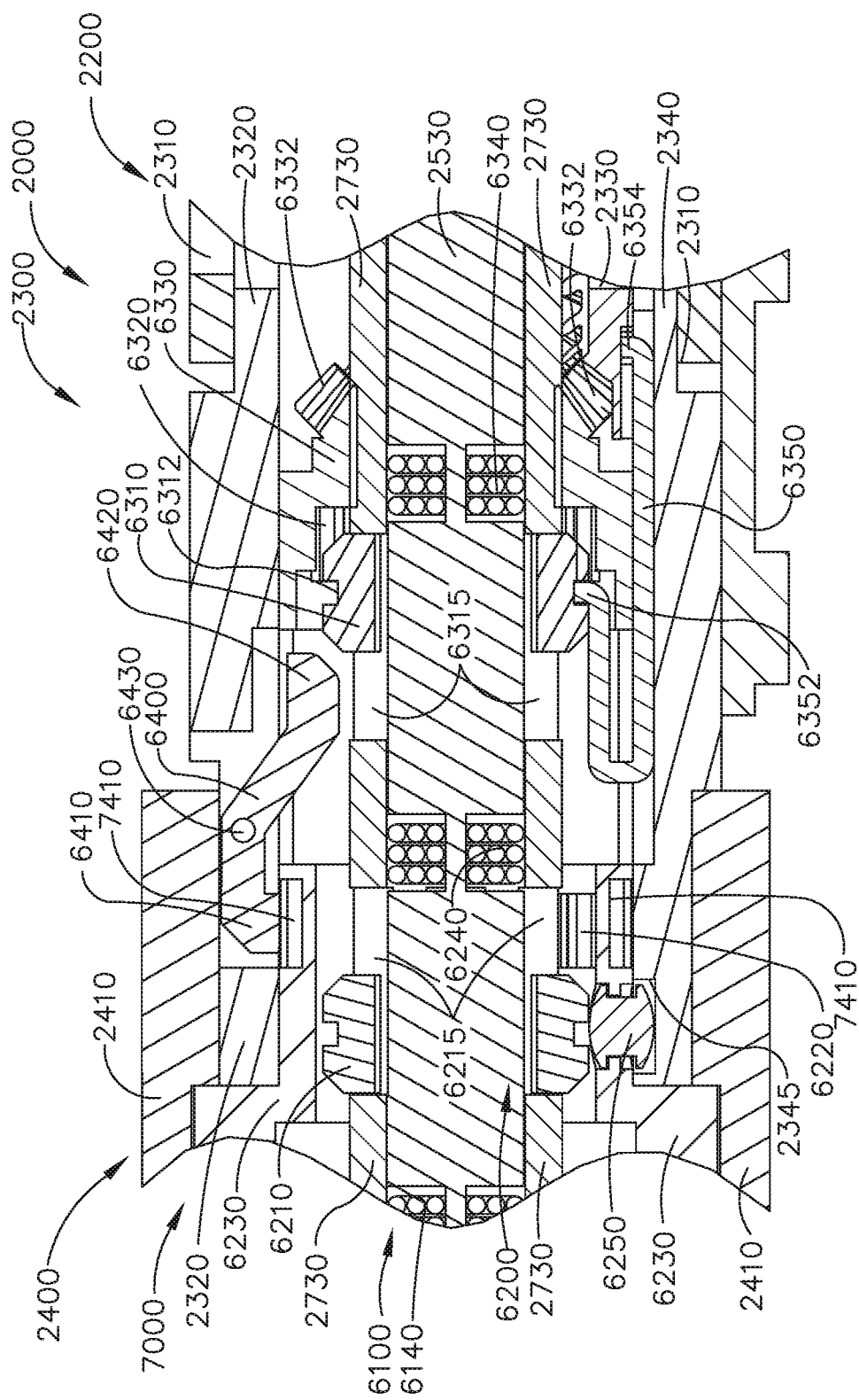
FIG. 35 depicts the second clutch of FIG. 27 in its unactuated condition and the third clutch of FIG. 27 in its actuated condition.
Figure 36:
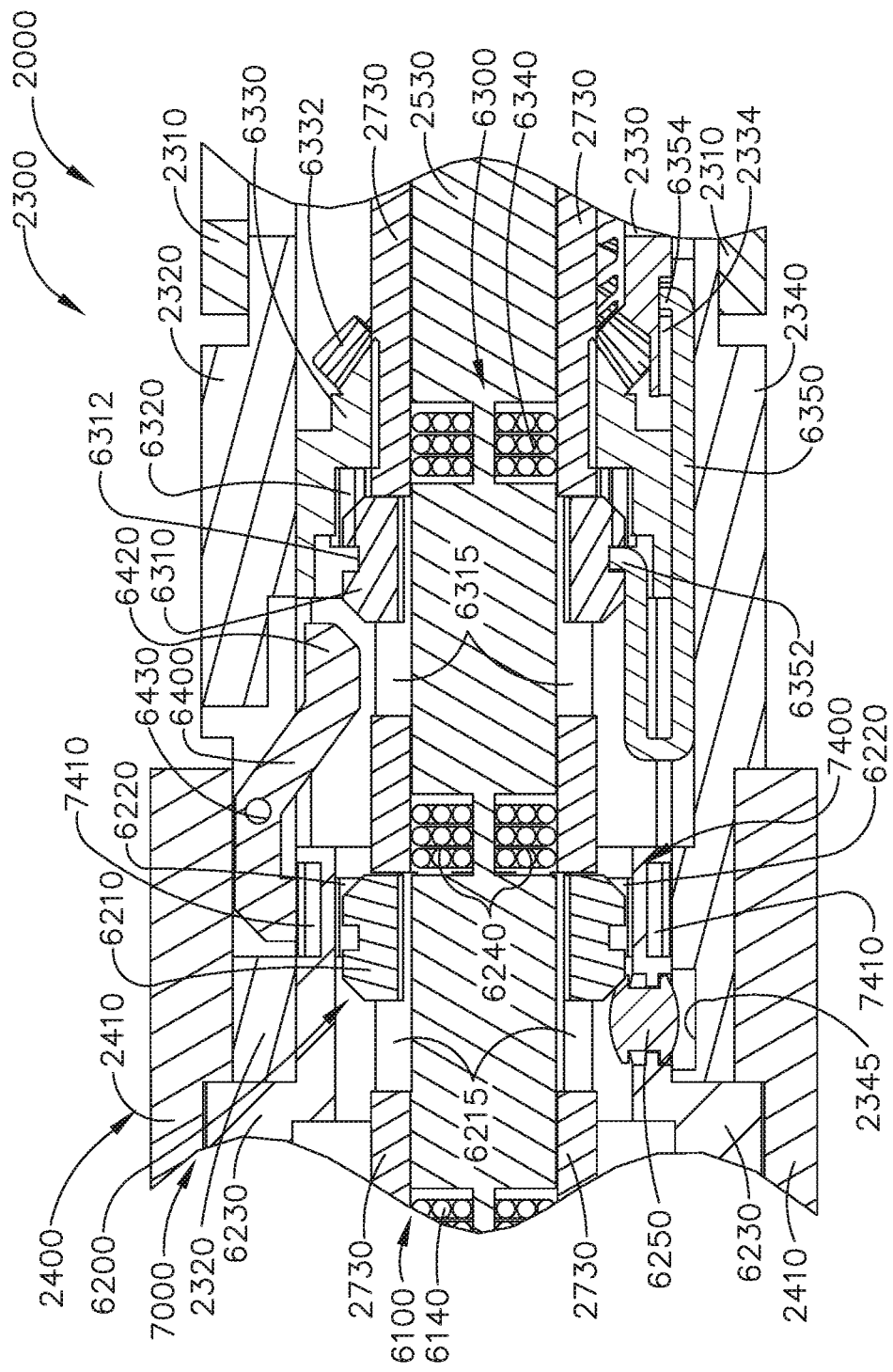
FIG. 36 depicts the second and third clutches of FIG. 27 in their actuated conditions and the end effector of FIG. 14 unlocked from the shaft assembly of FIG. 2.

As discussed above, referring to FIG. 34, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 34, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 35, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 34, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

Figure 37:
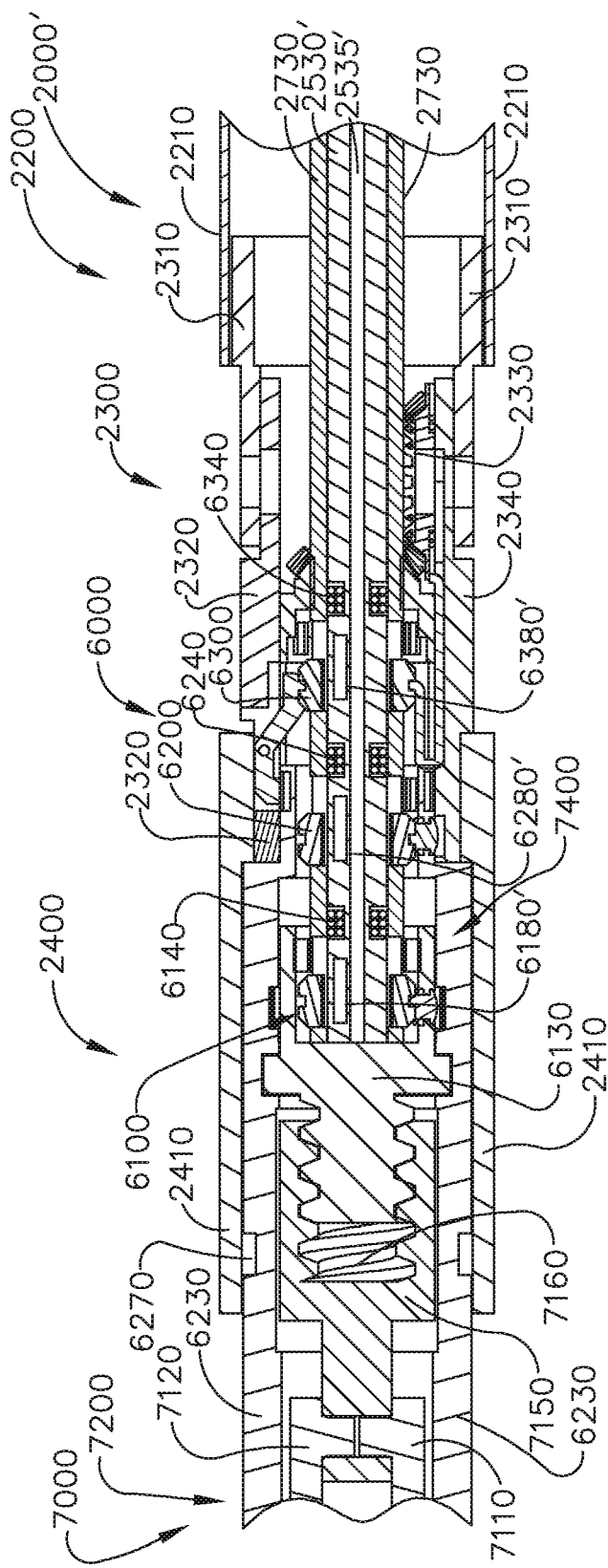
FIG. 37 is a partial cross-sectional view of a shaft assembly in accordance with at least one alternative embodiment comprising sensors configured to detect the conditions of the first, second, and third clutches of FIG. 27.

FIG. 37 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

Figure 38:
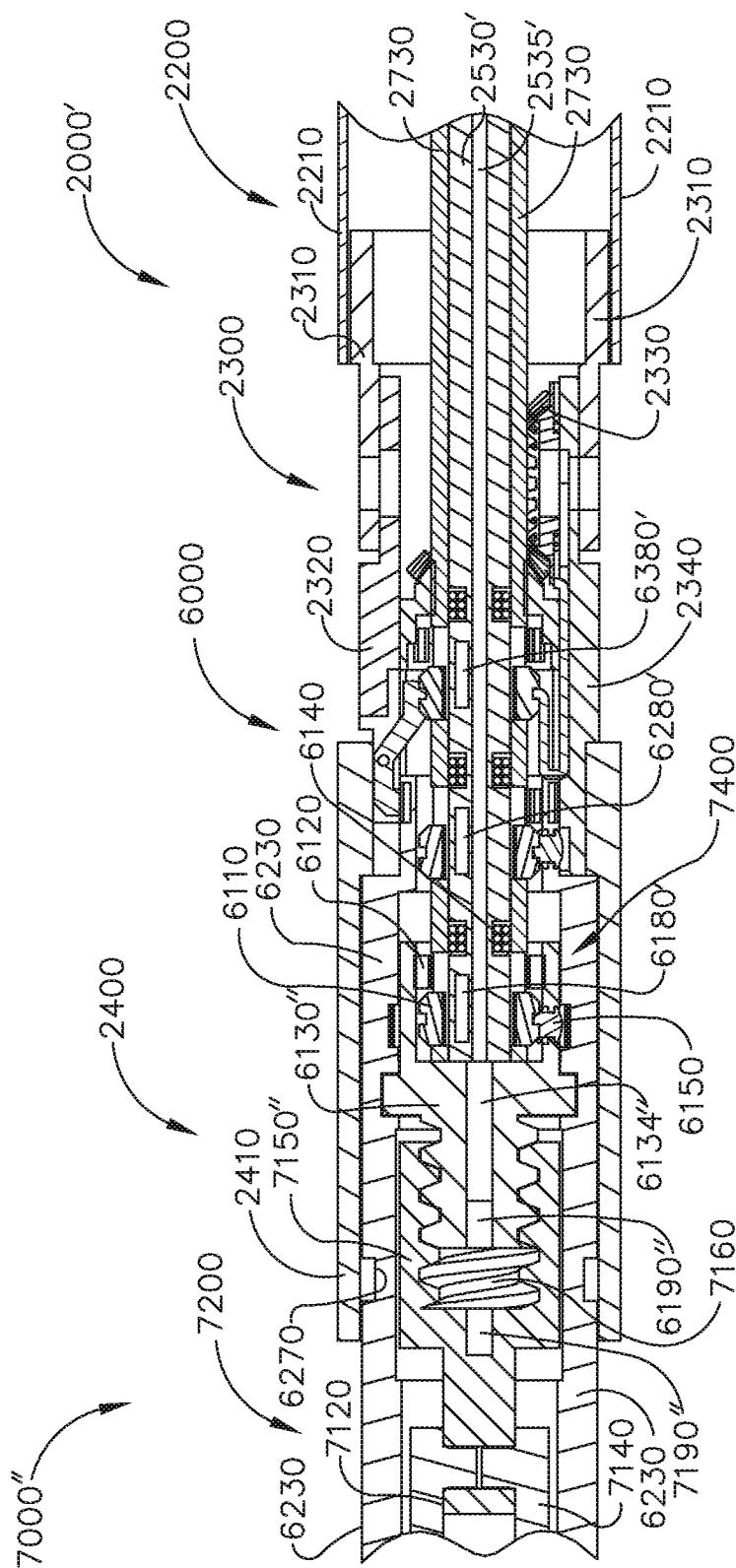
FIG. 38 is a partial cross-sectional view of a shaft assembly in accordance with at least one alternative embodiment comprising sensors configured to detect the conditions of the first, second, and third clutches of FIG. 27.

FIG. 38 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190"

and the control system 1800 are also configured to determine the distance between where the drive screw 6130″ is currently positioned and where the drive screw 6130″ should be positioned at the end of its closure stroke in order to calculate the amount of closure stroke of the drive screw 6130″ that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

Figure 39:
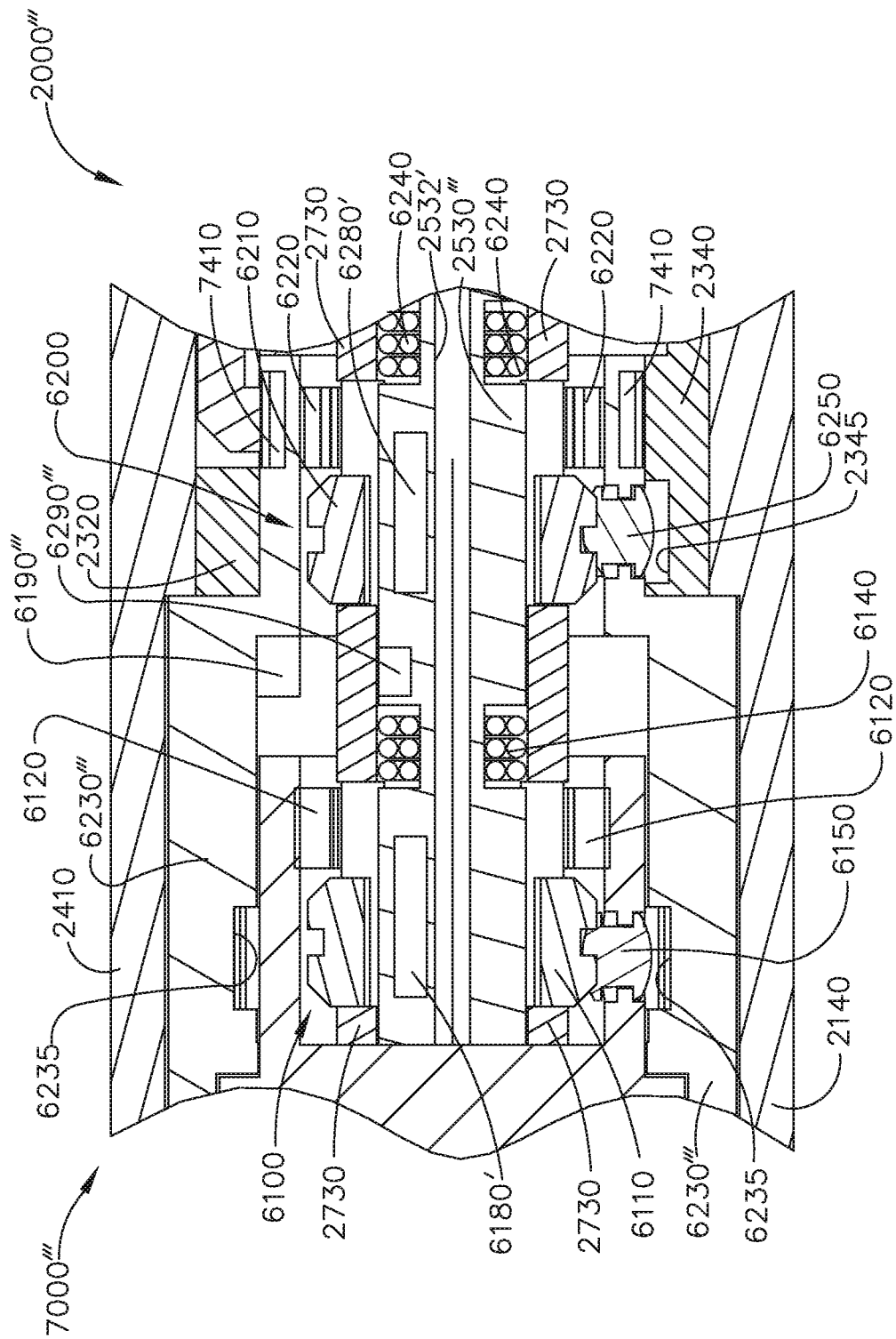
FIG. 39 depicts the first and second clutches of FIG. 38 in their unactuated conditions and a sensor in accordance with at least one alternative embodiment.

FIG. 39 depicts a shaft assembly 2000′″ and an end effector 7000′″ in accordance with at least one alternative embodiment. The shaft assembly 2000′″ is similar to the shaft assemblies 2000 and 2000′ in many respects, most of which will not be repeated herein for the sake of brevity. The end effector 7000′″ is similar to the end effectors 7000 and 7000″ in many respects, most of which will not be repeated herein for the sake of brevity. Similar to the end effector 7000, the end effector 7000′″ comprises a jaw assembly 7100 and a jaw assembly drive configured to move the jaw assembly 7100 between its open and closed configurations and, in addition, an end effector rotation drive that rotates the end effector 7000′″ relative to the distal attachment portion 2400 of the shaft assembly 2000′. The end effector rotation drive comprises an outer housing 6230′″ that is rotated relative to a shaft frame 2530′″ of the end effector 7000′″ by the second clutch assembly 6200. The shaft frame 2530′″ comprises a sensor 6290′″ positioned therein which is configured to detect the position of a magnetic element 6190′″ positioned in and/or on the outer housing 6230′″. The magnetic element 6190′″ can comprise a permanent magnet and/or can be comprised of iron, nickel, and/or any suitable metal, for example. In various instances, the sensor 6290′″ comprises a proximity sensor, for example, in signal communication with the control system 1800. In certain instances, the sensor 6290′″ comprises a Hall Effect sensor, for example, in signal communication with the control system 1800. In either event, the sensor 6290′″ is configured to communicate wirelessly with the control system 1800 via a wireless signal transmitter and receiver and/or via a wired connection extending through the shaft frame passage 2532′, for example. In various instances, the control system 1800 can use the sensor 6290′″ to confirm whether the magnetic element 6190′″ is rotating and, thus, confirm that the second clutch assembly 6200 is in its actuated state. Similarly, the control system 1800 can use the sensor 6290′″ to confirm whether the magnetic element 6190′″ is not rotating and, thus, confirm that the second clutch assembly 6200 is in its unactuated state. The control system 1800 can also use the sensor 6290′″ to confirm that the second clutch assembly 6200 is in its unactuated state by confirming that the second clutch 6210 is positioned adjacent the sensor 6290′″.

Figure 40:
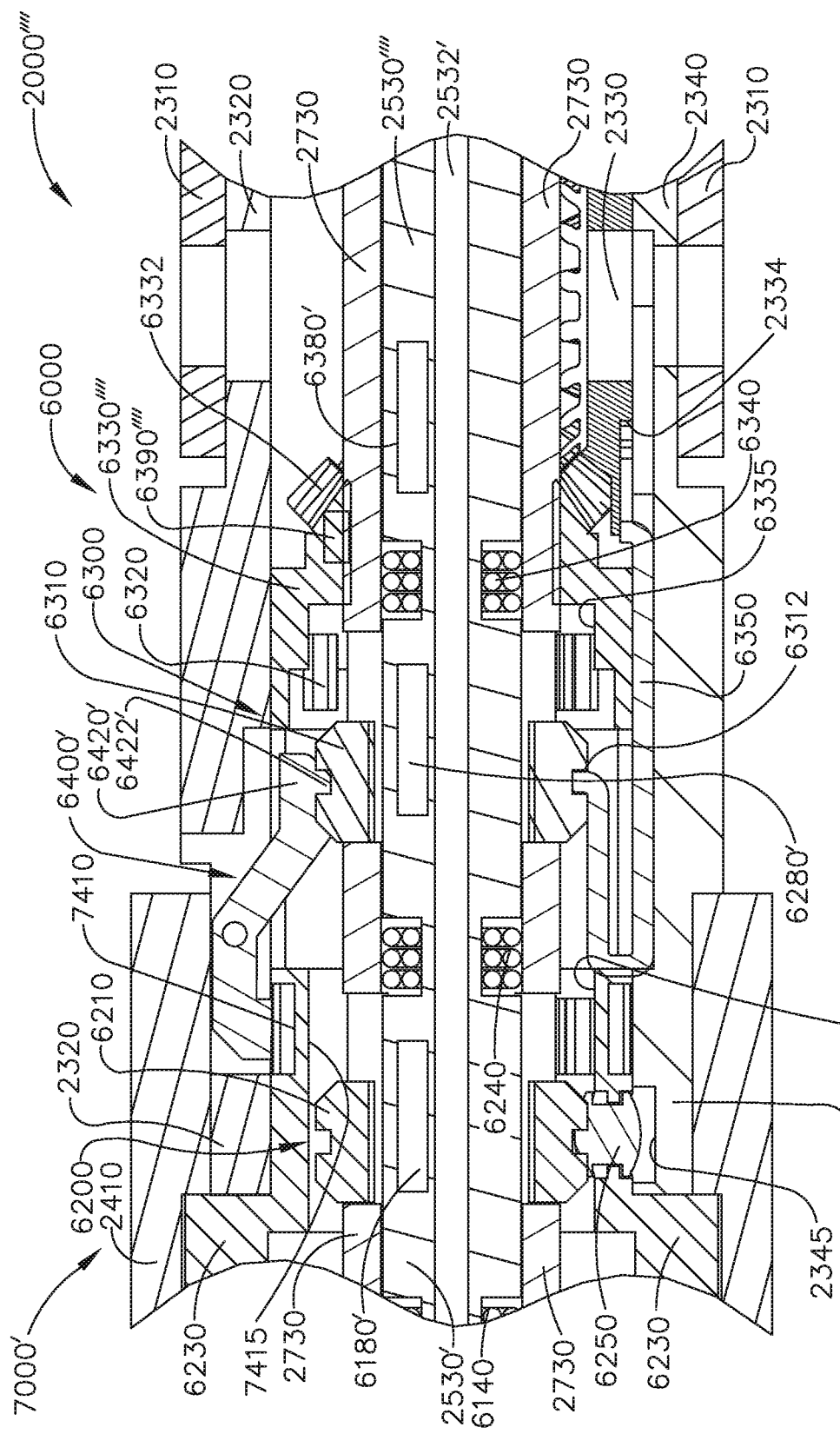
FIG. 40 depicts the second and third clutches of FIG. 38 in their unactuated conditions and a sensor in accordance with at least one alternative embodiment.

FIG. 40 depicts a shaft assembly 2000″″ in accordance with at least one alternative embodiment. The shaft assembly 2000″″ is similar to the shaft assemblies 2000, 2000′, and 2000′″ in many respects, most of which will not be repeated herein for the sake of brevity. Similar to the shaft assembly 2000, the shaft assembly 2000″″ comprises, among other things, an elongate shaft 2200, an articulation joint 2300, and a distal attachment portion 2400 configured to receive an end effector, such as end effector 7000′, for example. Similar to the shaft assembly 2000, the shaft assembly 2000″″ comprises an articulation drive, i.e., articulation drive 6330″″ configured to rotate the distal attachment portion 2400 and the end effector 7000′ about the articulation joint 2300. Similar to the above, a shaft frame 2530″″ comprises a sensor positioned therein configured to detect the position, and/or rotation, of a magnetic element 6390″″ positioned in and/or on the articulation drive 6330″″. The magnetic element 6390″ ″ can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532′, for example. In various instances, the control system 1800 can use the sensor to confirm whether the magnetic element 6390″″ is rotating and, thus, confirm that the third clutch assembly 6300 is in its actuated state. Similarly, the control system 1800 can use the sensor to confirm whether the magnetic element 6390″″ is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 40 once again, the shaft assembly 2000″″ comprises an end effector lock 6400′ configured to releasably lock the end effector 7000′, for example, to the shaft assembly 2000″″. The end effector lock 6400′ is similar to the end effector lock 6400 in many respects, most of which will not be discussed herein for the sake of brevity. Notably, though, a proximal end 6420′ of the lock 6400′ comprises a tooth 6422′ configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400′. Moreover, in such instances, the proximal movement of the third clutch 6310 into its engaged position rotates the end effector lock 6400′ into a locked position and into engagement with the lock notches 7410 to lock the end effector 7000′ to the shaft assembly 2000″″. Correspondingly, the distal movement of the third clutch 6310 into its disengaged position unlocks the end effector 7000′ and allows the end effector 7000′ to be disassembled from the shaft assembly 2000″″.

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces the current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

Figure 41:
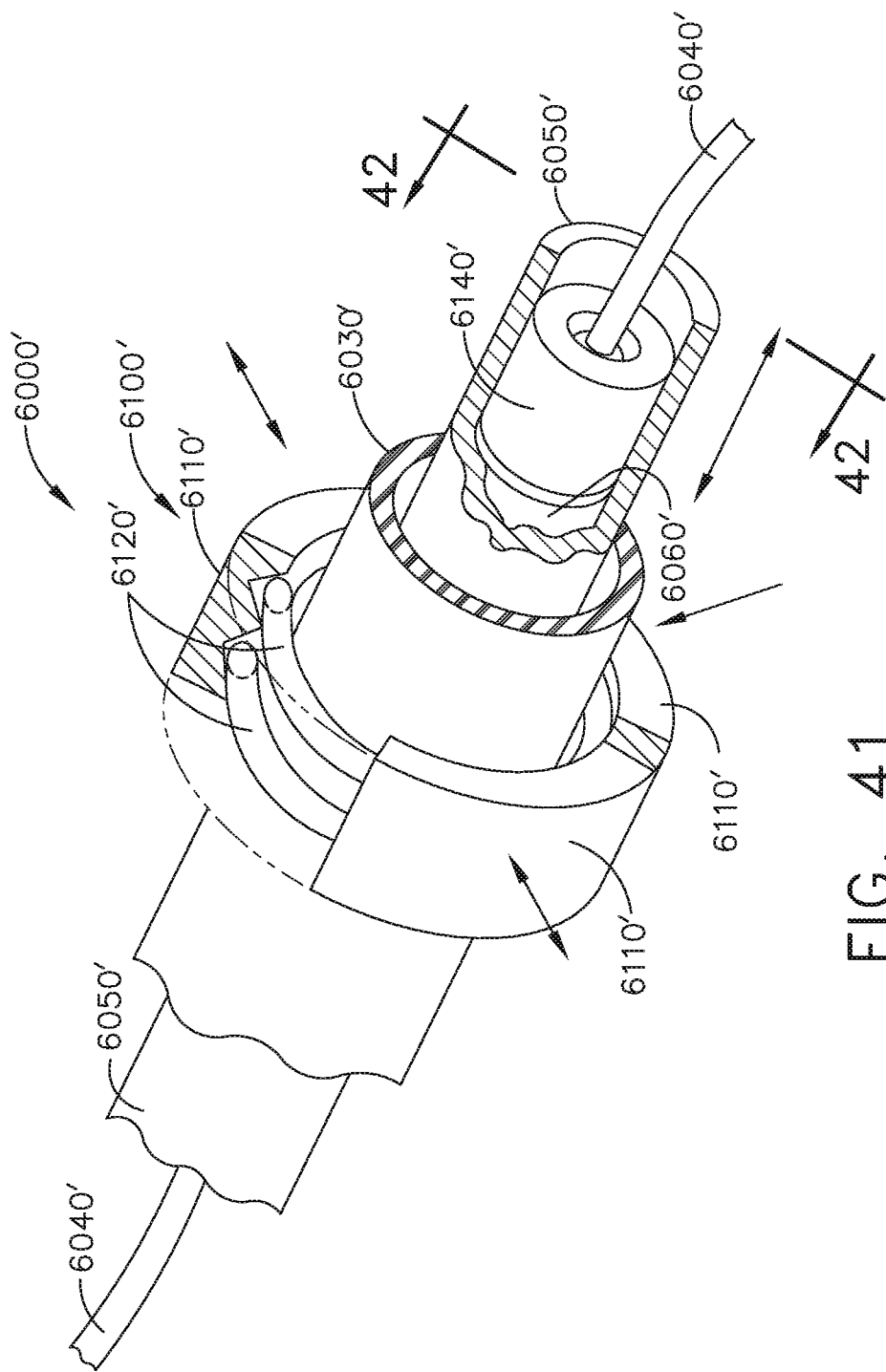
FIG. 41 is a partial cross-sectional view of a shaft assembly in accordance with at least one embodiment.
Figure 42:
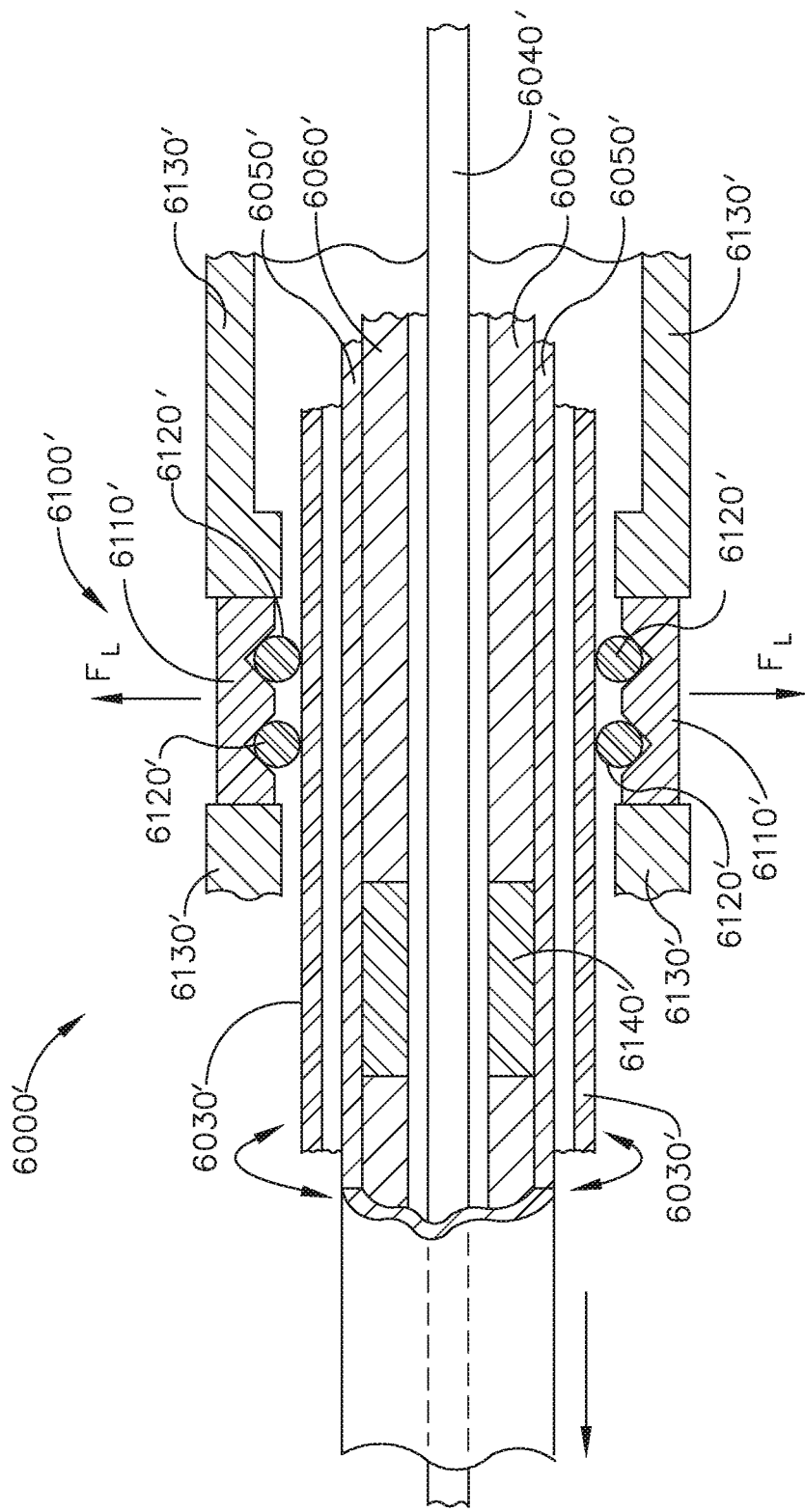
FIG. 42 is a partial cross-sectional view of the shaft assembly of FIG. 41 comprising a clutch illustrated in an unactuated condition.
Figure 43:
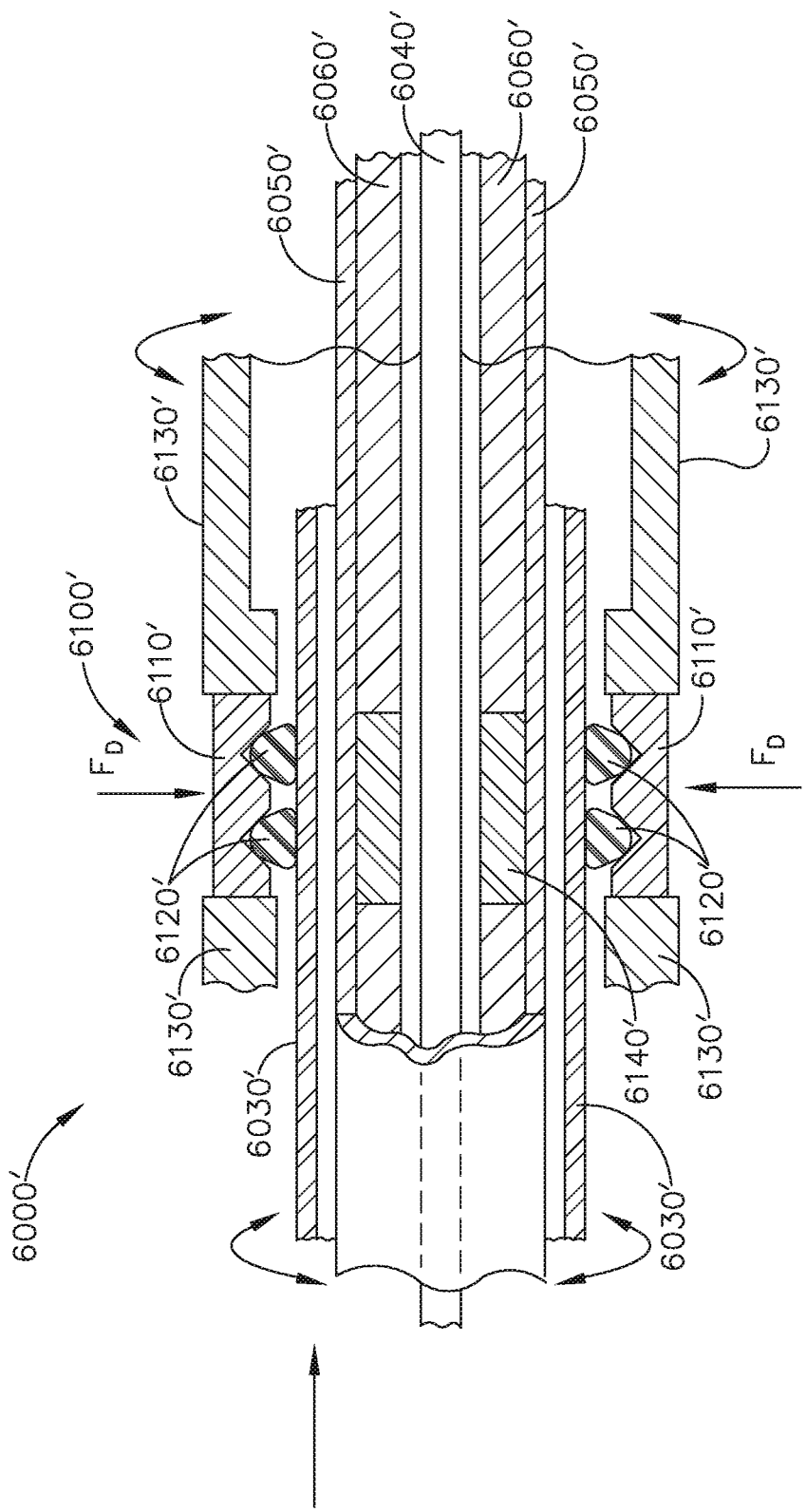
FIG. 43 is a partial cross-sectional view of the shaft assembly of FIG. 41 illustrating the clutch in an actuated condition.

FIGS. 41-43 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 42) and actuated positions (FIG. 43) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 42, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 43, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 42) and an actuated position (FIG. 43) by a clutch shaft 6060'. In at least one instance, the clutch shaft 6060' comprises a polymer cable, for example. When the clutch actuator 6140' is in its actuated position, as illustrated in FIG. 43, the clutch actuator 6140' pulls the clutch plates 6110' inwardly to compress the drive rings 6120', as discussed above. When the clutch actuator 6140' is moved into its unactuated position, as illustrated in FIG. 42, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

Figure 44:
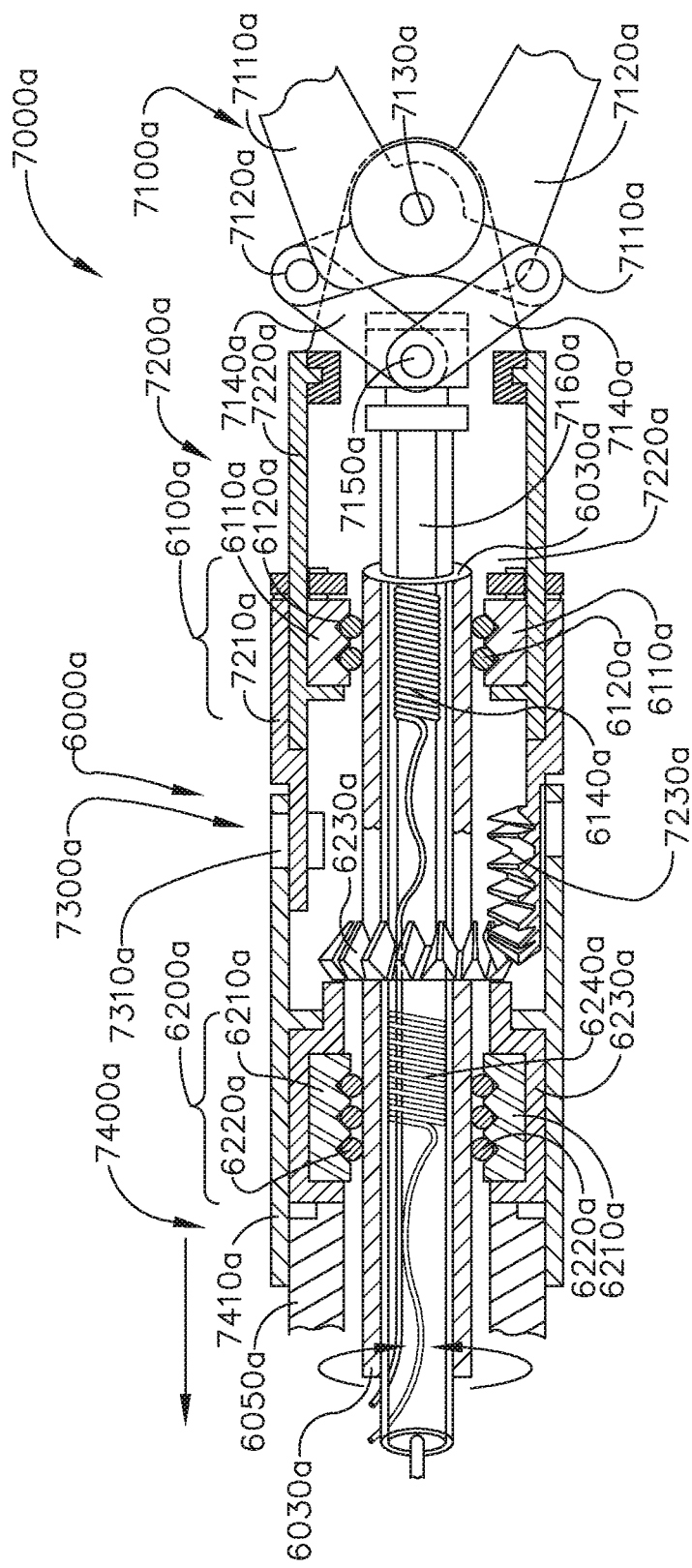
FIG. 44 is a partial cross-sectional view of a shaft assembly in accordance with at least one embodiment comprising first and second clutches illustrated in an unactuated condition.

FIG. 44 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch pates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch pates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 45-49. The shaft assembly 4000 is similar to the shaft assemblies 2000, 2000', 2000''', and 2000'''' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

Figure 48:
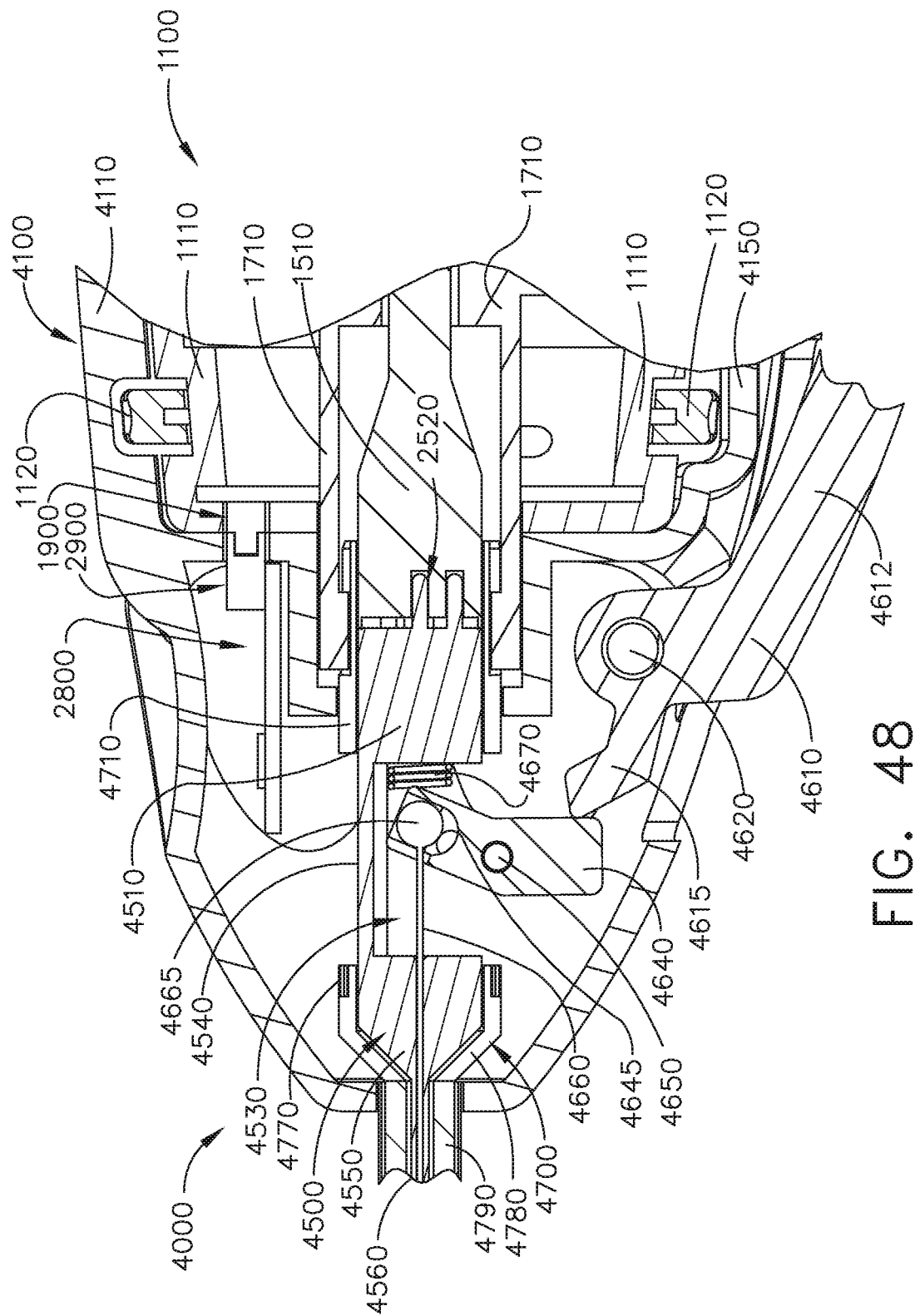
FIG. 48 is another partial cross-sectional view of the shaft assembly of FIG. 45 attached to the handle of FIG. 1.
Figure 49:
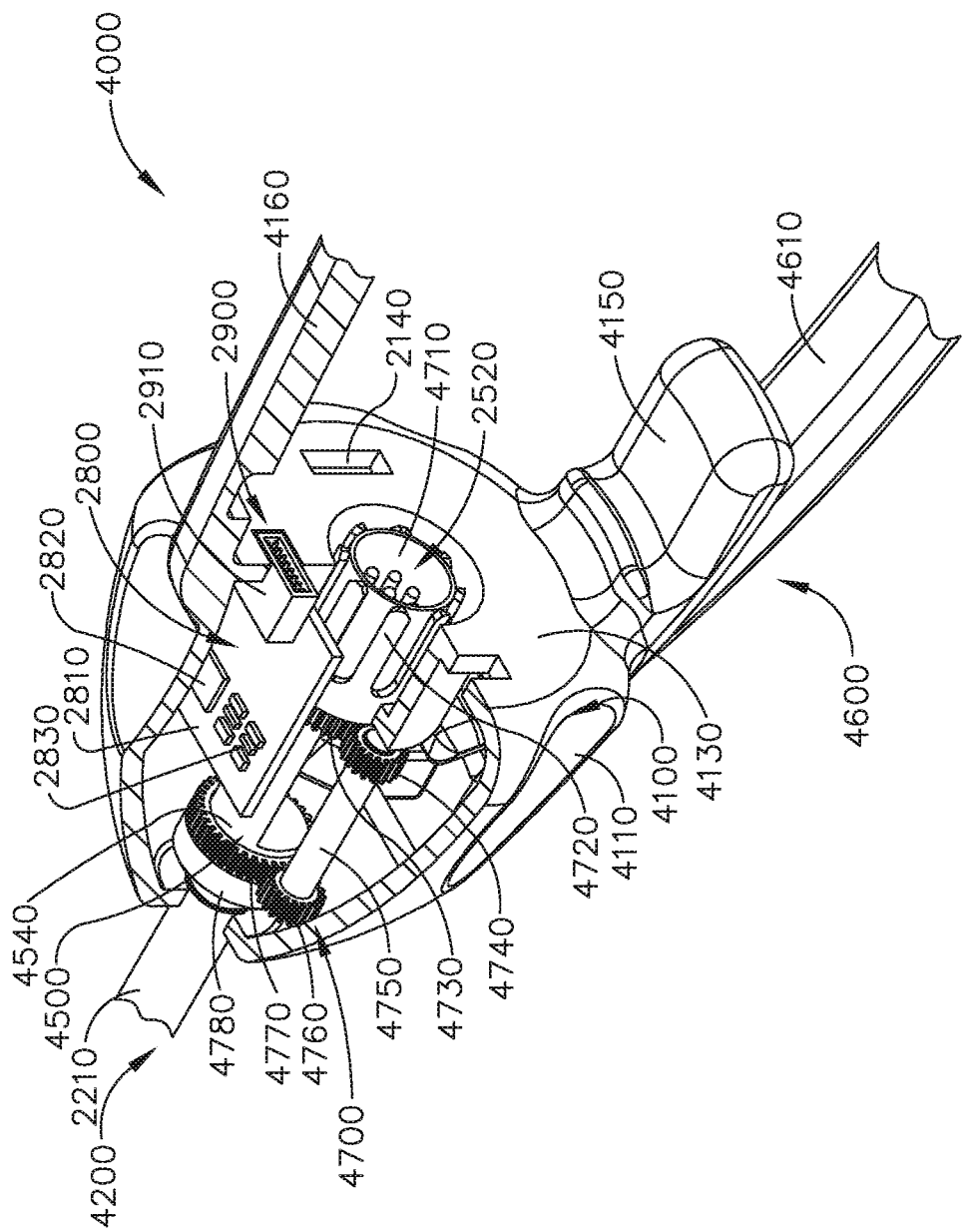
FIG. 49 is a partial cross-sectional perspective view of the shaft assembly of FIG. 45.

As discussed above, referring primarily to FIGS. 47-49, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 48, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 48 and 49, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 47 and 48, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing 4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 48), i.e., toward the stationary grip 4160, to close the jaw assembly 8100 of the end effector 8000.

Referring primarily to FIG. 48, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

Figure 50:
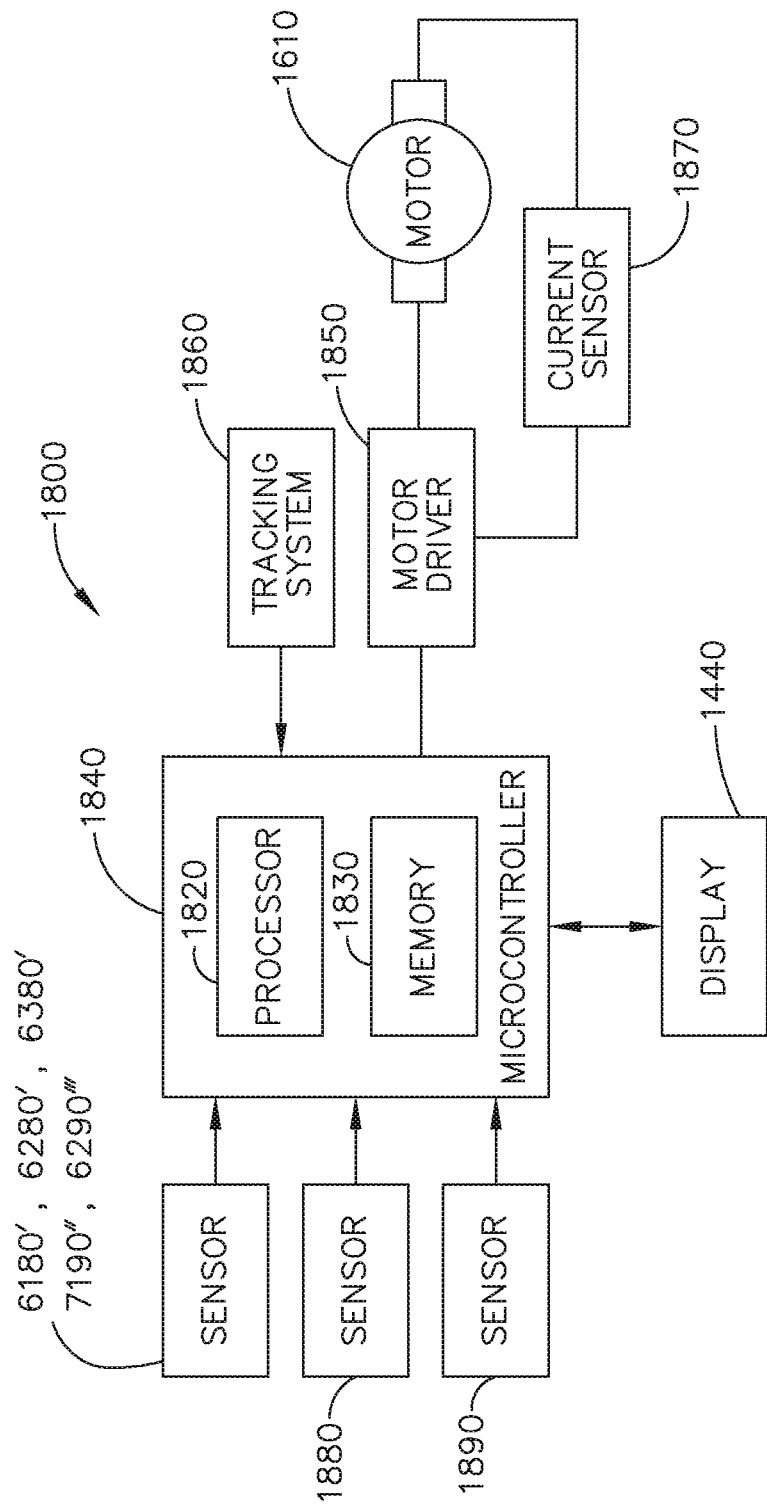
FIG. 50 is a schematic of the control system of the surgical system of FIG. 1.

FIG. 50 is a logic diagram of the control system 1800 of the surgical system depicted in FIG. 1 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190'', and/or 6290''', for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EE-PROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290''', for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290''', for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gauge or a micro-strain gauge, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610. The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

Figure 51:
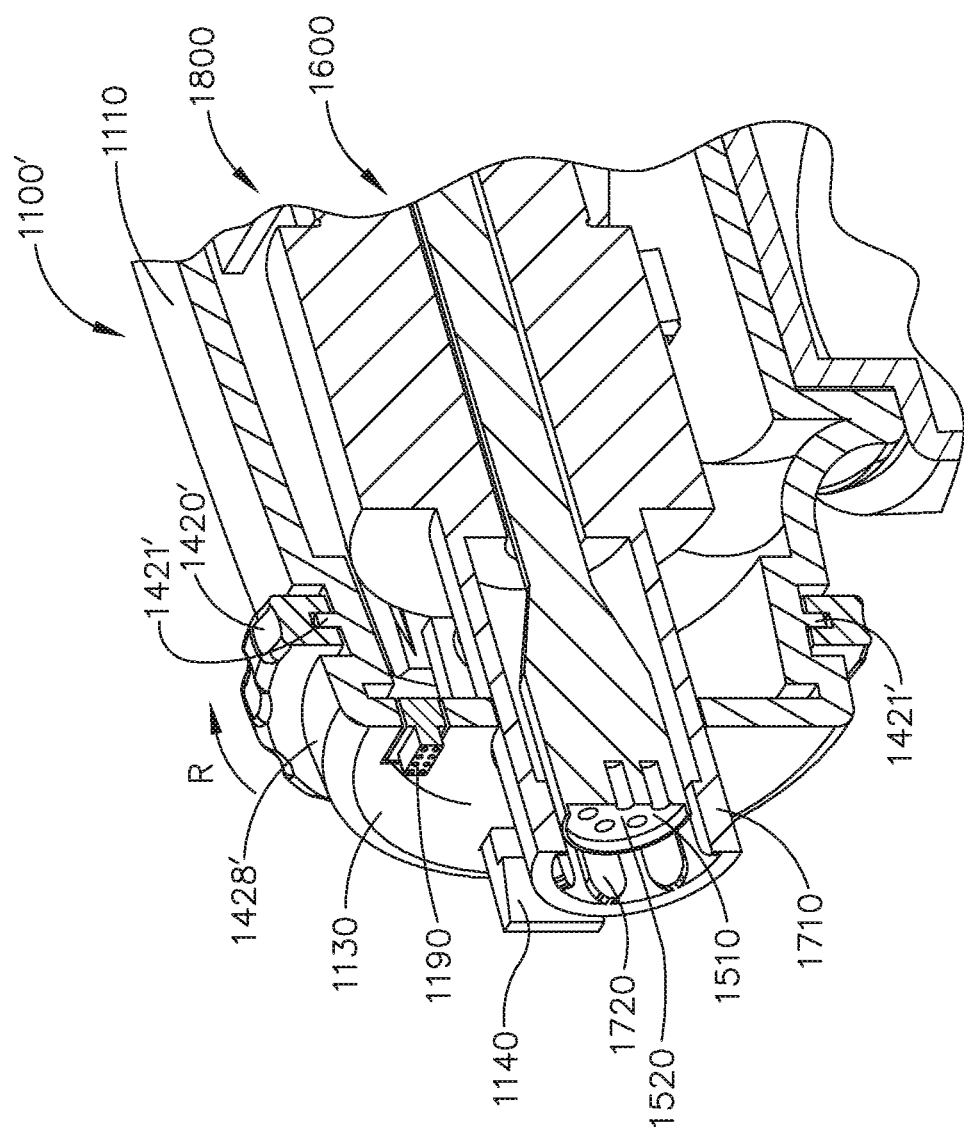
FIG. 51 is an elevational view of a handle in accordance with at least one embodiment and one of the shaft assemblies of the surgical system of FIG. 1.

A drive module 1100' in accordance with at least one alternative embodiment is illustrated in FIGS. 51-53. The drive module 1100' is similar to the drive module 1100 in many respects, most of which will not be discussed herein for the sake of brevity. The drive module 1100' comprises an actuator 1420' configured to control the rotation and articulation of the end effector 7000. Similar to the actuator 1420, discussed above, the actuator 1420' is rotatable about a longitudinal axis LA that extends through a shaft assembly attached to the drive module 1100. For instance, the longitudinal axis LA extends through the center, or substantially the center, of the elongate shaft 2200 of the shaft assembly 3000 (FIG. 1) when the shaft assembly 3000 is assembled to the drive module 1100'. The longitudinal axis LA also extends through the center, or substantially the center, of the end effector 7000 when the end effector 7000 is attached to the shaft assembly 3000, for example.

Figure 52A:
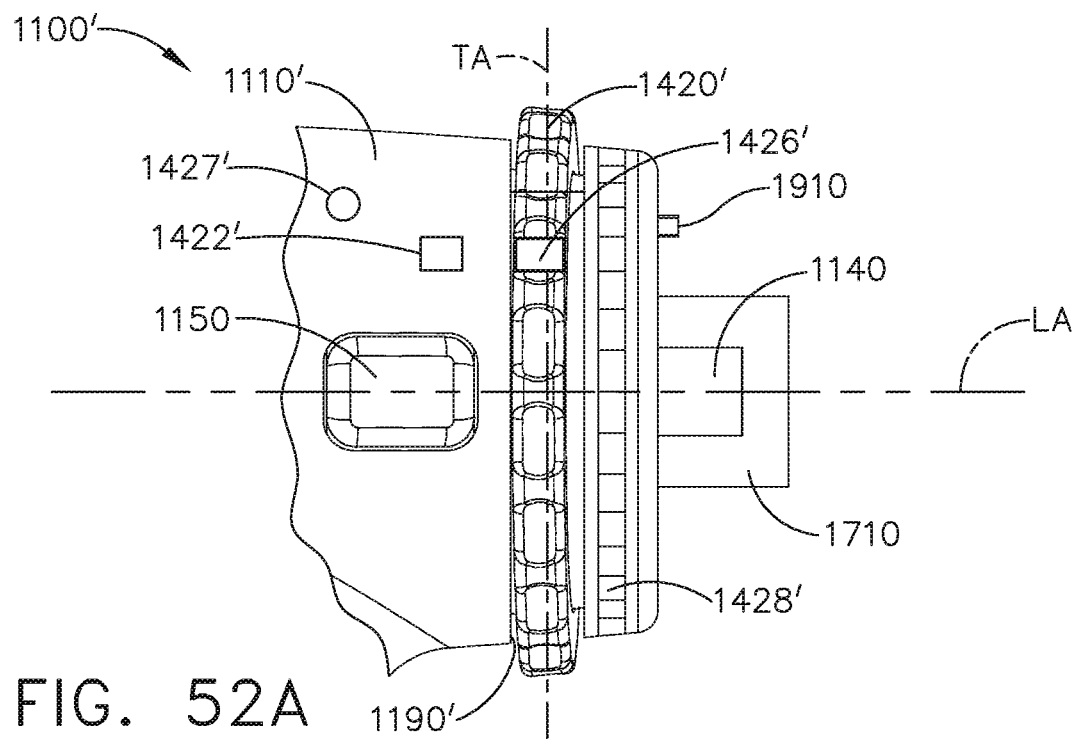
FIG. 52A is a partial top view of a drive module of the handle of FIG. 51 illustrated in a first rotation configuration.
Figure 52B:
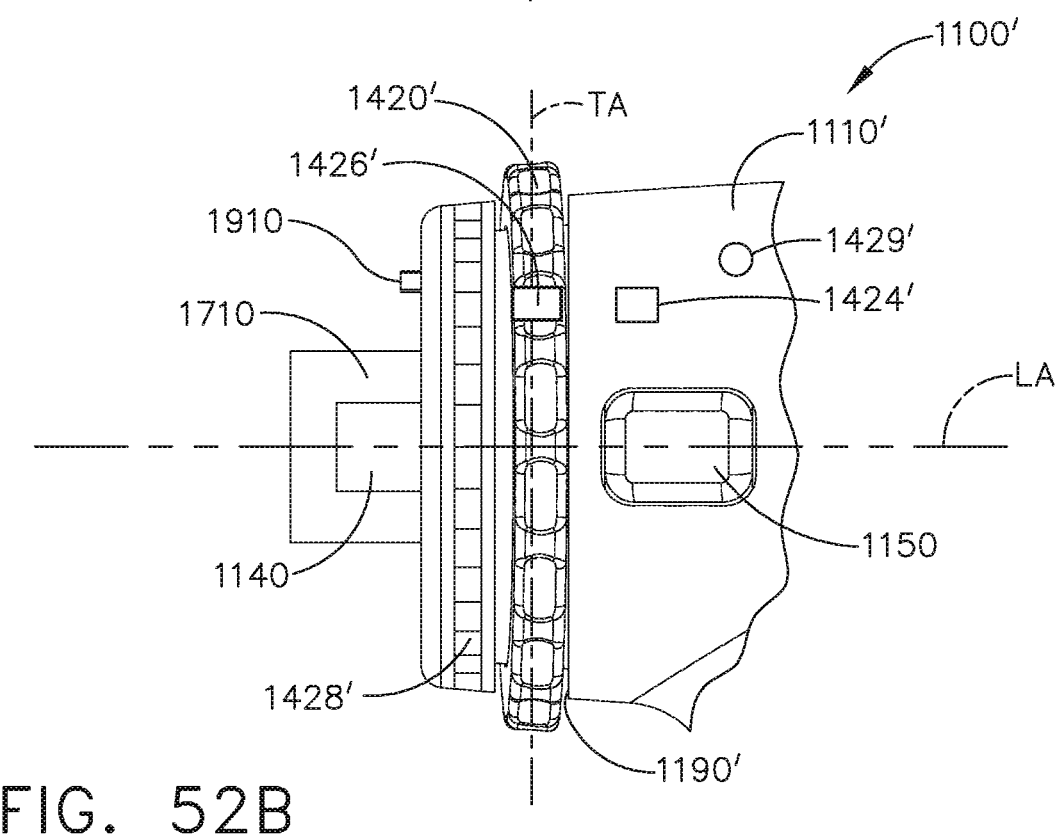
FIG. 52B is a partial top view of the drive module of FIG. 52A illustrated in a second rotation configuration.

The actuator 1420' is rotatable within a channel 1190' defined in the housing 1110 in a first direction to rotate the end effector 7000 in the first direction and, similarly, in a second, or opposite, direction to rotate the end effector 7000 in the second direction. Similar to the drive module 1100, the drive module 1100' comprises a sensor system in communication with the control system 1800 configured to detect the rotation of the actuator 1420' about the longitudinal axis LA. In at least one instance, the sensor system comprises a first sensor 1422' configured to detect the rotation of the actuator 1420' about the longitudinal axis LA in the first direction (FIG. 52A) and a second sensor 1424' configured to detect the rotation of the actuator 1420' about the longitudinal axis LA in the second direction (FIG. 52B). The first and second sensors 1422' and 1424' comprise Hall Effect sensors, for example, but could comprise any suitable type of sensor. In at least one such instance, further to the above, the actuator 1420' comprises a center magnetic element 1426' positioned in the top of the actuator 1420' which is detectable by the first and second sensors 1422' and 1424' to determine the rotation of the actuator 1420'. The center magnetic element 1426' can comprise a permanent magnet and/or can be comprised of iron and/or nickel, for example.

Further to the above, the control system 1800 is configured to control the motor assembly 1600 and the clutch system 6000 to rotate the end effector 7000 about the longitudinal axis LA in the first direction when the actuator 1420' is rotated about the longitudinal axis LA in the first direction. Similarly, the control system 1800 is configured to control the motor assembly 1600 and the clutch system 6000 to rotate the end effector 7000 about the longitudinal axis LA in the second direction when the actuator 1420' is rotated about the longitudinal axis LA in the second direction. By associating the rotation of the end effector 7000 about the longitudinal axis LA with the rotation of the actuator 1420' about the longitudinal axis LA, the clinician is provided with a system that is very intuitive to use.

As discussed above, the end effector 7000 is configured to rotate about a longitudinal axis within a socket defined in the distal attachment portion 2400 of the shaft assembly 2000. Depending on the amount of rotation desired, the end effector 7000 can be rotated less than 360 degrees or more than 360 degrees in either direction. In various instances, the end effector 7000 can be rotated through several rotations in either direction. In alternative embodiments, the rotation of the end effector 7000 about the longitudinal axis can be limited. In at least one embodiment, the shaft assembly 2000 comprises one or more stops which limit the rotation of the end effector 7000 to less than one rotation. In certain embodiments, the control system 1800 monitors the rotation of the drive shaft 1710, such as by an encoder and/or an absolute positioning sensor system, for example, and limits the rotation of the end effector 7000 by stopping or pausing the motor 1610 when the end effector 7000 has reached the end of its permitted range. In at least one instance, the control system 1800 can disengage the second clutch 6210 from the drive shaft 2730 to stop or pause the rotation of the end effector 7000 when the end effector 7000 has reached the end of its permitted range.

Further to the above, the drive module 1100' and/or a shaft module attached to the drive module 1100' can provide feedback to the clinician that the end effector 7000 has reached the end of its rotation. The drive module 1100' and/or the shaft module attached thereto can comprise an indicator light 1427', such as a red LED, for example, on a first side of the module housing 1110' which is illuminated by the control system 1800 when the end effector 7000 has reached the end of its permitted rotation in the first direction, as illustrated in FIG. 52A. In at least one instance, the drive module 1100' and/or the shaft module attached thereto can comprise an indicator light 1429', such as a red LED, for example, on a second side of the module housing 1110' which is illuminated by the control system 1800 when the end effector 7000 has reached the end of its permitted rotation in the second direction, as illustrated in FIG. 52B. In various instances, further to the above, the illumination of either the first light 1427' or the second light 1429' can indicate to the clinician that the motor 1610 has been paused and that the end effector 7000 is no longer rotating. In at least one instance, the first light 1427' and/or the second light 1429' can blink when the motor 1610 is paused.

In addition to or in lieu of the above, the drive module 1100' and/or the shaft assembly attached thereto can comprise an annular series, or array, of indicator lights 1428' extending around the perimeter thereof which is in communication with the control system 1800 and can indicate the rotational orientation of the end effector 7000. In at least one instance, the control system 1800 is configured to illuminate the particular indicator light which corresponds, or at least substantially corresponds, with the position in which the top of the end effector 7000 is oriented. In at least one instance, the center of the first jaw 7110 can be deemed the top of the end effector 7000, for example. In such instances, the illuminated light indicates the top-dead-center position of the end effector 7000. In other instances, the control system 1800 can illuminate the particular indicator light which corresponds, or at least substantially corresponds, with the position in which the bottom, or bottom-dead-center, of the end effector 7000 is oriented. In at least one instance, the center of the second jaw 7210 can be deemed the bottom of the end effector 7000, for example. As a result of the above, the illuminated indicator light can follow the rotation of the end effector 7000 around the array of indicator lights 1428'.

Figure 53A:
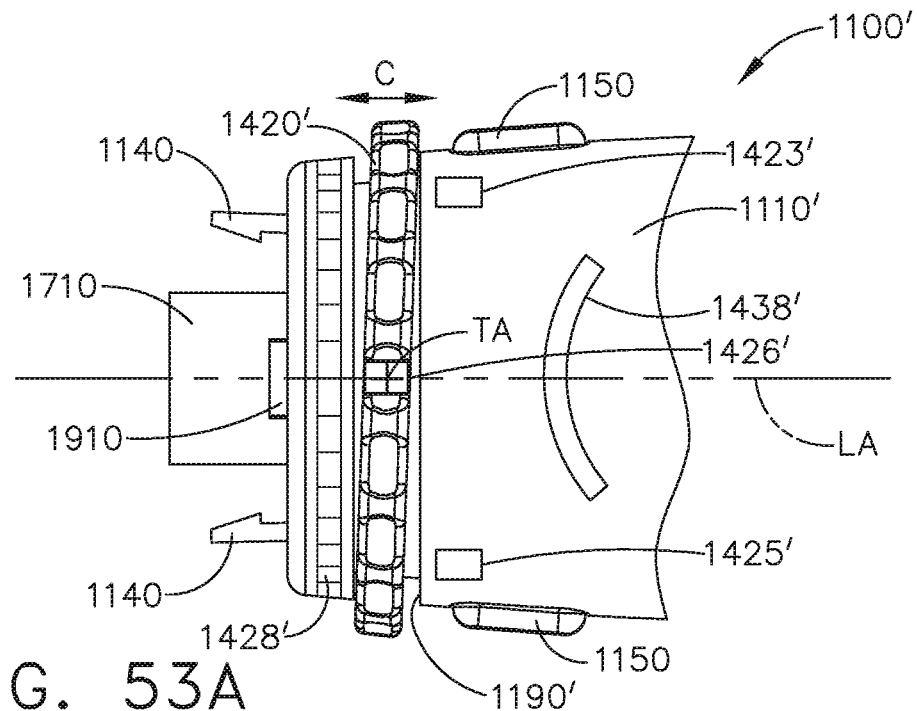
FIG. 53A is a partial top view of the drive module of FIG. 52A illustrated in a first articulation configuration.
Figure 53B:
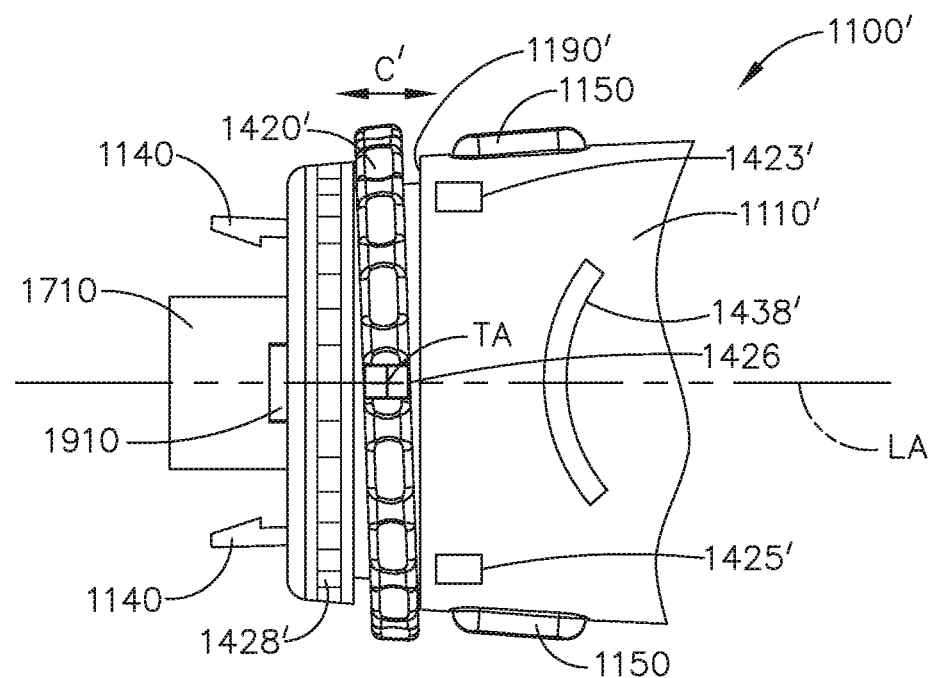
FIG. 53B is a partial top view of the drive module of FIG. 52A illustrated in a second articulation configuration.
Figure 54:
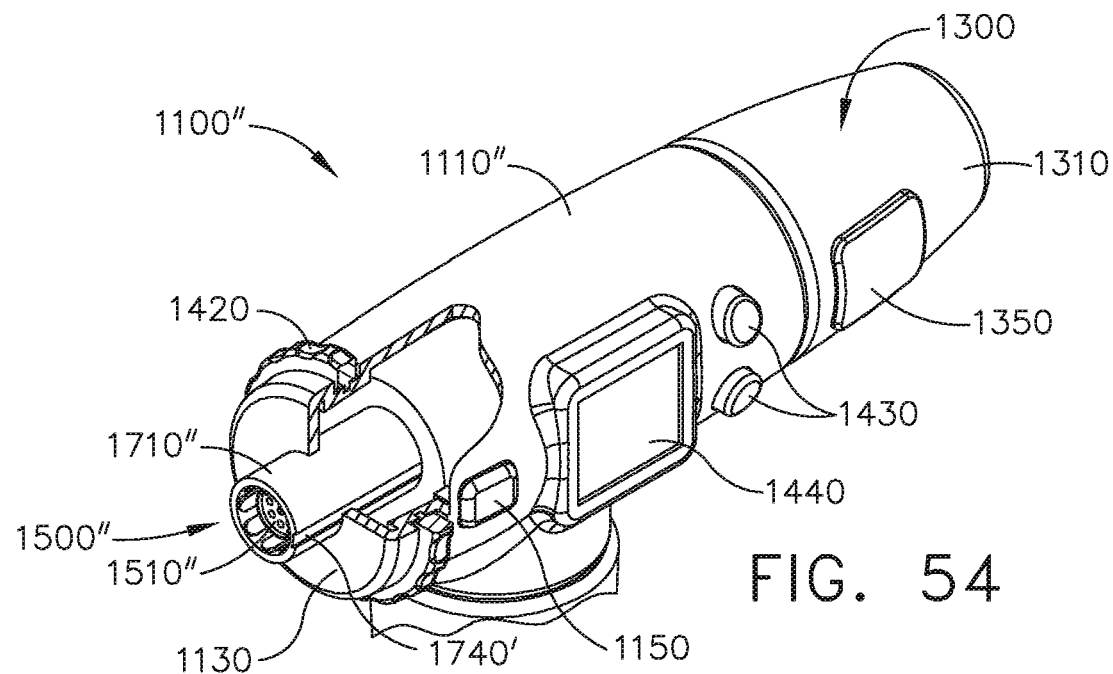
FIG. 54 is a partial cross-sectional perspective view of a drive module in accordance with at least one embodiment.

Further to the above, the actuator 1420' is also rotatable, or tiltable, about a transverse axis TA within the housing channel 1190'. The sensor system of the drive module 1100' is further configured to detect the rotation of the actuator 1420' about the transverse axis TA in a first tilt direction and a second tilt direction. In at least one instance, the sensor system comprises a first tilt sensor 1423' configured to detect the rotation of the actuator 1420' about the longitudinal axis TA in the first tilt direction (FIG. 53A) and a second tilt sensor 1425' configured to detect the rotation of the actuator 1420' in the second tilt direction (FIG. 53B). The first and second tilt sensors 1423' and 1425' comprise Hall Effect sensors, for example, but could comprise any suitable type of sensor. The actuator 1420' further comprises a first lateral magnetic element adjacent the first tilt sensor 1423', the motion of which is detectable by the first tilt sensor 1423'. The actuator 1420' also comprises a second lateral magnetic element adjacent the second tilt sensor 1425', the motion of which is detectable by the second tilt sensor 1425'. The first and second lateral magnetic elements can comprise a permanent magnet and/or can be comprised of iron and/or nickel, for example. As illustrated in FIGS. 53A and 53B, the lateral sides of the actuator 1420' are movable proximally and distally about the transverse axis TA and, as a result, the first and second lateral magnetic elements are also movable proximally and distally relative to the first and second tilt sensors. The reader should appreciate that, while the first and second lateral magnetic elements actually travel along arcuate paths about the transverse axis TA, the distances in which the first and second lateral magnetic elements move is small and, as a result, the arcuate motion of the first and second lateral magnetic elements approximates translation in the proximal and distal directions.

In various embodiments, further to the above, the entire actuator 1420' comprises a magnetic ring of material which is detectable by the tilt sensors 1423' and 1425' of the drive module 1100'. In such embodiments, the rotation of the actuator 1420' about the longitudinal axis LA would not create a compound motion relative to the tilt sensors when the actuator 1420' is tilted. The magnetic ring of material can comprise a permanent magnet and/or can be comprised of iron and/or nickel, for example.

In any event, when the sensor system detects that the actuator 1420' has been tilted in the first direction, as illustrated in FIG. 53A, the control system 1800 operates the motor assembly 1600 and the clutch system 6000 to articulate the end effector 7000 about the articulation joint 2300 in the first direction. Similarly, the control system 1800 operates the motor assembly 1600 and the clutch system 6000 to articulate the end effector 7000 about the articulation joint 2300 in the second direction when the sensor system detects that the actuator 1420' has been tilted in the second direction, as illustrated in FIG. 53B. By associating the rotation of the end effector 7000 about the articulation joint 2300 with the rotation of the actuator 1420' about the transverse axis TA, the clinician is provided with a system that is very intuitive to use.

Further to the above, the actuator 1420' comprises a biasing system configured to center the actuator 1420' in its unrotated and untilted position. In various instances, the biasing system comprises first and second rotation springs configured to center the actuator 1420' in its unrotated position and first and second tilt springs configured to center the actuator 1420' in its untilted position. These springs can comprise torsion springs and/or linear displacement springs, for example.

As discussed above, the end effector 7000 rotates relative to the distal attachment portion 2400 of the shaft assembly 3000. Such an arrangement allows the end effector 7000 to be rotated without having to rotate the shaft assembly 3000, although embodiments are possible in which an end effector and shaft assembly rotate together. That said, by rotating the end effector 7000 relative to the shaft assembly 3000, all of the rotation of the surgical system occurs distally relative to the articulation joint 2300. Such an arrangement prevents a large sweep of the end effector 7000 when the end effector 7000 is articulated and then rotated. Moreover, the articulation joint 2300 does not rotate with the end effector 7000 and, as a result, the articulation axis of the articulation joint 2300 is unaffected by the rotation of the end effector 7000. In order to mimic this arrangement, the transverse axis TA does not rotate with the actuator 1420'; rather, the transverse axis TA remains stationary with respect to the drive module 1100'. That said, in alternative embodiments, the transverse axis TA can rotate, or track the end effector 7000, when the articulation joint rotates with the end effector. Such an arrangement can maintain an intuitive relationship between the motion of the actuator 1420' and the motion of the end effector 7000.

Further to the above, the transverse axis TA is orthogonal, or at least substantially orthogonal, to the longitudinal axis LA. Similarly, the articulation axis of the articulation joint 2300 is orthogonal, or at least substantially orthogonal, to the longitudinal axis LA. As a result, the transverse axis TA is parallel to, or at least substantially parallel to, the articulation axis.

In various alternative embodiments, the tiltable actuator 1420' is only used to control the articulation of the end effector 7000 and is not rotatable about the longitudinal axis LA. Rather, in such embodiments, the actuator 1420' is only rotatable about the transverse axis TA. In at least one instance, the housing of the drive module 1100' comprises two posts 1421' (FIG. 51) about which the actuator 1120' is rotatably mounted which defines the transverse axis TA. The posts 1421' are aligned along a common axis. The above being said, the posts 1421', or any suitable structure, can be used in embodiments in which the actuator 1420' is both rotatable and tiltable to control the rotation and articulation of the end effector 7000. In at least one such instance, the actuator 1420' comprises an annular groove defined therein in which the posts 1421' are positioned.

In various instances, the drive module 1100 and/or the shaft assembly attached thereto can comprise a series, or array, of indicator lights 1438' which is in communication with the control system 1800 and can indicate the articulation orientation of the end effector 7000. In at least one instance, the control system 1800 is configured to illuminate the particular indicator light which corresponds, or at least substantially corresponds, with the position in which the end effector 7000 is articulated. As a result of the above, the illuminated indicator light can follow the articulation of the end effector 7000. Such an array of indicator lights can assist a clinician in straightening the end effector 7000 before attempting to remove the end effector 7000 from a patient through a trocar. In various instances, an unstraightened end effector may not pass through a trocar and prevent the removable of the end effector from the patient.

Figure 55:
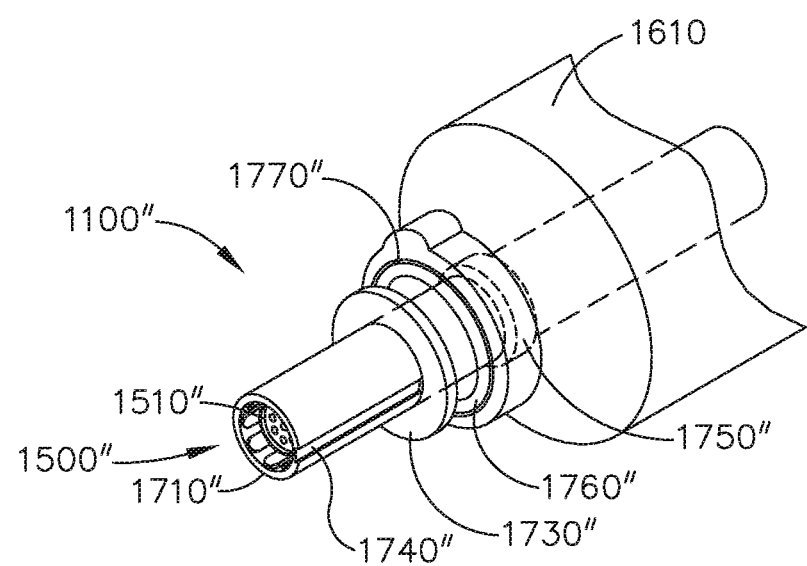
FIG. 55 is a partial perspective view of the drive module of FIG. 54 illustrated with some components removed.
Figure 56:
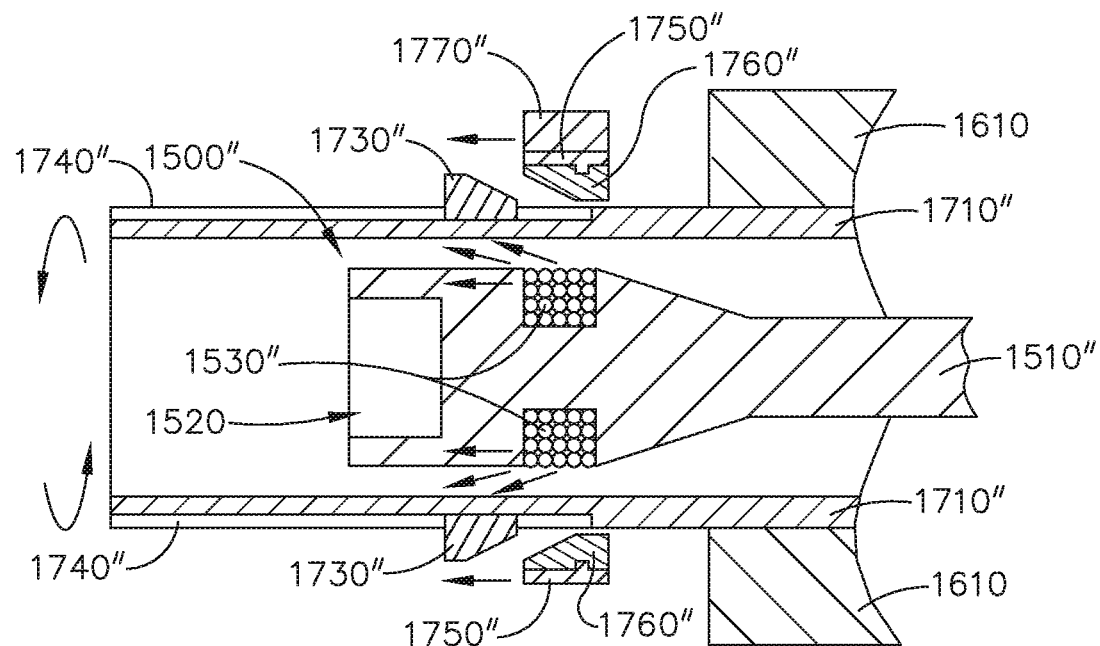
FIG. 56 is a partial cross-sectional view of the drive module of FIG. 54 illustrating an eccentric drive in a disengaged condition.
Figure 57:
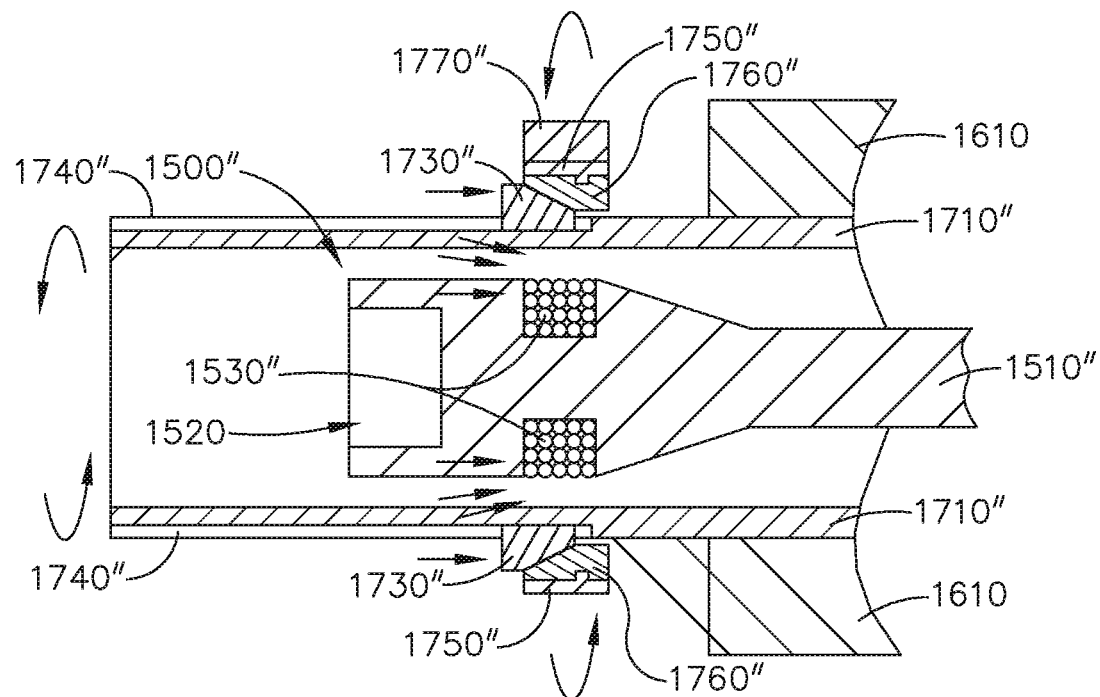
FIG. 57 is a partial cross-sectional view of the drive module of FIG. 54 illustrating the eccentric drive of FIG. 56 in an engaged condition.

A drive module 1100" in accordance with at least one alternative embodiment is illustrated in FIGS. 54-57. The drive module 1100" is similar to the drive modules 1100 and 1100' in many respects, most of which will not be discussed herein for the sake of brevity. The drive module 1100" comprises a feedback system configured to inform the clinician using the surgical instrument system that the drive shaft and/or any other rotatable component of the surgical instrument system is rotating. The feedback system can use visual feedback, audio feedback, and/or tactile feedback, for example. Referring primarily to FIG. 55, the drive module 1100" comprises a tactile feedback system which is operably engageable with the drive shaft 1710" of the drive module 1100". The tactile feedback system comprises a slideable clutch 1730", a rotatable drive ring 1750", and an eccentric, or offset, mass 1770" mounted to the drive ring 1750". The clutch 1730" is slideable between an unactuated position (FIG. 56) and an actuated position (FIG. 57) along the drive shaft 1710". The drive shaft 1710" comprises one or more slots 1740" defined therein which are configured to constrain the movement of the slideable clutch 1730" relative to the drive shaft 1710" such that the clutch 1730" translates longitudinally relative to the drive shaft 1710" but also rotates with the drive shaft 1710". The frame shaft 1510" of the handle frame 1500" comprises an electromagnet 1530" embedded therein which is configured to emit a first electromagnetic field to slide the clutch 1730" toward its actuated position, as illustrated in FIG. 57, and a second, or opposite, electromagnetic field to slide the clutch 1730" toward its unactuated position, as illustrated in FIG. 56. The clutch 1730" is comprised of a permanent magnet and/or a magnetic material such as iron and/or nickel, for example. The electromagnet 1530" is controlled by the control system 1800 to apply a first voltage polarity to a circuit including the electromagnet 1530" to create the first electromagnetic field and a second, or opposite, voltage polarity to the circuit to create the second electromagnetic field.

When the clutch 1730" is in its unactuated position, as illustrated in FIG. 56, the clutch 1730" is not operably engaged with the drive ring 1750". In such instances, the clutch 1730" rotates with the drive shaft 1710", but rotates relative to the drive ring 1750". Stated another way, the drive ring 1750" is stationary when the clutch 1730" is in its unactuated position. When the clutch 1730" is in its actuated position, as illustrated in FIG. 57, the clutch 1730" is operably engaged with an angled face 1760" of the drive ring 1750" such that the rotation of the drive shaft 1710" is transmitted to the drive ring 1750" via the clutch 1730" when the drive shaft 1710" is rotated. The eccentric, or offset, mass 1770" is mounted to the drive ring 1750" such that the eccentric mass 1770" rotates with the drive ring 1750". In at least one instance, the eccentric mass 1770" is integrally-formed with the drive ring 1750". When the drive ring 1750" and eccentric mass 1770" rotate with the drive shaft 1710", the eccentric mass 1770" creates a vibration that can be felt by the clinician through the drive module 1100" and/or the power modules assembled thereto. This vibration confirms to the clinician that the drive shaft 1710" is rotating. In at least one instance, the control system 1800 energizes the electromagnet 1530" when one of the clutches of the clutch system 6000 is energized. In such instances, the vibration can confirm to the clinician that the drive shaft 1710" is rotating and that one of the clutches in the clutch system 6000 is engaged with the drive shaft 1710". In at least one instance, the clutch 1730" can be actuated when the jaw assembly 7100, for example, has reached or is reaching its closed position such that the clinician knows that the tissue has been clamped within the jaw assembly 7100 and that the surgical instrument can be used to manipulate the tissue. The above being said, the tactile feedback system, and/or any other feedback system, of the drive module 1100" can be used to provide tactile feedback when appropriate.

Sterilization processes are part of customary surgical preparation procedures. A variety of sterilization processes exist for surgical instruments. Various methods include sterilization by way of autoclave which utilizes high heat and pressure, and sterilization utilizing steam, dry heat, and/or radiation, for example. However, one of the most widely used methods of sterilization is ethylene oxide processing. Ethylene oxide is an alkylating chemical compound which inhibits and disrupts the DNA of microorganisms in order to prevent reproduction of those organisms. Ethylene oxide processing is a highly effective sterilization process, but it does not come without cost. Some of the early steps involved during ethylene oxide processing involve heating the surgical instruments to a sustainable internal temperature and humidifying the surgical instruments. Often times, the surgical instruments undergo the heating and humidifying processes for anywhere from twelve to seventy-two hours during a single sterilization process. In addition to the heat and humidity, the potency of ethylene oxide tends to affect the soft electronic circuitry of powered surgical instruments. In the field of endoscopy, certain components of the powered endoscopy surgical instruments, such as display screens, for example, react poorly to the sterilization process when ethylene oxide is used. Improperly functioning display screens could result in difficulties and/or delays during a surgical procedure. Thus, a need exists for a surgical instrument system which incorporates a variety of cost-efficient disposable and replaceable components in order to avoid the damage caused by the sterilization process.

Figure 58:
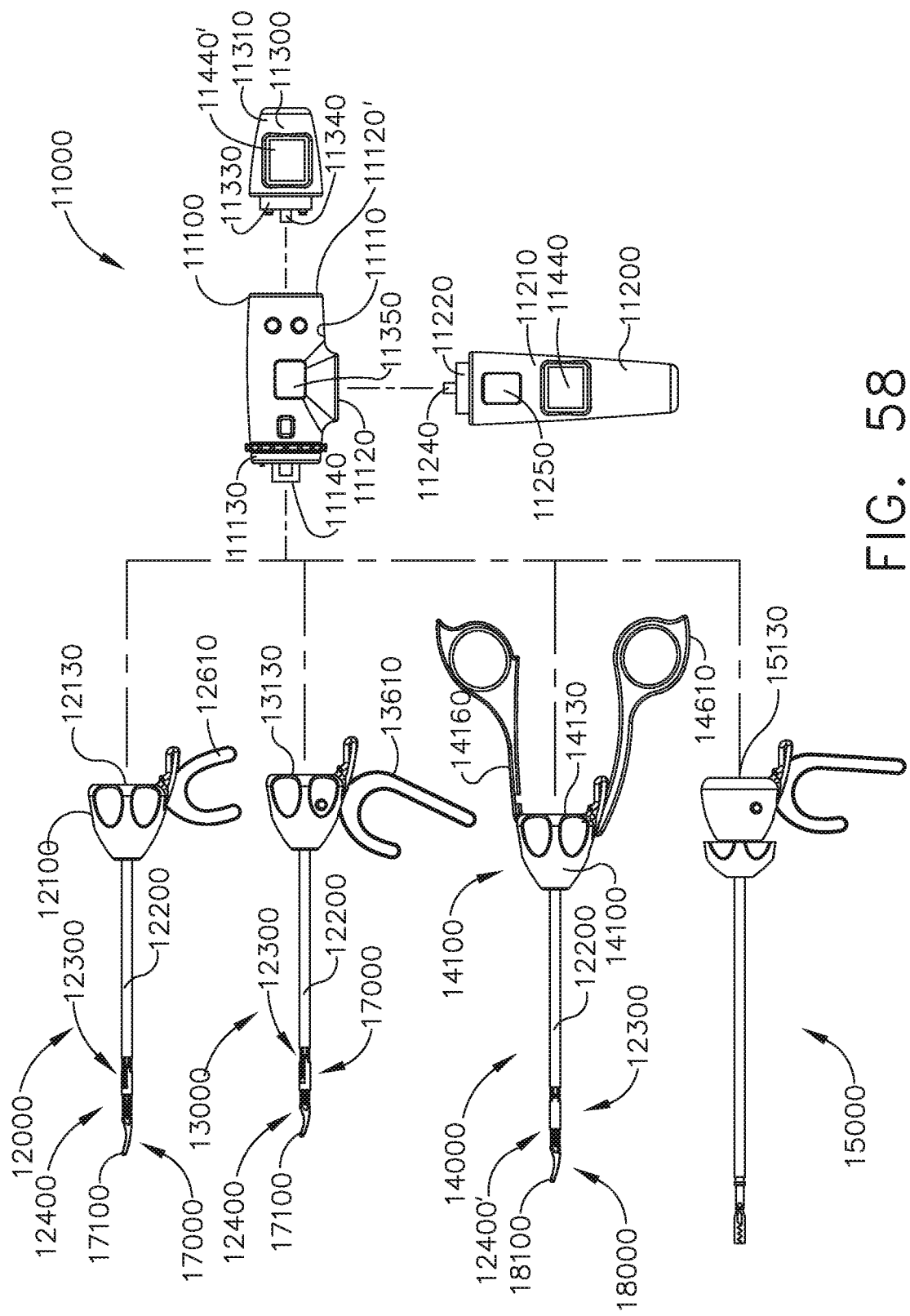
FIG. 58 illustrates a surgical instrument system comprising a handle and several shaft assemblies—each of which are selectively attachable to the handle in accordance with at least one embodiment.

A surgical instrument system is illustrated in FIG. 58. The surgical instrument system illustrated in FIG. 58 is similar to the surgical instrument system depicted in FIG. 1 in many respects, most of which will not be repeated herein out of the sake of brevity. The surgical instrument system comprises a variety of interchangeable shaft assemblies and power modules, as will be discussed in greater detail below. The surgical instrument system comprises a handle assembly 11000. The handle assembly 11000 is usable with a variety of interchangeable shaft assemblies, such as a shaft assembly 12000, a shaft assembly 13000, a shaft assembly 14000, a shaft assembly 15000, and/or other any other suitable shaft assembly. The interchangeable shaft assemblies 12000, 13000, 14000, and 15000 are similar to the shaft assemblies 2000, 3000, 4000, and 5000 in many respects. Similar to the shaft assembly 2000, the shaft assembly 12000 comprises a proximal end portion 12100 and an elongate shaft 12200 extending from the proximal end portion 12100. The shaft assembly 12000 also comprises an end effector 12400 which is rotatably attached to the elongate shaft 12200 by an articulation joint 12300. The end effector 12400 comprises a first jaw 17000 and a second jaw 17100. Similar to the shaft assembly 12000, the shaft assembly 13000 comprises a proximal end portion 13100, and an elongate shaft 13200 extending from the proximal end portion 13100. The shaft assembly 13000 is also configured for use with the end effector 12400 which is rotatably attached to the elongate shaft 13200 by an articulation joint 12300. Similar to the shaft assembly 12000, the shaft assembly 14000 comprises a proximal end portion 14100, and an elongate shaft 14200 extending from the proximal end portion 14100. The shaft assembly 14000 is also configured for use with an end effector 12400' which is rotatably attached to the elongate shaft 14200 by an articulation joint 12300. The end effector 12400' comprises a first jaw 18000 and a second jaw 18100. The shaft assembly 15000 comprises similar components to those of the shaft assemblies 12000, 13000, and 14000, many of which will not be discussed in detail for the sake of brevity.

Figure 76:
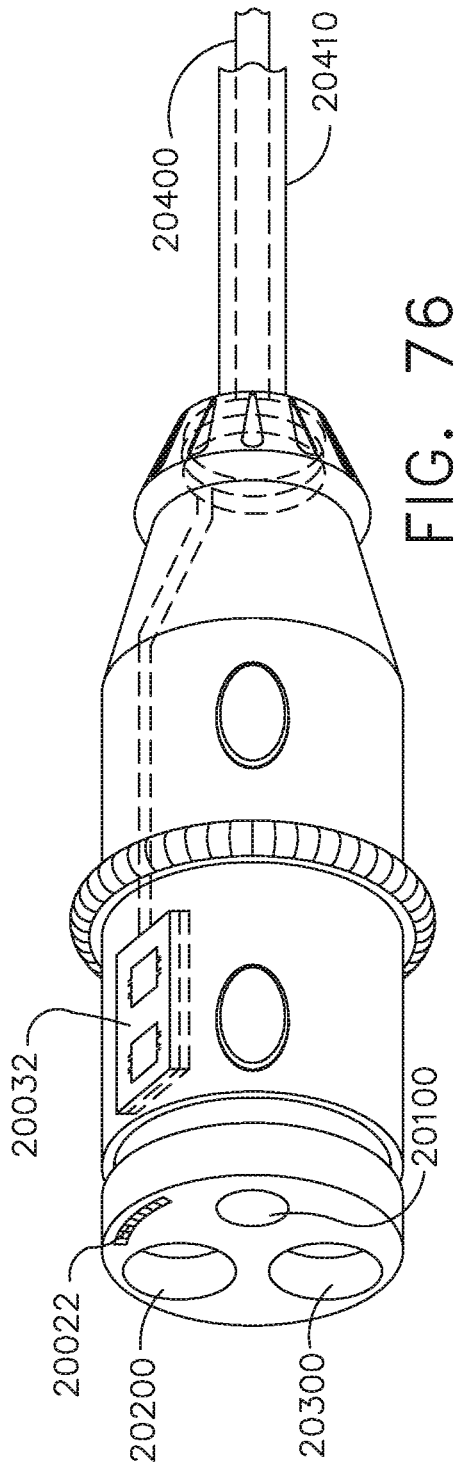
FIG. 76 illustrates a shaft assembly in accordance with at least one embodiment.
Figure 76A:
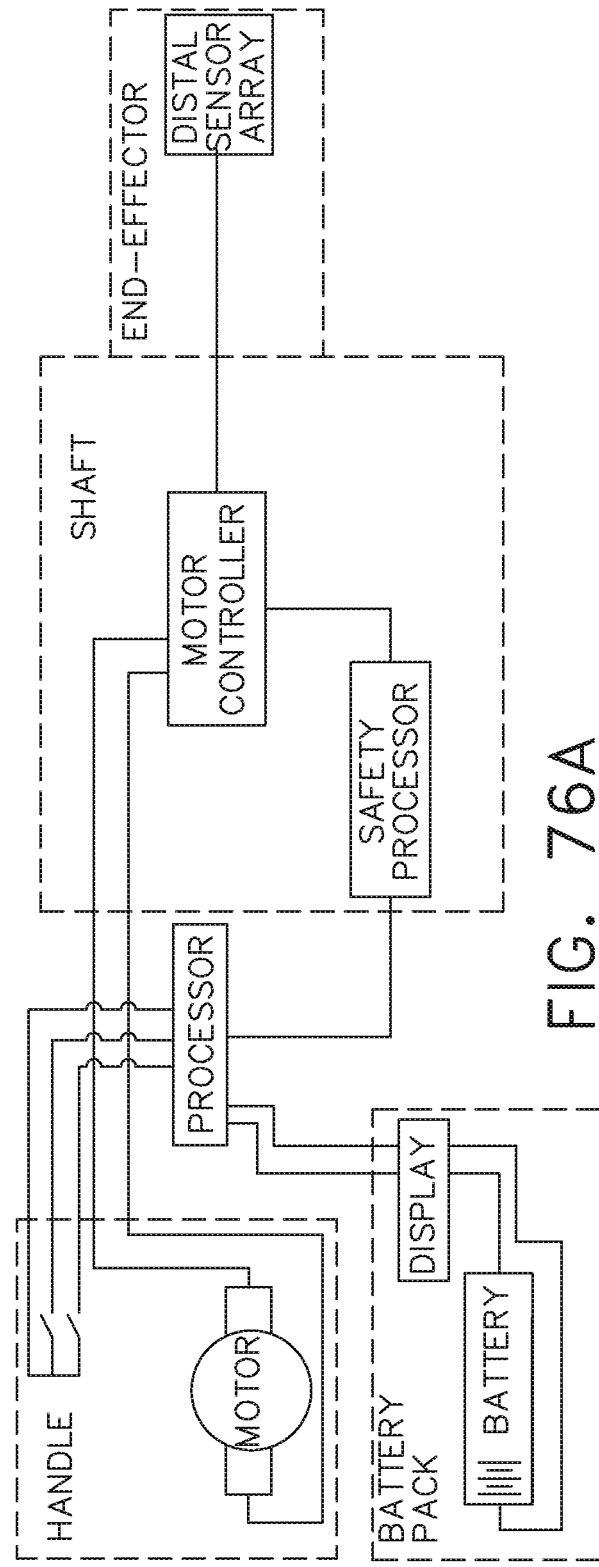
FIG. 76A is a block diagram illustrating the electrical connections of a surgical instrument system in accordance with at least one embodiment.

Still referring to FIG. 58, the handle assembly 11000 comprises a drive module 11100. The drive module 11100 comprises a distal mounting interface 11130 which allows for the selective and separate engagement of any one of the shaft assemblies 12000, 13000, 14000, and 15000 with the drive module 11100. Each of the shaft assemblies 12000, 13000, 14000, and 15000 comprises the same or a substantially similar proximal mounting interface which is configured to engage the distal mounting interface of the drive module 11100. Still referring to FIG. 58, the shaft assembly 12000 comprises a proximal mounting interface 12130 which is configured for attachment to the distal mounting interface 11130 of the drive module 11100 by at least one latch 11140 of the drive module 11100. Similarly, the shaft assembly 13000 comprises a proximal mounting interface 13130 which is configured for attachment to the distal mounting interface 11130 of the drive module 11100 by at least one latch 11140 of the drive module 11100. Also, similarly, the shaft assembly 14000 comprises a proximal mounting interface 14130 which is configured for attachment to the distal mounting interface 11130 of the drive module 11100 by at least one latch 11140 of the drive module 11100. Likewise, the shaft assembly 15000 comprises a proximal mounting interface 15130 which is configured for attachment to the distal mounting interface 11130 of the drive module 11100. The drive module 11100 is configured to electrically couple to each of the shaft assembles 12000, 13000, 14000, and 15000. The surgical instrument system comprises a motor positioned in the handle assembly 11000, as will be discussed in greater detail below. Each of the shaft assemblies 12000, 13000, 14000, and 15000 comprises a control circuit as will be discussed in greater detail below. The control circuit is configured to interact with the motor in order to control various functions of the surgical instrument system. The surgical instrument system further comprises a motor-control processor which is configured to communicate with the control circuit in order to control the motor. Referring to FIG. 76A, the processor is positioned in any suitable portion of the surgical instrument apart from the drive module 11100. For example, the processor is positioned in a shaft assembly of the surgical instrument system. The handle assembly 11000 is configured for use with at least one power module as will be discussed in greater detail below.

Figure 59:
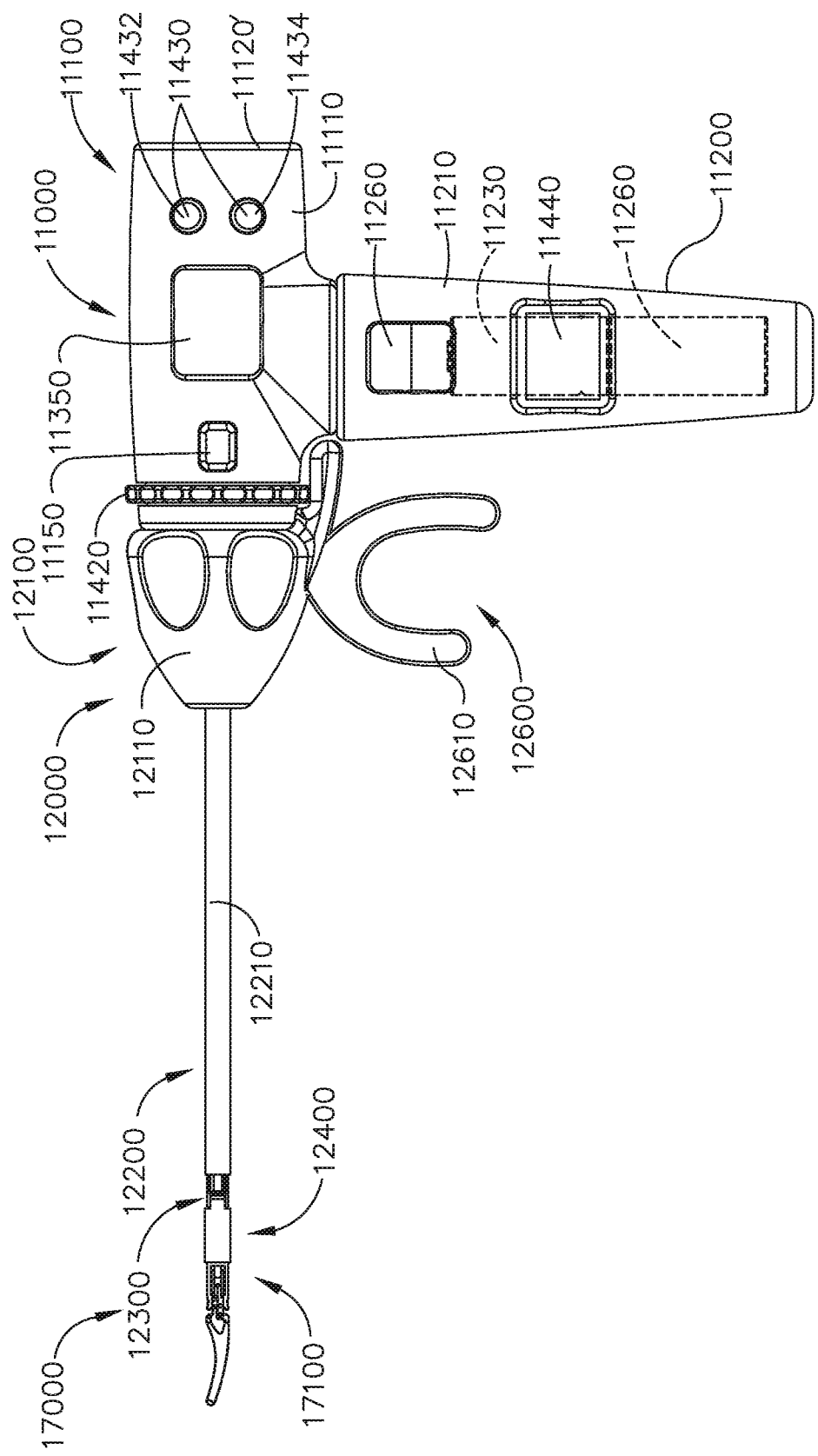
FIG. 59 is an elevational view of the handle and one of the shaft assemblies of the surgical instrument system of FIG. 58.

Referring to FIGS. 58 and 59, the drive module 11100 comprises a housing 11110 which is capable of use with a variety of power modules such as the power modules 11200 and 11300, for example. In various instances, each power module 11200 and 11300 comprises one or more battery cells, as illustrated in FIG. 59, which are configured to enable pistol, scissor, and/or pencil grip configurations comprising different load requirements. In particular, the housing 11110 comprises a first attachment portion 11120 and a second attachment portion 11120' which are configured to engage either the power module 11200 or the power module 11300 at either the bottom of the handle assembly 11000 or the proximal end of the handle assembly 11000 depending on which shaft assembly is attached to the handle assembly 11000. For example, when the shaft assembly 14000 is attached to the handle assembly 11000, a power module is attached to the proximal end of the handle assembly 11000 in a first configuration as illustrated in FIG. 58. As another example, when the shaft assembly 13000 is attached to the handle assembly 11000, a power module is attached to the bottom of the handle assembly 11000 in a second configuration. As illustrated in FIGS. 58 and 59, the first configuration and the second configuration are different from one another.

Still referring to FIG. 59, the drive module 11100 comprises a rotation actuator 11420 which is similar to the rotation actuator 1420, which is described in greater detail above. The drive module 11100 further comprises release actuators 11150 which, when depressed by a clinician, move the latches 11140 from their locked positions into their unlocked positions. The drive module 11100 comprises a first release actuator 11150 slideably mounted in an opening defined in the first side of the handle housing 11110 and a second release actuator 11150 slideably mounted in an opening defined in a second, or opposite, side of the handle housing 11110.

Figure 60:
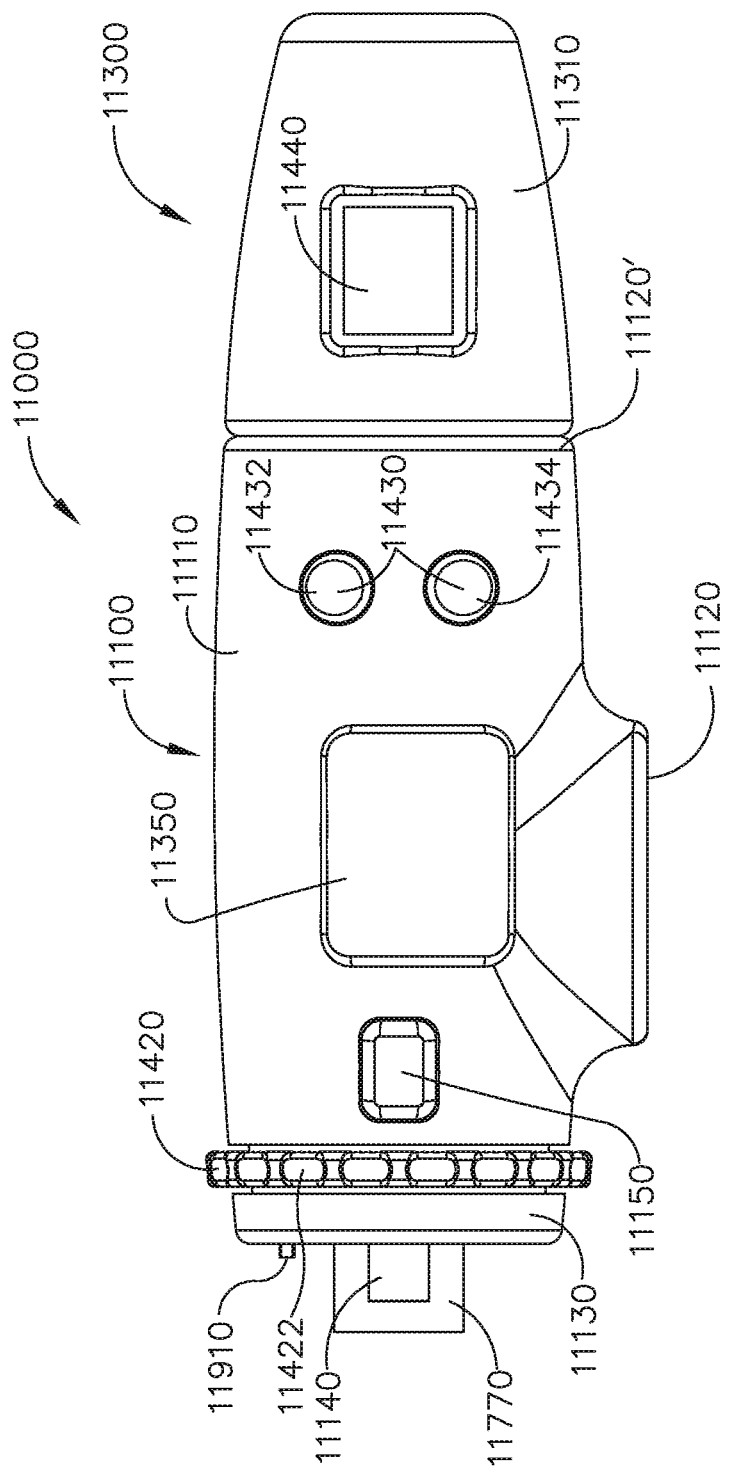
FIG. 60 is an elevational view of a drive module of the handle of FIG. 58.

Referring to FIG. 59 and FIG. 60, the drive module 11100 comprises an articulation actuator 11430. The articulation actuator 11430 comprises a first push button 11432 and a second push button 11434. The first push button 11432 is part of a first articulation control circuit and the second push button 11434 is part of a second articulation circuit of an input system similar to the input system 1400 discussed in greater detail above.

Referring again to FIG. 58, the surgical instrument system comprises a power module 11200. The power module 11200 comprises a housing 11210, a connector portion 11220, and at least one battery (as illustrated in at least FIG. 59). The connector portion 11220 is configured to be engaged with the first connector portion 11120 in order to attach the power module 11200 to the bottom of the handle assembly 11000. The power module 11200 comprises at least one latch 11240 positioned at the top of the power module 11200 which is configured to secure the power module 11200 to the bottom of the drive module 11100. More specifically, the latch 11240 is configured to securely attach the housing 11210 of the power module 11200 to the housing 11110 of the drive module 11100 located within the handle assembly 11000. The connector portion 11220 comprises a plurality of electrical contacts which enable an electrical connection between the power module 11200 and the drive module 11100. The power module 11200 comprises a release latch 11250 which is configured to release the power module 11250 from the drive module 11000.

Referring again to FIG. 58, the surgical instrument system comprises a power module 11300. The power module 11300 comprises a housing 11310, a connector portion 11320, and at least one battery. The connector portion 11320 is configured to be engaged with the second connector portion 11120' in order to attach the power module 11300 to the handle assembly 11000. The power module 11300 comprises at least one latch 11340 positioned at a distal end of the power module 11300 which is configured to secure the power module 11300 to the drive module 11100. More specifically, the latch 11340 is configured to securely attach the housing 11310 of the power module 11300 to the housing 11110 of the drive module 11100 located within the handle assembly 11000. The connector portion 11320 comprises a plurality of electrical contacts which enable an electrical connection between the power module 11300 and the drive module 11100.

Still referring to FIG. 58, the power module 11200 and the power module 11300 each comprise at least one display unit. The power module 11200 comprises a display unit 11440 located on the power module housing 11210. The power module 11300 comprises a display unit 11440'. The display units 11440 and 11440' can comprise any suitable display screen, for example, configured for use with a powered surgical device. In various instances, the display units 11440 and 11440' comprise an electrochromic display. The electrochromic display comprises an array of electrodes created from a metal oxide semi conductor. The electrodes are mounted on a flexible film comprising attachments of electrochromic molecules. As a charge is applied to the semi-conducting electrodes, the electrochromic molecules travel to the surface of the film to receive the charge. As the electrochromic molecules are charged, a change in color occurs in the molecules. Suitable versions of this type of display screen are available from Ntera and Seiko, for instance.

In certain instances, the display units 11440 and 11440' comprise an electrophoretic display. The electrophoretic display comprises titanium dioxide particles approximately one micrometer in diameter which are dispersed in a hydrocarbon oil, for example. A dark-colored dye is also added to the oil, along with surfactants and charging agents that cause the particles to take on an electric charge. The mixture of titanium dioxide particles and hydrocarbon oil is placed between two parallel conductive plates separated by a gap of 10 to 100 micrometers, for example. The parallel conductive plates comprise opposite charges from one another. When a voltage is applied across the two plates, the titanium dioxide particles migrate electrophoretically to the plate that bears the opposite charge from the charge of the particles. When the particles are located at the front (viewing) side of the display, it appears white, because light is scattered back to the viewer by the high-index titanium dioxide particles. When the particles are located at the rear side of the display, it appears dark, because the incident light is absorbed by the colored dye. If the rear electrode is divided into a number of small picture elements (pixels), then an image can be formed by applying the appropriate voltage to each region of the display to create a pattern of reflecting and absorbing regions.

Other suitable variations of display screens include various types of liquid-crystal displays including liquid-crystal character display modules, thin film transistor liquid-crystal displays, and/or any other suitable display screens. Liquid crystal character display modules are flat-panel displays which use the light-modulating properties of liquid crystals in order to produce images in color or monochrome by using a backlight or a reflector. Thin film transistor liquid-crystal displays use thin-film transistor technology to provide for improved image qualities including, but not limited to, contrast. Additional types of display screens comprise touch screen capable screens and/or active matrix backplanes comprising an amorphous silicon semiconductor or a polythiophene semiconductor, for example.

Figure 9:
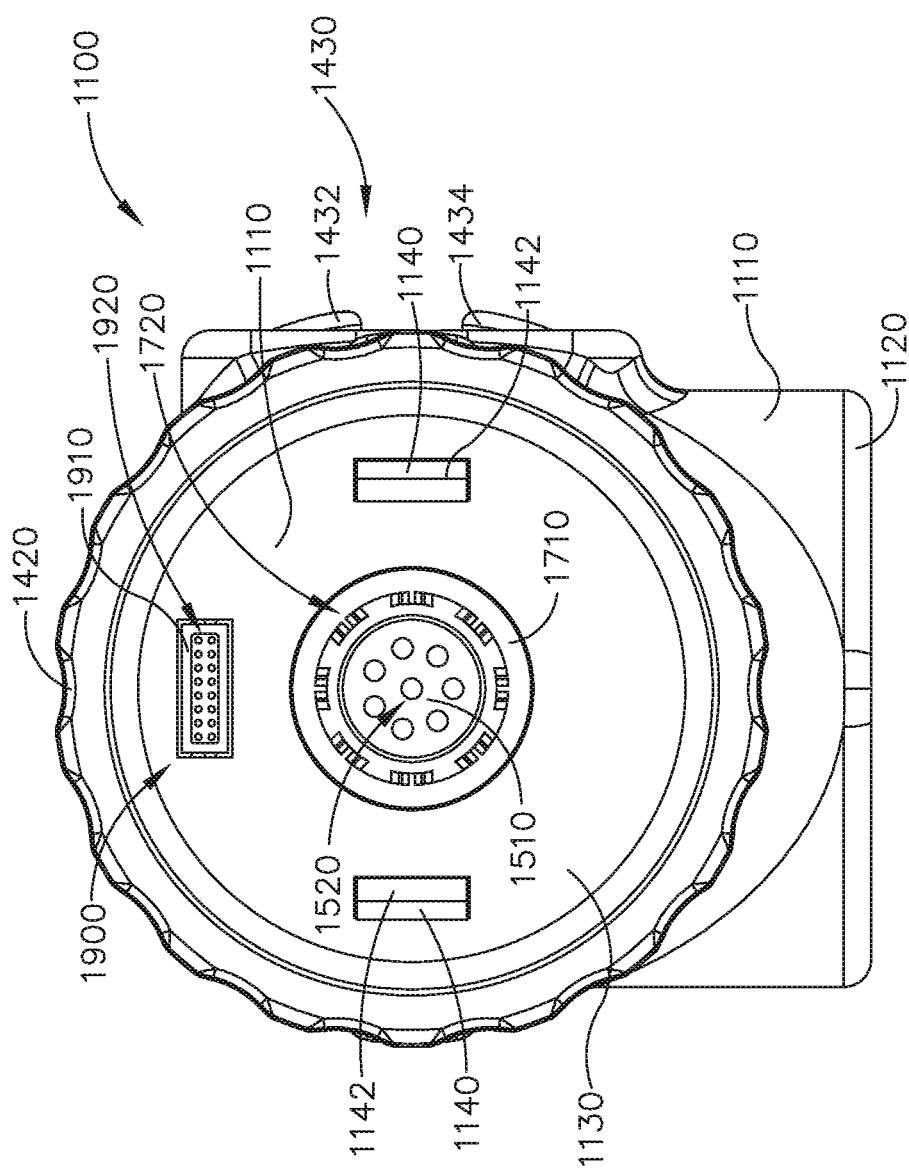
FIG. 9 is an end view of the drive module of FIG. 7.
Figure 61:
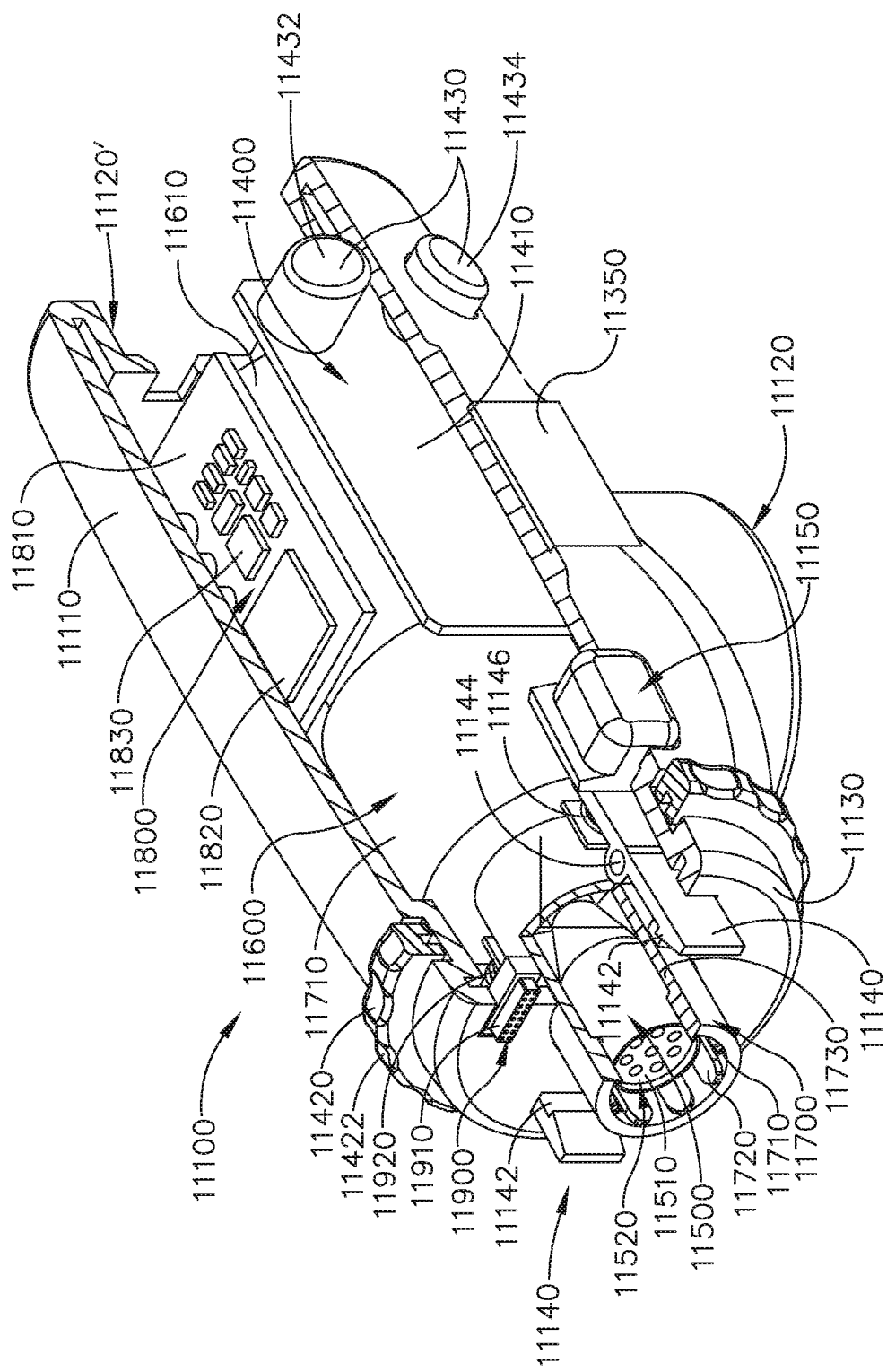
FIG. 61 is a cross-sectional perspective view of the drive module of FIG. 60.
Figure 62:
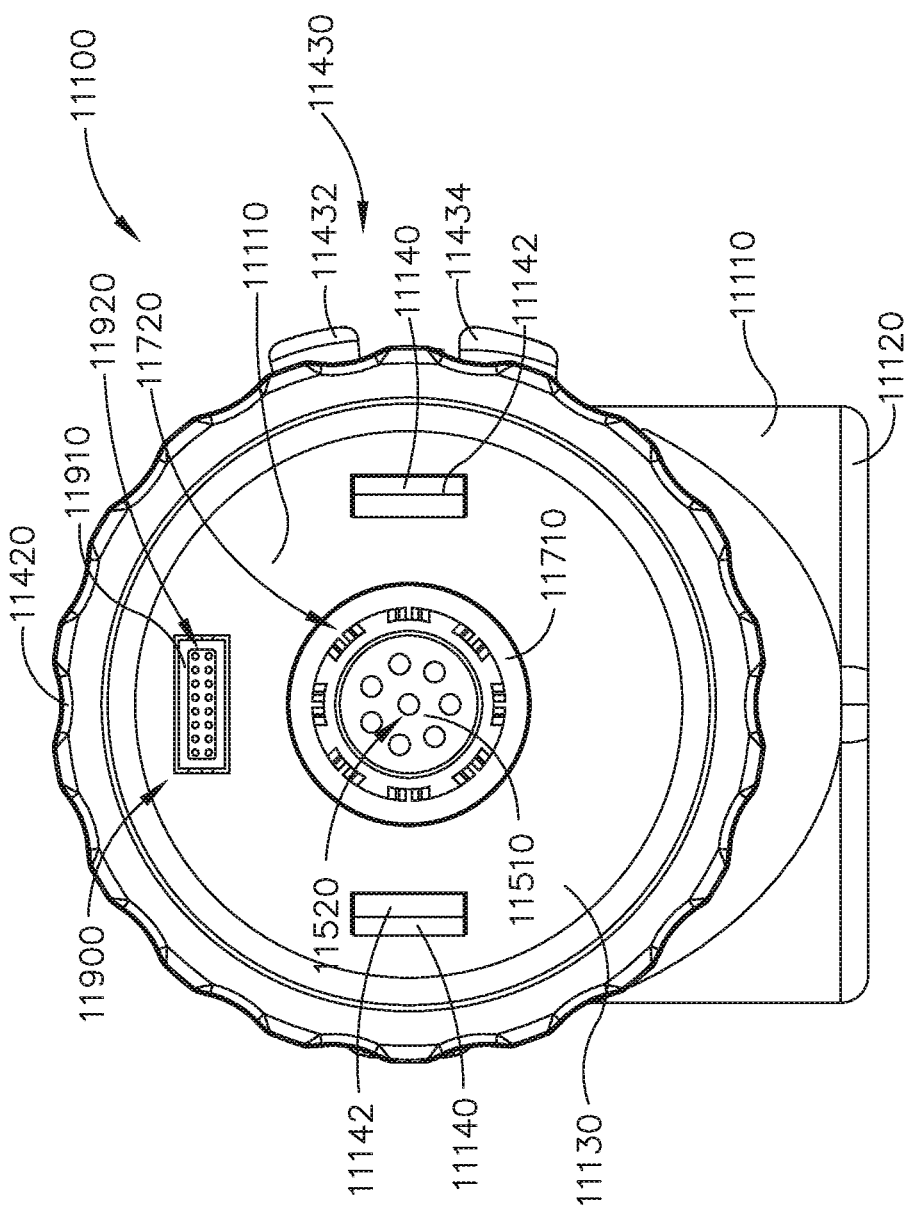
FIG. 62 is an end view of the drive module of FIG. 60.

Referring primarily to FIG. 59, the power module 11200 is attached to the handle assembly 11000 in a first orientation. When the power module 11200 is positioned in the first orientation, a first maximum level of power is supplied to the surgical instrument system. As seen in FIG. 59, the surgical instrument system comprises a pistol grip when the power module 11200 is attached to the surgical instrument. Still referring to FIG. 59, the power module 11200 comprises at least a first battery 11230 and a second battery 11260. Referring to FIG. 60, the power module 11300 comprises a housing 11310 which is configured to attach the power module 11300 to the handle assembly 11000 in a second orientation. The second orientation of the power module 11300 is configured to supply an appropriate amount of power when the surgical instrument comprises a pencil or wand grip configuration. The power module 11200 is configured to supply more power to the surgical instrument when the power 11200 is in the first orientation, and the power module 11300 is configured to supply less power to the surgical instrument in the second orientation. The use of various power modules ensures that the necessary amount of power for the operation of the surgical instrument system is provided. With respect to FIGS. 60-62, the drive module 11100 comprises the same and/or similar components as the drive module 1100 discussed in detail above with respect to FIGS. 7-9. That is, the drive module 11100 interacts with each of the shaft assemblies 12000, 13000, 14000, and 15000 in the same and/or a similar manner as the drive module 1100 interacts with the shaft assemblies 2000, 3000, 4000, and 5000.

Figure 63:
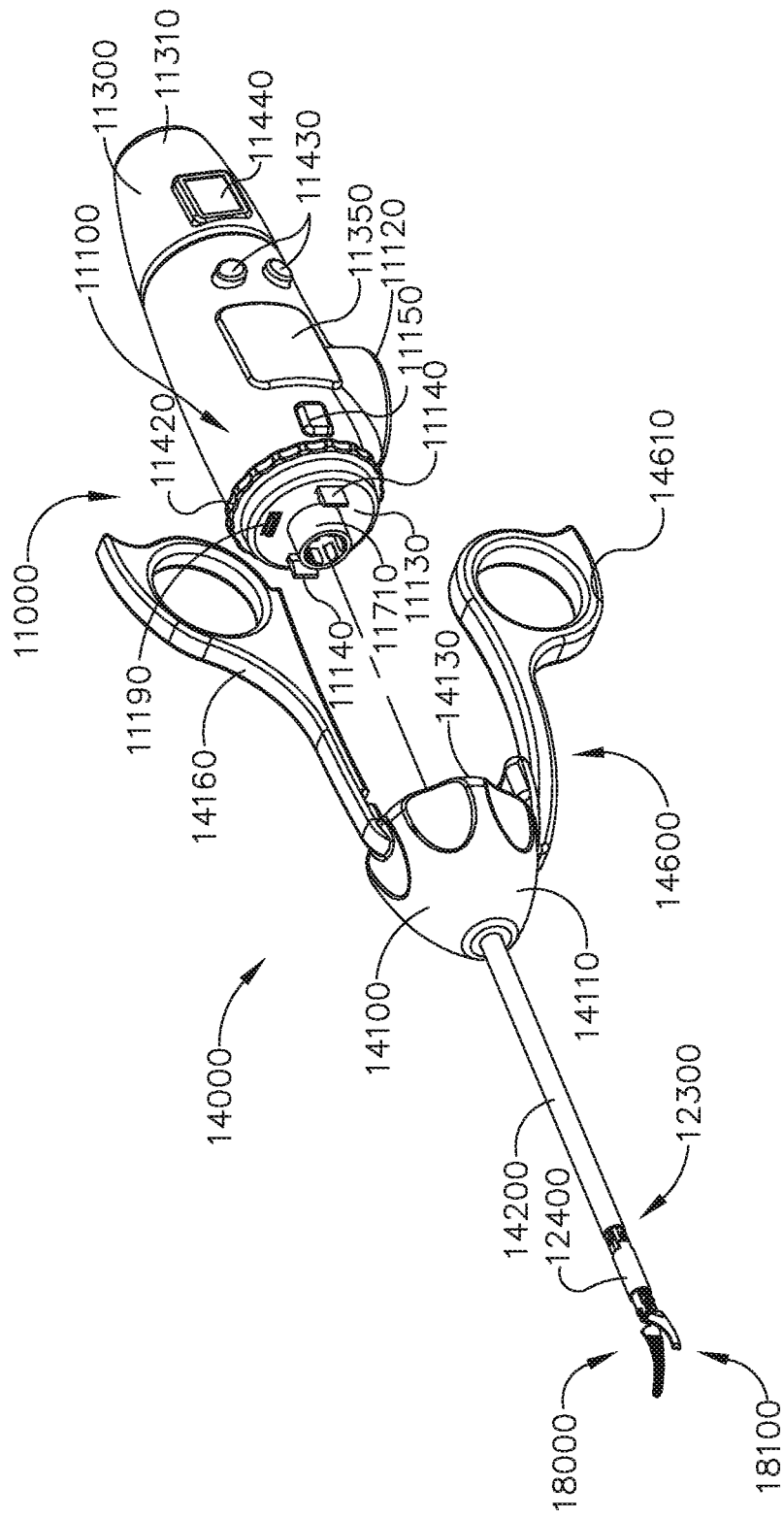
FIG. 63 is a perspective view of the handle drive module of FIG. 60 and one of the shaft assemblies of the surgical instrument system of FIG. 58.
Figure 64:
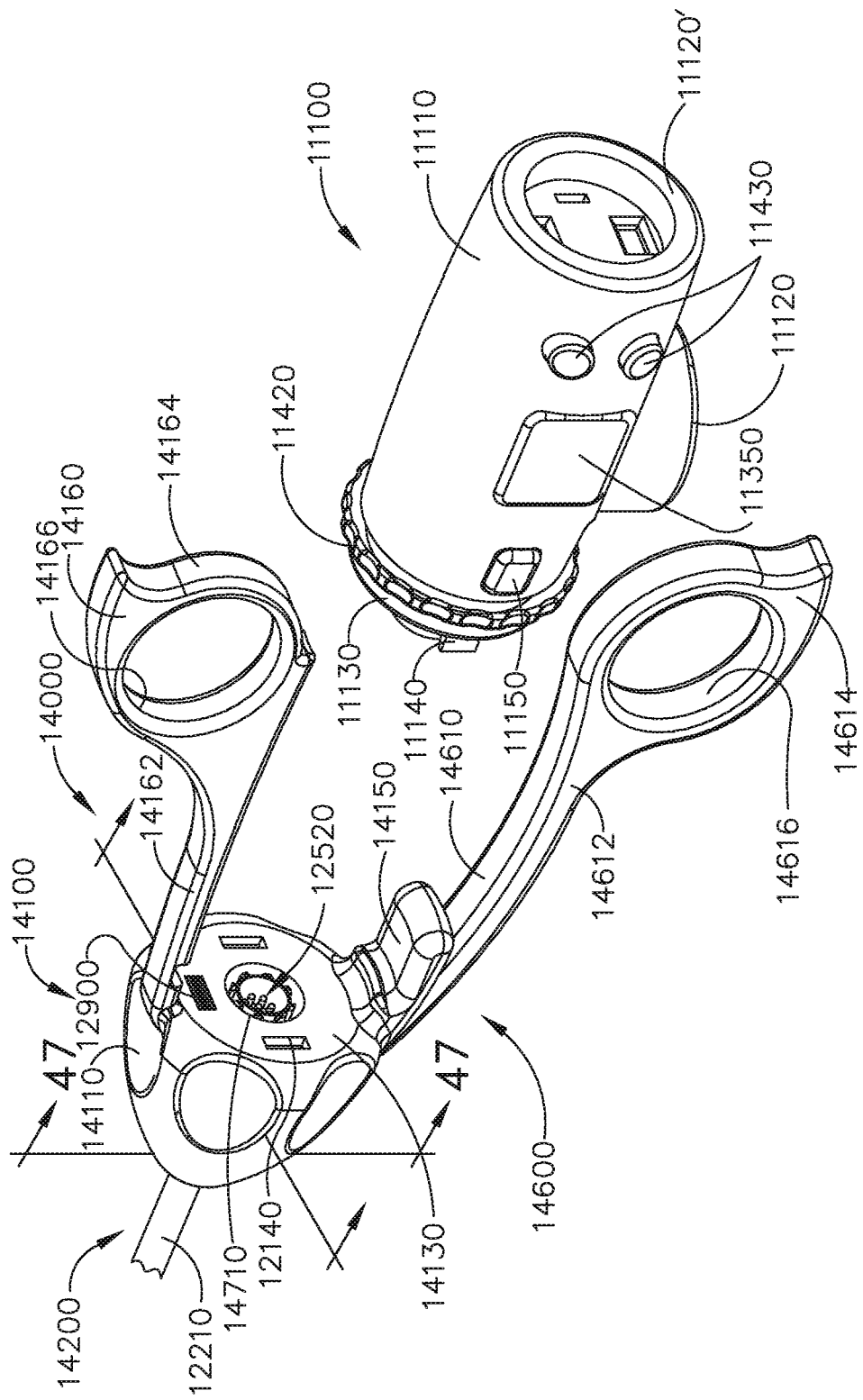
FIG. 64 is another perspective view of the handle drive module of FIG. 58 and the shaft assembly of FIG. 63.
Figure 65:
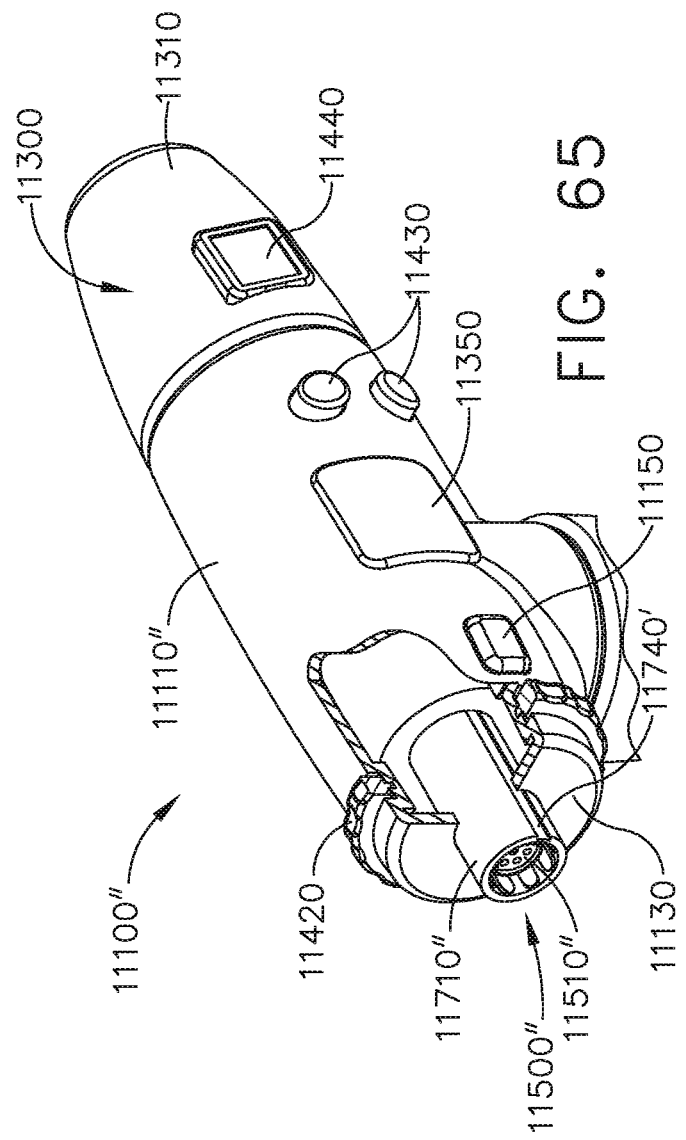
FIG. 65 is a partial cross-sectional perspective view of a handle drive module in accordance with at least one embodiment.

FIGS. 63-65 illustrate the surgical instrument system comprising the power module 11300 in the first orientation for use with the scissor grip configuration of the shaft assembly 14000. The surgical instrument system illustrated in FIGS. 63-65 is similar in some aspects to the surgical instrument system illustrated in FIGS. 45-47, which is discussed in greater detail above and is also configured for use with the power module 11300 which comprises the display unit 11440'. Various surgical instruments described herein are compatible with the power modules 11200 and 11300.

Figure 66:
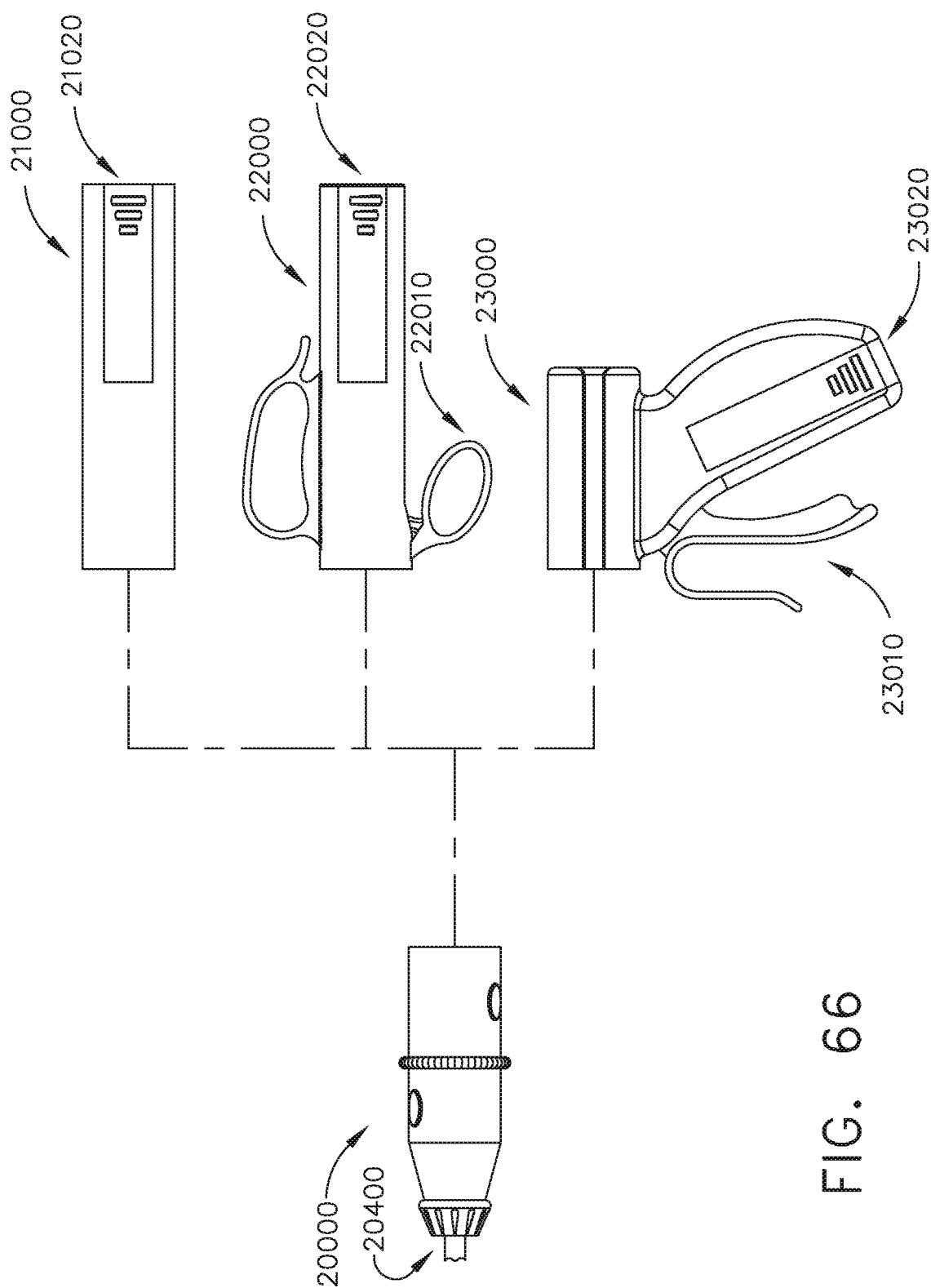
FIG. 66 illustrates a surgical instrument system comprising several handle assemblies and a shaft assembly selectively attachable to the handle assemblies in accordance with at least one embodiment.
Figure 68A:
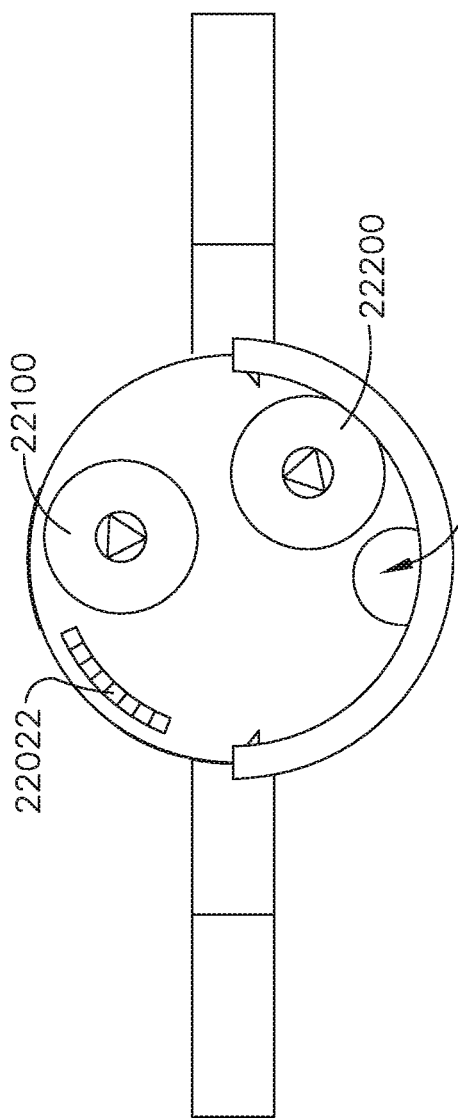
FIG. 68A is a proximal end view of the handle assembly of FIG. 66A.
Figure 68B:
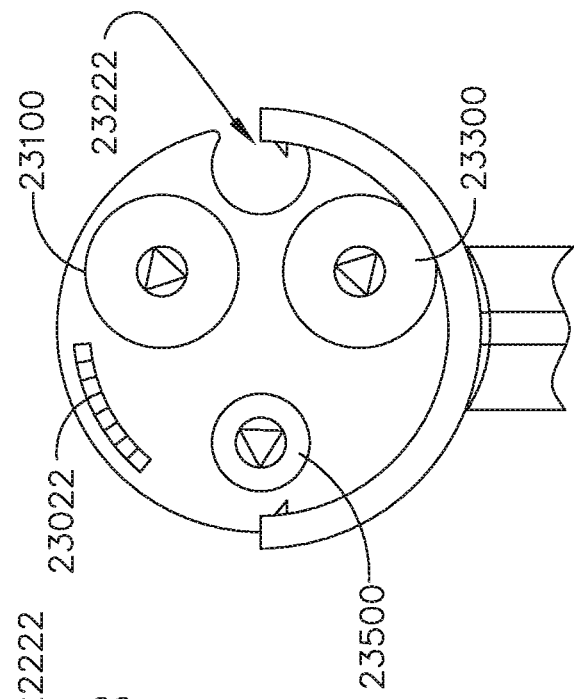
FIG. 68B is a proximal end view of the handle assembly of FIG. 66B.
Figure 68C:
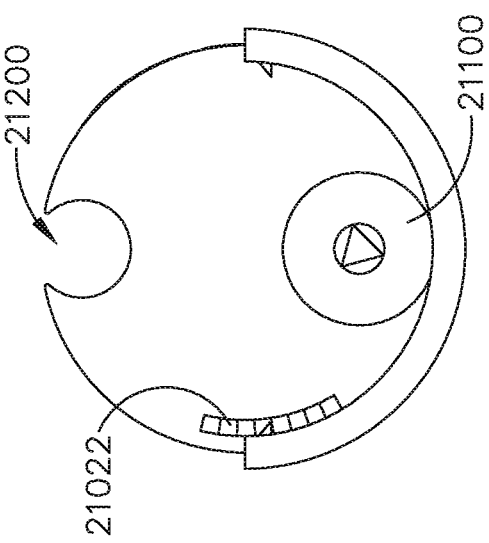
FIG. 68C is a proximal end view of the handle assembly of FIG. 66C.

Turning now to FIG. 66, a surgical instrument system can comprise a variety of handle assemblies such as a pencil grip handle, a scissor grip handle, a pistol grip handle, among others, and a shaft assembly, such as the shaft assembly 20000, for example, that can be used with each of the handle assemblies. The surgical instrument system comprises a first handle assembly 21000, which is a pencil grip handle. Referring primarily to FIGS. 66A and 68A, the first handle assembly 21000 comprises one electric drive motor, a first drive shaft 21100, and a first set of controls which controls the one electric drive motor. The drive shaft 21100 of the one drive motor is configured to be coupled with a drive system of the shaft assembly 20000 when the shaft assembly 20000 is attached to the handle assembly 21000. The drive motor used in connection with the surgical instrument system of FIG. 66 is similar in many respects to other motors discussed in detail above, such as the motor 1610, for example. The first handle assembly 21000 further comprises a plurality of electrical contacts 21022 for placing the handle assembly 21000 in electrical communication with the shaft assembly 20000 via electrical contacts 20022 defined thereon. Referring to FIGS. 66 and 66A, the first handle assembly 21000 further comprises an insertable power module 21020 at the proximal end of the handle assembly 21000.

Figure 66D:
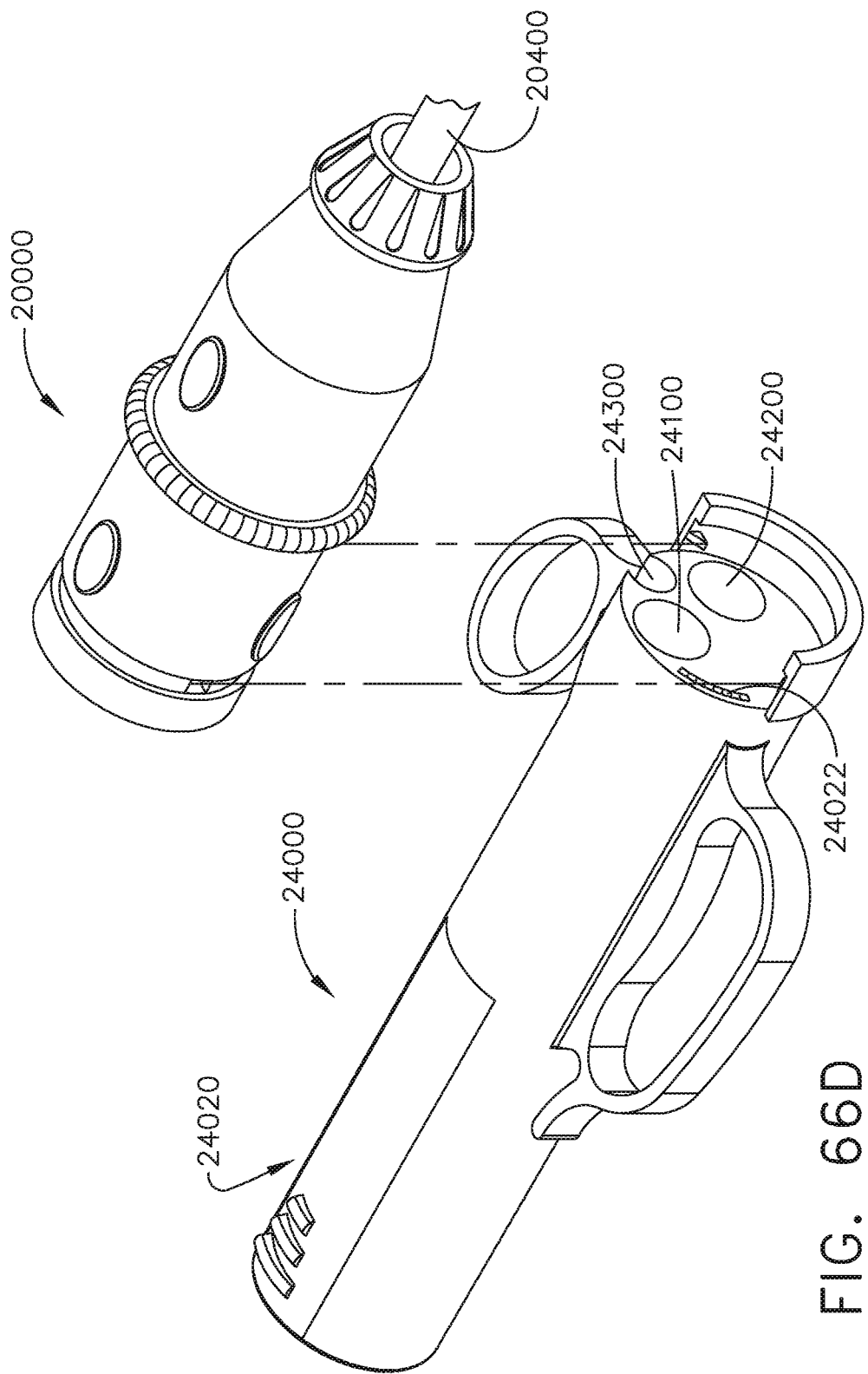
FIG. 66D is an elevational view of a handle assembly and the shaft assembly of FIG. 66 in accordance with at least one embodiment.
Figure 66E:
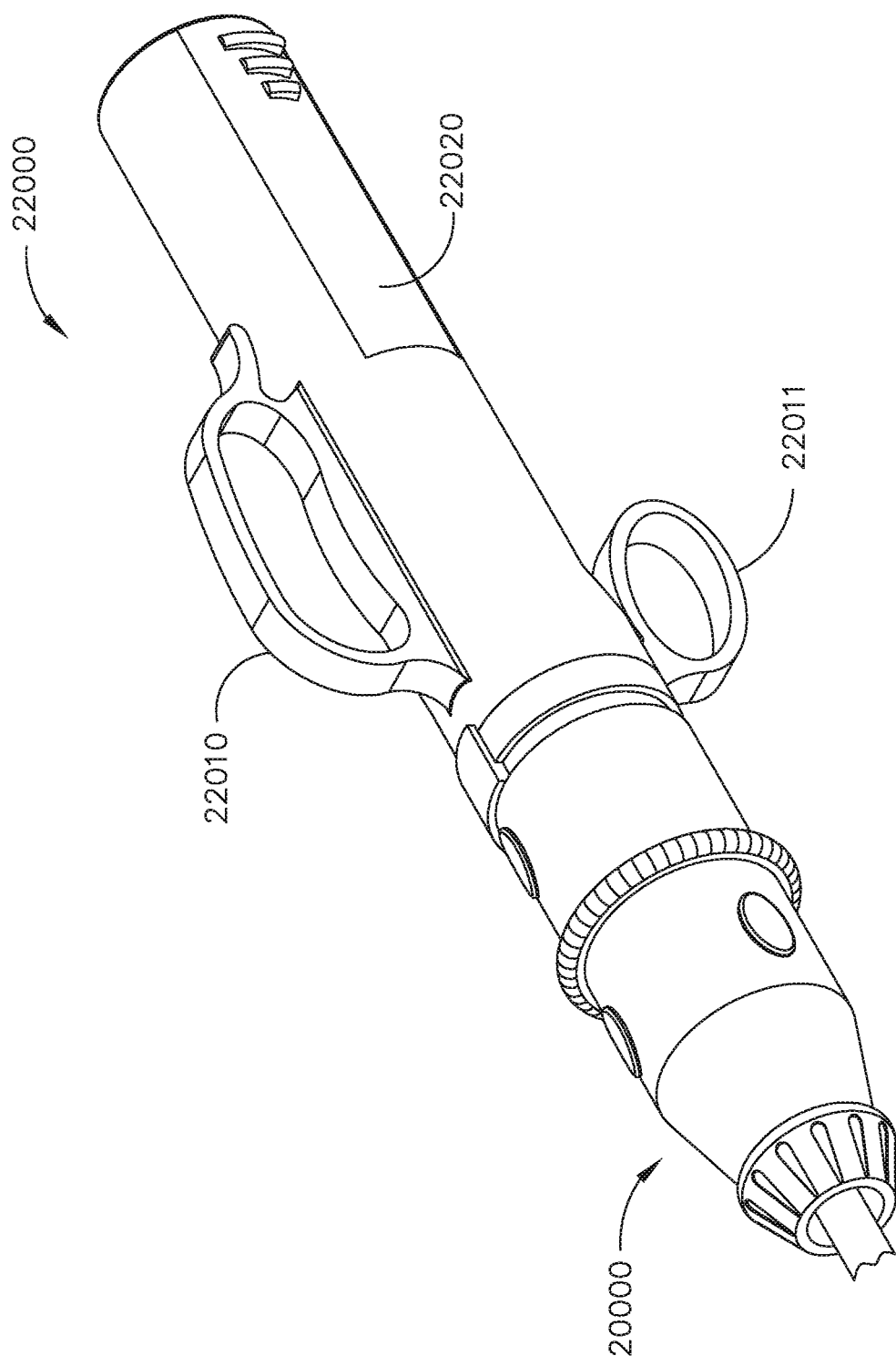
FIG. 66E is an elevational view of the handle assembly of FIG. 66B attached to the shaft assembly of FIG. 66 in accordance with at least one embodiment.
Figure 66F:
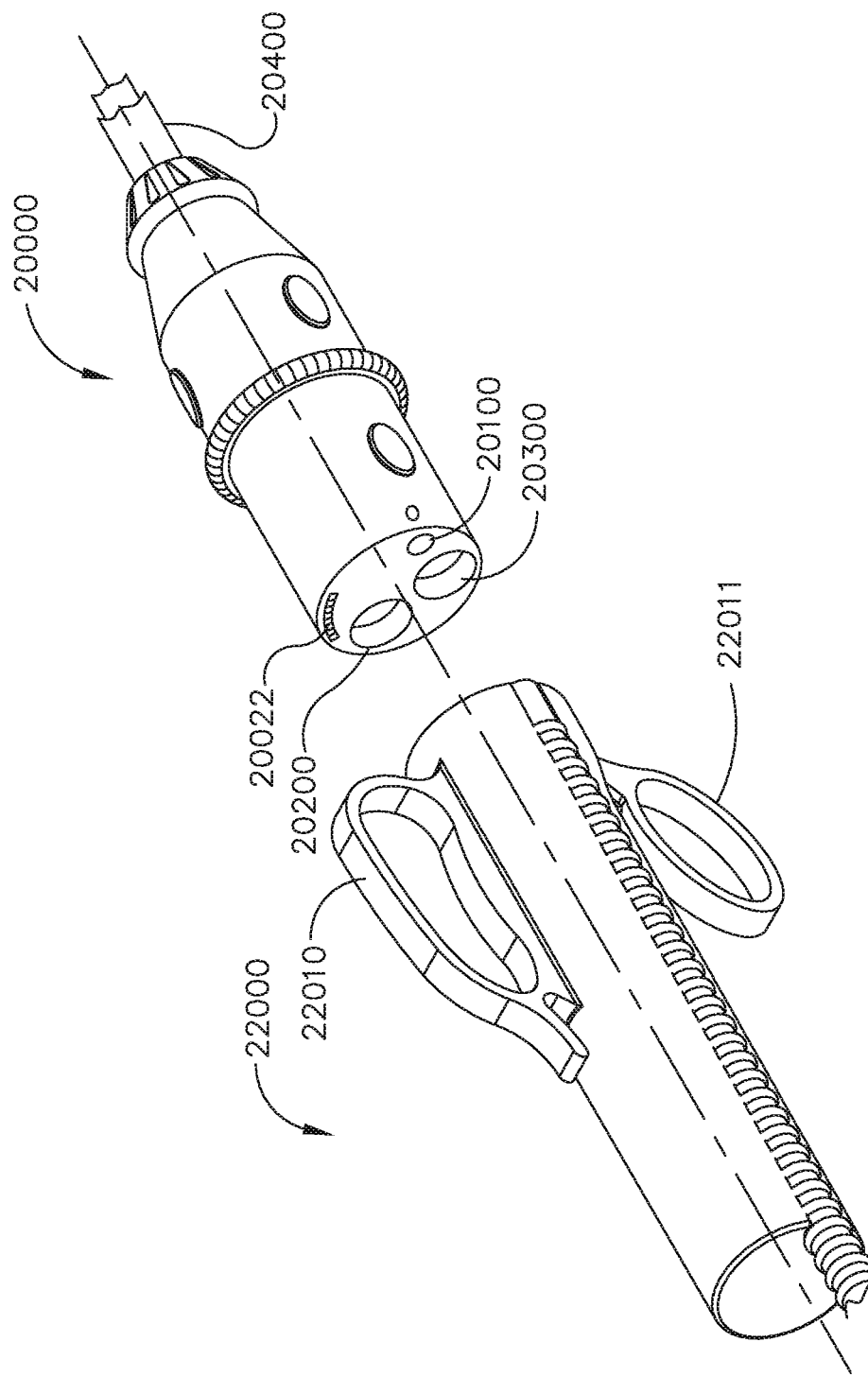
FIG. 66F is an elevational view of the handle assembly of FIG. 66B and the shaft assembly of FIG. 66 in accordance with at least one embodiment.

The surgical instrument system further comprises a second handle assembly 22000, which is a scissors grip handle. Referring primarily to FIG. 66B, the second handle assembly 22000 comprises first and second electric drive motors, a drive shaft 22100, a second drive shaft 22200, a first set of controls which controls the first drive motor, and a second set of controls which controls the second drive motor. The first drive shaft 22100 and the second drive shaft 22200 of the first and second drive motors can be coupled with two drive systems of the shaft assembly 20000. The first and second drive motors are similar in many respects to other motors discussed in detail above, such as the motor 1610, for example. The second handle assembly 22000 further comprises a plurality of electrical contacts 22022 for placing the handle assembly 22000 in electrical communication with the shaft assembly 20000 via electrical contacts 20022 defined thereon as seen in FIG. 66D. Referring primarily to FIGS. 66 and 66B, the second handle assembly 22000 further comprises an insertable power module 22020 at the proximal end of the handle assembly 22000.

Figure 66G:
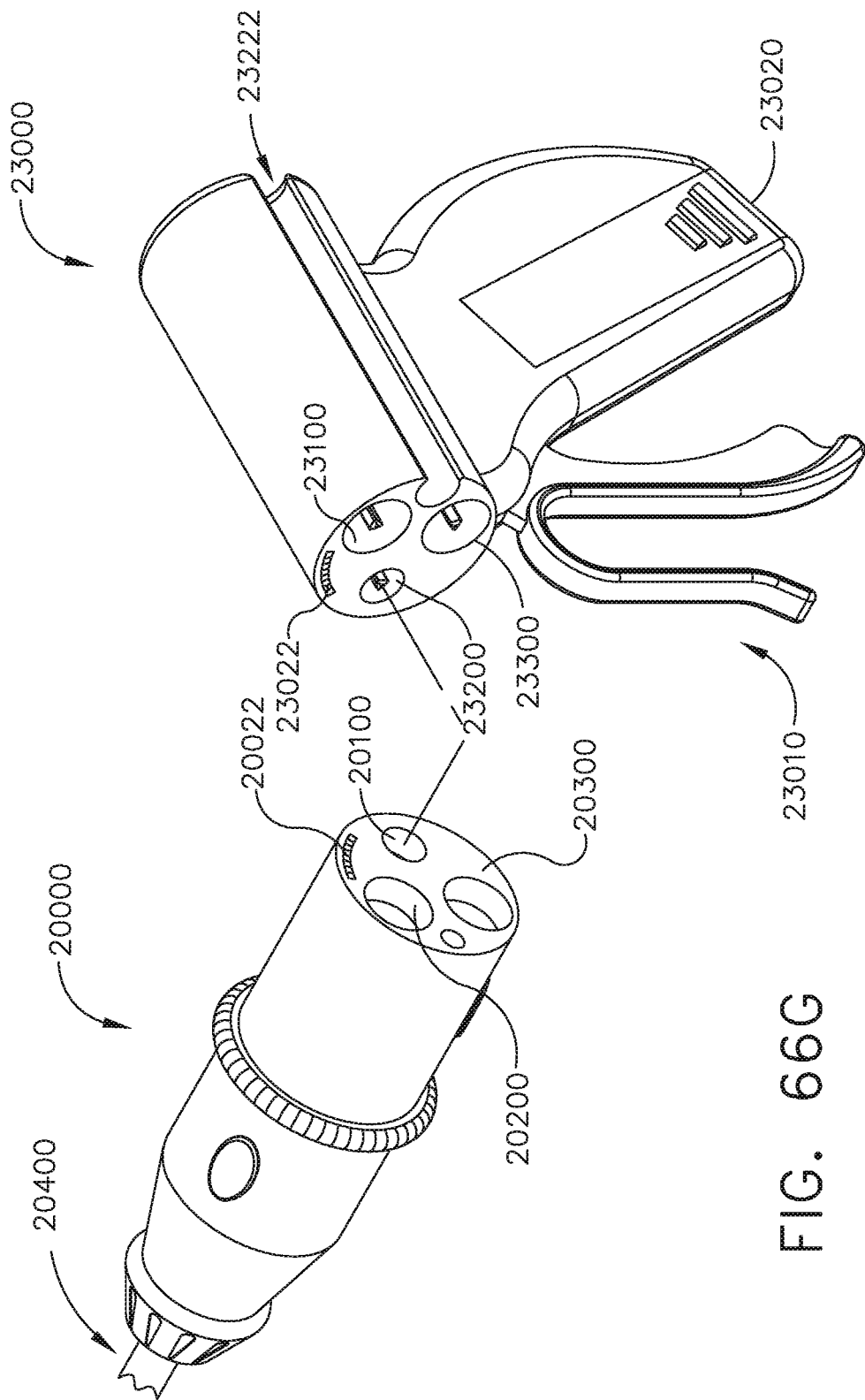
FIG. 66G is an elevational view of the handle assembly of FIG. 66C and the shaft assembly of FIG. 66 in accordance with at least one embodiment.
Figure 67:
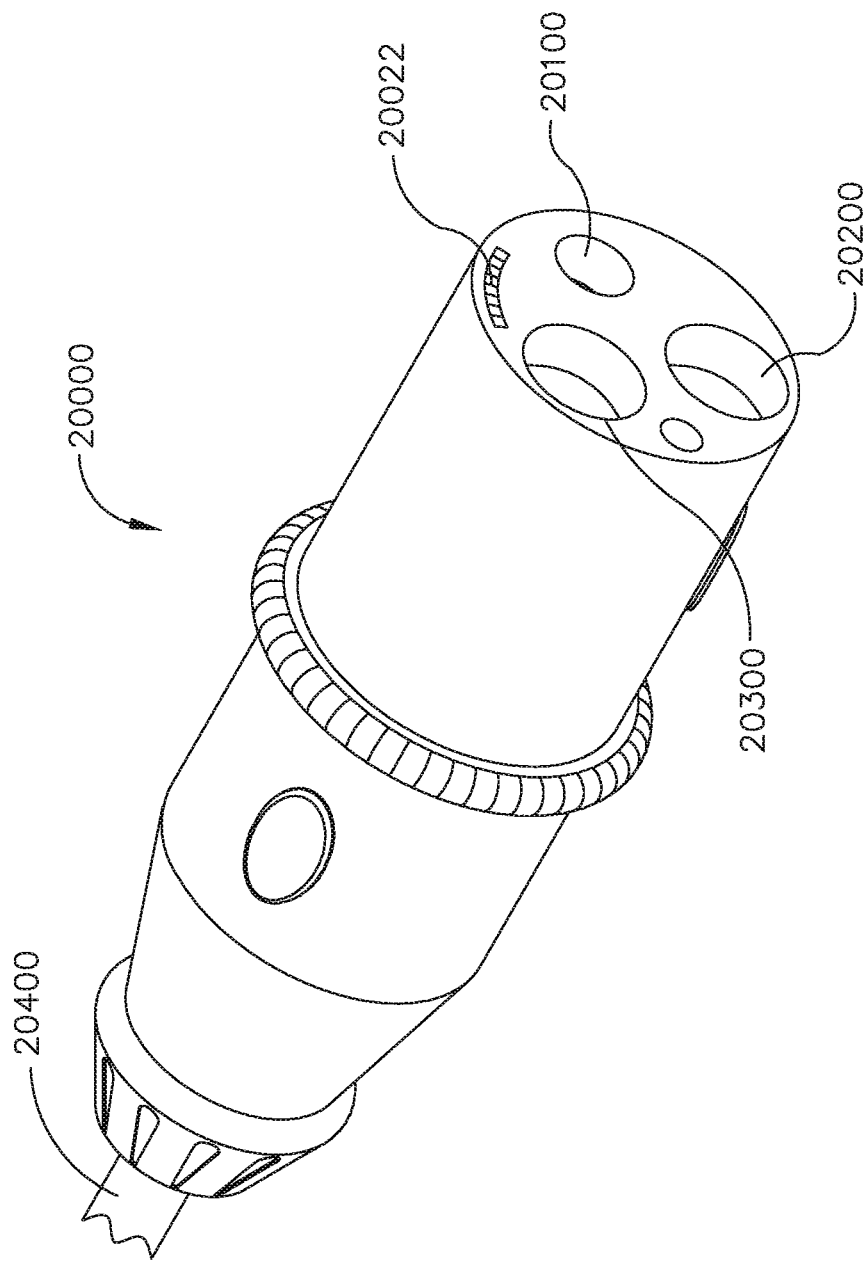
FIG. 67 is a perspective view of the shaft assembly of FIG. 66.

Referring to FIGS. 66 and 66C, the surgical instrument system further comprises a third handle assembly 23000, which is a pistol grip handle. The third handle assembly 23000 comprises first, second, and third electric drive motors, a first drive shaft 23100, a second drive shaft 23200, a third drive shaft 23300, a first set of controls which controls the first drive motor, a second set of controls which controls the second drive motor, and a third set of controls which controls the third drive motor. The third handle assembly 23000 comprises a third set of controls. The first drive shaft 23100, the second drive shaft 23200, and the third drive shaft 23300 can be coupled with the three drive systems of the shaft assembly 20000. The third handle assembly 23000 further comprises a plurality of electrical contacts 23022 for placing the handle assembly 23000 in electrical communication with the shaft assembly 20000 via electrical contacts 20022 defined thereon as seen in FIGS. 66C and 66G. The third handle assembly 23000 further comprises an insertable power module 23020 at the proximal end of the handle assembly 23000.

Further to the above, the shaft assembly 20000 comprises three drive systems which are drivable by a drive motor of a handle assembly—this is, of course, assuming that the handle assembly that the shaft assembly 20000 is attached to has a sufficient number of drive motors to drive all three drive systems of the shaft assembly 20000. Stated another way, the first handle assembly 21000 has only one drive motor to drive one of the drive systems of the shaft assembly 20000 and, similarly, the second handle assembly 22000 has only two drive motors to drive two of the drive systems of the shaft assembly 20000. Thus, two drive systems of the shaft assembly 20000 cannot be driven by the first handle assembly 21000 and one drive system of the shaft assembly 20000 cannot be driven by the second handle assembly 22000. In various instances, the undriven system, or systems, of the shaft assembly 20000 can remain inert while the other drive system, or systems, of the shaft assembly 20000 are being used. In at least one embodiment, the handle assemblies 21000 and 22000 can be configured to lock out the drive systems of the shaft assembly 20000 that aren't being used. In at least one instance, the handle assembly 21000 comprises two stationary posts extending therefrom which engage the second and third drive systems of the shaft assembly 20000 when the shaft assembly 20000 is assembled to the handle assembly 21000. The stationary posts prevent the second and third drive systems of the shaft assembly 20000 from being unintentionally actuated. Similarly, the handle assembly 22000 comprises one stationary post extending therefrom which engages the third drive system of the shaft assembly 20000 to prevent the third drive system from being unintentionally actuated. The third handle assembly 23000 does not comprise stationary posts to lock a drive system of the shaft assembly 20000 as all three drive systems of the shaft assembly 20000 are coupled to a drive motor in the third handle assembly 23000.

In addition to or in lieu of the above, the shaft assembly 20000 can comprise a second lock that is biased into a locked configuration to lock the second drive system in place and a third lock that is biased into a locked configuration to lock the third drive in place. When the shaft assembly 20000 is attached to the first handle assembly 21000, the shaft assembly 20000 does not receive electrical power from the first handle assembly 21000 to unlock the second lock or the third lock. When the shaft assembly 20000 is attached to the second handle assembly 22000, the shaft assembly 20000 receives electrical power from the second handle assembly 22000, via the electrical contacts 22022, and the second lock is unlocked so that the second drive system of the shaft assembly 20000 can be used by the second handle assembly 22000. That said, the second handle assembly 22000 does not receive electrical power from the second handle assembly 22000 to unlock the third lock as the second and third locks are part of separate and distinct circuits. When the shaft assembly 20000 is attached to the third handle assembly 23000, the shaft assembly 20000 receives power from the third handle assembly 23000, via the electrical contacts 23022, to unlock the second and third locks so that the second and third drive systems of the shaft assembly 20000 can be used by the third handle assembly 23000.

As discussed above and referring to FIG. 66, the shaft assembly 20000 is selectively attachable to the first handle assembly 21000, the second handle assembly 22000, and the third handle assembly 23000. That being said, the handle assemblies 21000, 22000, and 23000 are all configured to be held differently by a clinician. The pen configuration of the first handle assembly 21000 is configured to be held, or pinched, between the clinician's thumb and index finger on one hand. The scissors configuration of the second handle assembly 22000 is configured to be gripped by an outstretched hand of the clinician. The pistol configuration of the third handle assembly 23000 is configured to be gripped by a closed, clenched hand of the clinician. As a result, the handle configurations 21000, 22000, and 23000 can be configured such that the shaft assembly 20000 is attached thereto in different orientations to match the grip orientation of the clinician's hand. For instance, the shaft assembly 20000 is attached to the handle assembly 21000 in a first orientation and attached to the shaft assemblies 22000 and 23000 in a second orientation which is rotated 90 degrees from the first orientation. Such an arrangement matches the typical expectations of the clinician regarding the orientation of the shaft assembly 20000 relative to their hand. Similarly, the first set of controls on the first handle assembly 21000 for controlling the first drive motor can be oriented 90 degrees relative to the orientation of the first set of controls on the second handle assembly 22000 and the third handle assembly 23000. Moreover, it can be desirable for a certain function of the shaft assembly 20000 to be always coupled to a motor-driven drive system regardless of the handle assembly that it is attached to. To achieve this, in various instances, the shaft assembly 20000 may have to be attached to the handles 21000, 22000, and 23000 in different orientations to align the articulation drive system, for example, to a motor-driven drive system.

Further information regarding the different configurations of the handle assemblies 21000, 22000, and 23000 are presented in FIG. 69. For example, the pencil handle assembly 21000 comprises a motor-driven output which is configured to enable right and left articulation of the shaft 20400. The end effector can be manually rotated relative to the shaft 20400. The pencil handle assembly 21000 is not configured to perform any actuation motions of the end effector or rotation of the shaft 20400 as it does not comprise a motor driven output for the actuation motions of the end effector or the rotation of the shaft 20400. As another example, the scissor grip handle assembly 22000 comprises a motor-driven output which is configured to enable right and left articulation of the shaft 20400. The scissor grip handle assembly 22000 comprises another motor-driven output which is configured to enable a first actuation motion of the end effector. The scissor grip handle assembly 22000 is not configured to perform a second actuation motion of the end effector or rotation of the shaft 20400 as it does not comprise a motor-driven output for the second actuation motion of the end effector or the rotation of the shaft 20400. As another example, the pistol handle assembly 23000 comprises motor-driven outputs which are configured to enable right and left articulation of the shaft 20400. The pistol handle assembly also comprises motor-driven outputs which are configured to enable the first and second actuation motions of the end effector as well as rotation of the shaft 20400 via a motor and a shiftable transmission.

Figure 68D:
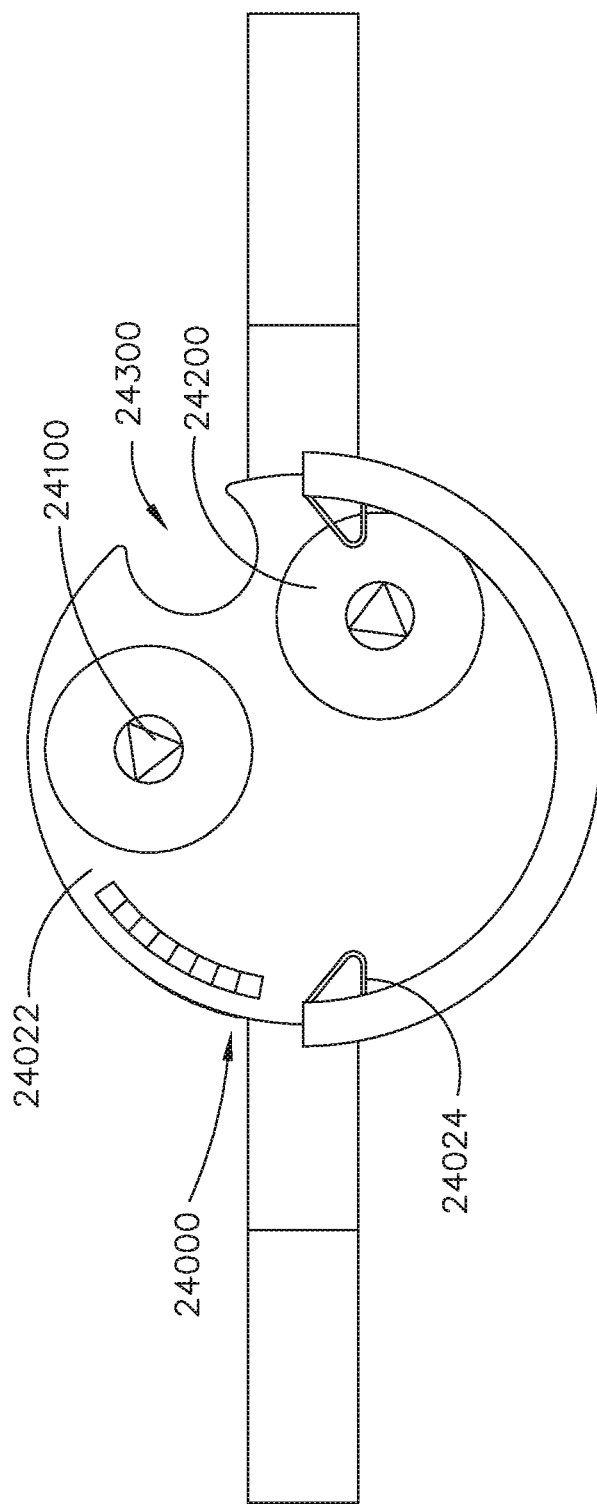
FIG. 68D is a proximal end view of the shaft assembly of FIG. 66D.

Referring primarily to FIGS. 66D and 68D, a handle assembly 24000, which is similar to the handle assembly 22000 in many respects, comprises at least one spring loaded pin 24024 which is configured to flex to allow the shaft assembly 20000 to be releasably held to the shaft assembly 20000. Such an arrangement can be adapted to the handle assemblies 21000, 22000, and 23000 to releasably hold the shaft assembly 20000 thereto. Similar to the handle assembly 22000, the handle assembly 24000 comprises a set of electrical contacts 24022, a first drive shaft 24100, and a second drive shaft 24200.

As discussed above, the shaft assembly 20000 comprises a first drive shaft 20100, a second drive shaft 20200, and a third drive shaft 20300, each of which enables a particular function of the surgical instrument system by establishing a mechanical connection with a drive shaft in any one of the handle assemblies 21000, 22000, and 23000—so long as the handle assembly has a sufficient number of drives to be coupled to. While the shaft assembly 20000 is attached to the first handle assembly 21000, certain functions of the surgical instrument and/or the end effector are enabled and certain functions of the surgical instrument and/or the end effector are locked out as seen in FIG. 69 and described in greater detail above. For example, the first handle assembly 21000 can drive the articulation system of the shaft 20400 with its one drive motor. All other functions of the shaft assembly 20000 would have to be performed by the manual manipulation of the first handle assembly 21000. Referring primarily to FIG. 66, the pencil grip configuration of the handle assembly 21000 does not afford a motor-driven output for actuating the end effector and/or rotating the shaft 20400.

The second handle assembly 22000 comprises two motors configured to drive two of the drives of the shaft assembly 20000. While the shaft assembly 20000 is attached to the second handle assembly 22000, certain functions of the surgical instrument and/or the end effector are enabled and certain functions of the surgical instrument and/or the end effector are locked out as seen in Table A of FIG. 69 and described in greater detail above. The first motor of the second handle assembly 22000 drives the articulation drive of the shaft assembly 20000 and the second motor of the second handle assembly 22000 drives a jaw assembly of the shaft assembly 20000 to move the jaw assembly between open and closed configurations. The third function of the shaft assembly 20000, i.e., the rotation of the jaw assembly about a longitudinal axis must be performed manually by rotating the second handle assembly 22000 about the longitudinal axis. The third handle assembly 23000 comprises three motors configured to drive all three of the drives of the shaft assembly 20000. While the shaft assembly 20000 is attached to the third handle assembly 23000 in the third orientation, none of the functions of the surgical instrument and/or the end effector are locked out as seen in Table A of FIG. 69 and described in greater detail above.

Figure 70:
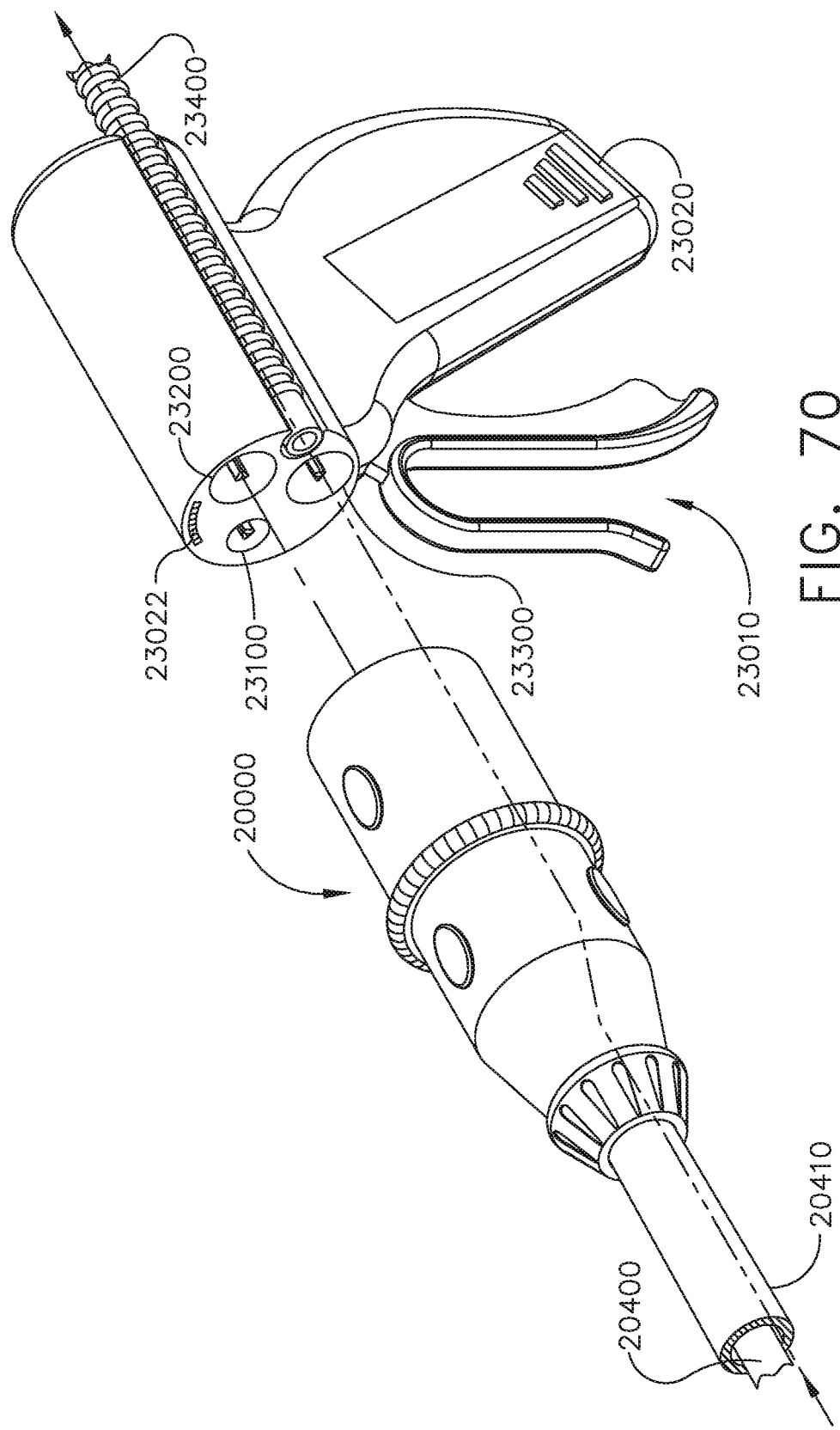
FIG. 70 is an exploded view of one of the handle assemblies and the shaft assembly of FIG. 66.
Figure 71:
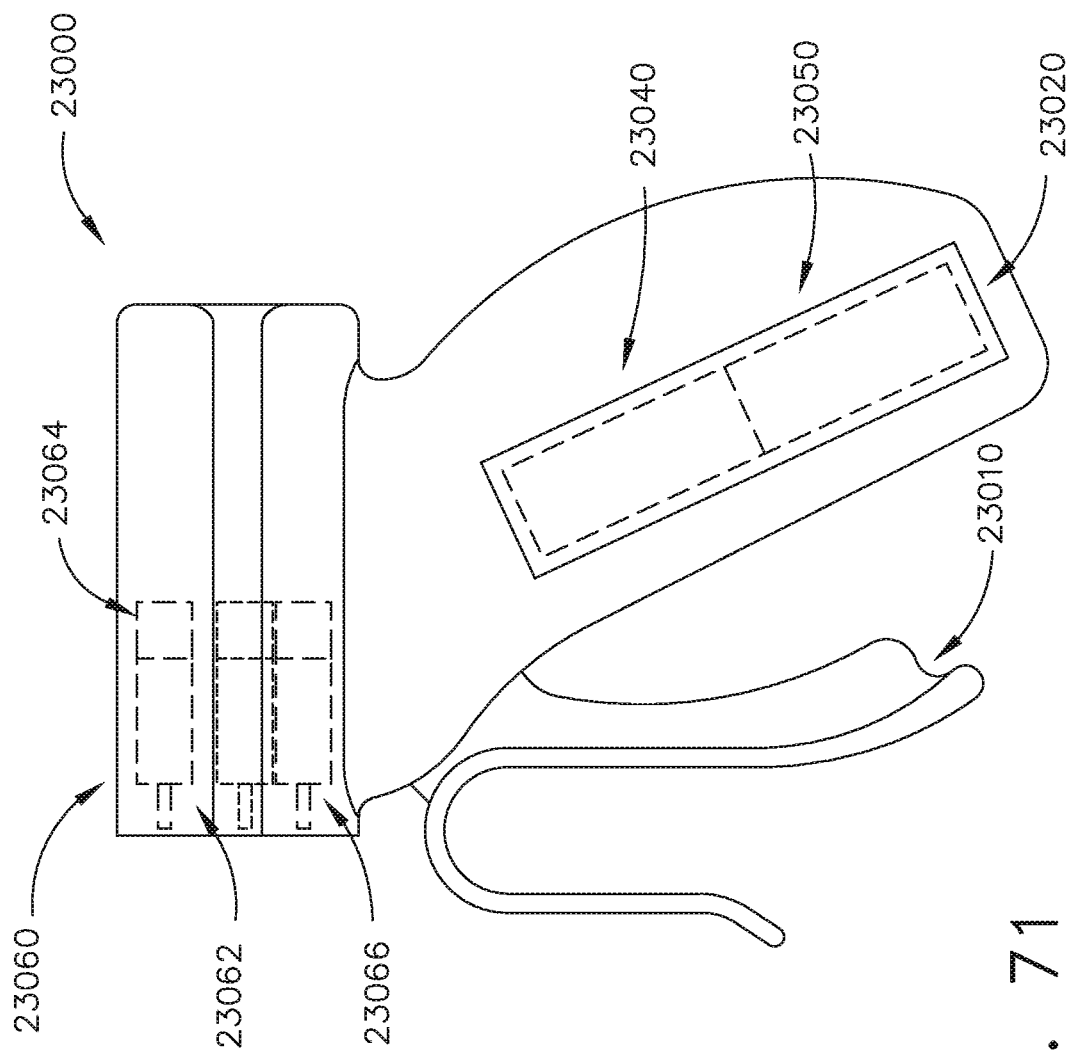
FIG. 71 depicts various aspects of the handle assembly of FIG. 70.

Referring to FIG. 70, the third handle assembly 23000 comprises a pistol grip configured for use with a smoke evacuation tube 23400. The smoke evacuation tube 23400 is configured to fit inside a groove 23420 within the handle assembly 23000. The shaft assembly 20000 further comprises a smoke evacuation tube 20410 which fits over the shaft 20400. Referring to FIG. 71, the third handle assembly 23000 comprises a first motor 23062 configured to power the right and left articulation of the end effector. The third handle assembly comprises a second motor configured to power the jaw drive of the shaft assembly 20000. The third handle assembly 23000 comprises a third motor configured to power the rotation of the end effector about the longitudinal axis. The handle assembly 23000 further comprises a first gear box 23064 to reduce the speed of the first motor and a second gear box 23068 to reduce the speed of the second motor. Still referring to FIG. 71, the insertable power module 23020 comprises at least two battery cells 23040 and 23050.

Figure 72:
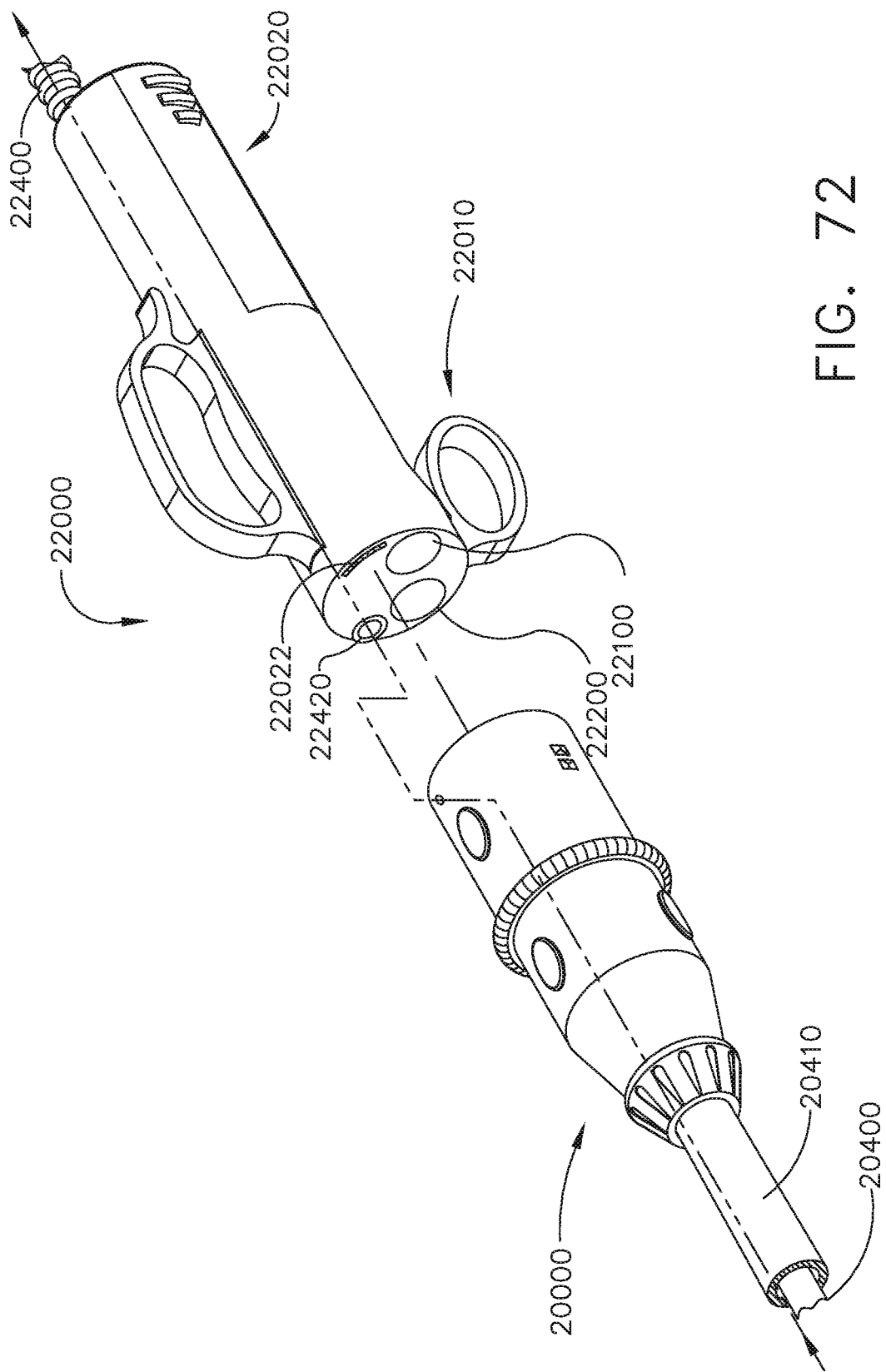
FIG. 72 is an exploded view of the handle assembly of FIG. 66B and the shaft assembly of FIG. 66.
Figure 73:
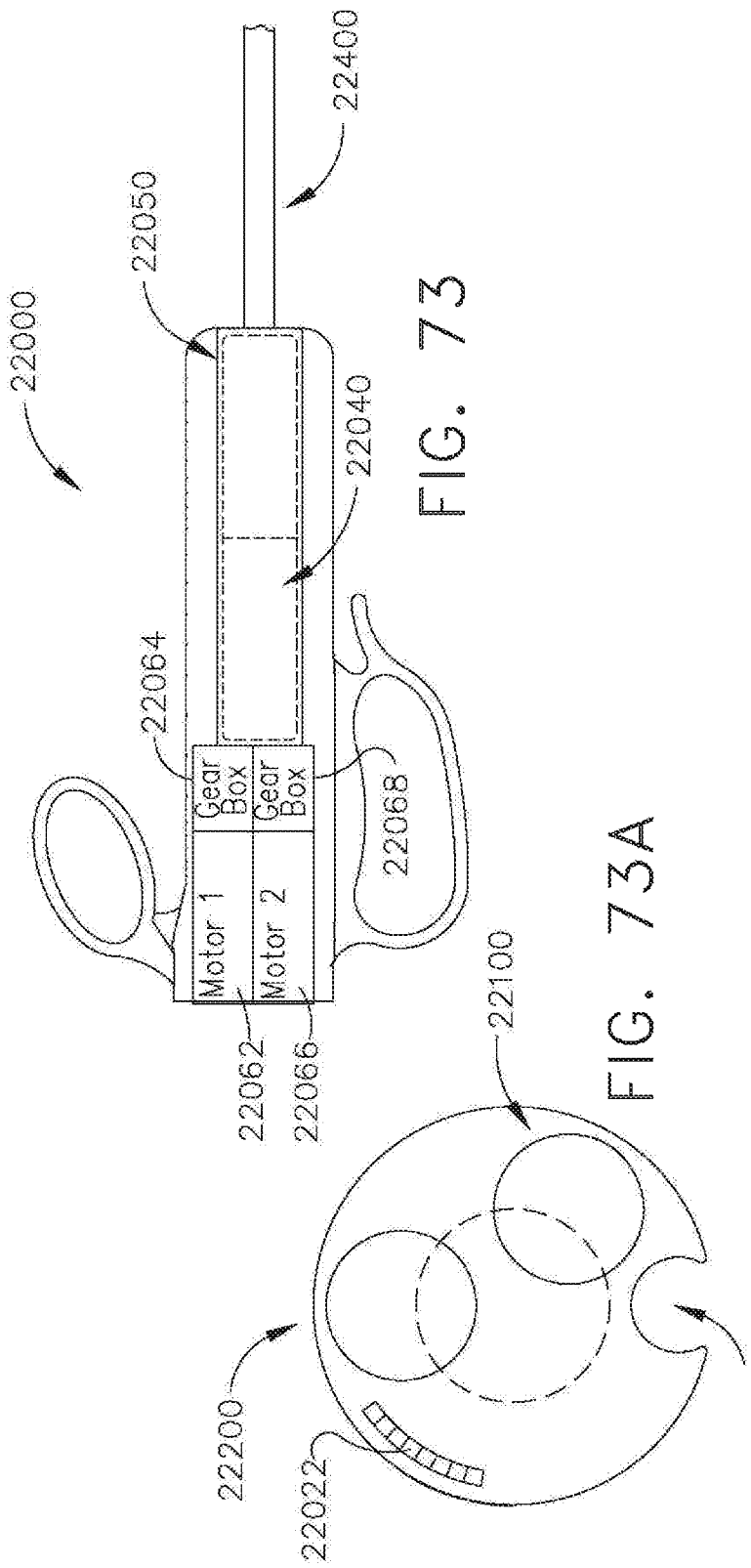
FIG. 73 depicts various aspects of the handle assembly of FIG. 72.

Referring to FIG. 72, the second handle assembly 22000 comprises a scissor grip configuration for use with a smoke evacuation tube 22400. The smoke evacuation tube 22400 is configured to fit inside a groove 22420 within the handle assembly 22000. Referring to FIG. 73, the handle assembly 22000 comprises a first motor 22062 and a second motor 22066 which are configured to power certain functions of the surgical instrument system as discussed above. Referring to FIG. 73B for example, the first motor 22062 is configured to power right and left articulation of the end effector, for example. The second motor 22066 is configured to power the jaw drive of the shaft assembly 20000. When the handle assembly 22000 is in use, the rotation of the end effector is performed manually by the clinician. The handle assembly 22000 further comprises a first speed reduction gear box 22064 and a second speed reduction gear box 22068 disposed within the handle assembly 22000. Still referring to FIG. 73, the insertable power module 22020 comprises at least two battery cells 22040 and 22050.

Figure 74:
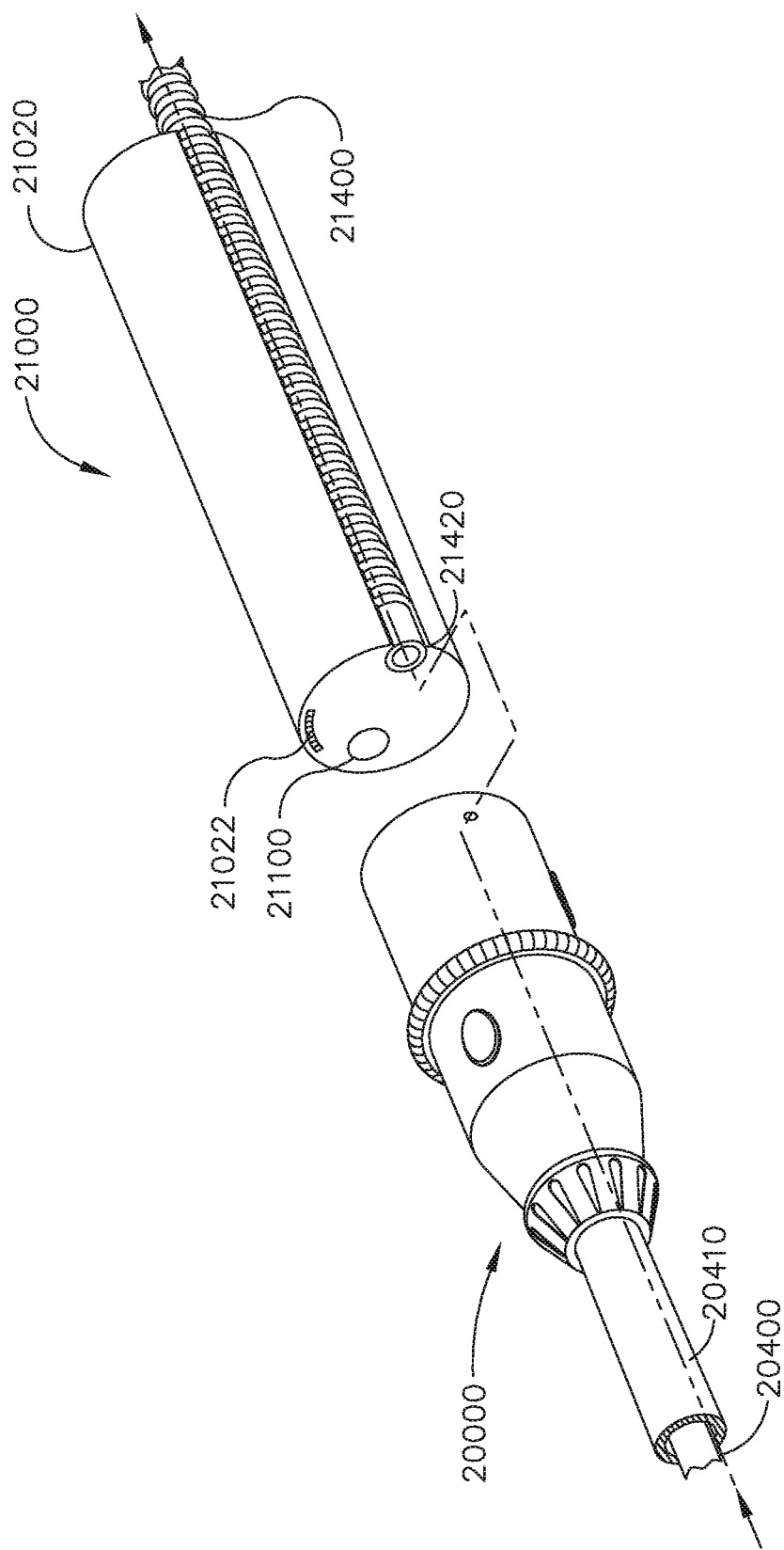
FIG. 74 is a partial exploded view the handle assembly of FIG. 66A and the shaft assembly of FIG. 66.
Figure 75:
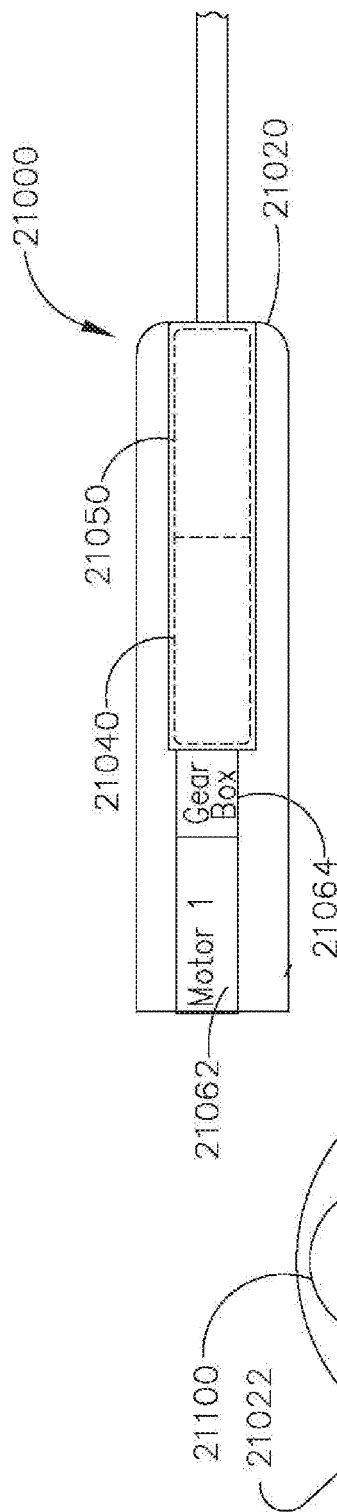
FIG. 75 depicts various aspects of the handle assembly of FIG. 74.

Referring to FIG. 74, the first handle assembly 21000 comprises a pencil grip configured for use with a smoke evacuation tube 21400. The smoke evacuation tube 21400 is configured to fit inside a groove 21420 within the handle assembly 21000. The shaft assembly 20000 further comprises a smoke evacuation tube 20410 which fits over the shaft 20400. Referring to FIG. 75, the handle assembly 21000 comprises a motor 21062 which is configured to power the right and left articulation of the end effector. When the handle assembly 21000 is in use, the rotation of the end effector is performed manually by the clinician, and certain functions such as a first actuation motion and a second actuation motion of the end effector are locked out as seen in FIG. 75B. The handle assembly 21000 further comprises a speed reduction gear box 21064 disposed within the handle assembly 21000. Still referring to FIG. 75, the insertable power module 21020 comprises at least two battery cells 21040 and 21050.

Figure 77:
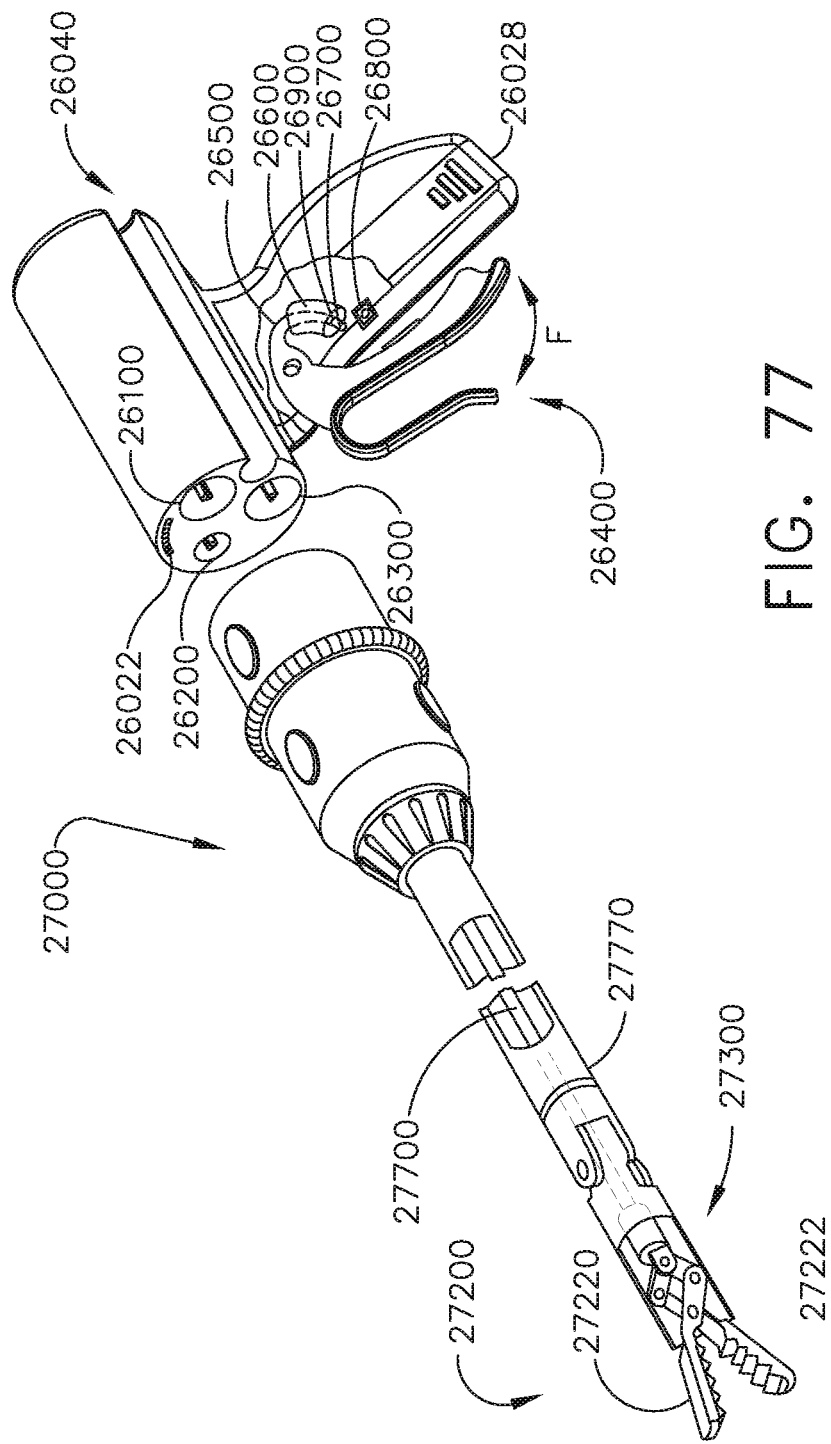
FIG. 77 illustrates a surgical system comprising a handle and a shaft assembly in accordance with at least one embodiment.

Referring to FIG. 77, various surgical instrument systems described herein comprise one or more feedback systems which are configured to alert the clinician as to the state of the surgical instrument system. The surgical instrument system comprises a handle assembly 26000 which includes a first drive 26100, a second drive 26200, and a third drive 26300 which are configured to permit drive systems within the handle assembly 26000 to be operably coupled to the drive systems of a shaft assembly 27000. The shaft assembly 27000 is similar to the shaft assembly 20000 in many respects. The handle assembly 26000 further comprises a plurality of electrical contacts 26022 configured to place the handle assembly 26000 in electrical communication with the shaft assembly 27000. The shaft assembly 27000 comprises an actuation rod 27700 extending within a shaft 27770, wherein the actuation rod 27700 is drivable by a drive system of the handle assembly 26000. The shaft assembly 27000 further comprises an end effector 27200 rotatably attached to the shaft 27770 about an articulation joint 27300. The end effector 27200 comprises a first jaw 27220 and a second jaw 27222 which are movable between open and closed positions in response to the motions of the actuation rod 27700. The handle assembly 26000 further comprises a curved trigger 26400 rotatably connected to the handle assembly 26000 which, as described in greater detail below, is used to control the drive system. The curved trigger 26400 comprises a curved trigger rod 26500 extending therefrom, as also discussed in greater detail below.

Figure 79:
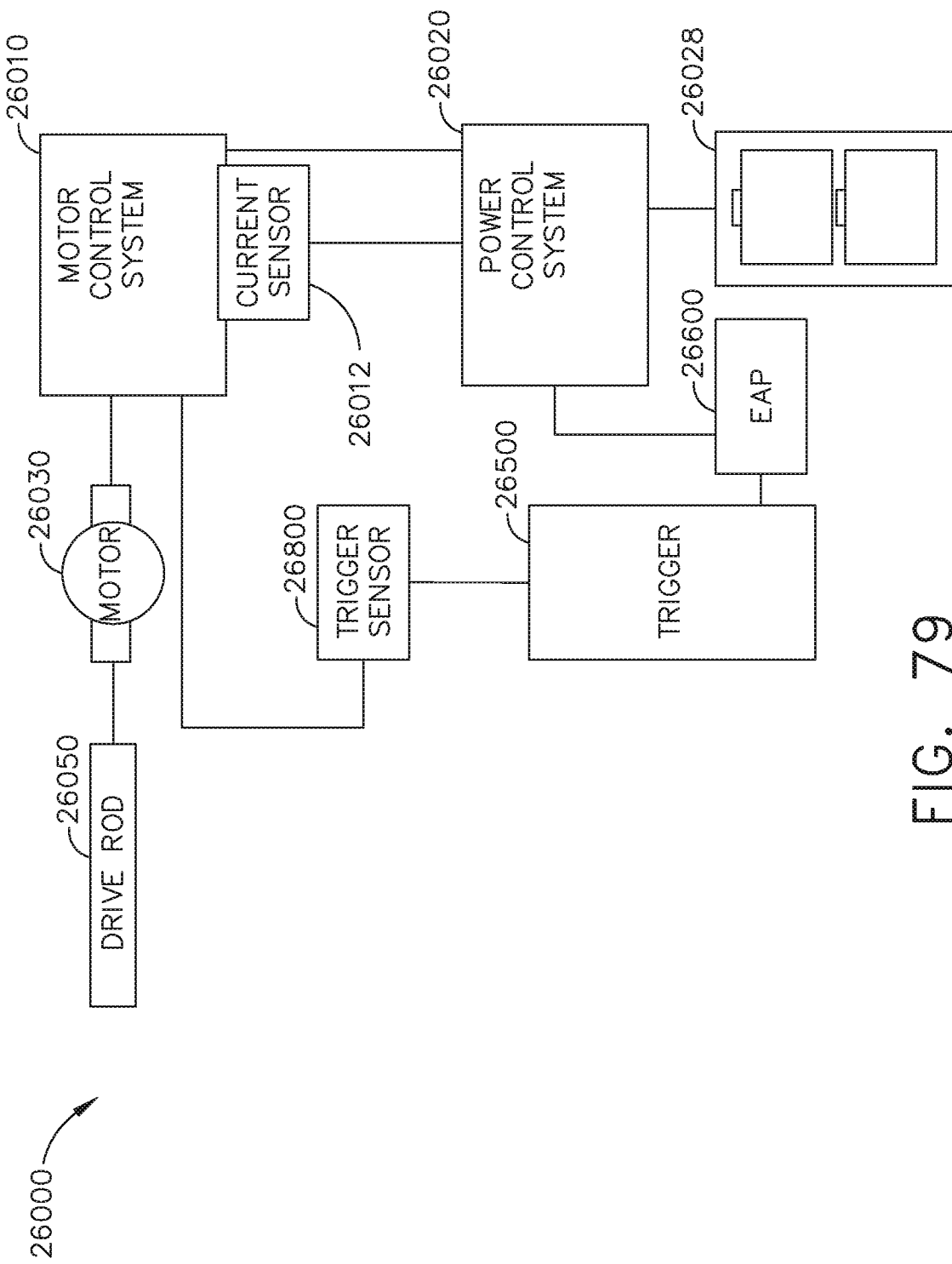
FIG. 79 is a block diagram illustrating various aspects of the handle and shaft assembly of FIG. 77 in accordance with at least one embodiment.

Referring to FIG. 79, further to the above, the handle assembly 26000 comprises a motor control system 26010 which is configured to run a motor 26030 configured to drive the drive system of the shaft assembly 27000 as mentioned above. The handle assembly 26000 further comprises a power module 26028 configured to supply power to the motor 26030 at the direction of a motor control system 26010. The handle assembly 26000 comprises a trigger sensor 26800 which is in communication with the motor control system 26010 and is configured to monitor the motion of the trigger 26400. The trigger sensor 26800 is configured to generate a voltage potential which is detectable by the motor control system 26010—the magnitude of which can be used to ascertain the actuation and/or position of the trigger 26400. In response to the signal from the trigger sensor 26800, the motor control system 26010 is configured to run the motor 26030 to drive the drive rod 26050. In various instances, the trigger sensor 26800 comprises a variable resistance sensor, for example, and the speed of the motor 26030 is responsive to the signal provided by the trigger sensor 26800.

As the drive rod 26050 is driven distally by the motor 26030, the drive rod 26050 experiences a force load. There is a wide range of acceptable force loads that the drive rod 26050 may experience during use. That said, such force loads can suggest certain information about the performance of the surgical system. For instance, force loads toward the top of the acceptable range can indicate that thick and/or dense tissue is captured within the end effector 27200 while force loads toward the bottom of the acceptable range can indicate that thin and/or less dense tissue is captured within the end effector 27200, for example. Without more, this information is not conveyed to the clinician as the trigger 26400 is not mechanically coupled to the drive rod 26050; rather, the trigger 26400 is electrically coupled to the motor 26030 via the motor control system 26010. Without this information, a clinician may not fully appreciate what is occurring within the surgical system. To this end, the surgical instrument system comprises means for detecting the force load experienced by the drive rod 26050 and communicating this information to the clinician. In at least one instance, the surgical instrument system comprises one or more load cells and/or strain gauges configured to detect the force load within the drive rod 26050. In addition to or in lieu of these mechanical detection systems, the motor control system 26010 is configured to monitor the current drawn by the electric motor 26030 during use and this information as a proxy for the force load being experienced by the drive rod 26050. Referring to FIG. 79, the handle assembly comprises a current sensor 26012 in communication with the power control system 26020, and/or the motor control system 26010, which is configured to monitor the amount of current drawn by the motor 26030. Discussed below are systems which can restore the clinician's sense for the loads being experienced within the drive system based on the load data supplied to the power control system 26020.

Referring to FIGS. 77A and 77B, the handle assembly 26000 further comprises an electroactive polymer (hereinafter "EAP") 26600 positioned within an aperture defined therein. The EAP 26600 is in signal communication with the power control system 26020 and is responsive to a voltage output provided by the power control system 26020. Referring primarily to FIG. 77B, the handle assembly 26000 comprises a curved cylinder 26900 which surrounds a portion of the curved trigger rod 26500 of the trigger 26400. More specifically, the curved trigger rod 26500 comprises a trigger bar 26550 extending through the curved cylinder 26900 positioned within the handle assembly 26000. The EAP 26600 is radially constrained by the sidewalls of the curved aperture defined in the handle 26000. The EAP 26600 reacts to the voltage potential applied thereto by the power control system 26020 and expands and contracts proportionately in size to the magnitude of the force being applied to the drive rod 26050. When the voltage applied to the EAP 26600 is increased, the walls of the handle assembly 26000 prevent the EAP 26600 from expanding. As a result, the EAP 26600 expands toward the trigger bar 26550 extending from the curved trigger 26500 and, thus, applies a compressive force to the trigger bar 26550. The compression force applied by the EAP 26600 on the trigger bar 26550 compresses the trigger bar 26550 which, in turn, creates a drag force between the EAP 26600 and the trigger bar 26550 when the trigger bar 26550 is moved by the trigger 26400. This drag force is felt by the clinician pulling the trigger 26400 and directly communicates the forces of the end effector 27200 to the clinician. As the magnitude of the load force experienced by the drive rod 26050 increases, the voltage applied to the EAP 26600 by the power control system 26020 increases, and the drag experienced by the trigger 26400 also increases. As the magnitude of the load force experienced by the drive rod 26050 decreases, the voltage applied to the EAP 26600 by the power control system 26020 decreases, and the drag experienced by the trigger 26400 also decreases. These relationships are linearly proportional; however, any proportional relationship could be used. Moreover, further to the above, the magnitude of the voltage potential applied to the EAP 26600 by the power control system 26020 is proportionately coupled to the motor current drawn by the motor 26030, the voltage supplied by the load cell circuit, and/or the voltage supplied by the strain gauge circuit, for example.

Turning to FIG. 78A, the EAP 26600 is shown in a non-energized state before the voltage potential is applied to the EAP 26600. As seen in FIG. 78A, there is space defined between the EAP 26600 within the curved cylinder 26900 and the curved trigger 26500. Referring to FIG. 78B, as the voltage potential is applied to the EAP 26600, the EAP 26600 constricts the trigger bar 26550 of the curved trigger 26500 which creates the drag force discussed above. The relationship between the forces on the end effector 27200 and/or the shaft 27770 and the compressive force on the curved trigger 26500 is further illustrated in FIGS. 80 and 81.

Figure 80:
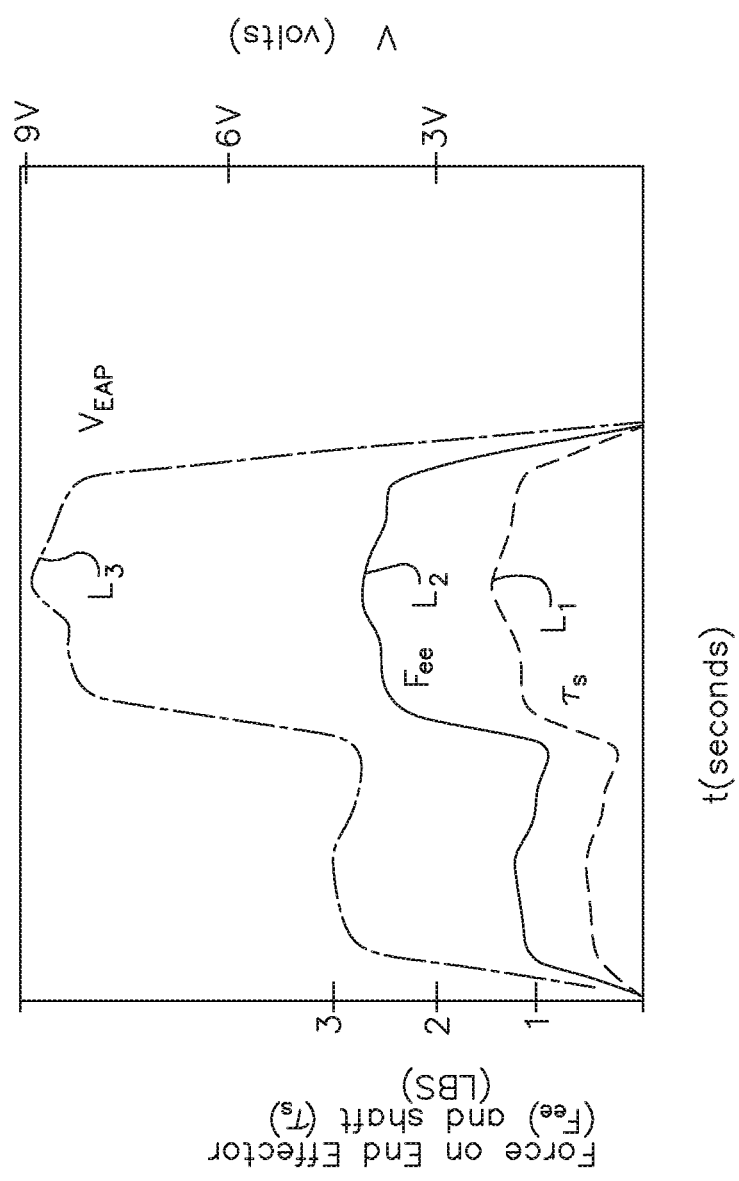
FIG. 80 is a graph illustrating the relationship between the forces experienced by an end effector and shaft of the surgical system of FIG. 77 and the voltage applied to the electroactive polymer over time.
Figure 81:
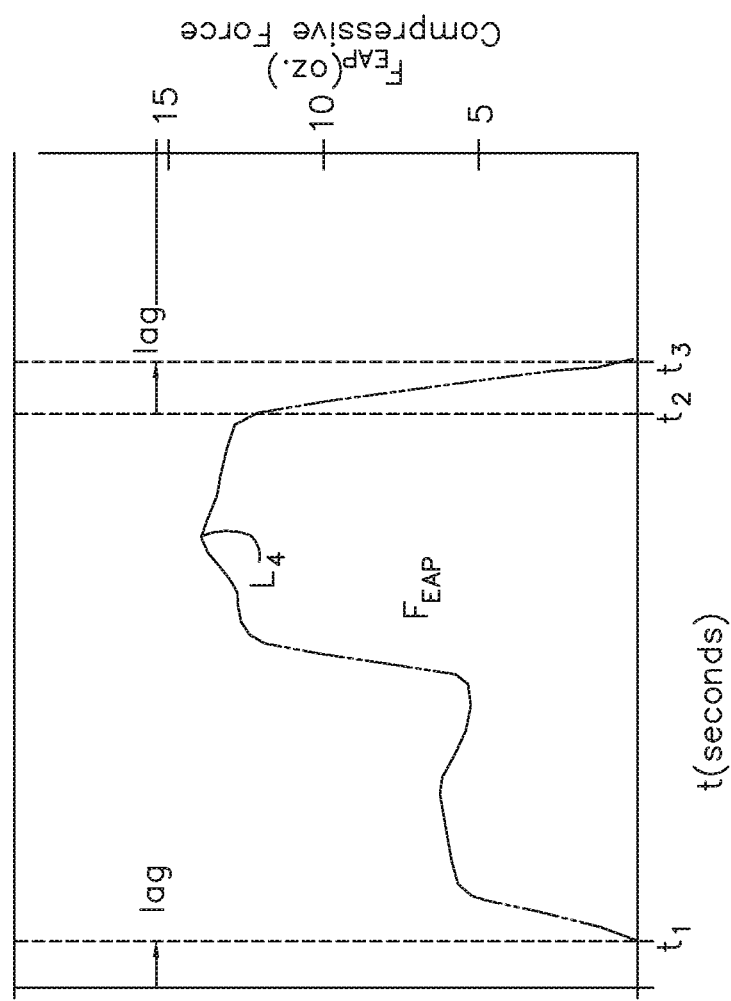
FIG. 81 is a graph illustrating the compressive force applied by the electroactive polymer over time.

Referring to FIG. 80, $L_1$ illustrates the torque experienced by the motor drive shaft. $L_2$ illustrates the load force experienced by the drive rod 26050. $L_3$ illustrates the voltage applied to the EAP 26600. The load force on the drive rod 26050 and the torque on the motor drive shaft are proportional to the amount of voltage applied to the EAP 26600. That is, as the load force and torque increase, as illustrated by way of $L_1$ and $L_2$ in FIG. 80, the voltage applied to the EAP 26600 also increases. Further to the above, there is a proportional relationship between the compressive force applied to the trigger 26500 and the voltage applied to the EAP 26600. As the voltage applied to the EAP 26600 increases, the drag force on the trigger 26500 increases, as discussed in greater detail above. The voltage applied to the EAP 26600 increases as a reaction to the amount of current flowing through the motor 26030 which is an indicator of the forces on the drive rod 26050 and the torques on the motor drive shaft. Referring to FIG. 81, $L_4$ illustrates the change in the voltage potential applied to the EAP 26600 over time.

Figure 86:
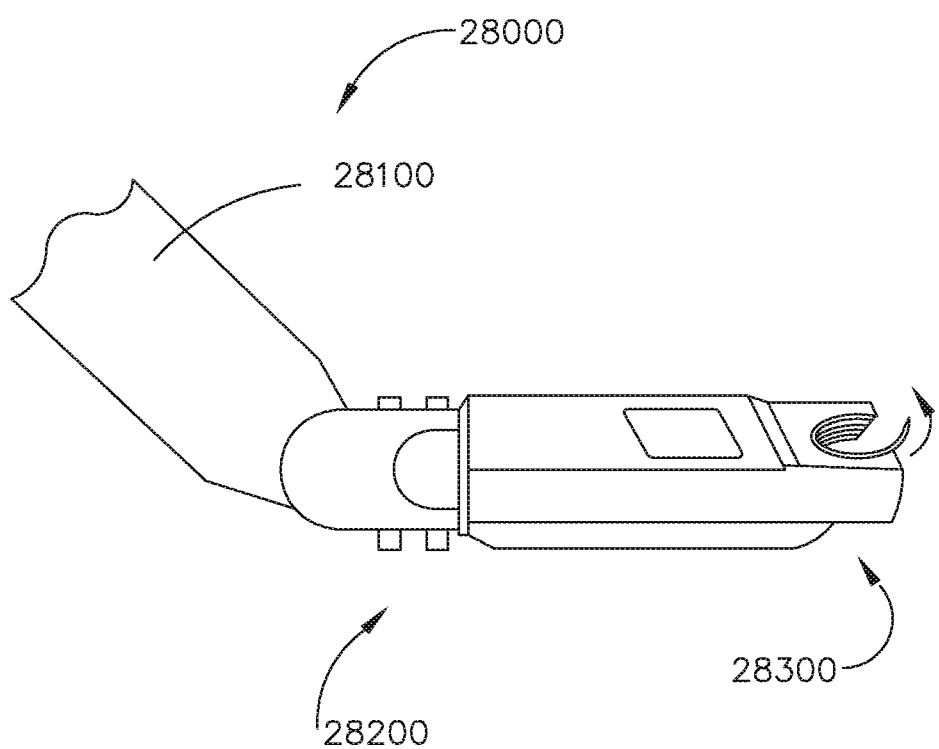
FIG. 86 is a partial perspective view of a distal attachment portion selectively attachable to the surgical system of FIG. 82.
Figure 87:
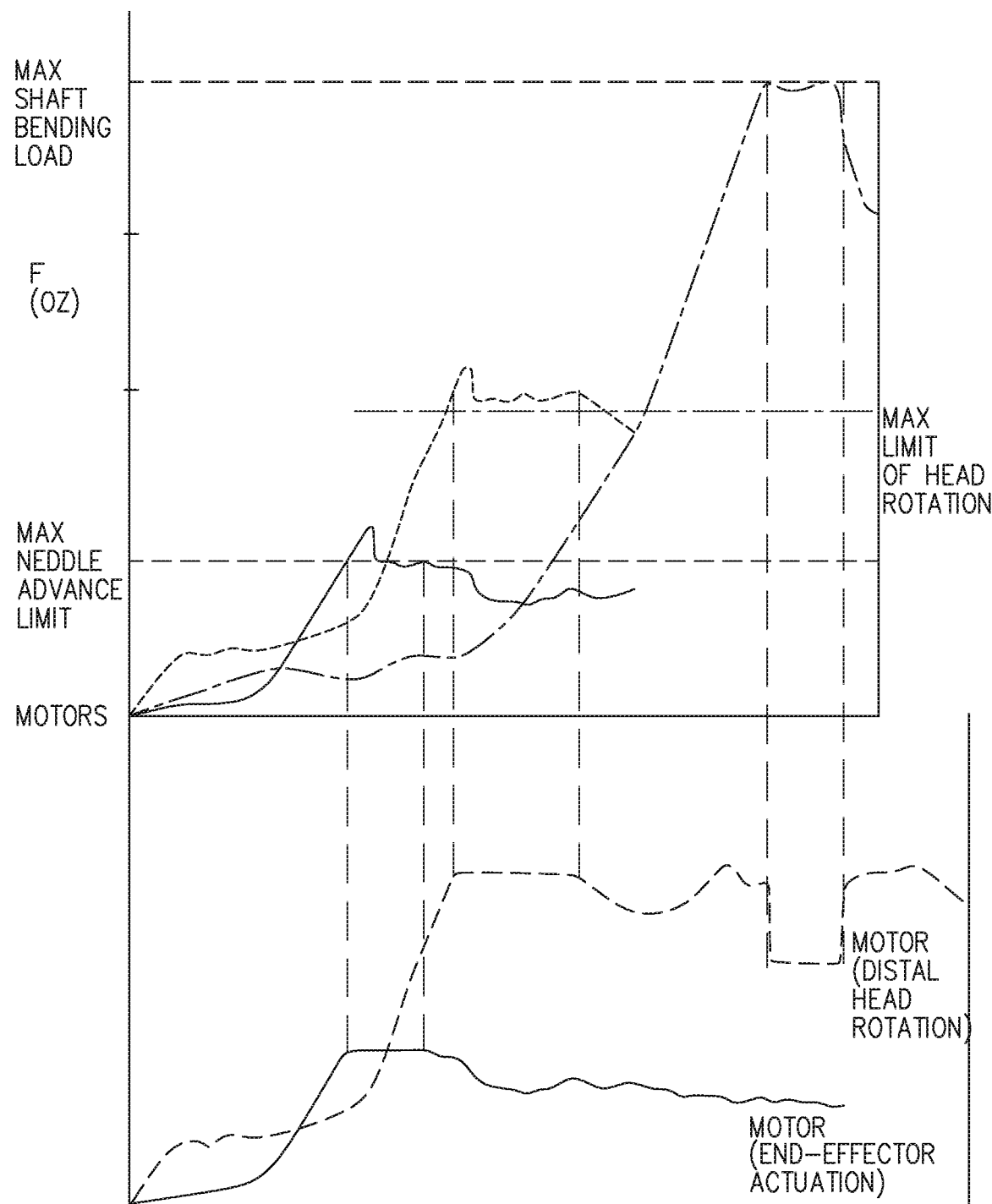
FIG. 87 is a graph illustrating possible drive force curves of the distal attachment portion of FIG. 86.

Turning to FIG. 86, additional feedback systems similar to those are configured for use with suturing devices. In particular, various surgical instrument systems are equipped with programs which are capable of measuring bending and axial loads applied to a suturing device shaft such as the shaft 28100 of the suturing device 28000 illustrated in FIG. 86. The suturing device 28000 comprises at least one motor configured to provide power to the suturing device during a surgical procedure. The suturing device 28000 further comprises a distal head 28300 rotatably connected to the shaft 28100 by an articulation joint 28200. The handle of the suturing device 28000 comprises a display which is configured to indicate a predefined proportion of loads to a user. The surgical instrument systems described herein are also configured for use with robotic surgical systems as well as cloud-based technology. Various applications disclosed which are incorporated by reference disclose situational awareness of an interactive HUB system which is configured to define various surgical steps. The devices, systems, and methods disclosed in the Subject Application can also be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated by reference in their entireties herein. Such surgical steps include providing the handle of the suturing device 28000 with and updated ration of the amount of the load being exerted as a portion of the suture stitch or knot tension. The tension is used by the user to create more standardization of the stitch to stitch tightness. Further uses are contemplated which include instructional uses for new users of the surgical instrument systems described herein. FIG. 87 further illustrates the relationship between the forces applied to the shaft 28100 and the distal head 28300 based on the different motors (e.g. the motor supplying power to perform an actuation motion of an end effector and the motor supplying power to perform a distal head rotation motion).

Figure 82:
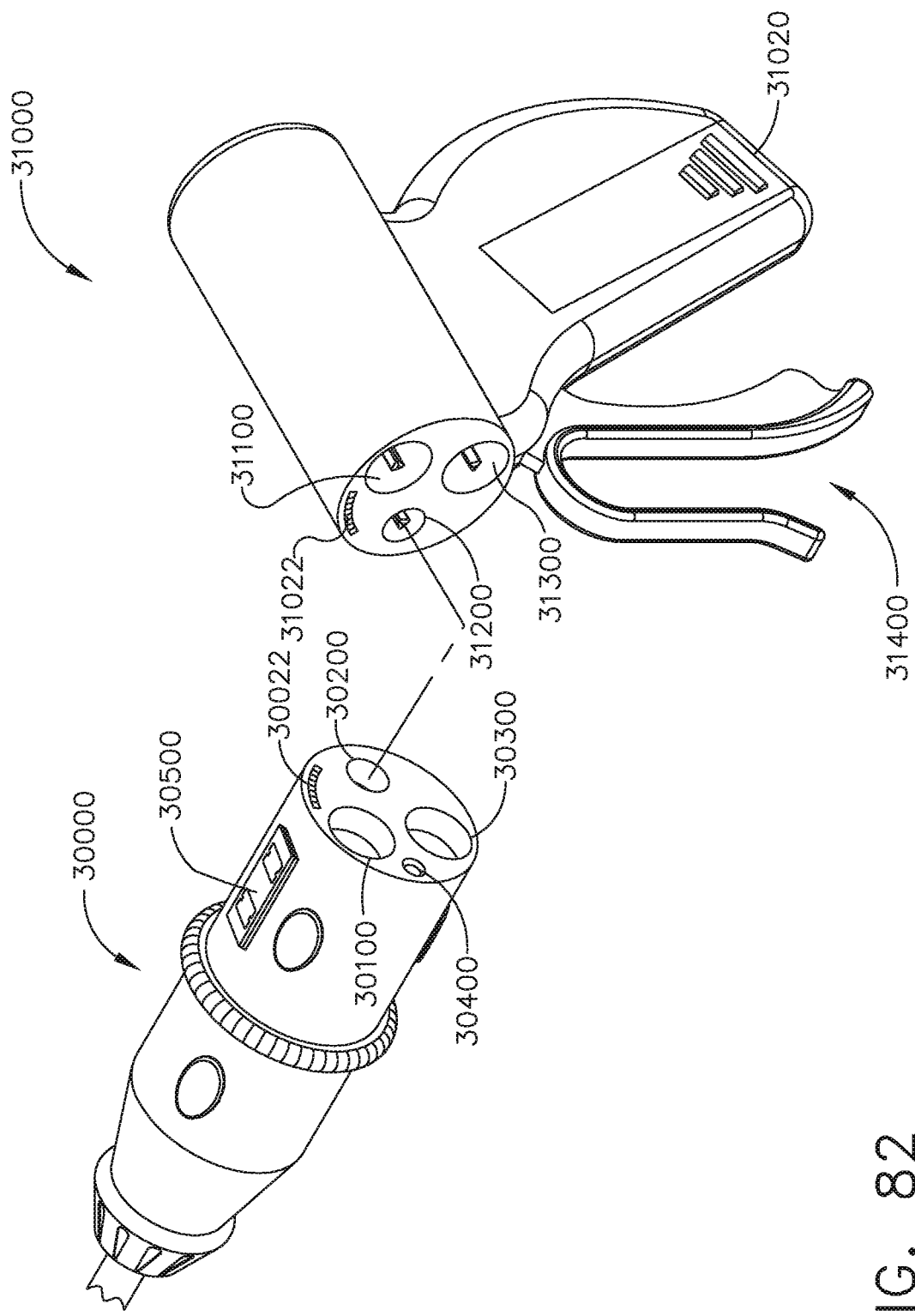
FIG. 82 illustrates a surgical system comprising a handle and a shaft assembly in accordance with at least one embodiment.

The surgical instrument systems discussed in greater detail above are configured for use with locking and safety mechanisms. The locking mechanisms comprise electrical sensing means configured to detect whether a modular attachment is in a usable or unusable state. The locking mechanisms further comprise electrical sensing means configured to detect whether a loadable mechanism is in a usable or unusable state. FIG. 82 illustrates an exemplary shaft assembly 30000 which is similar to the shaft assembly 20000. The locking mechanisms which will be discussed in greater detail below are configured for use with any of the surgical instrument systems described herein. The shaft assembly 30000 comprises a drive 30100, a second drive 30200, and a third drive 30300. The shaft assembly 30000 comprises a plurality of electrical contacts 30022 configured to place the shaft assembly 30000 in electrical communication with any of the handle assemblies described herein upon being attached thereto. The shaft assembly 30000 further comprises an on-board control circuit 30500. One example of a single use lockout 30400 is illustrated in FIG. 83. The single use lockout comprises a lock solenoid 30410, a lock spring 30420, and a lock pin 30430 as seen in FIGS. 84 and 85. The lock solenoid 30410 is energized upon power being supplied to the shaft assembly 30000.

In such instances, the lock solenoid 30410 is configured to push the lock pin 30430 outwardly into a locked position; however the lock pin 30430 is held in a staged position until the shaft assembly 30000 is detached from the handle. At such point, the lock spring 30420 can push the lock pin 30430 from its staged position into its locked position. In various instances, the shaft assembly 30000 comprises a lock shoulder 30440 configured to hold the lock pin 30430 in its locked position and prevent the lock pin 30430 from being reset. In such instances, the lock pin 30430 protrudes proximally from the housing of the shaft assembly 30000 which prevents the shaft assembly 30000 from being reattached to a handle. While the solenoid 30410 can drive the lock pin 30430 into its locked position in certain instances; in other instances, the solenoid 30410 holds the lock pin 30430 in its unlocked position until energized by the attachment of the shaft assembly 30000 to the handle wherein, at such point, the solenoid 30410 can release the lock pin 30430 such that the lock spring 30420 can move the lock pin 30430 into its staged position where the shaft assembly 30000 is attached to the handle and into its locked position once the shaft assembly 30000 is removed from the handle.

Other lockout mechanisms comprise a locking member which immobilizes a drive shaft of a surgical instrument if a modular shaft is attached to an incompatible handle can be used. For example, when a scissor grip handle is attached to an articulating clip applier shaft with distal head rotation, a lockout prevents distal head rotation drive because the scissor grip handle is used for only one drive system which is often the clip drive. In various instances, the lockout fixes the rotation of the distal head by engaging a lockout member into the drive shaft at the proximal end of the shaft. An additional locking mechanism for use with the surgical instrument systems described herein comprises a distal locking mechanism which prevents actuation motions of a clip applier or suturing device if a loaded cartridge is not in the jaws. A similar lockout mechanism comprises a distal locking mechanism which prevents actuation motions of a clip applier or suturing device if a spent cartridge is positioned in the jaws. The distal locking mechanism further comprises a means for sensing the engagement state of the distal lockout through a power system of the surgical instrument in order to prevent the activation of the motor or to instruct the motor to provide haptic vibration feedback that the handle assembly is incompatible with the attachment portion. Additional lockout assemblies include a modular lockout which prohibits or changes the operation of the motor if the shaft is detected to be in an unusable state.

Figure 88:
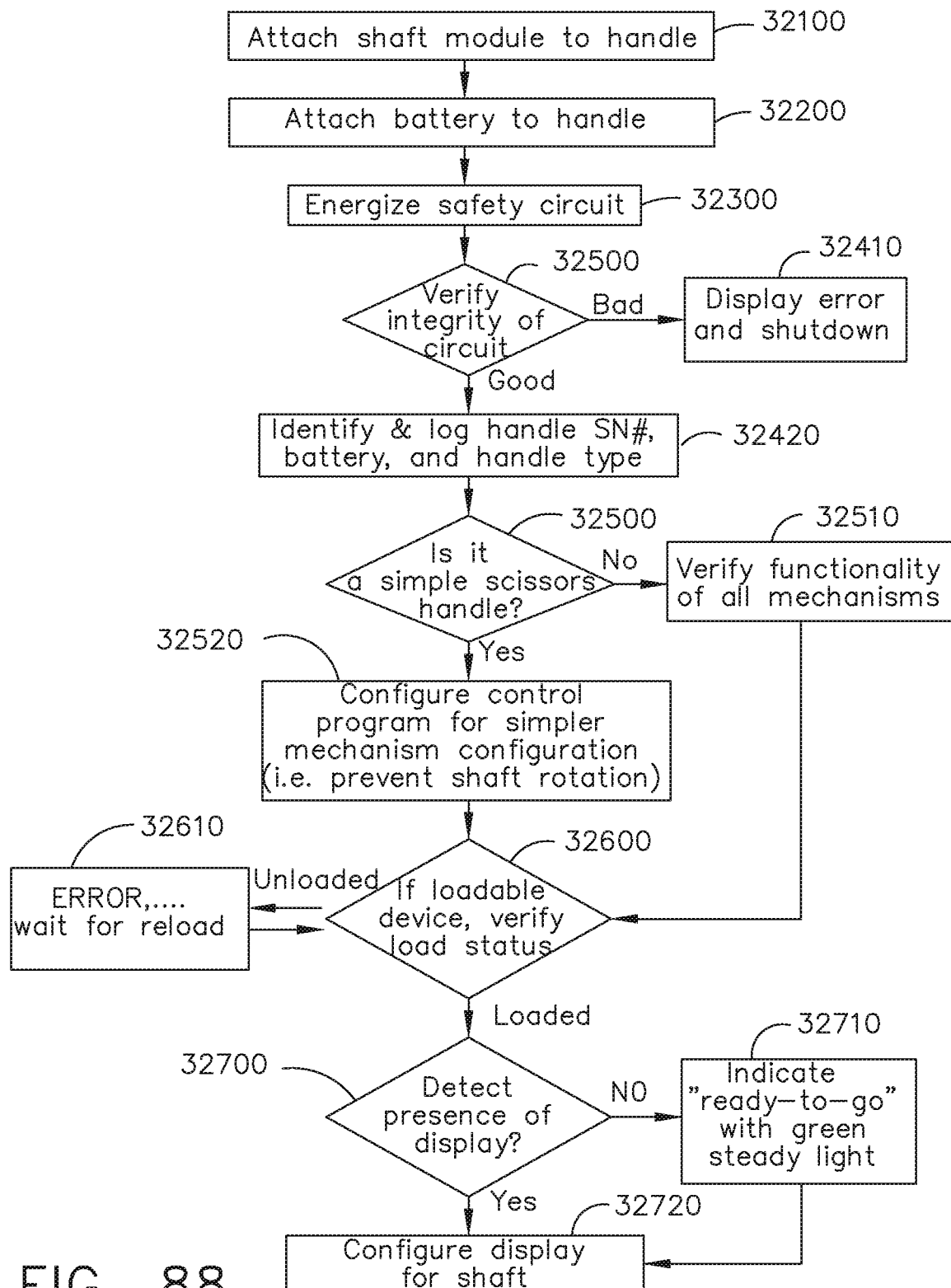
FIG. 88 is a flow chart illustrating a start-up process of a surgical instrument system in accordance with at least one embodiment.

Turning now to FIG. 88, an exemplary system for identifying the components of a surgical instrument system is disclosed. Step 32100 comprises attaching a shaft module to a handle assembly. Step 32200 comprises attaching a battery to a handle assembly. Step 32300 comprises energizing a safety circuit or watchdog processor wherein either is compatible with surgical instrument systems discussed in greater detail above. Decision 32400 comprises the verification of the integrity of the electrical circuit within the surgical instrument system. If the integrity of the circuit is bad, then the system is configured to display an error signal and shut down in step 32410. If the integrity of the circuit is good, the system is configured to identify and log a serial number associated with a handle assembly, battery, and/or shaft assembly, as illustrated in step 32420. Decision 32500 is configured to identify the type of handle assembly. For example, if the handle assembly is a simple scissors handle, the system is configured to control a program for a simple mechanism configuration which includes a shaft rotation lockout, as illustrated in step 32500. If the system determines that the handle assembly is not a simple scissors handle, then the system is configured to verify the functionality of all instrument mechanisms as illustrated in step 32510.

With further reference to FIG. 88, once the system identifies the type of handle assembly, the system is configured to determine whether the shaft assembly comprises a loadable portion in decision 32600, and is further configured to determine the status of the loadable portion. If the loadable portion is unloaded, the system is configured to generate an error message in step 32610 which indicates that the system is waiting for the loadable portion to be reloaded before a surgical procedure can continue. If the loadable portion is loaded, the system is configured detect whether a display unit is present during decision 32700. If the surgical instrument does not comprise a display unit, for example, the system is configured use a simple green light to indicate that the surgical instrument is ready for use. If the surgical instrument comprises a display unit, for example, the system configures the display unit for use with whatever shaft assembly is attached to the surgical instrument in step 32720. Additional systems comprise the identification of various compatible shaft assemblies and handle assemblies. Other systems comprise the identification of the status of a power module and the status of the power module. The verification processes described above are configured for use with any of the surgical instrument systems described herein. The surgical instruments, modules, systems, and methods disclosed herein can be used with the various disclosures incorporated by reference. The devices, systems, and methods disclosed in the Subject Application can also be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated by reference in their entireties herein.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118, 241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

EXAMPLES

Example 1

A surgical instrument system comprising a handle, and a shaft. The handle comprises a housing, a motor disposed within the handle, at least one control switch, and a motor-control processor in communication with the at least one control switch to control the motor, wherein the processor is not positioned in the handle. The surgical instrument system also comprises a disposable battery housing configured to be attached to the housing. The disposable battery housing comprises a disposable battery and a display unit.

Example 2

The surgical instrument system of Example 1, further comprising a controller.

Example 3

The surgical instrument system of Example 2, wherein the controller is located within the shaft.

Example 4

The surgical instrument system of Examples 2 or 3, wherein the controller comprises a control circuit configured to control the display unit on the disposable battery housing.

Example 5

The surgical instrument system of Examples 1, 2, 3, or 4, wherein the display unit on the disposable battery housing is touch screen capable.

Example 6

The surgical instrument system of Examples 1, 2, 3, 4, or 5, wherein the display unit comprises a multi-color display configured to indicate at least one function of the surgical instrument system to a user.

Example 7

A surgical instrument comprising a handle, a shaft, and a disposable power module. The handle comprises a housing, a motor located in the handle, and at least one control switch. The disposable power module comprises a disposable battery and a display unit. The surgical instrument also comprises a motor-control processor in communication with the at least one control switch to control the motor, wherein the processor is positioned in at least one of the shaft and the disposable power module.

Example 8

The surgical instrument of Example 7, further comprising a controller.

Example 9

The surgical instrument of Example 8, wherein the controller is located within the shaft.

Example 10

The surgical instrument of Examples 8 or 9, wherein the controller comprises a control circuit configured to control the display unit on the disposable power module.

Example 11

The surgical instrument of Examples 7, 8, 9, or 10, wherein the display unit on the disposable power module is touch screen capable.

Example 12

The surgical instrument of Examples 7, 8, 9, 10, or 11, wherein the display unit comprises a multi-color display configured to indicate at least one function of the surgical instrument.

Example 13

A surgical instrument comprising a housing, a handle attached to the housing, an end effector, a shaft, and a disposable battery comprising a multi-color display unit. The handle comprises a motor and at least one control switch. The shaft comprises a controller located within the shaft, wherein the controller is configured to control at least one function of the end effector.

Example 14

The surgical instrument of Example 13, wherein the controller comprises a control circuit configured to control the display unit on the disposable battery.

Example 15

The surgical instrument of Examples 13 or 14, wherein the end effector further comprises at least one sensor.

Example 16

The surgical instrument of Examples 13, 14, or 15, wherein the display unit on the disposable battery is touch screen capable.

Example 17

A sterilizable surgical instrument system comprising a handle assembly, a shaft attached to the distal end of the handle assembly, a disposable battery assembly, and an end effector attached to a distal end of the shaft. The handle assembly comprises a motor and at least one control switch. The shaft comprises a controller located within the shaft. The disposable battery assembly comprises a disposable battery and a display unit.

Example 18

The surgical instrument system of Example 17, wherein the controller comprises a control circuit configured to control the display unit on the disposable battery.

Example 19

The surgical instrument system of Examples 17 or 18, wherein the end effector further comprises at least one sensor.

Example 20

The surgical instrument system of Examples 17, 18, or 19, wherein the display unit on the disposable battery housing is touch screen capable.

Example 21

The surgical instrument system of Examples 17, 18, 19, or 20, wherein the display unit comprises a multi-color display configured to indicate at least one function of the surgical instrument system.

Example 22

A surgical instrument system comprising a handle assembly comprising a drive system including an electric motor, a battery comprising a first battery cell and a second battery cell, a first shaft assembly attachable to the handle assembly, and a second shaft assembly attachable to the handle assembly. The drive system utilizes a first power load from the battery to operate the first shaft assembly and the first power load is supplied by the first battery cell and not the second battery cell. The drive system comprises a second power load to operate the second shaft assembly which is different than the second power load and the second power load is supplied by the first battery cell and the second battery cell.

Example 23

A surgical instrument system comprising a handle assembly and a battery. The handle assembly comprises a housing and a drive system including an electric motor. The battery is insertable into the housing in a first orientation and a second orientation. The battery is configured to supply a first maximum power to the drive system when the battery is in the first orientation, wherein the battery is configured to supply a second maximum power when the battery is in the second orientation, and wherein the first orientation is different than the second orientation.

Example 24

The surgical instrument system of Example 23, wherein the battery is inserted into the handle in the first orientation when a first shaft assembly is attached to the handle, and wherein the battery is inserted into the second orientation when a second shaft assembly is attached to the handle.

Example 25

A surgical instrument system comprising a drive module comprising a drive module housing and a shaft assembly attachable to the drive module housing. The surgical instrument system also comprises a drive system and a battery attachable to the drive module housing. The drive system comprises an electric motor positioned in the drive module housing, a drive shaft in the shaft assembly which is operably couplable with the electric motor when the shaft assembly is attached to the drive module, and a control circuit including a microprocessor, wherein the microprocessor is positioned in the shaft assembly. The battery comprises a battery housing, at least one battery cell in the battery housing configured to supply power to the drive system when the battery is attached to the drive module housing, and a display in communication with control circuit when the battery is attached to the drive module housing.

Example 26

The surgical instrument system of Example 25, wherein the display comprises electrophoretic media.

Example 27

The surgical instrument system of Example 25, wherein the display comprises an active matrix backplane.

Example 28

The surgical instrument system of Example 27, wherein the active matrix backplane comprises an amorphous silicon semiconductor.

Example 29

The surgical instrument system of Example 27, wherein the active matrix backplane comprises a polythiophene semiconductor.

Example 30

The surgical instrument system of Example 27, wherein the display comprises an electrochromic display.

Example 31

The surgical instrument system of Example 27, wherein the display comprises a liquid-crystal display.

Example 32

The surgical instrument system of Example 27, wherein the display comprises a thin-film transistor liquid-crystal display.

Example 33

A surgical instrument system comprising a drive module comprising a drive module housing and a battery attachable to the drive module housing. The battery comprises a battery housing, at least one battery cell in the battery housing configured to supply power to the drive system when the battery is attached to the drive module housing, and a display in communication with a control circuit when the battery is attached to the drive module housing. The surgical instrument system also comprises a drive system, an electric motor positioned in the drive module housing and a control circuit including a microprocessor, wherein the microprocessor is positioned in the battery housing.

Example 34

The surgical instrument system of Example 33, wherein the display comprises electrophoretic media.

Example 35

The surgical instrument system of Example 33, wherein the display comprises an active matrix backplane.

Example 36

The surgical instrument system of Example 35, wherein the active matrix backplane comprises an amorphous silicon semiconductor.

Example 37

The surgical instrument system of Example 35, wherein the active matrix backplane comprises a polythiophene semiconductor.

Example 38

The surgical instrument system of Example 33, wherein the display comprises an electrochromic display.

Example 39

The surgical instrument system of Example 33, wherein the display comprises a liquid-crystal display.

Example 40

The surgical instrument system of Example 33, wherein the display comprises a thin-film transistor liquid-crystal display.

Example 41

A surgical instrument system, comprising a drive module comprising a drive module housing and a battery attachable to the drive module housing. The battery comprises a battery housing, at least one battery cell in the battery housing configured to supply power to the drive system when the battery is attached to the drive module housing, and a display in communication with a control circuit when the battery is attached to the drive module housing. The surgical instrument system also comprises a drive system, an electric motor positioned in the drive module housing, and a control system including a microprocessor, wherein the microprocessor is not positioned in the drive module.

Example 42

The surgical instrument system of Example 41, wherein the control system comprises at least one input on the drive module.

Example 43

The surgical instrument system of Example 41, wherein the control system comprises at least one switch on the drive module.

Example 44

A surgical instrument system comprising a drive module comprising a housing and an electric motor and a battery selectively attachable to the drive module. The battery comprises a housing comprising a connector configured to releasably connect the battery to the drive module, at least one battery cell, and an electronic display.

Example 45

The surgical instrument system of Example 44, wherein the display comprises electrophoretic media.

Example 46

The surgical instrument system of Example 44, wherein the display comprises an active matrix backplane.

Example 47

The surgical instrument system of Example 46, wherein the active matrix backplane comprises an amorphous silicon semiconductor.

Example 48

The surgical instrument system of Example 46, wherein the active matrix backplane comprises a polythiophene semiconductor.

Example 49

The surgical instrument system of Example 44, wherein the display comprises an electrochromic display.

Example 50

The surgical instrument system of Example 44, wherein the display comprises a liquid-crystal display.

Example 51

The surgical instrument system of Example 44, wherein the display comprises a thin-film transistor liquid-crystal display.

Example 52

A handle for use with a surgical instrument system, wherein the handle comprises a drive module and a sealed battery module. The a drive module comprises a housing and a sealed motor module removably positionable with the housing. The sealed motor module comprises a liquid-tight barrier, at least one electrical input extending through the liquid-tight barrier, and a rotatable output extending through the liquid-tight barrier. The sealed battery module comprises a housing comprising a connector configured to attach the sealed battery module to the drive module, a liquid-tight battery barrier, and at least one electrical output extending through the liquid-tight battery barrier.

Example 53

A surgical instrument system comprising a drive module comprising a drive system including an electric motor, a shaft attachable to the drive module, wherein the shaft comprises an end effector configured to treat the tissue of a patient. The surgical instrument system also comprises a battery attachable to the drive module and at least one electronic display system on at least one of the shaft and the battery. The surgical instrument system also comprises a control circuit comprising a processor, wherein the control circuit is configured to control the drive system, and wherein the control circuit is configured to communicate with the at least one electronic display system, and a power switch configured to place the battery in communication with the control circuit when the power switch is placed in an operational configuration, wherein the processor is configured to interrogate the shaft and the battery to assess the number of electronic display systems in the surgical instrument system.

Example 54

The surgical instrument system of Example 53, wherein the processor is configured to interrogate the shaft and the battery to assess the number of electronic display systems in the surgical instrument system when the power switch is moved into the operational configuration.

Example 55

The surgical instrument system of Example 53, wherein the processor is configured to interrogate the shaft and the battery to assess the number of electronic display systems in the surgical instrument system when the battery is assembled to the surgical instrument system.

Example 56

A surgical instrument system comprising a drive module comprising a drive system including an electric motor, a shaft attachable to the drive module, wherein the shaft comprises an end effector configured to treat the tissue of a patient, and a battery attachable to the drive module. The surgical instrument system also comprises at least one electronic display system on at least one of the drive module, the shaft, and the battery and a control circuit comprising a processor, wherein the control circuit is configured to control the drive system, wherein the control circuit is configured to communicate with the at least one electronic display system, and wherein the processor is configured to interrogate the shaft and the battery to assess the number of electronic display systems in the surgical instrument system.

Example 57

The surgical instrument system of Example 56, wherein the processor is configured to interrogate the drive module, the shaft, and the battery to assess the number of electronic display systems in the surgical instrument system when the battery is assembled to the surgical instrument system.

Example 58

A surgical instrument system comprising a drive module comprising a drive system including an electric motor, a shaft attachable to the drive module, wherein the shaft comprises an end effector configured to treat the tissue of a patient, and a battery attachable to the drive module. The surgical instrument system also comprises a control circuit comprising a processor, wherein the control circuit is configured to control the drive system during an operational sequence, and wherein the battery is configured to supply power to the control circuit during an initiation sequence, and a communications circuit configured to communicate with and receive data from an off-board control system during the initiation sequence, wherein the communications circuit is in communication with the control circuit, wherein the control circuit is configured to receive the data from the communications circuit, and wherein the control circuit is configured to modify the operational sequence using the data.

Example 59

The surgical instrument system of Example 58, wherein the initiation sequence is initiated by the assembly of the battery to the drive module.

Example 60

The surgical instrument system of Example 58, further comprising a switch configurable in an operational configuration, wherein the initiation sequence is initiated by placing the switch in the operational configuration.

Example 61

The surgical instrument system of Example 58, wherein the communications circuit comprises a wireless signal transmitter and a wireless signal receiver.

Example 62

The surgical instrument system of Example 58, wherein the operational sequence comprises an algorithm, and wherein the control circuit modifies the algorithm when modifying the operational sequence.

Example 63

The surgical instrument system of Example 62, wherein the control circuit deactivates a function of the surgical instrument system when modifying the algorithm.

Example 64

The surgical instrument system of Example 58, wherein the initiation sequence comprises an algorithm, and wherein the control circuit deactivates a function of the surgical instrument system when modifying the algorithm.

Example 65

A surgical instrument system, comprising a surgical instrument configured to perform at least three functions of an end effector, a first motor, a second motor, a third motor, and a first handle comprising a first number of controls, wherein each control corresponds to one of the three functions of the end effector. The surgical instrument system also comprises a second handle comprising a second number of controls and a shaft assembly attachable to the first handle and the second handle, wherein the shaft assembly is attachable to the first handle in a first orientation to engage one of the motors, and wherein the shaft assembly is attachable to the second handle in a second orientation to engage a different one of the motors, and wherein the surgical instrument system is configured to perform a different end effector function in the first orientation and the second orientation, and wherein certain end effector functions are locked out based on which motor is engaged in each orientation.

Example 66

The surgical instrument system of Example 65, wherein the first number of controls is different than the second number of controls.

Example 67

The surgical instrument system of Example 65 or 66, wherein the first orientation is different than the second orientation.

Example 68

The surgical instrument system of Examples 65, 66, or 67, wherein the first orientation prevents the surgical instrument from performing at least one function of the end effector.

Example 69

The surgical instrument system of Examples 65, 66, 67, or 68, wherein the second orientation prevents the surgical instrument from performing at least one function of the end effector.

Example 70

A surgical instrument system comprising a surgical instrument configured to perform at least three functions of an end effector and a motor operable in at least three states. The surgical instrument system also comprises a first handle comprising a first number of controls, wherein each control corresponds to a function of the end effector, a motor drive, and a first attachment portion, wherein the first attachment portion connects to the surgical instrument in a first orientation in order to enable a first set of end effector functions. The surgical instrument system also comprises a second handle comprising a second number of controls. The surgical instrument system also comprises a shaft assembly attachable to the first handle and the second handle, wherein the shaft assembly is attachable to the first handle in a first orientation, and wherein the shaft assembly is attachable to the second handle in a second orientation. The surgical instrument system also comprises an end effector attachable to the shaft assembly.

Example 71

The surgical instrument system of Example 70, wherein the first number of controls is different than the second number of controls.

Example 72

The surgical instrument system of Examples 70 or 71, wherein the first orientation is different than the second orientation.

Example 73

The surgical instrument system of Examples 70, 71, or 72, wherein the first orientation prevents the surgical instrument from performing at least one function of the end effector.

Example 74

The surgical instrument system of Examples 70, 71, 72, or 73, wherein the second orientation prevents the surgical instrument from performing at least one function of the end effector.

Example 75

A surgical instrument system comprising a surgical instrument configured to perform at least three functions of an end effector, a first motor, a second motor, and a third motor. The surgical instrument system further comprises a first handle comprising a first number of controls, wherein each control corresponds to an end effector function, a second handle comprising a second number of controls, and a third handle comprising a third number of controls. The surgical instrument system also comprises a shaft assembly attachable to each of the handles, wherein the shaft assembly is attachable to each of the handles in a different orientation, and wherein the surgical instrument system is configured to perform a different end effector function in each different orientation, and wherein certain end effector functions are locked out based on which motor is engaged in each orientation.

Example 76

A surgical instrument system, comprising a surgical instrument configured to perform at least three functions of an end effector. The surgical instrument system also comprises a first handle comprising a first number of controls, wherein each control corresponds to an end effector function, a second handle comprising a second number of controls, and a third handle comprising a third number of controls. The surgical instrument system also comprises a shaft assembly attachable to each of the handles, wherein the shaft assembly is attachable to each of the handles in a different orientation, and wherein the surgical instrument system is configured to perform a different end effector function in each different orientation, and wherein certain end effector functions are locked out based on which handle is attached to the end effector.

Example 77

A surgical instrument system comprising a first shaft assembly configured to perform a first function, a second function, and a third function and a second shaft assembly configured to perform the first function and the second function, but not the third function. The surgical instrument system also comprises a handle, wherein the first shaft assembly and the second shaft assembly are selectively and separately attachable to the handle, wherein the handle comprises a first electric motor configured to drive the first function, a second electric motor configured to drive the second function, a third electric motor configured to drive the third function when the first shaft assembly is attached to the handle, and a lockout configured to prevent the third electric motor from being operated when the second shaft assembly is attached to the handle.

Example 78

The surgical instrument system of Example 77, wherein the first shaft assembly is attachable to the handle in a first orientation and the second shaft assembly is attachable to the handle in a second orientation, and wherein the first orientation is different than the second orientation.

Example 79

A surgical instrument system comprising a first shaft assembly configured to perform a first function, a second function, and a third function, a second shaft assembly configured to perform the first function and the second function, and a handle, wherein the first shaft assembly and the second shaft assembly are selectively, and separately, attachable to the handle. The handle comprises a first control configured to control the first function, a second control configured to control the second function, and a third control configured to control the third function when the first shaft assembly is attached to the handle, and locking means for locking out the third control when the second shaft assembly is attached to the handle.

Example 80

The surgical instrument system of Example 79, wherein the handle further comprises a microprocessor comprising input gates and output gates, wherein the first control, the second control, and the third control are in signal communication with the microprocessor via the input gates, and wherein the locking means comprises deactivating the input gate associated with the third control when the second shaft assembly is attached to the handle.

Example 81

The surgical instrument system of Example 79, wherein the handle further comprises a microprocessor comprising input gates and output gates, wherein the shaft assembly is in signal communication with the microprocessor via the output gates, and wherein the locking means comprises deactivating the output gate associated with the third function when the second shaft assembly is attached to the handle.

Example 82

A surgical instrument system comprising a shaft assembly configured to perform a first function, a second function, and a third function. The surgical instrument system also comprises a first handle comprising a first control for controlling the first function, a second control for controlling the second function, and a third control for controlling the third function when the shaft assembly is operably coupled to the first handle. The surgical instrument system also comprises a second handle comprising a first control for controlling the first function, a second control for controlling the second function, and a lockout for preventing the shaft assembly from performing the third function when the shaft assembly is operably coupled to the second handle.

Example 83

The surgical instrument system of Example 82, wherein the shaft assembly is attachable to the first handle in a first orientation and the handle in a second orientation, and wherein the first orientation is different than the second orientation.

Example 84

The surgical instrument system of Examples 82 or 83, wherein the shaft assembly comprises a longitudinal axis, an end effector, and an articulation joint, wherein the end effector comprises a jaw movable between an open position and a closed position, wherein the first function comprises moving the jaw, wherein the second function comprises articulating the end effector about the articulation joint, and wherein the third function comprises rotating the shaft assembly about the longitudinal axis.

Example 85

A surgical instrument system comprising a shaft assembly configured to perform a first function, a second function, and a third function. The surgical instrument system also comprises a first handle comprising a first motor for driving the first function, a second motor for driving the second function, and a third motor for driving the third function when the shaft assembly is operably coupled to the first handle. The surgical instrument system also comprises a second handle comprising a first motor for driving the first function, a second motor for driving the second function, and a lockout for preventing the shaft assembly from performing the third function when the shaft assembly is operably coupled to the second handle.

Example 86

The surgical instrument system of Example 85, wherein the shaft assembly is attachable to the first handle in a first orientation and the second handle in a second orientation, and wherein the first orientation is different than the second orientation.

Example 87

The surgical instrument system of Examples 85 or 86, wherein the shaft assembly comprises a longitudinal axis, an end effector, and an articulation joint, wherein the end effector comprises a jaw movable between an open position and a closed position, wherein the first function comprises moving the jaw, wherein the second function comprises articulating the end effector about the articulation joint, and wherein the third function comprises rotating the shaft assembly about the longitudinal axis.

Example 88

The surgical instrument system of Examples 85, 86, or 87, wherein the shaft assembly comprises a first drive system for performing the first function, a second drive system for performing the second function, and a third drive system for performing the third function, and wherein the lockout comprises a locking element configured to engage the third drive and prevent the third drive from driving the third function.

Example 89

A surgical instrument system comprising a shaft assembly, a first handle, and a second handle. The shaft assembly is configured to perform a first function, a second function, and a third function and comprises a first drive configured to perform the first function, a second drive configured to perform the second function, a third drive configured to perform the third function, and a lockout, wherein the lockout is selectively switchable between an unlocked configuration and a locked configuration, wherein the lockout prevents the shaft assembly from performing the third function when the lockout is in the locked configuration, and wherein the lockout permits the shaft assembly to perform the third function when the lockout is in the unlocked configuration. The first handle comprises a first motor for driving the first function, a second motor for driving the second function, a third motor for driving the third function when the shaft assembly is operably coupled to the first handle, and a control system configured to place the lockout in the unlocked configuration. The second handle comprises a first motor for driving the first function, a second motor for driving the second function, and a control system configured to place the lockout in the locked configuration.

Example 90

A surgical instrument system comprising a first handle comprising a first gripping portion and a first shaft lock, and a second handle comprising a second gripping portion and a second shaft lock. The surgical instrument system also comprises a shaft assembly selectively, and separately, attachable to the first handle and the second handle, wherein the first shaft lock holds the shaft assembly to the first handle in a first orientation when the shaft assembly is attached to the first handle, wherein the second shaft lock holds shaft assembly to the second handle in a second orientation when the shaft assembly is attached to the second handle, and wherein the first orientation is different than the second orientation.

Example 91

The surgical instrument system of Example 90, wherein the shaft assembly comprises a housing and an array of lock apertures extending around the housing, and wherein the first shaft lock and the second shaft lock engage the lock apertures.

Example 92

The surgical instrument system of Example 91, wherein the first shaft lock comprises an arcuate ridge including a first end and a second end, a first lock shoulder at the first end, wherein the first lock shoulder is positionable in a lock aperture, and a second lock shoulder at the second end, wherein the second lock shoulder is positionable in a lock aperture.

Example 93

The surgical instrument system of Examples 91 or 92, wherein the second shaft lock comprises an arcuate ridge including a first end and a second end, a first lock shoulder at the first end, wherein the first lock shoulder is positionable in a lock aperture, and a second lock shoulder at the second end, wherein the second lock shoulder is positionable in a lock aperture.

Example 94

A surgical instrument system comprising a shaft assembly comprising three drive functions, a first handle, and a second handle. The shaft assembly is selectively attachable to the first handle, wherein the first handle comprises a drive system configured to drive all three drive functions of the shaft assembly when the shaft assembly is attached to the first handle. The shaft assembly is selectively attachable to the second handle, wherein the second handle comprises a drive system configured to drive less than all three functions of the shaft assembly when the shaft assembly is attached to the second handle.

Example 95

The surgical instrument system of Example 94, wherein the shaft assembly comprises a first drive system configured to perform a first drive function of the three drive functions, a second drive system configured to perform a second drive function of the three drive functions, and a third drive system configured to perform a third drive function of the three drive functions.

Example 96

The surgical instrument system of Example 95, wherein the second handle comprises a housing and a lock projection, and wherein the lock projection is configured to engage the second drive system to prevent the operation of the second drive system when the shaft assembly is assembled to the second handle.

Example 97

The surgical instrument system of Example 96, wherein the second handle comprises another lock projection, and wherein the another lock projection is configured to engage the third drive system to prevent the operation of the third drive system when the shaft assembly is assembled to the second handle.

Example 98

The surgical instrument system of Examples 96 or 97, wherein the lock projection extends from the housing.

Example 99

The surgical instrument system of Examples 96, 97, or 98, wherein the lock projection is integrally formed with the housing.

Example 100

The surgical instrument system of Examples 94, 95, 96, 97, 98, or 99, wherein the first handle comprises a pistol grip and the second handle comprises a scissors grip.

Example 101

The surgical instrument system of Examples 94, 95, 96, 97, 98, or 99, wherein the first handle comprises a pistol grip and the second handle comprises a pencil grip.

Example 102

The surgical instrument system of Examples 94, 95, 96, 97, 98, 99, 100, or 101, wherein the shaft assembly comprises a clip applier.

Example 103

A surgical instrument system comprising a shaft assembly comprising three drive functions requiring power above a power threshold, a first handle, and a second handle. The shaft assembly is selectively attachable to the first handle, wherein the first handle comprises a drive system configured to drive all three drive functions of the shaft assembly at or above the power threshold when the shaft assembly is attached to the first handle. The shaft assembly is selectively attachable to the second handle, wherein the second handle comprises a drive system configured to drive less than all three functions of the shaft assembly at or above the power threshold when the shaft assembly is attached to the second handle, and wherein the second handle is configured to disable the drive functions receiving power below the power threshold.

Example 104

A surgical instrument system comprising a handle assembly. The handle assembly comprises an actuation trigger comprising a curved proximal portion and a curved cylinder surrounding the curved proximal portion of the actuation trigger, wherein the curved cylinder comprises at least one electroactive polymer. The surgical instrument system also comprises a motor, a shaft attached to the handle assembly, an end effector attached to a distal end of the shaft, an actuation rod configured to transmit an actuation force to the end effector, and a sensor system configured to detect the magnitude of the actuation force, wherein the electroactive polymer is responsive to the actuation force, and wherein the electroactive polymer provides tactile feedback to a user of the surgical instrument system by applying forces to the actuation trigger.

Example 105

The surgical instrument system of Example 104, wherein the forces applied to the actuation trigger by the electroactive polymer are proportional to the actuation force.

Example 106

The surgical instrument system of Example 105, wherein the forces applied to the actuation trigger by the electroactive polymer are directly proportional to the actuation force.

Example 107

The surgical instrument system of Example 106, wherein the forces applied to the actuation trigger by the electroactive polymer are linearly proportional to the actuation force.

Example 108

The surgical instrument system of Example 106, wherein the forces applied to the actuation trigger by the electroactive polymer are non-linearly proportional to the actuation force.

Example 109

The surgical instrument system of Examples 104, 105, 106, 107, or 108, further comprising a power source and a control system in communication with the sensor system, the curved cylinder, and the power source, wherein the control system is configured to apply a voltage potential to the curved cylinder in response to the actuation force detected by the sensor system.

Example 110

The surgical instrument system of Example 109, wherein the voltage potential is proportional to the actuation force.

Example 111

The surgical instrument system of Example 110, wherein the voltage potential is linearly proportional to the actuation force.

Example 112

The surgical instrument system of Examples 109, 110, or 111, wherein the curved cylinder expands in proportion to the magnitude of the voltage potential applied to the curved cylinder.

Example 113

The surgical instrument system of Examples 104, 105, 106, 107, 108, 109, 110, 111, or 112, wherein the handle comprises a cavity comprising a sidewall, wherein the curved cylinder is positioned in the cavity, and wherein the sidewall prevents the expansion of the curved cylinder when a voltage potential is applied to the curved cylinder such that a gripping force is applied to the curved proximal portion.

Example 114

The surgical instrument of Examples 104, 105, 106, 107, 108, 109, 110, 111, 112, or 113, wherein the end effector comprises a crimping mechanism configured to apply a clip to the tissue of a patient, and wherein the crimping mechanism is driven by the actuation rod.

Example 115

The surgical instrument of Examples 104, 105, 106, 107, 108, 109, 110, 111, 112, or 113, wherein the end effector is configured to apply staples to the tissue of a patient, and wherein the staples are pushed out of a staple cartridge by the actuation rod.

Example 116

The surgical instrument of Examples 104, 105, 106, 107, 108, 109, 110, 111, 112, or 113, wherein the end effector comprises a needle configured to apply a suture to the tissue of a patient, and wherein the needle is driven by the actuation rod.

Example 117

The surgical instrument of Examples 104, 105, 106, 107, 108, 109, 110, 111, 112, or 113, wherein the end effector comprises jaws configured to grasp tissue, and wherein the actuation rod closes the jaws.

Example 118

The surgical instrument of Examples 104, 105, 106, 107, 108, 109, 110, 111, 112, or 113, wherein the end effector comprises jaws configured to dissect tissue, and wherein the actuation rod opens the jaws.

Example 119

The surgical instrument of Examples 104, 105, 106, 107, 108, 109, 110, 111, 112, or 113, wherein the end effector is configured to ablate tissue with electrical energy.

Example 120

The surgical instrument of Examples 104, 105, 106, 107, 108, 109, 110, 111, 112, or 113, wherein the end effector comprises at least one electrode and is configured to apply RF energy to tissue.

Example 121

The surgical instrument of Examples 104, 105, 106, 107, 108, 109, 110, 111, 112, or 113, wherein the handle comprises a transducer, and wherein the end effector is configured to apply vibrational energy to tissue.

Example 122

The surgical instrument of Examples 104, 105, 106, 107, 108, 109, 110, 111, 112, or 113, wherein the end effector comprises a knife configured to cut tissue, and wherein the knife is pushed distally by the actuation rod.

Example 123

A surgical instrument system comprising a handle assembly wherein the handle assembly comprises an actuation trigger and a cylinder surrounding a portion of the actuation trigger, wherein the cylinder comprises at least one electroactive polymer. The surgical instrument system also comprises a power source, a motor, an actuation member configured to transmit an actuation force, a sensor system configured to detect the magnitude of the actuation force, and a control system in communication with the sensor system and the cylinder, wherein the control system is configured to apply a voltage potential from the power source to the cylinder in response to the actuation force, and wherein the cylinder applies a gripping force to the actuation trigger indicative of the magnitude of the actuation force.

Example 124

A surgical instrument system comprising a handle assembly wherein the handle assembly comprises an actuation trigger and an electroactive polymer actuator. The surgical instrument system also comprises a voltage source, an electric motor, an actuation member configured to transmit an actuation force, a sensor system configured to detect the magnitude of the actuation force, and a control system in communication with the sensor system and the electroactive polymer actuator, wherein the control system is configured to apply a voltage potential from the voltage source to the electroactive polymer actuator in response to the actuation force, and wherein the electroactive polymer actuator applies a gripping force to the actuation trigger which is proportional to the magnitude of the actuation force.

Example 125

A surgical instrument system comprising a handle assembly wherein the handle assembly comprises an actuation trigger and an electroactive polymer actuator.

The surgical instrument system also comprises a power source, an electric motor configured to draw an electrical current from the power source, an actuation member operably coupled to the electric motor which is configured to transmit an actuation force, a sensor system configured to detect the magnitude of the electrical current, and a control system in communication with the sensor system and the electroactive polymer actuator, wherein the control system is configured to apply a voltage potential to the electroactive polymer actuator in response to the electrical current, and wherein the electroactive polymer actuator applies a gripping force to the actuation trigger which is proportional to the magnitude of the electrical current.

Example 126

A robotic surgical instrument system comprising a surgical robot and a console configured to control the surgical robot. The console comprises an actuation trigger and an electroactive polymer actuator. The robotic surgical instrument system comprises a power source, an electric motor configured to draw an electrical current from the power source, an actuation member operably coupled to the electric motor which is configured to transmit an actuation force, a sensor system configured to detect the magnitude of the electrical current, and a control system in communication with the sensor system and the electroactive polymer actuator, wherein the control system is configured to apply a voltage potential to the electroactive polymer actuator in response to the electrical current, and wherein the electroactive polymer actuator applies a gripping force to the actuation trigger which is proportional to the magnitude of the electrical current.

Example 127

A robotic surgical instrument system comprising a surgical robot and a console configured to control the surgical robot. The console comprises an actuation trigger and an electroactive polymer actuator. The robotic surgical instrument system also comprises a voltage source, an electric motor, an actuation member configured to transmit an actuation force, a sensor system configured to detect the magnitude of the actuation force, and a control system in communication with the sensor system and the electroactive polymer actuator, wherein the control system is configured to apply a voltage potential from the voltage source to the electroactive polymer actuator in response to the actuation force, and wherein the electroactive polymer actuator applies a gripping force to the actuation trigger which is proportional to the magnitude of the actuation force.

Example 128

A surgical instrument system comprising a handle assembly which comprises an actuation trigger and an electroactive polymer actuator. The surgical instrument system also comprises a voltage source, an electric motor, an actuation member configured to transmit an actuation force, a sensor system configured to detect the magnitude of the actuation force, and a control system in communication with the sensor system and the electroactive polymer actuator, wherein the control system is configured to apply a voltage potential from the voltage source to the electroactive polymer actuator in response to the actuation force, and wherein the electroactive polymer actuator applies a friction force to the actuation trigger which is proportional to the magnitude of the actuation force.

Example 129

A surgical instrument system comprising a handle assembly which comprises an actuation trigger and an electroactive polymer actuator. The surgical instrument system also comprises a voltage source, an electric motor, an actuation member configured to transmit an actuation force, a sensor system configured to detect the magnitude of the actuation force, and a control system in communication with the sensor system and the electroactive polymer actuator, wherein the control system is configured to apply a voltage potential from the voltage source to the electroactive polymer actuator in response to the actuation force, and wherein the electroactive polymer actuator applies a resistance force to the actuation trigger which is proportional to the magnitude of the actuation force.

Example 130

A surgical instrument system comprising a handle assembly which comprises an actuation trigger and an electroactive polymer actuator. The surgical instrument system also comprises a power source, an electric motor configured to draw an electrical current from the power source, an actuation member operably coupled to the electric motor which is configured to transmit an actuation force, a sensor system configured to detect the magnitude of the electrical current, and a control system in communication with the sensor system and the electroactive polymer actuator, wherein the control system is configured to apply a voltage potential to the electroactive polymer actuator in response to the electrical current, and wherein the electroactive polymer actuator applies a resistance force to the actuation trigger which is proportional to the magnitude of the electrical current.

Example 131

A surgical instrument system comprising a surgical instrument and a housing which comprises a handle assembly, at least one motor, and a drive shaft. The surgical instrument system also comprises a shaft assembly configured to be attached to a distal end of the housing, wherein the shaft assembly comprises a control circuit and a locking mechanism, wherein the locking mechanism prevents movement of the drive shaft if the shaft assembly is not attached to the surgical instrument in an orientation which enables operation of the surgical instrument, and wherein the locking mechanism further comprises sensing means for determining whether the locking mechanism is actively engaged and an end effector attachable to a distal end of the shaft assembly.

Example 132

The surgical instrument system of Example 131, wherein the control circuit further comprises at least one safety feature.

Example 133

The surgical instrument system of Examples 131 or 132, wherein the locking mechanism is configured to prevent the actuation of the surgical instrument.

Example 134

The surgical instrument system of Examples 131, 132, or 133, wherein the locking mechanism is configured to prevent activation of the motor.

Example 135

The surgical instrument system of Examples 131, 132, 133, or 134, wherein the locking mechanism prevents movement of the shaft assembly when the shaft assembly is not attached to the housing.

Example 136

The surgical instrument system of Examples 131, 132, 133, 134, or 135, wherein the locking mechanism is configured to detect whether the end effector is in a usable state.

Example 137

The surgical instrument system of Examples 131, 132, 133, 134, 135, or 136, wherein the sensing means is configured to enable haptic feedback of the motor in order to alert a user of a state of the surgical instrument.

Example 138

A surgical instrument comprising a housing which comprises a handle assembly, at least one motor, and a drive shaft. The surgical instrument also comprises a shaft assembly configured to be attached to a distal end of the housing, wherein the shaft assembly comprises a control circuit, and a locking mechanism, wherein the locking mechanism prevents movement of the drive shaft if the shaft assembly is not attached to the surgical instrument in an orientation which enables operation of the surgical instrument. The surgical instrument also comprises an end effector attachable to a distal end of the shaft assembly.

Example 139

The surgical instrument of Example 138, wherein the control circuit further comprises at least one safety feature.

Example 140

The surgical instrument of Examples 138 or 139, wherein the locking mechanism is configured to prevent the actuation of the surgical instrument.

Example 141

The surgical instrument of Examples 138, 139, or 140, wherein the locking mechanism is configured to prevent activation of the motor.

Example 142

The surgical instrument of Examples 138, 139, 140, or 141, wherein the locking mechanism prevents movement of the shaft assembly when the shaft assembly is not attached to the housing.

Example 143

The surgical instrument of Examples 138, 139, 140, 141, or 142, wherein the locking mechanism is configured to detect whether the end effector is in a usable state.

Example 144

The surgical instrument of Examples 138, 139, 140, 141, 142, or 143, wherein the sensing means is configured to enable haptic feedback of the motor in order to alert a user of a state of the surgical instrument.

Example 145

A surgical assembly comprising a surgical instrument and a housing which comprises a handle, at least one motor, and a drive shaft assembly. The surgical assembly also comprises a shaft assembly configured to be attached to a distal end of the housing, wherein the shaft assembly comprises a control circuit and a locking mechanism, wherein the locking mechanism prevents movement of the drive shaft if the shaft assembly is not attached to the surgical instrument in an orientation which enables operation of the surgical instrument and wherein the locking mechanism further comprises an electrical sensor for determining whether the locking mechanism is actively engaged within the surgical instrument. The surgical assembly also comprises an end effector attachable to a distal end of the shaft assembly.

Example 146

The surgical assembly of Example 145, wherein the control circuit further comprises at least one safety feature.

Example 147

The surgical assembly of Examples 145 or 146, wherein the locking mechanism is configured to prevent the actuation of the surgical instrument.

Example 148

The surgical assembly of Examples 145, 146, or 147, wherein the locking mechanism is configured to prevent activation of the at least one motor.

Example 149

The surgical assembly of Examples 145, 146, 147, or 148, wherein the locking mechanism prevents movement of the shaft assembly when the shaft assembly is not attached to the housing.

Example 150

The surgical assembly of Examples 145, 146, 147, 148, or 149, wherein the locking mechanism is configured to detect whether the end effector is in a usable state.

Example 151

The surgical assembly of Examples 145, 146, 147, 148, 149, or 150, wherein the electrical sensor is configured to enable haptic feedback of the motor in order to alert a user of a state of the surgical instrument.

Example 152

A surgical instrument configured to apply clips to the tissue of a patient, comprising an end effector which comprises a replaceable clip cartridge comprising a plurality of clips removably stored therein, an actuator configured to deploy the clips, and a lockout configurable in a locked configuration and an unlocked configuration, wherein the lockout is in the locked configuration when the replaceable clip cartridge is not in the end effector, wherein the lockout prevents the actuator from being actuated when the lockout is in the locked configuration, wherein the lockout is in the unlocked configuration when the replaceable clip cartridge is positioned in the end effector, and wherein the lockout permits the actuator to deploy the clips when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the locked configuration.

Example 153

A surgical instrument configured to apply clips to the tissue of a patient, comprising an end effector which comprises a replaceable clip cartridge comprising a plurality of clips removably stored therein, an actuator configured to deploy the clips, a lockout configurable in a locked configuration and an unlocked configuration, wherein the lockout is in the locked configuration when the replaceable clip cartridge is not in the end effector, wherein the lockout prevents the actuator from being actuated when the lockout is in the locked configuration, wherein the lockout is in the unlocked configuration when the replaceable clip cartridge is positioned in the end effector, and wherein the lockout permits the actuator to deploy the clips when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit provides haptic feedback to the user of the surgical instrument when the sensing system determines that the lockout is in the locked configuration.

Example 154

A surgical instrument configured to apply clips to the tissue of a patient comprising an end effector which comprises a replaceable clip cartridge comprising a plurality of clips removably stored therein, an actuator configured to deploy the clips, and a lockout configurable in a locked configuration and an unlocked configuration, wherein the lockout is in the locked configuration when the replaceable clip cartridge has been completely expended, wherein the lockout prevents the actuator from being actuated when the lockout is in the locked configuration, wherein the lockout is in the unlocked configuration when the replaceable clip cartridge is positioned in the end effector and has not been completely expended, and wherein the lockout permits the actuator to deploy the clips when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the locked configuration.

Example 155

A surgical instrument system configured to apply clips to the tissue of a patient comprising a shaft assembly which comprises a longitudinal axis, an end effector, an articulation joint rotatably connecting the end effector to the shaft, a rotation drive shaft configured to rotate the shaft about the longitudinal axis, a clip firing drive shaft configured to deploy the clips, and an articulation drive shaft configured to articulate the end effector relative to the shaft. The end effector comprises a clip cartridge comprising a plurality of clips removably stored therein and an actuator configured to deploy the clips. The surgical instrument system also comprises a first handle which comprises a rotation drive system configured to drive the rotation drive shaft, a clip firing drive system configured to drive the clip firing drive shaft, and an articulation drive system configured to drive the articulation drive shaft. The surgical instrument system also comprises a second handle comprising a rotation drive lockout configured to lock the rotation drive shaft, a clip firing drive system configured to drive the clip firing drive shaft, and an articulation drive lockout configured to lock the articulation drive shaft.

Example 156

A surgical instrument configured to apply a suture to the tissue of a patient, comprising an end effector which comprises a replaceable suture cartridge comprising a suture removably stored therein, an actuator configured to deploy the suture, and a lockout configurable in a locked configuration and an unlocked configuration, wherein the lockout is in the locked configuration when the replaceable suture cartridge is not in the end effector, wherein the lockout prevents the actuator from being actuated when the lockout is in the locked configuration, wherein the lockout is in the unlocked configuration when the replaceable suture cartridge is positioned in the end effector, and wherein the lockout permits the actuator to deploy the suture when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the locked configuration.

Example 157

A surgical instrument configured to apply a suture to the tissue of a patient comprising an end effector which comprises a replaceable suture cartridge comprising a suture removably stored therein, an actuator configured to deploy the suture, a lockout configurable in a locked configuration and an unlocked configuration, wherein the lockout is in the locked configuration when the replaceable suture cartridge is not in the end effector, wherein the lockout prevents the actuator from being actuated when the lockout is in the locked configuration, wherein the lockout is in the unlocked configuration when the replaceable suture cartridge is positioned in the end effector, and wherein the lockout permits the actuator to deploy the suture when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit provides haptic feedback to the user of the surgical instrument when the sensing system determines that the lockout is in the locked configuration.

Example 158

A surgical instrument configured to apply a suture to the tissue of a patient comprising an end effector which comprises a replaceable suture cartridge comprising a suture removably stored therein, an actuator configured to deploy the suture, a lockout configurable in a locked configuration and an unlocked configuration, wherein the lockout is in the locked configuration when the replaceable suture cartridge has been completely expended, wherein the lockout prevents the actuator from being actuated when the lockout is in the locked configuration, wherein the lockout is in the unlocked configuration when the replaceable suture cartridge is positioned in the end effector and has not been completely expended, and wherein the lockout permits the actuator to deploy the suture when the lockout is in the unlocked configuration. The surgical instrument also comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the locked configuration.

Example 159

A surgical instrument system configured to treat the tissue of a patient, comprising a shaft assembly which comprises a longitudinal axis, an end effector comprising a movable member and an actuator configured to deploy the plurality of surgical clips, an articulation joint rotatably connecting the end effector to the shaft, a rotation drive shaft configured to rotate the shaft about the longitudinal axis, a firing drive shaft configured to deploy the movable member, and an articulation drive shaft configured to articulate the end effector relative to the shaft. The surgical instrument system also comprises a first handle comprising a rotation drive system configured to drive the rotation drive shaft, a firing drive system configured to drive the firing drive shaft, and an articulation drive system configured to drive the articulation drive shaft. The surgical instrument system also comprises a second handle comprising a rotation drive lockout configured to lock the rotation drive shaft and a firing drive system configured to drive the firing drive shaft.

Example 160

A surgical instrument system configured to treat the tissue of a patient comprising a shaft assembly which comprises a longitudinal axis, an end effector comprising a movable member and an actuator configured to deploy a plurality of clips, an articulation joint rotatably connecting the end effector to the shaft, a rotation drive shaft configured to rotate the shaft about the longitudinal axis, a firing drive shaft configured to deploy the movable member, and an articulation drive shaft configured to articulate the end effector relative to the shaft. The surgical instrument system also comprises a first handle comprising a rotation drive system configured to drive the rotation drive shaft, a firing drive system configured to drive the firing drive shaft, and an articulation drive system configured to drive the articulation drive shaft. The surgical instrument system also comprises a second handle comprising an articulation drive lockout configured to lock the articulation drive shaft and a firing drive system configured to drive the firing drive shaft.

Example 161

A surgical instrument system configured to treat the tissue of a patient comprising a shaft assembly configured to perform a first function, a second function, and a third function wherein the shaft assembly comprises a first drive shaft configured to perform the first function, a second drive shaft configured to perform the second function, and a third drive shaft configured to perform the third function. The surgical instrument system also comprises a first handle and a second handle. The first handle comprises a first drive system configured to drive the first drive shaft, a second drive system configured to drive the second drive shaft, and a third drive system configured to drive the third drive shaft. The second handle comprises a first drive lockout configured to lock the first drive shaft and a second drive system configured to drive the second drive shaft.

Example 162

The surgical instrument system of Example 161, wherein the second handle comprises a drive lockout configured to lock the third drive shaft.

Example 163

A surgical instrument system configured to treat the tissue of a patient, comprising a shaft assembly which comprises a first drive system configured to perform a first function, a second drive system configured to perform a second function, a first lockout configured to selectively engage the first drive system and prevent the first drive system from performing the first function, and a second lockout configured to selectively engage the second drive system and prevent the second drive system from performing the second function. The surgical instrument system also comprises a first handle comprising a first operating system configured to operate the first drive system and a second operating system configured to operate the second drive system, wherein the first lockout and the second lockout are disengaged when the shaft assembly is assembled to the first handle. The surgical instrument system also comprises a second handle comprising a first operating system configured to operate the first drive system but not comprising a second operating system configured to operate the second drive system, wherein the first lockout is disengaged and the second lockout is engaged when the shaft assembly is assembled to the second handle.

Example 164

The surgical instrument system of Example 163, wherein the first lockout and the second lockouts are in their engaged states when the shaft assembly is not assembled to either the first handle or the second handle.

Example 165

A surgical instrument system, comprising a handle comprising a drive system including an electric motor and a shaft assembly attachable to the handle, wherein the shaft assembly comprises a drive shaft that is operably engaged with the drive system when the shaft assembly is attached to the handle, wherein the drive system is configured to drive the drive shaft when the shaft assembly is in a usable condition. The surgical instrument system also comprises a sensor system configured to evaluate the condition of the shaft assembly and a control system in communication with the drive system and the sensor system, wherein the control system is configured to prevent the operation of the electric motor if the shaft assembly is in an unusable condition.

Example 166

The surgical instrument system of Example 165, further comprising a haptic feedback system in communication with the control system, wherein the control system is configured to actuate the haptic feedback system to provide haptic feedback to the user of the surgical instrument system when the sensor system detects that the shaft assembly is in an unusable condition.

Example 167

The surgical instrument system of Examples 165 or 166, wherein the handle further comprises a second drive system, wherein the shaft assembly further comprises a second drive shaft operably engageable with the second drive system when the shaft assembly is attached to the handle, and wherein the control system is configured to use the second drive system when the sensor system detects that the shaft assembly is in an unusable condition.

Example 168

A surgical instrument system comprising a handle which comprises a housing, a handle electrical connector, a drive system including an electric motor, and a power source. The surgical instrument system also comprises a shaft assembly operably attachable to the handle, wherein the shaft assembly comprises a connector attachable to the housing when the shaft assembly is attached to the handle, a drive shaft engageable with the drive system when the shaft assembly is attached to the handle, a shaft electrical connector configured to be electrically coupled with the handle electrical connector when the shaft assembly is attached to the handle, and a shaft control system in communication with the shaft electrical connector, wherein the shaft control system is configured to receive power from the power source through the shaft electrical connector. The surgical instrument system also comprises a lockout in communication with the shaft control system, wherein the lockout comprises a solenoid, a lock element movable between an unlocked position, a hold position, and a locked position, a catch configured to releasably hold the lock element in the unlocked position, wherein the solenoid is configured to release the catch and allow the lock element to be moved into the hold position when the shaft control system receives power from the power source, and a biasing member configured to move the lock element into the hold position when the catch releases the lock element and while the shaft assembly is attached to the handle, wherein the biasing member is configured to move the lock element into the locked position once the shaft assembly is detached from the handle, and wherein the lock element prevents the shaft assembly from being re-attached to the handle once the lock element is in the locked position.

Example 169

The surgical instrument system of Example 168, wherein the shaft assembly comprises an unreleasable catch configured to hold the lock element in the locked position.

Example 170

A surgical instrument system comprising a handle and a shaft assembly operably attachable to the handle. The handle comprises a housing and a power source. The shaft assembly comprises a connector attachable to the housing when the shaft assembly is attached to the handle, a shaft control system configured to receive power from the power source when the shaft assembly is attached to the handle, and a lockout in communication with the shaft control system. The lockout comprises a lock element movable between an unlocked position, a hold position, and a locked position, a catch configured to releasably hold the lock element in the unlocked position, wherein the catch is configured to allow the lock element to be moved into the hold position when the shaft control system receives power from the power source, and a biasing member configured to move the lock element into the hold position when the catch releases the lock element and while the shaft assembly is attached to the handle, wherein the biasing member is configured to move the lock element into the locked position once the shaft assembly is detached from the handle, and wherein the lock element prevents the shaft assembly from being re-attached to the handle once the lock element is in the locked position.

Example 171

The surgical instrument system of Example 170, wherein the shaft assembly comprises an unreleasable catch configured to hold the lock element in the locked position.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument system, comprising:
a surgical instrument configured to perform at least three motor-driven functions of an end effector;
a first motor;
a second motor;
a third motor;
a first handle, comprising:
a first number of controls, wherein each control of said first number of controls corresponds to one of said three motor-driven functions of the end effector;
a second handle, comprising:
a second number of controls; and
a shaft assembly attachable to said first handle and said second handle, wherein said shaft assembly is attachable to said first handle in a first orientation to engage one of said first, second, or third motors, wherein said shaft assembly is attachable to said second handle in a second orientation to engage a different one of said first, second, or third motors, wherein the surgical instrument system is configured to perform a first motor-driven end effector function in said first orientation and a second motor-driven end effector function in said second orientation, wherein said first motor-driven end effector function is different than said second motor-driven end effector function, and wherein certain motor-driven end effector functions are locked out based on which motor is engaged in each orientation.

2. The surgical instrument system of claim 1, wherein said first number of controls is different than said second number of controls.

3. The surgical instrument system of claim 1, wherein said first orientation is different than said second orientation.

4. The surgical instrument system of claim 1, wherein said first orientation prevents said surgical instrument from performing at least one motor-driven function of the end effector.

5. The surgical instrument system of claim 1, wherein said second orientation prevents said surgical instrument from performing at least one motor-driven function of the end effector.

6. A surgical instrument system, comprising:
a surgical instrument configured to perform at least three motor-driven functions of an end effector;
a first handle comprising a first number of controls, wherein each control of said first number of controls corresponds to a motor-driven end effector function;
a second handle comprising a second number of controls;
a third handle comprising a third number of controls; and
a shaft assembly attachable to each of said first, second and third handles, wherein said shaft assembly is attachable to each of said first, second and third handles in a different orientation, wherein said surgical instrument system is configured to perform a different motor-driven end effector function in each said different orientation, and wherein certain motor-driven end effector functions are locked out based on which handle is attached to the end effector.

7. A surgical instrument system, comprising:
a first shaft assembly configured to perform a first motor-driven function, a second motor-driven function, and a third motor-driven function;
a second shaft assembly configured to perform said first motor-driven function and said second motor-driven function, but not said third motor-driven function; and
a handle, wherein said first shaft assembly and said second shaft assembly are selectively, and separately, attachable to said handle, wherein said handle comprises:
a first electric motor configured to drive said first motor-driven function;
a second electric motor configured to drive said second motor-driven function;

a third electric motor configured to drive said third motor-driven function when said first shaft assembly is attached to said handle; and a lockout configured to prevent said third electric motor from being operated when said second shaft assembly is attached to said handle.

8. The surgical instrument system of claim 7, wherein said first shaft assembly is attachable to said handle in a first orientation and said second shaft assembly is attachable to said handle in a second orientation, and wherein said first orientation is different than said second orientation.

9. A surgical instrument system, comprising:
a first shaft assembly configured to perform a first motor-driven function, a second motor-driven function, and a third motor-driven function;
a second shaft assembly configured to perform said first motor-driven function and said second motor-driven function; and
a handle, wherein said first shaft assembly and said second shaft assembly are selectively, and separately, attachable to said handle, wherein said handle comprises:
a first control configured to control said first motor-driven function;
a second control configured to control said second motor-driven function;
a third control configured to control said third motor-driven function when said first shaft assembly is attached to said handle; and
locking means for locking out said third control when said second shaft assembly is attached to said handle.

10. The surgical instrument system of claim 9, wherein said handle further comprises a microprocessor comprising input gates and output gates, wherein said first control, said second control, and said third control are in signal communication with said microprocessor via said input gates, and wherein said locking means comprises deactivating an input gate of said input gates associated with said third control when said second shaft assembly is attached to said handle.

11. The surgical instrument system of claim 9, wherein said handle further comprises a microprocessor comprising input gates and output gates, wherein said first control, said second control, and said third control are in signal communication with said microprocessor via said output gates, and wherein said locking means comprises deactivating an output gate of said output gates associated with said third motor-driven function when said second shaft assembly is attached to said handle.

12. A surgical instrument system, comprising:
a shaft assembly configured to perform a first function, a second function, and a third function, wherein said shaft assembly comprises:
a first drive configured to perform said first function;
a second drive configured to perform said second function;
a third drive configured to perform said third function; and
a lockout, wherein said lockout is selectively switchable between an unlocked configuration and a locked configuration, wherein said lockout prevents said shaft assembly from performing said third function when said lockout is in said locked configuration, and wherein said lockout permits said shaft assembly to perform said third function when said lockout is in said unlocked configuration;
a first handle, comprising:
a first motor for driving said first function;
a second motor for driving said second function;
a third motor for driving said third function when said shaft assembly is operably coupled to said first handle; and
a control system configured to place said lockout in said unlocked configuration; and
a second handle, comprising:
a first motor for driving said first function;
a second motor for driving said second function; and
a control system configured to place said lockout in said locked configuration.

13. A surgical instrument system, comprising:
a first handle comprising a first gripping portion and a first shaft lock;
a second handle comprising a second gripping portion and a second shaft lock; and
a shaft assembly selectively, and separately, attachable to said first handle and said second handle, wherein said first shaft lock holds said shaft assembly to said first handle in a first orientation when said shaft assembly is attached to said first handle, wherein said second shaft lock holds shaft assembly to said second handle in a second orientation when said shaft assembly is attached to said second handle, wherein said first orientation is different than said second orientation, wherein said first orientation and said second orientation correspond to different surgical instrument functions, and wherein said different surgical instrument functions are each carried out by separate drive systems.

14. The surgical instrument system of claim 13, wherein said shaft assembly comprises a housing and an array of lock apertures extending around said housing, and wherein said first shaft lock and said second shaft lock engage said lock apertures.

15. A surgical instrument system, comprising:
a first handle comprising a first gripping portion and a first shaft lock;
a second handle comprising a second gripping portion and a second shaft lock; and
a shaft assembly selectively, and separately, attachable to said first handle and said second handle, wherein said first shaft lock holds said shaft assembly to said first handle in a first orientation when said shaft assembly is attached to said first handle, wherein said second shaft lock holds shaft assembly to said second handle in a second orientation when said shaft assembly is attached to said second handle, and wherein said first orientation is different than said second orientation, wherein said first shaft lock comprises:
an arcuate ridge including a first end and a second end;
a first lock shoulder at said first end, wherein said first lock shoulder is positionable in a lock aperture; and
a second lock shoulder at said second end, wherein said second lock shoulder is positionable in a lock aperture.

16. A surgical instrument system, comprising:
a first handle comprising a first gripping portion and a first shaft lock;
a second handle comprising a second gripping portion and a second shaft lock; and
a shaft assembly selectively, and separately, attachable to said first handle and said second handle, wherein said first shaft lock holds said shaft assembly to said first handle in a first orientation when said shaft assembly is attached to said first handle, wherein said second shaft lock holds shaft assembly to said second handle in a second orientation when said shaft assembly is attached to said second handle, and wherein said first orientation is different than said second orientation, wherein said second shaft lock comprises:

an arcuate ridge including a first end and a second end;

a first lock shoulder at said first end, wherein said first lock shoulder is positionable in a lock aperture; and a second lock shoulder at said second end, wherein said second lock shoulder is positionable in a lock aperture.

\* \* \* \* \*